(12) United States Patent
Ozaki et al.

(10) Patent No.: US 6,784,192 B2
(45) Date of Patent: Aug. 31, 2004

(54) PIPERIDINE COMPOUND AND PHARMACEUTICAL COMPOSITION THEREOF

(75) Inventors: Fumihiro Ozaki, Ibaraki (JP); Toshihiko Kaneko, Ibaraki (JP); Mutsuko Tabata, Ibaraki (JP); Yoshinori Takahashi, Ibaraki (JP); Kazuki Miyazaki, Ibaraki (JP); Junichi Kamata, Ibaraki (JP); Ichiro Yoshida, Ibaraki (JP); Masayuki Matsukura, Ibaraki (JP); Hiroyuki Suzuki, Ibaraki (JP); Takashi Yoshinaga, Ibaraki (JP); Hiroki Ishihara, Ibaraki (JP); Hiroshi Katoh, Ibaraki (JP); Kohei Sawada, Ibaraki (JP); Tatsuhiro Onogi, Ibaraki (JP); Kiyoaki Kobayashi, Ibaraki (JP); Miyuki Ohkubo, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/181,560

(22) PCT Filed: Jan. 18, 2001

(86) PCT No.: PCT/JP01/00287

§ 371 (c)(1),
(2), (4) Date: Jul. 19, 2002

(87) PCT Pub. No.: WO01/53288

PCT Pub. Date: Jul. 26, 2001

(65) Prior Publication Data

US 2003/0220368 A1 Nov. 27, 2003

(30) Foreign Application Priority Data

Jan. 20, 2000 (JP) .......................................... 2000-012175

(51) Int. Cl.[7] .................... A61K 31/445; C07D 401/02; C07D 401/06

(52) U.S. Cl. ........................ 514/318; 514/312; 546/153; 546/193; 546/194

(58) Field of Search ................................. 514/312, 318; 546/153, 193, 194

(56) References Cited

U.S. PATENT DOCUMENTS

| | | | |
|---|---|---|---|
| 4,409,228 A | 10/1983 | Nisato et al. | ................ 514/318 |
| 4,665,187 A | 5/1987 | Böttcher et al. | ............. 546/255 |
| 5,604,245 A | 2/1997 | Le Fur et al. | ............... 514/318 |
| 5,665,719 A | 9/1997 | Pettibone et al. | ......... 514/227.8 |
| 5,958,924 A | 9/1999 | McCort et al. | ......... 514/253.04 |
| 6,130,232 A | 10/2000 | Mase et al. | ................. 514/318 |

FOREIGN PATENT DOCUMENTS

| | | |
|---|---|---|
| AU | A-70939/91 | 5/1991 |
| AU | 9170939 A | 5/1991 |
| EP | 0 021 973 A2 | 1/1981 |
| EP | 21973 A2 | 1/1981 |
| EP | 236140 A2 | 9/1987 |
| EP | 356230 A1 | 2/1990 |
| EP | 0 356 230 A1 | 2/1990 |
| EP | 0 506 545 A2 | 9/1992 |
| EP | 506545 A2 | 9/1992 |
| EP | 0 577 325 A1 | 1/1994 |
| EP | 577325 A1 | 1/1994 |
| EP | 0 976 732 A1 | 2/2000 |
| FR | 2467849 A | 4/1981 |
| FR | 2 467 849 | 4/1981 |
| FR | 2761067 A | 9/1998 |
| FR | 2 761 067 | 9/1998 |
| JP | 62-281858 | 12/1987 |
| JP | 64-63518 A | 3/1989 |
| JP | 64-63518 | 3/1989 |

(List continued on next page.)

OTHER PUBLICATIONS

Tabusa et al. "Carbostyril derivatives . . . " CA 109:6428 (1988).*
Kitazawa et al. "Preparation of 1,4–disubstituted cyclic . . . " CA 129:302552 (1998).*
Poss et al. "Preparation of cyclic amino substituted . . . " CA 133:135229 (2000).*
Fujio et al. "Preparation of fused heterocyclic compounds . . . " CA 138:4615 (2002).*
Shimada et al. "Nonischemic ST–segment elevation induced by . . . " CA 132:106293 (1999).*
Sindrup et., Pain, vol. 83, pp. 389–400, (1999).
Kalso et al., European Journal of Pain, vol. 2, pp. 3–14, (1998).
Kingery, W., Pain, vol. 73, pp. 123–139, (1997).

Primary Examiner—Ceila Chang
(74) Attorney, Agent, or Firm—Birch, Stewart, Kolasch & Birch, LLP

(57) ABSTRACT

The present invention provides a novel compound having a superior Na+ channel inhibitory activity. Namely, it provides a compound represented by the following formula (I), a salt thereof or a hydrate of them.

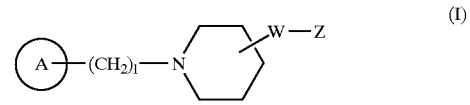

(I)

In the formula, the ring A represents a ring represented by the formula:

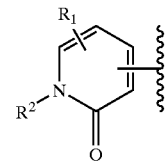

(wherein $R^1$ represents a hydrogen atom etc.; and $R^2$ represents indicates a hydrogen atom and the like) etc.; W represents an optionally substituted $C_{1-6}$ alkylene group etc.; Z represents an optionally substituted $C_{6-14}$ aromatic hydrocarbon cyclic group etc.; and l represents an integer from 0 to 6.

26 Claims, No Drawings

FOREIGN PATENT DOCUMENTS

| | | | |
|---|---|---|---|
| JP | 2-264773 A | 10/1990 | |
| JP | 2-264773 | 10/1990 | |
| JP | 6-501242 | 2/1994 | |
| JP | 7-502273 | 3/1995 | |
| JP | 8-511014 | 11/1996 | |
| JP | 9-505597 | 6/1997 | |
| WO | 0 236 140 A2 | 9/1987 | |
| WO | WO94/29305 | 12/1994 | |
| WO | 94/29305 A1 | 12/1994 | |
| WO | WO95/02405 | 1/1995 | |
| WO | 95/02405 A1 | 1/1995 | |
| WO | 95/23507 A1 | 9/1995 | |
| WO | WO95/23507 | 9/1995 | |
| WO | WO96/13479 | 5/1996 | |
| WO | 97/10238 A1 | 3/1997 | |
| WO | WO97/10238 | 3/1997 | |
| WO | 97/13766 A1 | 4/1997 | |
| WO | WO97/13766 | 4/1997 | |
| WO | 98/07703 A1 | 2/1998 | |
| WO | WO98/07703 | 2/1998 | |
| WO | 98/43956 A1 | 10/1998 | |
| WO | WO98/43956 | 10/1998 | |
| WO | WO99/31062 | 6/1999 | |
| WO | 99/31602 A1 | 6/1999 | |
| WO | 99/50263 A1 | 10/1999 | |
| WO | WO99/50263 | 10/1999 | |
| WO | WO00/34278 | 6/2000 | |
| WO | 00/34278 A1 | 6/2000 | |

\* cited by examiner

PIPERIDINE COMPOUND AND PHARMACEUTICAL COMPOSITION THEREOF

This application is the national phase under 35 U.S.C. § 371 of PCT International Application No. PCT/JP01/00287 which has an International filing date of Jan. 18, 2001, which designated the United States of America.

TECHNICAL FIELD

The present invention relates to a novel piperidine compound, a salt thereof or a hydrate of them, a production process thereof, and a pharmaceutical composition comprising these compounds and the like and a preparation thereof.

PRIOR ART

The atrial fibrillation, which is one type of arrhythmia, is a condition in which the atrium does not carry out regular excitation and contraction in accordance with stimulation from the sinoatrial node, and frequently repeats the excitation at random, and is classified in paroxysmal atrial fibrillation and chronic atrial fibrillation. In many cases, crisis occurs as the complication of organic heart diseases, such as mitral valve disease, coronary artery disease, hypertensive heart disease, thyrotoxicosis (which are four major basic diseases), increases, and lone atrial fibrillation only causing atrial fibrillation is also reported. Further, a condition in heart failure is often exhibited in addition to palpitation and chest discomfort, and thrombus is formed in the left atrium, which can provoke thromboembolism in various organs of system. Although the treatment of atrial fibrillation (the termination of paroxysm, the prevention of recurrence, and the like) differs in the cases of paroxysmal atrial fibrillation and chronic atrial fibrillation, the effectiveness of non-medication is insufficient in both cases, and the administration of an antiarrhythmic drug is designated as the first choice at present. There are known antiarrhythmics, such as Class I drugs of Vaughan Williams classification (Class I: a drug suppressing the conduction in atrial muscle by selective blocking of $Na^+$ channel and inhibiting the reentry circuit), Class II drugs (Class II: β-adrenergic receptor blocker), Class III drugs (Class III: a drug of selectively blocking $K^+$ channel and prolonging the action potential duration), Class IV drugs (Class IV: Ca+ channel blocker), and the like. However, a drug of inhibiting the reentry circuit of potential in atrial muscle is effective for termination of atrial fibrillation, and it is considered that the class I antiarrhythmic drug and the class III antiarrhythmic drug are effective. Concerning this kind of antiarrhythmics, many reports have been hitherto disclosed, and, for example, the inventions relating to piperidine compounds as antiarrhythmics are disclosed in Japanese patent Application No. 62-281858, JP-A 6-501242, JP-A 7-502273, JP-A 8-511014 etc., in addition to the inventions relating to the antiarrhythmics disclosed in JP-A 9-505597, JP-A 8-511014, WO96/13479, etc.

However, since the class I antiarrhythmic drug has a negative inotropic effect (the reduction of the pumping function of heart) based on the $Na^+$ channel inhibitory action, it has been a problem in that it causes the deterioration or exasperation of heart failure. To the contrary, the class III antiarrhythmic drug does not exhibit such an effect and is superior in only extending the refractory period, but a conventional class III antiarrhythmic drug is not always effective in the termination rate of atrial fibrillation, extends also the refractory period of atrial muscle, and often extends the refractory period of atrial muscle at a normal time than at tachycardia (reverse use-dependency), and therefore it has been a problem to induce ventricular arrhythmia at a dose of showing a medicinal effect.

On the other hand, it is also known that the compound having the $Na^+$ channel inhibitory action is useful for remedy of various neuralgia (for example, postherpetic neuralgia, diabetic neuralgia, HIV neuralgia etc.). For example, Lidoderm in remedy for postherpetic neuralgia, Carbamazepine in trigeminal neuralgia, $Na^+$ channel inhibitor as antiarrhythmic (for example, Mexiletin), $Na^+$ channel inhibitors as antidepressant and anticonvulsant (for example, Amitriptyline, Carbamazepine) and the like are used as various antineuralgic remedies. In addition to these, there are several reports (Pain. 83 (1999) 389–400: European Journal of Pain 2 (1998) 3–14; Pain. 73 (1997) 123–139) concerning the fact that arrhythmia drug (Mexiletine, Lidocaine) is effective as analgesic.

However, since a conventional $N^+$ channel inhibitor has an equal effect to the heart and nerves in the remedy of a conventional neuralgia, the dose of a $Na^+$ channel inhibiting compound cannot be increased, and a distinct analgesic effect could not be exhibited.

A drug which exhibits a superior $Na^+$ channel inhibitory action, that satisfies the requirements of pharmacological activity, a dose, safety and the like, as pharmaceuticals, and effective in clinical use, has been not found. Namely, it is the object of the present invention to investigate and find a superior $Na^+$ channel inhibiting compound which solves the above-mentioned problems.

DISCLOSURE OF THE INVENTION

The present inventors have intensively studied in view of the above-mentioned circumstances, and as a result, have succeeded in synthesizing a compound which is a quite novel piperidine compound represented by the formula (I):

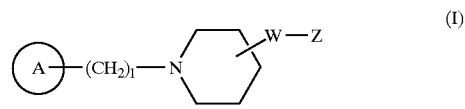

(wherein the ring A indicates a ring represented by the formula:

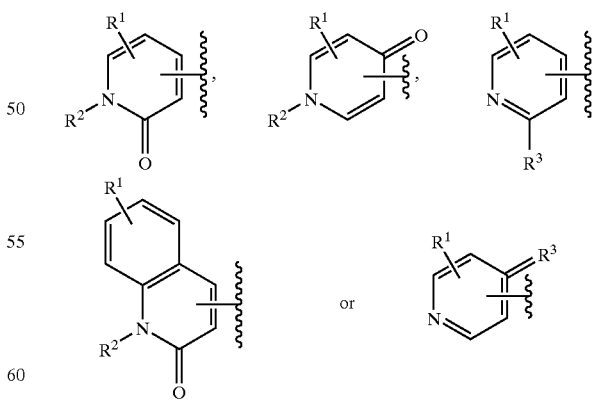

(wherein $R^1$ means (1) a hydrogen atom, (2) a halogen atom, (3) a cyano group, (4) an optionally substituted $C_{1-6}$ alkyl group, (5) an optionally substituted $C_{2-6}$ alkenyl group, (6) an optionally substituted $C_{2-6}$ alkynyl group, (7) an optionally substituted $C_{3-8}$ cycloalkyl group, (8) an optionally substituted $C_{3-8}$ cycloalkenyl group, (9) an optionally substituted $C_{1-6}$ alkoxy group, (10) an optionally substituted $C_{1-6}$ alkylthio group, (11) an optionally substituted $C_{1-6}$ alkylsulfinyl group, (12) an optionally substituted $C_{1-6}$ alkylsulfonyl group, (13) an optionally substituted $C_{6-14}$ aromatic hydrocarbon cyclic group or (14) an optionally substituted 5- to 14-membered aromatic heterocyclic group;

$R^2$ means (1) a hydrogen atom, (2) an optionally substituted $C_{1-6}$ alkyl group, (3) an optionally substituted $C_{2-6}$ alkenyl group, (4) an optionally substituted $C_{2-6}$ alkynyl group, (5) an optionally substituted $C_{3-8}$ cycloalkyl group, (6) an optionally substituted $C_{3-8}$ cycloalkenyl group, (7) an optionally substituted amino group, (8) an optionally substituted $C_{6-14}$ aromatic hydrocarbon cyclic group or (9) an optionally substituted 5- to 14-membered aromatic heterocyclic group; and $R^3$ means (1) an optionally substituted $C_{1-6}$ alkoxy group, (2) an optionally substituted $C_{2-6}$ alkenyloxy group, (3) an optionally substituted $C_{3-7}$ cycloalkyloxy group or (4) an optionally substituted $C_{3-7}$ cycloalkenyloxy group);

W means (1) a single bond, (2) an optionally substituted $C_{1-6}$ alkylene group, (3) an optionally substituted $C_{2-6}$ alkenylene group, (4) an optionally substituted $C_{2-6}$ alkynylene group or (5) a group represented by the formula —U—V— (wherein U means (i) a single bond, (ii) an oxygen atom, (iii) a sulfur atom, (iv) a group represented by the formula —NH—, (v) an optionally substituted $C_{1-6}$ alkylene group, (vi) an optionally substituted $C_{2-6}$ alkenylene group or (vii) an optionally substituted $C_{2-6}$ alkynylene group; V means (i) a single bond, (ii) an optionally substituted $C_{1-6}$ alkylene group, (iii) an optionally substituted $C_{2-6}$ alkenylene group, (iv) an optionally substituted $C_{2-6}$ alkynylene group, (v) an oxygen atom, (vi) a sulfur atom, or (vii) a group represented by the formula —CO—, (viii) —SO— or (ix) —SO$_2$—, provided that the case where U and V mean the same group in the above definition is excluded, and one of U and V means a single bond, an optionally substituted $C_{1-6}$ alkylene group, an optionally substituted $C_{2-6}$ alkenylene group or an optionally substituted $C_{2-6}$ alkynylene group);

Z means (1) an optionally substituted $C_{6-14}$ aromatic hydrocarbon cyclic group, (2) an optionally substituted 5- to 14-membered aromatic heterocyclic group or (3) a group represented by the formula —N(R$^4$)R$^5$ (wherein R$^4$ and R$^5$ may be the same as or different from each other and each represents (i) a hydrogen atom, (ii) an optionally substituted $C_{1-6}$ alkyl group, (iii) an optionally substituted $C_{2-6}$ alkenyl group, (iv) an optionally substituted $C_{2-6}$ alkynyl group, (v) an optionally substituted $C_{3-8}$ cycloalkyl group, (vi) an optionally substituted $C_{3-8}$ cycloalkenyl group, (vii) an optionally substituted $C_{6-14}$ aromatic hydrocarbon cyclic group, (viii) an optionally substituted 5- to 14-membered aromatic heterocyclic group or (ix) a $C_{1-6}$ aliphatic acyl group, or (x) R$^4$ and R$^5$ may be bound together to form a 3-to 8-membered nitrogen-containing cyclic group); and l represents an integer of (0 to 6), and further, have found that these compounds, etc. have a superior N$^+$ channel inhibitory action, and are useful for treating or preventing a disease against which the Na$^+$ channel inhibitory action is useful for the treatment and prevention (for example, arrhythmia (in addition to this, the removal of a patient's stress caused by an attack of atrial fibrillation, for example, palpitation, chest discomfort, heart failure, thrombus in left atrium, thromboembolism, seizure), various neuralgia (for example, diabetic neuralgia, HIV neuralgia, postherpetic neuralgia etc.) etc.). Thus, they have completed the present invention.

Namely, the present invention is 1) a compound represented by the above-mentioned formula (I), a salt thereof or a hydrate of them; 2) in the above-mentioned 1), W may be a group represented by the formula —CH$_2$—, —CH$_2$—CH$_2$—, —(CH$_2$)$_3$—, —(CH$_2$)$_4$—, —(CH$_2$)$_5$—, —CH=CH—, —C≡C—, —CO—, —O—, —O—CH$_2$—, —CH$_2$—O—, —CH$_2$—CO—, —(CH$_2$)$_2$—CO—, —CH$_2$—CH(CN)—, —CH$_2$—CH(OH)—, —SO$_2$—, —CH$_2$—SO$_2$—, —NH—CO—, —CH$_2$—NH—CO—, —NH—SO$_2$— or —CH$_2$—NH—SO$_2$—, 3) in the above-mentioned 1), w may be a group represented by the formula —CH$_2$—CH$_2$—, —CH=CH—, —CH—CH— or —CH$_2$—O—, 4) in the above-mentioned 1), Z may be an optionally substituted $C_{6-14}$ aromatic hydrocarboncyclic group or an optionally substituted 5- to 14-membered aromatic heterocyclic group, 5) in the above-mentioned 1), Z may be an optionally substituted phenyl group, pyridyl group or thienyl group, 6) in the above-mentioned 1), Z may be a $C_{6-14}$ aromatic hydrocarbon cyclic group or a 5- to 14-membered aromatic heterocyclic group, and the ring may be respectively substituted with one or more groups selected from (1) a hydroxyl group, (2) a halogen atom, (3) a cyano group, (4) an optionally substituted $C_{1-6}$ alkyl group, (5) an optionally substituted $C_{3-8}$ cycloalkyl group, (6) an optionally substituted $C_{1-6}$ alkoxy group, (7) an optionally substituted $C_{3-8}$ cycloalkyloxy group, (8) an optionally substituted $C_{1-6}$ alkylthio group, (9) an optionally substituted $C_{6-14}$ aryloxy group, (10) an optionally substituted 5- to 14-membered hetero aryloxy group, (11) an optionally substituted amino group, (12) an optionally substituted 5- to 14-membered aromatic heterocyclic group, (13) an optionally substituted 5- to 14-membered non aromatic heterocyclic group, (14) a $C_{1-6}$ alkylsulfonyl group and (15) a $C_{1-4}$ alkylenedioxy group, 7) in the above-mentioned 1), Z may be a group represented by the formula —N(R$^4$)R$^5$ (wherein R$^4$ and R$^5$ have the same meanings as defined above, respectively), 8) in the above 7), R$^4$ and R$^5$ may be the same as or different from each other and each represents a hydrogen atom, an optionally substituted $C_{1-6}$ alkyl group, an optionally substituted $C_{2-6}$ alkynyl group, an optionally substituted $C_{6-14}$ aryl $C_{1-6}$ alkyl group or an optionally substituted heteroaryl $C_{1-6}$ alkyl group, 9) in the above-mentioned 7), R$^4$ and R$^5$ may be bound together to form an optionally substituted 3- to 8-membered nitrogen-containing cyclic group, 10) in the above-mentioned 9), Z may be a piperidyl group which may be an optionally substituted piperidyl group, an optionally substituted piperazyl group or an optionally substituted morpholinyl group, 11) in the above-mentioned 1), l may be an integer of 1, 12) in the above-mentioned 1), the ring A may be a ring represented by the formula:

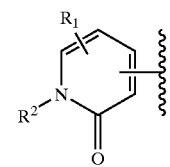

(wherein R¹ and R² have the same meanings as defined above, respectively), 13) in the above-mentioned 12), R¹ may be a hydrogen atom, a halogen atom or a $C_{1-6}$ alkyl group, 14) in the above-mentioned 12), R¹ may be a hydrogen atom, 15) in the above-mentioned 12), R² may be a hydrogen atom or an optionally substituted $C_{1-6}$ alkyl group, 16) in the above-mentioned 1), the ring A may be a ring represented by the formula:

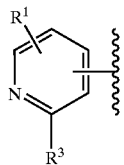

wherein R¹ and R³ have the same meanings as defined above, respectively, 17) in the above-mentioned 16), R³ may be a hydroxyl group or a $C_{1-6}$ alkoxy group, 18) in the above-mentioned 1), the bonding position of the group —W—Z may be 2- or 4-position of a piperidine ring. Further, the present invention is 19) a compound represented by the above-mentioned formula:

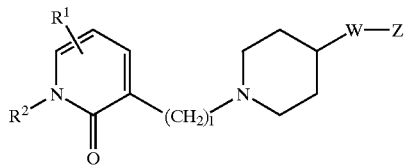

(wherein R¹, R², W, Z and l have the same meanings as defined in the above claim 1), a salt thereof or a hydrate of them, 20) a compound represented by the formula:

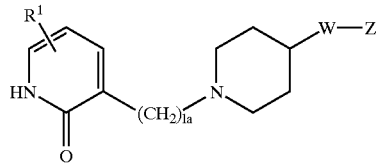

(wherein R¹, W and Z have the same meanings as defined in the above claim 1, respectively; and la represents an integer of 1 or 2), a salt thereof or a hydrate of them, 21)

1-[(2-oxo-1,2-dihydro-3-pyridinyl)methyl]-4-[2-[2-(cyclohexylmethyloxy)phenyl]ethyl]piperidine,
1-[(5-chloro-2-oxo-1,2-dihydro-3-pyridinyl)methyl]-4-[2-[2,3-(methylenedioxy)phenyl]ethyl]piperidine,
1-[(5-chloro-2-oxo-1,2-dihydro-3-pyridinyl)methyl]-4-[2-(2-(fluorophenyl)ethyl]piperidine,
1-[(5-chloro-2-oxo-1,2-dihydro-3-pyridinyl)methyl]-4-[2-[2-(isobutyloxy)phenyl]ethyl]piperidine,
1-[(5-chloro-2-oxo-1,2-dihydro-3-pyridinyl)methyl]-4-[(E)-2-(2-fluorophenyl)-1-ethenyl]piperidine,
1-[(5-fluoro-2-oxo-1,2-dihydro-3-pyridinyl)methyl]-4-[(E)-2-(2-fluorophenyl)-1-ethenyl]piperidine,
1-[(2-oxo-1,2-dihydro-3-pyridinyl)methyl]-4-[(E)-2-[2-(benzyloxy)phenyl]-1-ethenyl]piperidine,
1-[(2-oxo-1,2-dihydro-3-pyridinyl)methyl]-4-[(E)-2-[2-(cyclohexylmethyloxy)phenyl]-1-ethenyl]piperidine,
1-[(2-oxo-1,2-dihydro-3-pyridinyl)methyl]-4-[(Z)-2-[2-(cyclohexylmethyloxy)phenyl]-1-ethenyl]piperidine,
1-[(5-fluoro-2-oxo-1,2-dihydro-3-pyridinyl)methyl]-4-[(E)-2-[(2-cyclohexylmethyloxy)phenyl]-1-ethenyl]piperidine,
1-[(2-oxo-1,2-dihydro-3-pyridinyl)methyl]-4-[2-(2-cyclohexylmethyloxy)phenyl]-1-ethynyl]piperidine,
1-[(5-chloro-2-oxo-1,2-dihydro-3-pyridinyl)methyl]-4-[2,4-(difluorophenoxy)methyl]piperidine or
1-[(5-chloro-2-oxo-1,2-dihydro-3-pyridinyl)methyl]-4-[2,5-(difluorophenoxy)methyl]piperidine, a salt thereof or a hydrate of them, 22) a process for producing the compound described in the above-mentioned 1), a salt thereof or a hydrate of them, which comprises the step of reacting a compound represented by the formula:

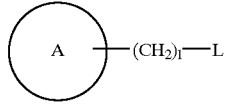

(wherein the ring A and l have the same meaning as in the fore-mentioned definition according to claim 1, respectively; and L represents a leaving group), a salt thereof or a reactive derivative of them, with a compound represented by the formula:

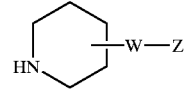

(wherein W and Z have the same meanings as defined in the above claim 1, respectively), 23) a pharmaceutical composition comprising a compound represented by the formula:

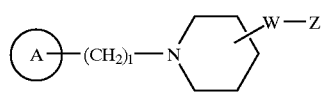

(I)

(in the formula, the respective symbols have the same meanings as defined in the above claim 1), a salt thereof or a hydrate of them, 24) the composition in the above-mentioned 23) may be a sodium channel inhibitor or a potassium channel inhibitor, 25) the composition in the above-mentioned 23) may be an agent for preventing or treating arrhythmia, 26) the composition in the above-mentioned 23) may be the class III antiarrhythmic drug of Vaughan Williams classification, 27) the composition in the above-mentioned 23) may be an analgesic, 28) the composition in the above-mentioned 23) may be an agent for treating or preventing neuralgia, further, 29) the neuralgia in the above-mentioned 28) may be diabetic neuralgia, HIV neuralgia, postherpetic neuralgia, trigeminal neuralgia, stump pain, postspinal injury pain, thalamic pain or post-stroke pain.

The present invention provides use of the compound represented by the above formula (I), a salt thereof or a hydrate of them, for producing a sodium channel inhibitor or a potassium channel inhibitor, an agent for treating or preventing arrhythmia, the class III antiarrhythmic drug of Vaughan Williams classification, an analgesic, and an agent for treating or preventing neuralgia.

Further, the present invention provides a method for preventing or treating a disease against which a sodium channel inhibitiory action or a potassium channel inhibitory action is effective for the prevention or therapy, by administering a pharmacologically effective amount of the compound represented by the above formula (I), a salt thereof or a hydrate of them to a patient.

Further, the present invention provides a method for preventing or treating arrhythmia, the class III antiarrhythmia drug of Vaughan Williams classification, pain and neuralgia, by administering a pharmacologically effective amount of the compound represented by the above formula (I), a salt thereof or a hydrate of them to a patient.

The meanings of the symbols, terms etc. described in the specification of the present application are indicated below, and the present invention is illustrated in detail.

The structural formula of a compound sometimes represents a fixed isomer in the specification of the present application for convenience, but the present invention includes all of geometrical isomers which occur in the structure of the compound, optical isomers based on an asymmetric carbon, stereo-isomers, the isomers of tautomers and the like, and a mixture of the isomers. The present invention is not limited to the description of the formulae for convenience, and may include one of the isomers and a mixture thereof. Accordingly, in the compounds of the present invention, there may exist an optical activator and a racemic body which have an asymmetric carbon atom in the molecule, but they are not limited in the present invention, and both of them are included therein. Further, polymorphism sometimes exists, but is not similarly limited, and any of crystal forms may be single or a mixture of crystal forms, and may be a hydrate in addition to an anhydride. A so-called metabolite which is occurred by decomposing the compounds according to the present invention in vivo is also included within the scope of claim for patent of the present application.

The "arrhythmia" in the specification of the present application is a general name of cases in which tuning function among cardiac functions exhibits abnormality (stimulant genesis abnormality and stimulant conduction abnormality), and includes, for example, sinus arrhythmia, premature beat, atrial fibrillation, paroxysmal supraventricular tachycardia, sinoatrial block, atrioventricular block and the like. The compounds according to the present invention are specifically effective for atrial fibrillation among arrhythmia.

The "neuralgia" in the specification of the present application is dolorific symptom (true and sequential) derived from nerve, and means pain which occurs in the running path of nerve or distribution region thereof. For example, it includes affections such as diabetic neuralgia, HIV neuralgia, postherpetic neuralgia, trigeminal neuralgia, stump pain, postspinal injury pain, thalamic pain, poststroke pain and the like. "Analgesic" means a drug which mitigates or removes pain by changing the perception of rociceptive stimuli without causing anesthetic condition and unconsciousness.

The "Halogen atom" used in the specification of the present application refers to atoms such as fluorine atom, chlorine atom, bromine atom and iodine atom.

The "$C_{1-6}$ alkyl group" used in the specification of the present application refers to an alkyl group having 1 to 6 carbon atoms, and examples thereof include linear or branched alkyl groups such as methyl group, ethyl group, n-propyl group, isopropyl group, n-butyl group, isobutyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-ethylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl, 2-ethylbutyl group, 2-methylpentyl group, and 3-methylpentyl group.

The "$C_{2-6}$ alkenyl group" used in the specification of the present application refers to an alkenyl group having 2 to 6 carbon atoms, and examples thereof include linear or branched alkenyl groups such as vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group and 1,6-hexanedienyl group.

The "$C_{2-6}$ alkynyl group" used in the specification of the present application refers to an alkynyl group having 2 to 6 carbon atoms, and examples thereof include linear or branched alkynyl groups such as ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexanediynyl group and 1,6-hexanediynyl group.

The "$C_{1-6}$ alkoxy group" used in the specification of the present application refers to a "$C_{1-6}$ alkyloxy group" in which oxygen atom is bound to a group having the same meaning as the $C_{1-6}$ alkyl group in the above definition, and examples thereof include methoxy group, ethoxy group, n-propoxy group, isopropoxy group, n-butoxy group, isobutoxy group, sec-butoxy group, tert-butoxy group, n-pentyloxy group, isopentyloxy group, sec-pentyloxy group, n-hexoxy group, isohexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group etc.

The "$C_{1-6}$ alkenyloxy group" used in the specification of the present application refers to a group in which an oxygen atom is bound to a group having the same meaning as the $C_{1-6}$ alkenyl group in the above definition, and examples of a preferable group include vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexanedienyloxy group, 1,6-hexanedienyloxy group etc.

Examples of the "$C_{1-6}$ alkylthio group" used in the specification of the present application include, for example, methylthio group, ethylthio group, n-propylthio group, isopropylthio group, n-butylthio group, isobutylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, 2-ethylpropylthio group, n-hexylthio group, 1-methyl-2-ethylpropylthio group, 1-ethyl-2-ethylpropylthio group, 1,1,2-trimethylpropylthio group, 1-propylpropylthio group, 1-methylbutylthio group, 2-methylbutylthio group, 1,1-dimethylbutylthio group, 1,2-dimethylbutylthio group, 2,2-dimethylbutylthio group, 1,3-dimethylbutylthio group, 2,3-dimethylbutylthio group, 2-ethylbutylthio group, 2-methylpentylthio group, 3-methylpentylthio group.

The "$C_{3-8}$ cycloalkyl group" used in the specification of the present application refers to a cycloalkyl group in which the ring is formed by 3 to 8 carbon atoms, and examples thereof include cyclopropyl group, cyclobutyl group, cyclopentyl group, cyclohexyl group, cycloheptyl group, cyclooctyl group etc. Further, the "$C_{3-8}$ cycloalkane group" used in the specification of the present application refers to a ring which corresponds to the above-mentioned $C_{3-8}$ cycloalkyl group.

The "$C_{3-8}$ cycloalkenyl group" used in the specification of the present application refers to a cycloalkenyl group in which the ring is formed by 3 to 8 carbon atoms, and for example, groups represented by the formula:

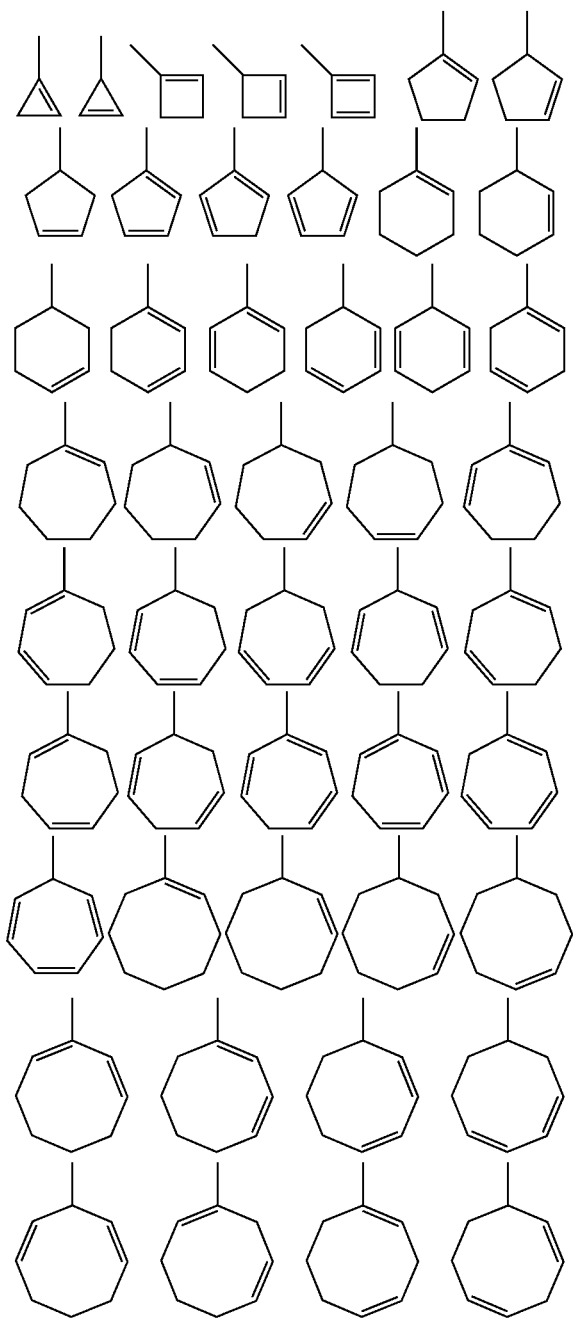

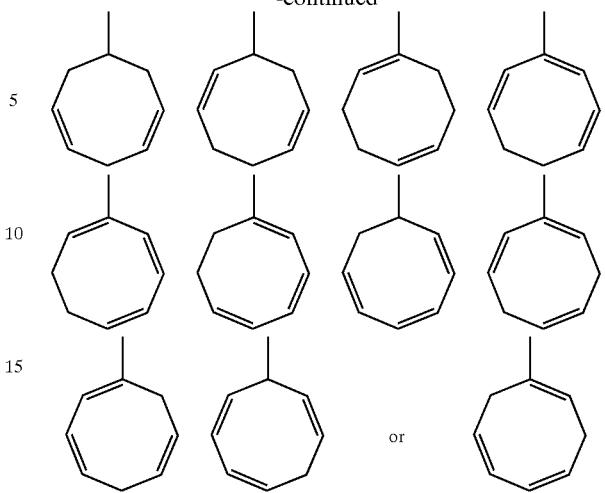

are mentioned.

Examples of the "$C_{6-14}$ aromatic hydrocarbon cyclic group" used in the specification of the present application refers to mono-cyclic, di-cyclic or tri-cyclic $C_{6-14}$ aromatic hydrocarbon cyclic groups such as phenyl group, indenyl group, 1-naphthyl group, 2-naphthyl group, azulenyl group, hepthalenyl group, biphenyl group, indathenyl group, acenaphthyl group, fluorenyl group, phenalenyl group, phenanthrenyl group, anthracenyl group, cyclopentacyclooctenyl group and benzocyclooctenyl group.

The "5- to 14-membered aromatic heterocyclic group" used in the specification of the present application means a mono-cyclic, di-cyclic or tri-cyclic 5- to 14-membered aromatic heterocyclic group containing any one or more hetero atoms selected from nitrogen atom, sulfur atom and oxygen atom, and the examples thereof include (i) aromatic heterocyclic groups containing nitrogen such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthylidinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, imidazopyridinyl group, imidazopyrimidinyl group, a pyrazolopyridinyl group and pyrazolopyridinyl group; (ii) aromatic heterocyclic groups containing sulfur such as thienyl group and benzothienyl group; (iii) aromatic heterocyclic groups containing oxygen such as furyl group, pyranyl group, cyclopentapyranyl group, benzofuranyl group and isobenzofuranyl group; (iv) aromatic heterocyclic groups containing 2 or more different kinds of hetero atoms selected from nitrogen atom, sulfur atom and oxygen atom, such as thiazolyl group, isothiazolyl group, benzothiazolyl group, benzthiazolyl group, phenothiazinyl group, isoxazolyl group, furazanyl group, phenoxazinyl group, oxazolyl group, benzooxazolyl group, oxadiazolyl group, pyrazolooxazolyl group, imidazothiazolyl group, thienofuranyl group, furopyrrolyl group and pyridoxazinyl group.

The "5- to 14-membered non-aromatic heterocyclic ring" used in the specification of the present application means a mono-cyclic, di-cyclic or tri-cyclic 5- to 14-membered non-aromatic heterocyclic ring containing any of one or more of hetero atoms selected from nitrogen atom, sulfur atom and oxygen atom, and the examples thereof include pyrrolidine, pyrroline, piperidine, piperazine, imidazoline, pyrazolidine, imidazolidine, morpholine, tetrahydrofuran, tetrahydropyran, aziridine, oxirane, oxathiorane, pyridone ring, and condensed rings such as phthalimide ring and succinimide ring.

The "hydrocarbon group" used in the specification of the present application specifically refers to a $C_{1-6}$ alkyl group, a $C_{2-6}$ alkenyl group, a $C_{2-6}$ alkynyl group, a $C_{3-8}$ cycloalkyl or a $C_{3-8}$ cycloalkenyl group, and the respective meanings are as described above.

In the compound represented by the above formula (I) according to the present invention, a particularly preferable aspect of each group are as follows.

In a group represented by the formula:

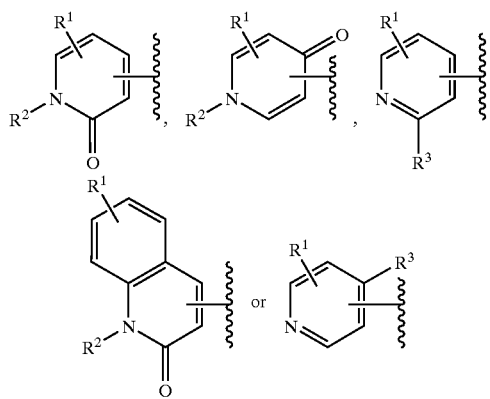

(wherein $R^1$, $R^2$ and $R^3$ have the same meanings as defined in the above claim 1) indicated by A in the above formula (I), the preferable atom of the "halogen atom" indicated by $R^1$ includes fluorine atom, chlorine atom and bromine atom, and fluorine atom and chlorine atom are more preferable.

The "$C_{1-6}$ alkyl group" in the "$C_{1-6}$ alkyl group which may be substituted" shown by the above-mentioned $R^1$ or $R^2$ is preferably methyl group, ethyl group, n-propyl group, isopropyl group, n-butyl group, isobutyl group, sec-butyl group, tert-butyl group, n-pentyl group, n-hexyl group etc. Further, the "$C_{2-6}$ alkenyl group" in the "$C_{2-6}$ alkenyl group which may be substituted" shown by $R^1$ or $R^2$ is preferably vinyl group, allyl group, 1-propenyl group, 2-propenyl group, isopropenyl group, 1-butenyl group, 2-butenyl group, 3-butenyl group, 1-pentenyl group, 1-hexenyl group etc. Further, the "$C_{2-6}$ alkynyl group" in the "$C_{2-6}$ alkynyl group which may be substituted" shown by the above $R^1$ or $R^2$ is preferably ethynyl group, 1-propynyl group, 2-propynyl group, 1-butynyl group, 2-butynyl group, 3-butynyl group, 1-pentynyl group, 1-hexynyl group etc.

The "$C_{3-8}$ cycloalkyl group" in the "$C_{3-8}$ cycloalkyl group which may be substituted" by the above-mentioned $R^1$ or $R^2$ is preferably cyclopropyl group, cyclobutyl group, cyclopentyl group, cyclohexyl group etc. Further, the "$C_{3-8}$ cycloalkenyl group" in the "$C_{3-8}$ cycloalkenyl group which may be substituted" shown by $R^1$ or $R^2$ is preferably cyclobutenyl group, cyclopentenyl group, cyclohexenyl group etc.

The "$C_{1-6}$ alkoxy group" in the "$C_{1-6}$ alkoxy group which may be substituted" shown by the above-mentioned $R^1$ or $R^3$ is preferably methoxy group, ethoxy group, n-propoxy group, isopropoxy group, n-butoxy group, isobutoxy group, sec -butoxy group, tert-butoxy group, n-pentyloxy group, isopentyloxy group, sec-pentyloxy group, n-hexoxy group, isohexoxy group etc. Further, the "$C_{2-6}$ alkenyloxy group" in the "$C_{2-6}$ alkenyloxy group which may be substituted" shown by the above-mentioned $R^3$ is preferably vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexanedienyloxy group, 1,6-hexanedienyloxy group etc.

The "$C_{1-6}$ alkylthio group" in the "$C_{1-6}$ alkylthio group which may be substituted" shown by the above-mentioned $R^1$ is preferably methylthio group, ethylthio group, n-propylthio group, isopropylthio group, n-butylthio group, isobutylthio group, sec-butylthio group, tert-butylthio group, n-pentylthio group, n-hexylthio group etc.

The "$C_{1-6}$ alkylsulfinyl group" in the "$C_{1-6}$ alkyl sulfinyl group which may be substituted" shown by the above-mentioned $R^1$ is preferably methylmethylsulfinyl group, ethylsulfinyl group, n-propylsulfinyl group, isopropylsulfinyl group, n-butylsulfinyl group, isobutylsulfinyl group, sec-butylsulfinyl group, tert-butylsulfinyl group, n-pentylsulfinyl group, n-hexylsulfinyl group etc.

The "$C_{1-6}$ alkylsulfonyl group" in the "$C_{1-6}$ alkylsulfonyl group which may be substituted" shown by the above-mentioned $R^1$ is preferably methylmethylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, n-hexylsulfonyl group etc.

The "$C_{6-14}$ aromatic hydrocarbon cyclic group" in the "$C_{6-14}$ aromatic hydrocarbon cyclic group which may be substituted" shown by the above-mentioned $R^1$ or $R^2$ is preferably phenyl group, naphthyl group etc. Further, the "5- to 14-membered aromatic heterocyclic group" in the "5- to 14-membered aromatic heterocyclic group which may be substituted" shown by the above-mentioned $R^1$ or $R^2$ is preferably pyridyl group, pyrazyl group, pyrinidyl group, pyridazinyl group, thienyl group, thiazolyl group, imidazolyl group, furyl group etc.

As the preferable substituent of the amino group in the "amino group which may be substituted" shown by the above-mentioned $R^2$, for example, (1) a $C_{1-6}$ alkyl group which may be substituted (for example, methyl group, ethyl group, n-propyl group, isopropyl group, n-butyl group, isobutyl group, sec-butyl group, tert-butyl group, n-pentyl group, n-hexyl group etc. which may be substituted, respectively), (2) a $C_{2-6}$ alkenyl group which may be substituted (for example, vinyl group, allyl group, 1-propenyl group, 2-propenyl group, isopropenyl group, 1-butenyl group, 2-butenyl group, 3-butenyl group, 1-pentenyl group, 1-hexenyl group etc. which may be substituted, respectively), (3) a $C_{2-6}$ alkynyl group which may be substituted (for example, ethynyl group, 1-propynyl group, 2-propynyl group, 1-butynyl group, 2-butynyl group, 3-butynyl group, 1-pentynyl group, 1-hexynyl group etc. which may be substituted, respectively), (4) a $C_{3-8}$ cycloalkyl group which may be substituted (for example, cyclopropenyl, cyclopropyl group, cyclobutyl group, cyclopentyl group, cyclohexyl group etc. which may be substituted, respectively), (5) a $C_{3-8}$ cycloalkenyl group which may be substituted (for example, cyclobutenyl group, cyclopentenyl group, cyclohexenyl group etc. which may be substituted, respectively), (6) anacyl group, (7) a carbamoyl group which may be substituted, etc. may be proposed. The relevant amino group may have one or two groups selected from these groups as substituents, and more preferable examples of the amino group includes unsubstituted amino group, methylamino group, dimethylamino group, ethylamino group, diethylamino group, n-propylamino group, di(n-propyl)amino group, isopropylamino group, di(isopropyl)amino group etc.

The "$C_{3-7}$ cycloalkyloxy group" in the "$C_{3-7}$ cycloalkyloxy group which may be substituted" shown by the above-mentioned $R^3$ is preferably cyclopropyloxy group, cyclobutyloxy group, cyclopentyloxy group, cyclohexyloxy group etc. Further, the "$C_{3-7}$ cycloalkenyloxy group" in the "$C_{3-7}$ cycloalkenyloxy group which may be substituted" shown by the above-mentioned $R^3$ is preferably cyclobutenyloxy group, cyclopentenyloxy group, cyclohexenyloxy group etc.

The preferable examples of a "substituent" of the $C_{1-6}$ alkyl group, the $C_{2-6}$ alkenyl group, the $C_{2-6}$ alkynyl group, the $C_{3-8}$ cycloalkyl group, the $C_{3-8}$ cycloalkenyl group, the $C_{1-6}$ alkoxy group, the $C_{1-6}$ alkylthio group, the $C_{1-6}$ alkylsufinyl group, the $C_{1-6}$ alkylsulfonyl group, the $C_{6-14}$ aromatic hydrocarbon cyclic group, the 5- to 14-membered aromatic heterocyclic group, the $C_{2-6}$ alkenyloxy group, the $C_{3-7}$ cycloalkyloxy group, the $C_{3-7}$ cycloalkenyloxy group shown by the above-mentioned $R^1$, $R^2$ or $R^3$ and optionally substituted respectively include (1) a hydroxyl group, (2) a halogen atom (for example, fluorine atom, chlorine atom, bromine atom, iodine atom), (3) a cyano group, (4) a nitro group, (5) a $C_{1-6}$ alkyl group (for example, methyl group, ethyl group, n-propyl group, isopropyl group, n-butyl group, isobutyl group, sec-butyl group, tert-butyl group, n-pentyl group, n-hexyl group etc.), (6) a $C_{2-6}$ alkenyl group (for example, vinyl group, allyl group, 1-propenyl group, 2-propenyl group, isopropenyl group, 1-butenyl group, 2-butenyl group, 3-butenyl group, 1-pentenyl group, 1-hexenyl group etc.), (7) a $C_{2-6}$ alkynyl group (for example, ethynyl group, 1-propynyl group, 2-propynyl group, 1-butynyl group, 2-butynyl group, 3-butynyl group, 1-pentynyl group, 1-hexynyl group etc.), (8) a $C_{3-8}$ cycloalkyl group (for example, cyclopropyl group, cyclobutyl group, cyclopentyl group, cyclohexyl group etc.), (9) a $C_{1-6}$ alkoxy group (for example, methoxy group, ethoxy group, n-propoxy group, isopropoxy group etc.), (10) a $C_{1-6}$ alkylthio group (for example, methylthio group, ethylthio group etc.), (11) a 5- to 14-membered non-aromatic heterocyclic group (for example, piperidyl group, piperazyl group, morpholinyl group etc.), (12) a $C_{6-14}$ aromatic heterocyclic group (for example, phenyl group, naphthyl group etc.), (13) a 5- to 14-membered aromatic hydrocarbon group (for example, pyridyl group, thienyl group, furyl group, thiazolyl group etc.), (14) an amino group which may be substituted (for example, amino group which may be substituted with one or two groups selected from a $C_{1-6}$ alkyl group, a $C_{1-6}$ alkenyl group, a $C_{1-6}$ alkynyl group, a $C_{3-8}$ cycloalkyl group, a $C_{3-8}$ cycloalkenyl group, an acyl group, carbamoyl group which may be substituted, a $C_{1-6}$ alkyl sulfonyl group etc. (for example, unsubstituted amino group, methylamino group, dimethylamino group, ethylamino group, diethylamino group, n-propylamino group, di(n-propyl)amino group, isopropylamino group, di(isopropyl) amino group etc.), or the substituents are bound together to form a nitrogen-containing cyclic group which contains the nitrogen atoms to which they bound). It may have one or more groups selected from these groups, as the substituent.

Examples of the more preferable group as the above-mentioned $R^1$ include a hydrogen atom or a halogen atom (for example, fluorine atom, chlorine atom, bromine atom etc.) Further, examples of the more preferable group as $R^2$ include a hydrogen atom, a $C_{1-6}$ alkyl group, a halogenated $C_{1-6}$ alkyl group, a $C_{1-6}$ alkoxy $C_{1-6}$ alkyl group, a $C_{3-8}$ cycloalkyl $C_{1-6}$ alkyl group, an aralkyl group (for example, benzyl group, phenethyl group etc.), a mono($C_{1-6}$ alkyl) amino $C_{1-6}$ alkyl group and a di($C_{1-6}$ alkyl) aminoalkyl group, and a hydrogen atom is most preferable. Further, examples of the more preferable group as $R^3$ include a $C_{1-6}$ alkoxy group which may be optionally substituted, and methoxy group is most preferable.

In the compound represented by the above formula (I) according to the present invention, a preferable aspect of the ring A is a ring represented by the formula:

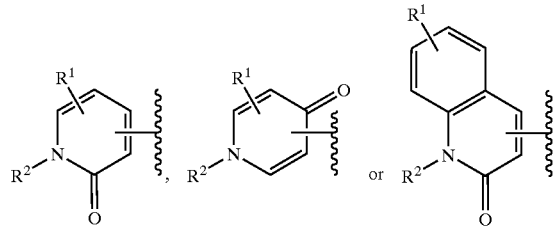

wherein $R^1$, $R^2$ and $R^3$ have the same meanings as defined in the above-mentioned claim 1. Particularly, a ring represented by the formula:

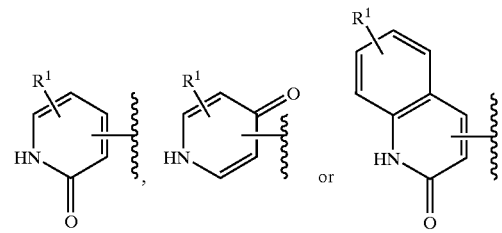

is preferable.

Examples in "$C_{1-6}$ alkylene group which may be substituted", "$C_{2-6}$ alkenylene group which may be substituted" or "$C_{2-6}$ alkynylene group which may be substituted" shown by W in the above formula (I) include a group which may be optionally substituted and represented by the formula —$CH_2$—, —$CH_2$—$CH_2$—, —$(CH_2)_3$—, —$(CH_2)_4$—, —$(CH_2)_5$—, —$(CH_2)_6$—, —CH=CH—, —CH=CH—$CH_2$—, —$CH_2$—CH=CH—, —$CH_2$—$CH_2$—CH=CH—, —$CH_2$—CH=CH—$CH_2$—, —C≡C—, —$CH_2$—C≡C—, —C≡C—$CH_2$— or —$CH_2$—C≡C—$CH_2$—. Further, examples of the "substituent" of the $C_{1-6}$ alkylene group, $C_{2-6}$ alkenylene group and $C_{2-6}$ alkynylene group include a hydroxyl group, a halogen atom, a cyano group, a $C_{6-14}$ aromatic hydrocarbon cyclic group (for example, phenyl group etc.), a 5- to 14-membered aromatic heterocyclic group (for example, pyridyl group, thienyl group, furyl group etc.) etc., and a hydroxyl group and a cyano group are preferable.

Examples of the preferable group as W in the above formula (I) include a group which may be optionally substituted and represented by the formula —$CH_2$—, —$CH_2$—$CH_2$—, —$(CH_2)_3$—, —$(CH_2)_4$—, —$(CH_2)_5$—, —$(CH_2)_6$—, —CH=CH—, —CH=CH—$CH_2$—, —$CH_2$—CH=CH—, —$CH_2$—$CH_2$—CH=CH—, —$CH_2$—CH=CH—$CH_2$—, —C≡C—, —$CH_2$—C≡C—, —C≡C—$CH_2$— or —$CH_2$—C≡C—$CH_2$—, or a group represented by the formula —$CH_2$—CO—, —$CH_2$—$CH_2$—CO—, —$(CH_2)_3$—CO—, —CH=CH—CO—, —CH=CH—$CH_2$—CO—, —C≡C—CO—, —$CH_2$—O—, —O—$CH_2$—, —$CH_2$—$CH_2$—O—, —$(CH_2)_3$—O—, —CH—CH—O, —CH=CH—$CH_2$—O—, —C≡C—O—, —CH$_2$—SO$_2$—, —CH$_2$—CH$_2$—SO$_2$—, —(CH$_2$)$_3$—SO$_2$—, —CH=CH—SO$_2$—, —CH=CH—CH$_2$—SO$_2$—, —C≡C—SO$_2$—, —CH$_2$—NH—CO—, —CH$_2$—CH$_2$—NH—CO—, —(CH$_2$)$_3$—NH—CO—, —CH=CH—NH—CO—, —CH=CH—CH$_2$—NH—CO—, —C≡C—NH—CO—, —CH$_2$—NH—SO$_2$—, —CH$_2$—CH$_2$—NH—SO$_2$—, —(CH$_2$)$_3$—NH—SO$_2$—, —CH=CH—NH—SO$_2$—, —CH=CH—CH$_2$—NH—SO$_2$— or —C≡C—NH—SO$_2$—, and a group represented by the formula —CH$_2$—CH$_2$—, —CH=CH—, —C≡C—, —CH$_2$—O— etc. are more preferable.

Preferable examples of the "C$_{6-14}$ aromatic hydrocarbon cyclic group" in a "C$_{6-14}$ aromatic hydrocarbon cyclic group which may be substituted" shown by Z in the above formula (I) include phenyl group, naphthyl group (for example, 1-naphthyl group, 2-naphthyl group etc.), azulenyl group, hepthalenyl group etc.

Examples of a preferable group as the "5- to 14-membered aromatic heterocyclic group which may be substituted" shown by Z in the above formula (I) include pyrrolyl group, pyridyl group, thienyl group, pyridazyl group, pyrimidyl group, pyrazyl group, imidazolyl group, pyrazolyl group, indolyl group, quinolyl group, quinazolyl group, thiazolyl group, benzothienyl group etc.

When Z in the above formula (I) is a "C$_{6-14}$ aromatic hydrocarbon cyclic group which may be substituted" or a "5- to 14-membered aromatic heterocyclic group which may be substituted", the "substituent" includes one or more groups selected from (1) a hydroxyl group, (2) a halogen atom (for example, fluorine atom, chlorine atom and a bromine atom), (3) nitrile group, (4) a hydrocarbon group which may be substituted with one or more groups selected from (i) a halogen atom, (ii) a C$_{6-14}$ aromatic hydrocarbon cyclic group (phenyl group, naphthyl group) which may be substituted with a halogen atom (for example, fluorine atom and chlorine atom), (iii) a 5- to 14-membered aromatic heterocyclic group (for example, pyridyl group, thienyl group, furyl group, thiazolyl group etc.) which may be substituted with a halogen atom (for example, fluorine atom, chlorine atom etc.), (iv) a C$_{1-6}$ alkylsulfonyl group etc., such as a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group, (5) a C$_{1-6}$ alkoxy group (methoxy group, ethoxy group, n-propoxy group, isopropoxy group) which may be substituted with one or more groups selected from (i) a hydroxyl group, (ii) a halogen atom (for example, fluorine atom, chlorine atom etc.), (iii) a C$_{1-6}$ alkoxy group, (iv) a sulfonyl group substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group), (v) an amino group substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group) etc., (6) a C$_{3-7}$ cycloalkyloxy group which may be substituted with (i) a hydroxyl group, (ii) a halogen atom (for example, fluorine atom, chlorine atom etc.), (iii) a C$_{1-6}$ alkoxy group, (iv) a sulfonyl group substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group)., (v) an amino group substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group) etc., (7) a C$_{6-14}$ aryloxy group (for example, phenoxy group) which may be substituted with a halogen atom (for example, fluorine atom, chlorine atom etc.), (8) a heteroaryloxy group (for example, pyridyloxy group, thienyloxy group, furyloxy group etc.) which may be substituted with a halogen atom (for example, fluorine atom, chlorine atom etc.), (9) a hydrocarbonthio group (for example, methylthio group, ethylthio group, n-propylthio group, isopropylthio group etc.) which may be substituted with a group selected from (i) a hydroxyl group, (ii) a halogen atom (for example, fluorine atom, chlorine atom etc.), (iii) a C$_{1-6}$ alkoxy group, (iv) a sulfonyl group substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group) and (v) an amino group which may be substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group), (10) an acyl group represented by the formula —CO—N(R$^6$)R$^7$ (wherein R$^6$ and R$^7$ are the same as or different from each other and each indicates (i) a hydrogen atom or (ii) a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group) which may be substituted with a halogen atom (for example, fluorine atom, chlorine atom etc.), or R$^6$ and R$^7$ may be bound together to form a 3- to 7-membered nitrogen-containing non-aromatic heterocyclic ring (for example, piperidine, piperazine, morpholine ring etc.) which contains one or two atoms selected from a nitrogen atom, a sulfur atom and an oxygen atom), (11) a 5- to 14-membered aromatic group (for example, phenyl group, naphthyl group, pyridyl group, thienyl group, furyl group, thiazolyl group etc.) which may be substituted with a group selected from (i) a hydroxyl group, (ii) a halogen atom (for example, fluorine atom, chlorine atom etc.), (iii) a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group) which may be substituted with a halogen atom (for example, fluorine atom, chlorine atom etc.), (iv) a C$_{1-6}$ alkoxy group (methoxy group, ethoxy group, n-propoxy group, isopropoxy group etc.) and (v) a C$_{1-6}$ alkoxy group (methoxy group, ethoxy group, n-propoxy group, isopropoxy group etc.) substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group) which may be substituted with a halogen atom (for example, fluorine atom, chlorine atom etc.), (12) a 3 to 8-membered non-aromatic heterocyclic group (piperidyl group, piperazyl group, morpholinyl group etc.) which contains one or two atoms selected from nitrogen atom, sulfur atom and an oxygen atom, (13) a sulfonyl group substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group), (14) a sulfonamide group which may be substituted with a hydrocarbon group (a C$_{1-6}$ alkyl group, a C$_{2-6}$ alkenyl group, a C$_{2-6}$ alkynyl group, a C$_{3-8}$ cycloalkyl group or a C$_{3-8}$ cycloalkenyl group), and (15) a C$_{1-4}$alkylenedioxy group (for example, methylenedioxy group, ethylenedioxy group and propylenedioxy group). For example, a hydroxyl group, nitrile group, a halogen atom (fluorine atom, chlorine atom, blomide atom), methyl group, ethyl group, n-butyl group, trifluoromethyl group, methoxy group, ethoxy group, cyclopropylmethoxy group, 2,2,2-trifluoroethyoxy group, 2-methoxyethoxy group, 2-hydroxyethoxy group, 2-(N,N-dimethylamino)ethoxy group, phenoxy group, phenyl group, imidazolyl group, pyrazolyl group, thiazolyl group, methoxyphenyl group, piperidyl group, piperazyl group, morpholinyl group, N-acetylpiperazyl group, methylsulfonyl group, amino group, trifluoroacetylamino group, methylsulfonyl group, ethylsulfonyl group, alkylenedioxy group etc. may be proposed. Here, the "C$_{1-6}$ alkyl group", "C$_{2-6}$ alkenyl group", "$C_{2-6}$ alkynyl group", "$C_{3-8}$ cycloalkyl group" and "$C_{3-8}$ cycloalkenyl group" listed as a "hydrocarbon group" have the same meanings as defined above, respectively.

In the group represented by the formula —$N(R^4)R^5$ (wherein $R^4$ and $R^5$ have the same meanings as defined above) shown by Z in the above formula (I), the "$C_{1-6}$ alkyl group" in the "$C_{1-6}$ alkyl group which may be substituted" shown by $R^4$ or $R^5$ is preferably methyl group, ethyl group, n-propyl group, isopropyl group, n-butyl group, isobutyl group, sec-butyl group, tert-butyl group, n-pentyl group, n-hexyl group etc., the "$C_{2-6}$ alkenyl group" in the "$C_{2-6}$ alkenyl group which may be substituted" is preferably vinyl group, allyl group, 1-propenyl group, 2-propenyl group, isopropenyl group, 1-butenyl group, 2-butenyl group, 3-butenyl group, 1-pentenyl group, 1-hexenyl group etc., and the "$C_{2-6}$ alkynyl group" in the "$C_{2-6}$ alkynyl group which may be substituted" is preferably ethynyl group, 1-propynyl group, 2-propynyl group, 1-butynyl group, 2-butynyl group, 3-butynyl group, 1-pentynyl group, 1-hexynyl group etc. Further, the "$C_{3-8}$ cycloalkyl group" in the "$C_{3-8}$ cycloalkyl group which may be substituted" shown by $R^4$ or $R^5$ is preferably cyclopropyl group, cyclobutyl group, cyclopentyl group, cyclohexyl group etc., and the "$C_{3-8}$ cycloalkenyl group" in the "$C_{3-8}$ cycloalkenyl group which may be substituted" is preferably cyclobutenyl group, cyclopentenyl group, cyclohexenyl group etc. Further, the "$C_{6-14}$ aromatic hydrocarbon cyclic group" in the "$C_{6-14}$ aromatic hydrocarbon cyclic group which may be substituted" shown by $R^4$ or $R^5$ is preferably phenyl group, naphthyl group etc. The "5- to 14-membered aromatic heterocyclic group" in the "5- to 14-membered aromatic heterocyclic group which may be substituted" is preferably pyridyl group, pyrazyl group, pyrimidyl group, pyridazinyl group, thienyl group, thiazolyl group, imidazolyl group, furyl group etc.

When the above-mentioned $R^4$ or $R^5$ are the same as or different from each other and each is a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted or a $C_{3-8}$ cycloalkenyl group which may be substituted, preferable examples of the "substituent" include (1) a hydroxyl group, (2) a halogen atom (for example, fluorine atom, chlorine atom, bromine atom, iodine atom), (3) a $C_{1-6}$ alkoxy group which may be substituted (for example, a methoxy group, a methoxy group, ann-propoxy group, anisopropoxy group, an n-butoxy group, a tert-butoxy group etc. which may be substituted with a halogen atom, respectively), (4) a $C_{6-14}$ aromatic hydrocarbon cyclic group which may be substituted (for example, a 5- to 14-membered aromatic group which may be substituted with any one or more groups selected from a hydroxyl group, a halogen atom, a hydrocarbon group which may be substituted with a halogen atom, a $C_{1-6}$ alkoxy group which may be substituted with a halogen atom, and a 5- to 14-membered aromatic group), (5) a 5- to 14-membered aromatic heterocyclic group which may be substituted (for example, a 5- to 14-membered aromatic group which may be substituted with any one or more of groups selected from a hydroxyl group, a halogen atom, a hydrocarbon group which may be substituted with a halogen atom, a $C_{1-6}$ alkoxy group which may be substituted with a halogen atom and a 5- to 14-membered aromatic group, etc.) etc. Specific examples thereof include one or two groups selected from ethyl group, 2-methylpropyl group, isopropyl group, n-pentyl group, n-octyl group, tert-butyl group, hydroxy-tert-butyl group, cyclohexyl group, cyclopropylmethyl group, 1-cyclopropylethyl group, 2-cyclopropylethyl group, 2,2,2-trifluoroethyl group, morpholylethyl group, hydroxyethyl group, hydroxypropyl group, 5-phenylpentyl group, 2-propyn-1-yl group, 1,2-dimethylpropyl group, 2-ethyl-n-butyl group, benzyl group, phenethyl group, a halogenated benzyl group, hydroxybenzyl group, o-phenylbenzyl group, methyl sulfonylbenzyl group, methylsulfonylaminobenzyl group, pyridylmethyl group, furylmethyl group, N-methylpyrolylethyl group, diphenylmethyl group, methylenedioxyphenylmethyl group, methoxypyridylmethyl group and dimethylaminomethyl group.

When the above-mentioned $R^4$ or $R^5$ are the same as or different from each other and each is an optionally substituted $C_{6-14}$ aromatic hydrocarbon cyclic group 5- to 14-membered aromatic heterocyclic group, the preferable examples of the "substituent" include (1) hydroxy group, (2) a halogen atom, (3) nitrile group, (4) a hydrocarbon group which may be substituted with such as a halogen atom, a 5- to 14-membered aromatic group which may be substituted with a halogen atom and a $C_{1-6}$ alkylsulfonyl group, (5) a $C_{1-6}$ alkoxy group which may be substituted with such as a hydroxyl group, a halogen atom, a $C_{1-6}$ alkoxy group, a sulfonyl group substituted with a hydrocarbon group and an amino group which may be substituted with a hydrocarbon group, (6) a $C_{3-7}$ cycloalkyloxy group which may be substituted with such as a hydroxyl group, a halogen atom, a $C_{1-6}$ alkoxy group, a sulfonyl group substituted with a hydrocarbon group and an amino group which may be substituted with a hydrocarbon group, (7) a ($C_{6-10}$ aryl)-oxy group which may be substituted with a halogen atom etc., (8) a (5- to 14-membered heteroaryl)-oxy group which may be substituted with a halogen atom etc., (9) a hydrocarbon-thio group which may be substituted with a group selected from a hydroxyl group, a halogen atom, a $C_{1-6}$ alkoxy group, a sulfonyl group substituted with a hydrocarbon group and an amino group which may be substituted with a hydrocarbon group, (10) an acyl group represented by the formula —CO—$N(R^{12})R^{13}$ (wherein $R^{12}$ and $R^{13}$ are the same as or different from each other and each indicates a hydrogen atom or a hydrocarbon group which may be substituted with a halogen atom, and further, in the formula —CO—$N(R^{12})R^{13}$, $R^{12}$ and $R^{13}$ may be bound together to form a 3- to 7-membered nitrogen-containing non-aromatic heterocyclic ring containing one or two atoms selected from a nitrogen atom, an oxygen atom and a sulfur atom), (11) a 5- to 14-membered aromatic group which may be substituted with a group selected from a hydroxyl group, a halogen atom, a hydrocarbon group which may be substituted with a halogen atom and a hydrocarbon $C_{1-6}$ alkoxy group which may be substituted with a halogen atom, (12) a 3 to 7-membered non-aromatic heterocyclic group which contains one or two atoms selected from a nitrogen atom, an oxygen atom and a sulfur atom, (13) a sulfonyl group substituted with a hydrocarbon group, (14) a sulfoneamide group which may be substituted with a hydrocarbon group, (15) a $C_{1-2}$ alkylenedioxy group, etc.

The "$C_{1-6}$ aliphatic acyl group" shown by the above-mentioned $R^4$ or $R^5$ means a carbonyl group which was substituted with groups such as a $C_{1-6}$ alkyl group, a $C_{2-6}$ alkenyl group, a $C_{2-6}$ alkynyl group, a $C_{1-6}$ alkoxy-$C_{1-6}$ alkyl group, a $C_{1-6}$ alkoxy group, a $C_{6-14}$ aryl group, a 5- to 14-membered aromatic heterocyclic group etc., and as the preferable examples, acetyl group, ethylcarbonyl group etc. are listed.

In the above formula (I), Z may indicate a 3- to 8-membered nitrogen-containing cyclic group obtained by $R^4$ and $R^5$ in the formula —$N(R^4)R^5$ bound together, and the preferable examples of the group include piperidyl group, piperazyl group, morpholinyl group etc.

In the above formula (I), the symbol l indicates an integer of 0, 1, 2, 3, 4, 5 or 6, an integer of 1 to 3 is preferable, an integer of 1 or 2 is more preferable, and an integer of 1 is further preferable.

As the more preferable aspect of the compound represented by the above formula (I) according to the present invention, a compound represented by the formula:

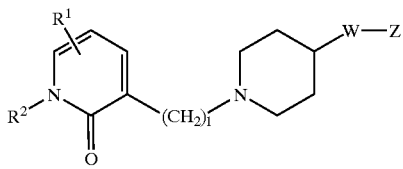

(wherein $R^1$, $R^2$, W, Z and l have the same meanings as defined above, respectively), a salt thereof or a hydrate of them may be proposed, and as the particularly preferable aspect, a compound represented by the formula:

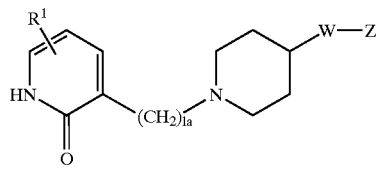

(wherein $R^1$, W and Z have the same meanings as defined in the above claim 1), a salt thereof or a hydrate of them may be proposed.

The "salt" according to the specification of the present application is not specifically limited so far as it forms a salt with a compound according to the present invention and is pharmacologically acceptable. Preferably, a salt of a hydrogen halide acid (for example, hydrogen fluoride, hydrogen chloride, hydrogen bromide, hydrogen iodide, etc.), an inorganic acid salt (for example, sulfate, nitrate, perchlorate, phosphate, carbonate, bicarbonate etc.), an organic acid salt (for example, acetate, trifluoroacetate, oxalate, maleate, tartarate, fumarate, citrate etc.), a salt of an organosulfonic acid (for example, methanesulfonate, trifluoromethanesulfonate, ethanesulfonate, benzenesulfonate, toluenesulfonate, camphorsulfonate etc.), a salt of amino acid (for example, aspartate, glutamate etc.), a quaternary ammonium salt, an alkali metal salt (for example, sodium salt, potassium salt etc.), an alkali earth metal salt (for example, magnesium salt, calcium salt etc.), etc. may proposed. Hydrogen chloride, oxalate, trifluoroacetate etc. are more preferable.

The typical process for producing the compound represented by the above formula (I) according to the present invention is shown below.

Production process 1

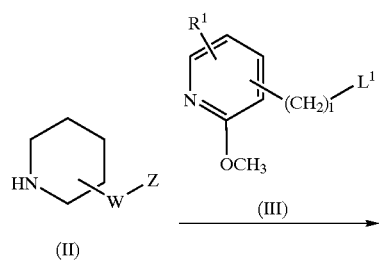

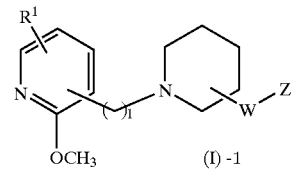

In the formula, $R^1$, W, Z and l have the same meanings as defined above; and $L^1$ indicates a leaving group (for example, a halogen atom, tosylate etc.) or an aldehyde group. The compound (I)-1 according to the present invention can be produced by condensing a piperidine derivative (II) with a pyridine derivative (III) in a solvent by the reductive amination method, or by condensing them in the presence of a base. When the reductive amination method is used, the solvent used is not specifically limited so far as it does not inhibit the reaction and dissolves a starting substance to an extent. For example, ethers such as tetrahydrofuran (THF), dioxane and diethylene glycol dimethyl ether, halogenated carbons such as dichloromethane, chloroform and dichloroethane, ethyl acetate, dimethylformamide (DMF), dimethyl sulfoxide (DMSO), 1-methylpyrrolidone, acetonitrile etc. are preferable. As the reducing agent, metal hydrides such as sodium borohydride, sodium triacetoxyborohydride etc. can be used. Further, a catalytic reduction method which conventionally used can be carried out. The amount of the reducing agent used is 1 to 5 equivalents to a raw material. The reaction temperature is conventionally from −50° C. to are flux temperature of the solvent, and preferably about 0 to about 25° C. All of the organic solvents which are inert to reaction can be used in case of the condensation in the presence of a base, and for example, benzene, dichloromethane, acetonitrile, THF, dioxane, dimethylformamide, dimethyl sulfoxide, 1-methylpyrrolidone etc. may be proposed. The base used is not specifically limited, but sodium hydride, potassium, tert-butoxide, lithium diisopropylamide, potassium carbonate, sodium hydroxide etc. are preferable. The amount of the base used is 1 to 10 equivalent to a raw material. The reaction temperature is conventionally from −50° C. to are flux temperature of the solvent, and preferably 20 to 80° C.

The production process is shown below when W is a "hydrocarbon chain which may be substituted" in the above formula (I).

Production process 2

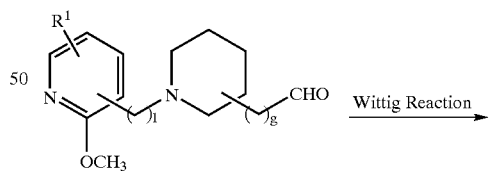

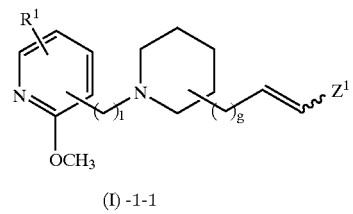

In the formula, $R^1$ and l have the same meanings as defined above; $Z^1$ indicates a 5- to 14-membered aromatic group which may be substituted; and g indicates 0, 1 and 2.

The pyridylpiperidine derivative (I)-1-1 according to the present invention can be produced by carrying out Wittig reaction or an analogous reaction to the piperidine aldehyde derivative (IV) in an organic solvent. The solvent used is not specifically limited so far as it does not inhibit the reaction and dissolves a starting substance to an extent. For example, ethers such as tetrahydrofuran, dioxane and diethylene glycol dimethyl ether, ethyl acetate, dimethylformamide, dimethyl sulfoxide, toluene, benzene etc. are preferable. The Wittig reagent which is commercially available is bought and those which are not commercially available can be easily prepared according to a conventional method. The amount of the Wittig reagent used is 1 to 2 equivalents to a raw material. Examples of the base used are preferably sodium hydride, potassium tert-butoxide, potassium methoxide, sodium ethoxide, lithium diisopropylamide, diazabicycloundecene, n-butyl lithium, sodium hydroxide etc. The amount of the base used is 1 to 2 equivalents to a raw material. The reaction temperature is conventionally from −70° C. to a reflux temperature of the solvent, and preferably about −40 to about 60° C.

Production process 3

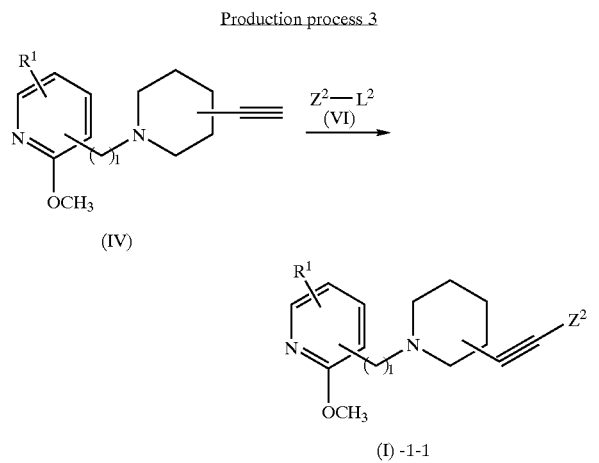

In the formula, $R^1$ and l have the same meanings as defined above, $Z^2$ indicates a 5- to 14-membered aromatic group which may be substituted; and $L^2$ indicates a leaving group (for example, a halogen atom, triflate etc.). The compound (I)-1-2 according to the present invention can be produced by reacting (VI) (for example, aryl halide, aryl triflate etc.) to an alkynylpiperidine derivative (V) in a solvent in the presence of a catalyst. The solvent used is not specifically limited so far as it does not inhibit the reaction and dissolves a starting substance to an extent. For example, ethers such as tetrahydrofuran (THF), dioxane and diethylene glycol dimethyl ether, halogenated carbons such as dichloromethane, chloroform and dichloroethane, ethyl acetate, dimethylformamide, dimethyl sulfoxide, toluene, benzene, 1-methylpyrrolidone etc. are preferable. The present reaction can be carried out in the presence of a reagent of either of tetrakis(triphenylphosphine)palladium or dichlorobis(triphenylphosphine)palladium(II) in a catalytic amount, cupric iodide and a tertiary amine. As the tertiary amine used, for example, triethylamine, diisopropylethylamine, dimethylaniline, diazabicycloundecene etc. are preferable. The amount of the catalyst used is about 0.001 to about 0.1 mol % based on a raw material. The reaction is carried out under a nitrogen flow, and the reaction temperature is conventionally from −20° C. to a reflux temperature of the solvent, and preferably about 80 to about 140° C.

Production process 4

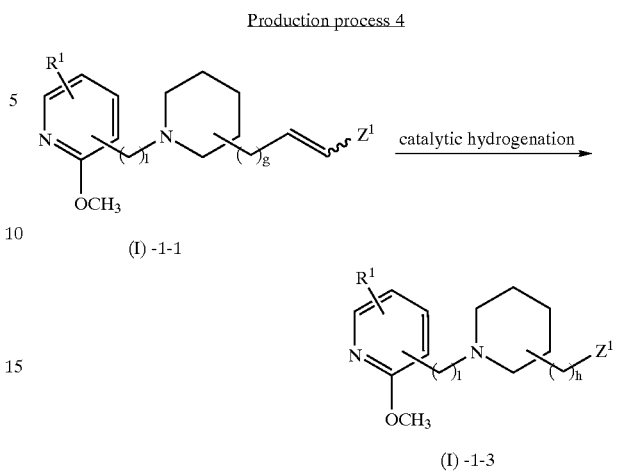

In the formula, $R^1$, l, g and $Z^1$ have the same meanings as defined above, and h indicates an integer of any one of 1 to 3. The compound (I)-1-3 according to the present invention can be produced by carrying out the catalytic reduction of the pyridylpiperidine derivative (I)-1-1 obtained in the reaction 2. The solvent used is not specifically limited so far as it does not inhibit the reaction and dissolves a starting substance to an extent. For example, ethers such as tetrahydrofuran (THF), dioxane and diethylene glycol dimethyl ether, halogenated carbons such as dichloromethane, chloroform and dichloroethane, ethyl acetate, dimethylformamide, dimethyl sulfoxide, ethanol, methanol etc. are preferable. In the present reaction, a good result can be also obtained by adding an appropriate amount of an acid to the reaction solution. As the catalyst used, palladium carbon (Pd—C), Raney-Nickel, platinum oxide ($PtO_2$) etc. are preferable. The reaction temperature is generally from 0° C. to 120° C., and preferably about 25° C. The hydrogen pressure during reduction is 1 to 140 kg/cm$^2$, and preferably 1 to 3 kg/cm$^2$.

Production process 5

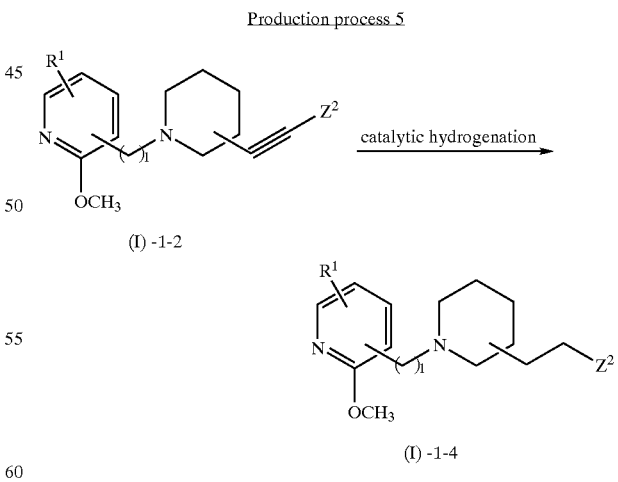

In the formula, $R^1$, l and $Z^2$ have the same meanings as defined above. The compound (I)-1-4 according to the present invention can be produced by carrying out the catalytic hydrogenation of (I)-1-2 obtained in the "reaction 3". The present reaction can be carried out under the same condition as in the "reaction 4".

Production process 6

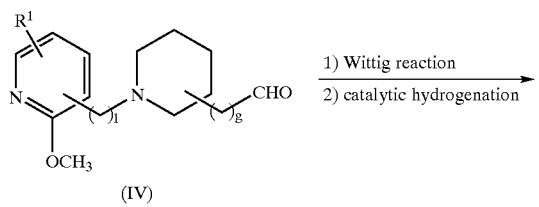

In the formula, $R^1$, l, g, h and $Z^1$ have the same meanings as defined above. The compound (I)-1-3 according to the present invention can be produced by reacting a Wittig reagent with the piperidinealdehyde derivative (IV) in the presence of a base and carrying out the catalytic hydrogenation of the pyridylpiperidine derivative (I)-1-1 obtained, without separation. The Wittig reaction can be carried out according to the method described in the reaction 2, and the catalytic hydrogenation can be carried out according to the method described in the "reaction 4".

Production process 7

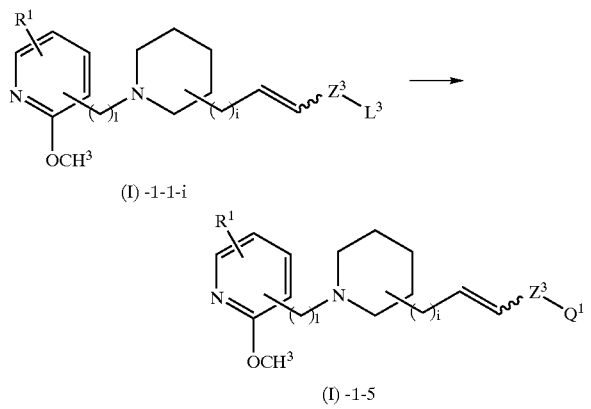

In the formula, $R^1$, l, i and $Z^1$ have the same meanings as defined above; $L^3$ indicates a leaving group (for example, a halogen atom, triflate etc.), and $Q^1$ and $Z^3$ indicate a 5- to 14-membered aromatic group which may be substituted. The compound (I)-1-5 according to the present invention can be produced in the presence of a palladium catalyst from the compound (I)-1-1-i in which $Z^1$ is represented by $Z^3$—$L^3$ among the compound (I)-1-1 obtained in the "reaction 2". As the aryl metal compound used for the reaction, for example, aryltributyltin, aryl boric acid, other conventionally-used arylalkoxyborane, arylalkylborane, etc. are listed. The amount of the aryl metal compound used is conventionally 1 to 5 equivalents to a raw material, and preferably about 2 equivalents. As the catalyst used, for example, tetrakis(triphenylphosphine)palladium, dichlorobis(triphenylphosphine)-palladium(II) etc. are mentioned. The amount of the catalyst used is about 0.05 mol % to a raw material. The solvent used is not specifically limited so far as it does not inhibit the reaction and dissolves a starting substance to an extent. For example, tetrahydrofuran (THF), dioxane, diethylene glycol dimethyl ether, toluene, benzene etc. are preferable. When aryl boric acid is used as the aryl metal compound, aqueous sodium carbonate, methanol and a mixture of organic solvents are preferable. The reaction temperature is conventionally from room temperature to 150° C., and preferably from 80 to 130° C. The compound (I)-1-5 obtained by the present production process can be used as a raw material in the reaction 4.

Production process 8

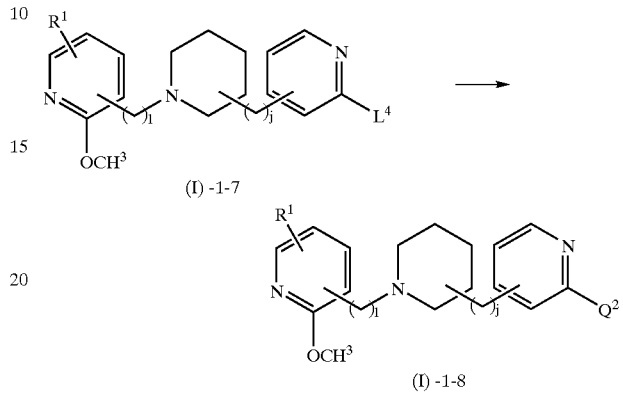

In the formula, $R^1$ and l have the same meanings as defined above; j indicates an integer of any one of 1 to 3; $L^4$ indicates a leaving group (for example, a halogen atom, tosylate, triflate etc.); and $Q^2$ indicates a substituent (for example, a $C_{1-6}$ alkoxy group, an alkylamino group etc.). The compound (I)-1-8 according to the present invention can be also produced by further reacting the pyridine derivative (I)-1-7 which has the eliminating group $L^4$ at 2-position of the aromatic groups represented by Z and $Z^1$ among the compound obtained in the above-mentioned reactions 1 or 4, with a nucleophile. As the nucleophile used, alkoxides obtained by reacting bases such as sodium hydride, potassium tert-butoxide, sodium metal, lithium metal and sodium diisopropylamide with alcohols such as methanol, ethanol and dimethylaminoethanol, and additionally, primary or secondary amines such as piperidine and morpholine are preferable. When an amine is used as the nucleophile, a good result can be obtained even if a base having a weak nucleophilic property such as potassium carbonate, diisopropylethylamine and triethylamine coexist. The amount of the nucleophile used is 1 to a greatly excessive amount for a raw material. The solvent used is not specifically limited so far as it does not inhibit the reaction and dissolves a starting substance to an extent. For example, ethers such as tetrahydrofuran (THF), dioxane and diethylene glycol dimethyl ether, halogenated carbons such as dichloromethane, chloroform and dichloroethane, and additionally, ethyl acetate, dimethylformamide, dimethylsulfoxide, 1-methylpyrrolidone etc. are preferable. When an alkoxide is used as the nucleophile, an alcohol can be used as the solvent. The reaction temperature is generally from 0 to 200° C., and preferably from 100 to 170° C.

Production process 9

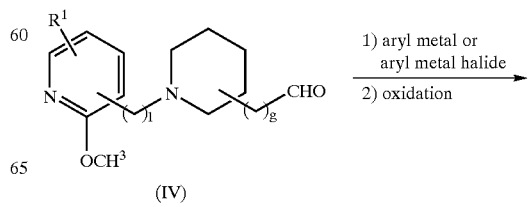

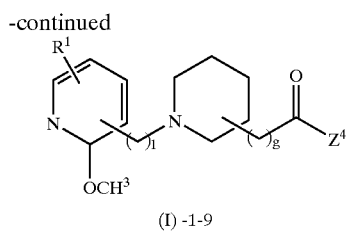

(I)-1-9

In the formula, $R^1$, l and g have the same meanings as defined above; j indicates an integer of anyone of 1 to 3, and $Z^4$ indicates a 5- to 14-membered aromatic group which may be substituted. The compound (I)-1-9 according to the present invention can be produced by reacting an aryl metal or an aryl metal halide with the aldehyde derivative (IV) by 1,2-addition to give an intermediate and oxidizing it. The aryl metal or aryl metal halide used in the 1,2-addition reaction is bought when it is commercially available, and can be prepared according to a conventional method to be used when it is not commercially available. The amount of the aryl metal or aryl metal halide used is 1 to 5 equivalents to a raw material. The solvent used is not specifically limited so far as it does not inhibit the reaction and dissolves a starting substance to an extent. For example, ethers such as tetrahydrofuran (THF), dioxane and diethylene glycol dimethyl ether, toluene, benzene etc. are preferable. The reaction temperature is generally from −78 to 0° C. As an oxidant used for oxidation reaction, for example, Swern oxidant which is adjusted by sulfur trioxide-pyridine complex, chlorochromic acid pyridinium, manganese dioxide, di(chromic acid)pyridinium, oxalyl chloride-dimethyl sulfoxide etc. are preferable. The solvent used in the oxidation reaction is not specifically limited so far as it does not inhibit the reaction and dissolves a starting substance to an extent. For example, ethers such as tetrahydrofuran (THF), dioxane and diethylene glycol dimethyl ether, halogenated carbons such as dichloromethane, chloroform and dichloroethane, and additionally, acetonitrile, ethyl acetate, dimethylformamide, dimethyl sulfoxide, 1-methylpyrrolidone etc. are preferable. The reaction temperature is generally from 0° C. to a reflux temperature of the solvent.

Production process 10

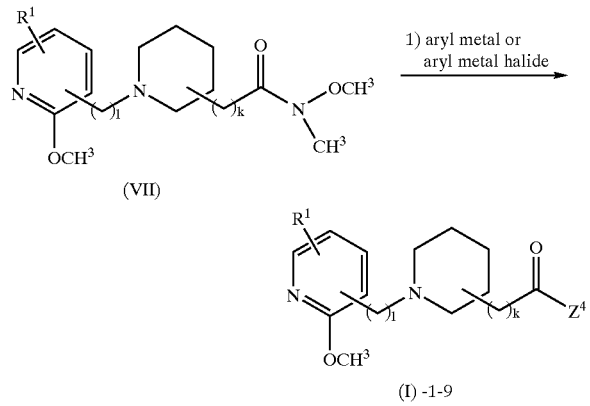

In the formula, $R^1$, l and $Z^4$ have the same meanings as defined above; and k indicates an integer of any of 0 to 2. The compound (I)-1-9 according to the present invention can be produced by reacting an aryl metal or an aryl metal halide with the amide derivative (VII). The aryl metal or aryl metal halide used is bought when it is commercially available, and can be prepared according to a conventional method to be used when it is not commercially available. The amount of the aryl metal or aryl metal halide used is about 1 to about 2 equivalents to a raw material. The solvent used is not specifically limited so far as it does not inhibit the reaction and dissolves a starting substance to an extent. For example, ethers such as tetrahydrofuran (THF), dioxane and diethylene glycol dimethyl ether, toluene, benzene etc. are preferable. The reaction temperature is conventionally from −78 to 0° C.

Production process 11

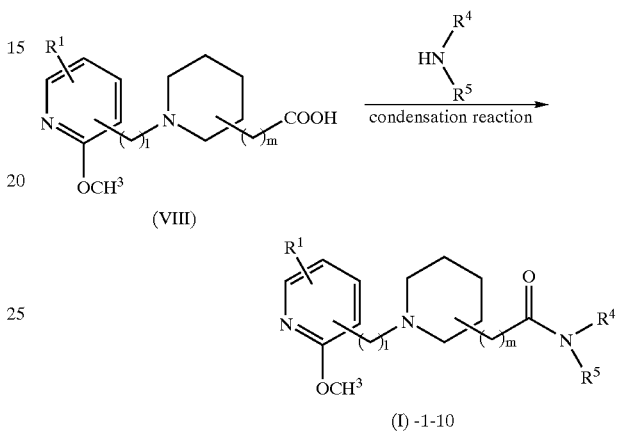

In the formula, $R^1$, $R^4$, $R^5$ and l have the same meanings as defined above; and m indicates an integer of any one of 0, 1 and 2. The compound (I)-1-10 according to the present invention can be produced by carrying out the condensation reaction of the carboxylic acid derivative (VIII) and an amine represented by the formula $NH(R^4)R^5$ in an organic solvent. The solvent used is not specifically limited so far as it does not inhibit the reaction and dissolves a starting substance to an extent. For example, ethers such as tetrahydrofuran (THF), dioxane and diethylene glycol dimethyl ether, halogenated carbons such as dichloromethane, chloroform and dichloroethane, and additionally, ethyl acetate, dimethylformamide, dimethyl sulfoxide, ethanol, methanol etc. are preferable. As the condensation reaction, reactions conventionally carried out can be used. For example, a DCC method, a DCC-HOBt method, a DCC-HOSu method, and an improved method in accordance with these methods (for example, a WSC-HOBt method) etc. can be used. The amount of a condensing agent used is 1 to 5 equivalents to the raw material (VIII). Further, after a carboxylic acid-piperidine derivative is made as a reactive derivative conventionally used, it can be also carried out by reacting the derivative with an amine. As there active derivative used, for example, an acid chloride obtained by treating with thionyl chloride etc., an acid anhydride introduced by reacting isobutyloxycarbonyl chloride (IBCF), 1-ethoxycarbonyl-2-ethoxy-1,2-dihydroquinoline (EEDQ), ethyl chlorocarbonate etc. with the carboxylic acid derivative (VIII), those which is obtained by converting the carboxylic acid derivative (VIII) into an acid azide by using diphenylphosphoryl azide (DPPA), etc. are preferable. Further, they can be introduced to active esters such as p-nitrophenylester (ONp) and N-hydroxysuccinimide (ONSu). The compound (I)-1-10 according to the present invention can be obtained by reacting the reactive derivative with the amine $NH(R^4)R^5$ in an organic solvent.

Production process 13

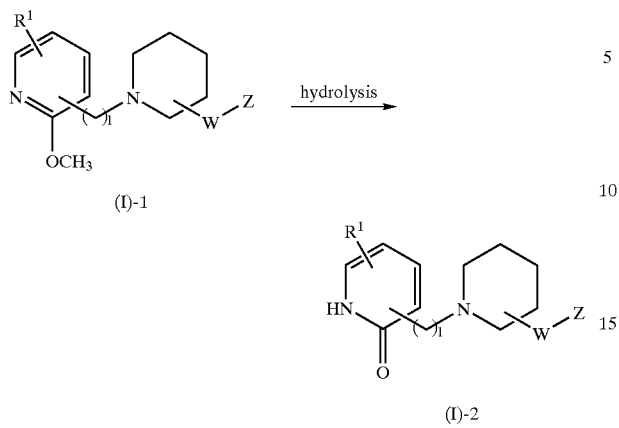

In the formula $R^1$, W, Z and l have the same meanings as defined above. The pyridonepiperidine derivative (I)-2 being the compound according to the present invention can be produced by hydrolyzing the pyridylpiperidine derivative (I)-1. The present reaction can be carried out by interacting 2 equivalents to a greatly excessive amount of an appropriate acid in water or a mixed solvent of water and organic solvents such as methanol, ethanol, dioxane and tetrahydrofuran. As the acid used, for example, hydrochloric acid, hydrobromic acid, sulfuric acid, nitric acid, trifluoroacetic acid etc. are preferable, and an acid may be generated in the reaction system by adding thionyl chloride in an alcohol solvent. The reaction temperature is generally from a room temperature to a reflux temperature. Further, the present reaction can be carried out by interacting 2 equivalents to a greatly excessive amount of trimethylsilyl iodide or trimethylsilane chloride-sodium iodide in an organic solvent such as dichloromethane, chloroform, dichloroethane and acetonitrile. The reaction temperature is generally from −78° C. to a reflux temperature of the solvent and preferably from −20° C. to room temperature.

Production process 13

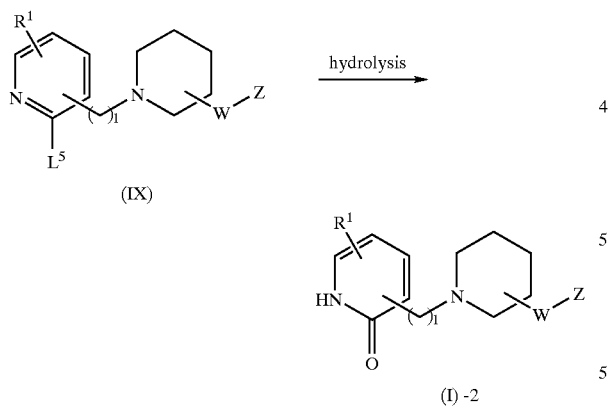

In the formula, $R^1$, W, Z and l have the same meanings as defined above; and $L^5$ indicates a leaving group (for example, a halogen atom etc.). The pyridonepiperidine derivative (I)-2 being the compound according to the present invention can be produced by hydrolyzing the 2-substituted pyridine derivative (X). The solvent used is not specifically limited so far as it does not inhibit the reaction and dissolves a starting substance to an extent. For example, tert-butanol etc. are preferable. The base used for hydrolysis reaction is not specifically limited, but potassium tert-butoxide is preferable. The reaction temperature is generally from room temperature to a reflux temperature of the solvent, and preferably from 100 to 140° C.

Production Process 14

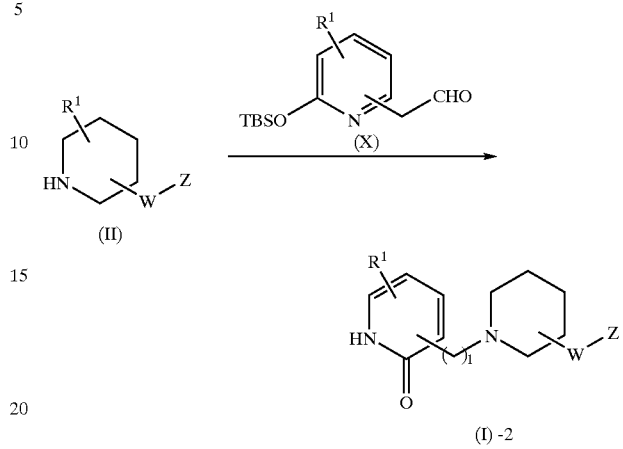

In the formula, $R^1$, W, Z and l have the same meanings as defined above. Further, TBSO- in the formula means tert-butyldimethylsilyl ether. The compound (I)-2 according to the present invention can be produced by condensing the piperidine derivative (II) and the pyridine derivative (X) in an organic solvent by reductive amination. The solvent used is not specifically limited so far as it does not inhibit the reaction and dissolves a starting substance to an extent. For example, ethers such as tetrahydrofuran, dioxane and diethylene glycol dimethyl ether, halogenated carbons such as dichloromethane, chloroform and dichloroethane, and additionally, ethyl acetate, dimethylformamide, dimethyl sulfoxide etc. are preferable. As the reducing agent used, for example, metal hydrides such as sodium borohydride and triacetoxy sodium boronhydride are preferable. Further, a catalytic reduction method which conventionally used can be carried out. The amount of the metal halide used is 1 to 5 equivalents to a raw material. In the present reaction, the tert-butyldimethylsilyl group is naturally deprotected by the acidity of the silica gel used at a step of purifying the product. The reaction temperature is generally from −50° C. to a reflux temperature of the solvent, and preferably about 0 to about 25° C.

Production process 15

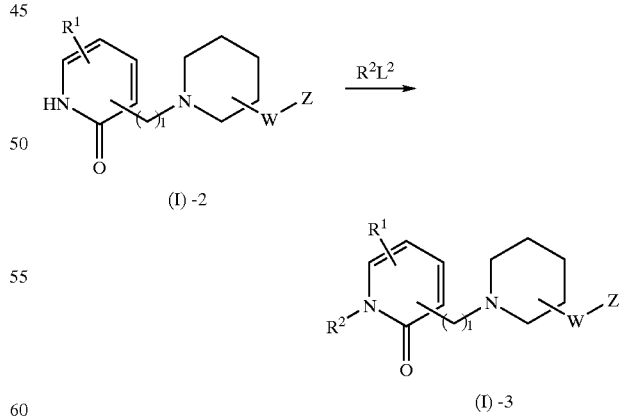

In the formula, $R^1$, $R^2$, W, Z and l have the same meanings as defined above; and $L^2$ indicates a leaving group (for example, a halogen atom, a tosylate, a mesylate etc.). The N-substituted pyridonepiperidine derivative (I)-3 being the compound according to the present invention can be produced by interacting a compound $R^2L^2$ with the pyridone-piperidine derivative (I)-2 together with an appropriate base in an organic solvent. The solvent used is not specifically limited so far as it does not inhibit the reaction and dissolves a starting substance to an extent. For example, dimethylformamide, dimethyl sulfoxide, 1-methylpyrrolidone, ethers such as tetrahydrofuran (THF), dioxane and diethylene glycol dimethyl ether, halogenated carbons such as dichloromethane, chloroform and dichloroethane, and additionally, ethyl acetate, ethanol, methanol etc. are preferable. As the base used, for example, sodium hydride, potassium tert-butoxide, potassium methoxide, lithium diisopropylamide, potassium carbonate, sodium hydroxide etc. are preferable. The amount of the base used is 1 to 10 equivalents to a raw material. The amount of the compound, $R^2L^2$ used is 1 equivalent to a greatly excessive amount to a raw material. The reaction temperature is generally from a room temperature to a reflux temperature.

Production process 16

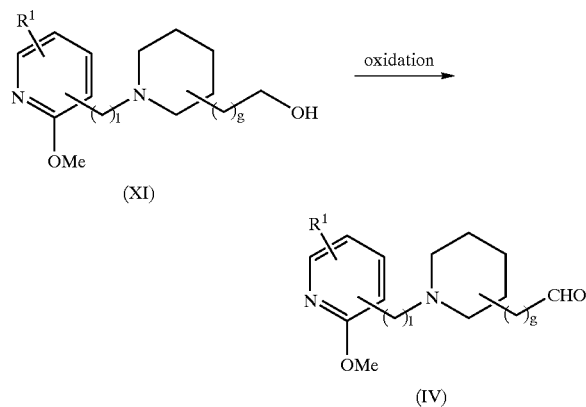

In the formula, $R^1$, 1 and g have the same meanings as defined above. The piperidinealdehyde derivative (IV) which is a raw material in the above-mentioned "reactions 2, 4 and 7" can be produced by oxidizing the alcohol derivative (XI). The solvent used is not specifically limited so far as it does not inhibit the reaction and dissolves a starting substance to an extent. For example, dimethylformamide, dimethyl sulfoxide, 1-methylpyrrolidone, ethers such as tetrahydrofuran, dioxane and diethyleneglycol dimethyl ether, halogenated carbons such as dichloromethane, chloroform and dichloroethane, and additionally, ethyl acetate, acetonitrile, toluene etc. are preferable. As oxidation methods used for oxidation reaction, for example, an oxidation method using chlorochromic acid pyridinium, manganese dioxide and di(chromic acid)pyridinium as an oxidant, oxidation methods such as Swern oxidation, Jones oxidation, Corey-Khim oxidation and the like are preferable. The reaction temperature is conventionally from −50° C. to a reflux temperature of the solvent.

Production process 17

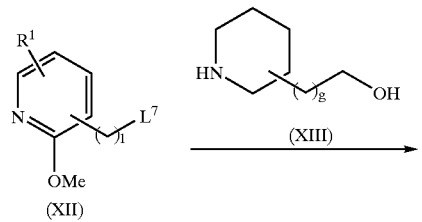

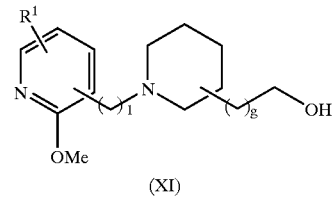

In the formula, $R^1$, 1 and g have the same meanings as defined above; and $L^7$ indicates a leaving group (for example, a halogen atom, tosylate etc.) or an aldehyde group. The pyridylpiperidine derivative (XI) which is a raw material for the above-mentioned "reaction 16" can be produced by condensing the piperidine derivative (XIII) and the pyridine derivative (XII) by reductive amination, or by condensing them in the presence of a base. The present reaction can be carried out under the same condition as in the above-mentioned "reaction 1". The commercially available product of the pyridine derivative (XII) is bought, and those which are not commercially available can be easily prepared according to a conventional method to be used.

Production Process 18

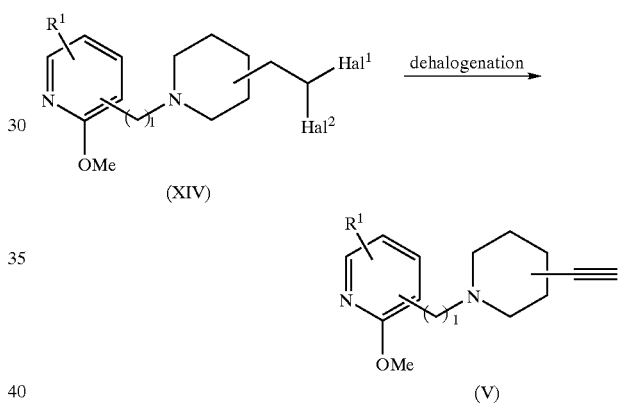

In the formula, $R^1$ and 1 have the same meanings as defined above; and each of $Hal^1$ and $Hal^2$ indicates the same or different halogen atom. The alkynylpiperidine derivative (V) which is a raw material in the above-mentioned "reaction 3" can be produced by carrying out the dehalogenation reaction of the olefin derivative (XIV). The solvent used is not specifically limited so far as it does not inhibit the reaction and dissolves a starting substance to an extent. For example, ethers such as tetrahydrofuran (THF), dioxane and diethylene glycol dimethyl ether, toluene etc. are preferable. As the base used, for example, n-butyllithium, sec-butyllithium, tert-butyllithium, etc. are preferable. The amount of the base used is 1 to 10 equivalents to a raw material. The reaction temperature is generally from −100 to −50° C.

Production process 19

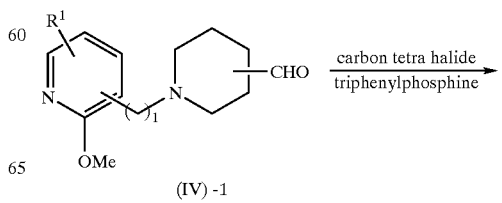

-continued

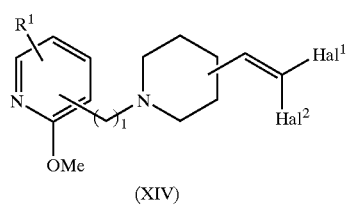

(XIV)

In the formula, $R^1$, 1 $Hal^1$ and $Hal^2$ have the same meanings as defined above. The olefin derivative (XIV) which is a raw material in the above-mentioned "reaction 18" can be produced by interacting the piperidinealdehyde derivative (IV)-1 and carbon tetra halide in the presence of triphenylphosphine. The solvent used is not specifically limited so far as it does not inhibit the reaction and dissolves a starting substance to an extent. For example, 1-methylpyrrolidone, ethers such as tetrahydrofuran (THF), dioxane and diethylene-glycol dimethyl ether, halogenated carbons such as dichloromethane, chloroform and dichloroethane, and additionally, ethyl acetate, acetonitrile, toluene etc. are preferable. As the base added, for example, tertiary amines such as triethylamine and diisopropylethylamine are preferable. The amount of the base used is 2 equivalents to a greatly excessive amount to a raw material. The reaction temperature is conventionally from −50 to 80° C., and preferably about 0° C.

Production process 20

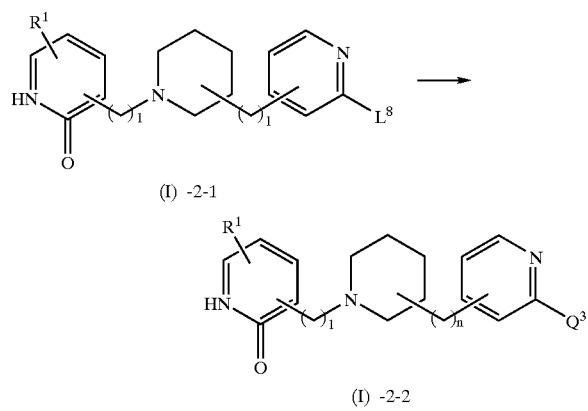

In the formula, $R^1$ and 1 have the same meanings as defined above; $L^8$ indicates a leaving group (for example, a halogen atom, tosylate, mesylate, triphlate etc.); $Q^3$ indicates a substituent (for example, a $C_{1-6}$ alkoxy group, an alkylamino group etc.); and n indicates an integer of 1 to 3. In the pyridonpiperidine derivative (I)-2 obtained in each of the above-mentioned "reactions 13, 14 and 15", the compound (I)-2-1 in which Z is a pyridyl group having a leaving group at 2-position can be converted into the compound (I)-2-2 according to the present invention, by being reacted with an appropriate nucleophile. The present reaction can be carried out under the similar condition as in the above-mentioned "reaction 8".

Production process 21

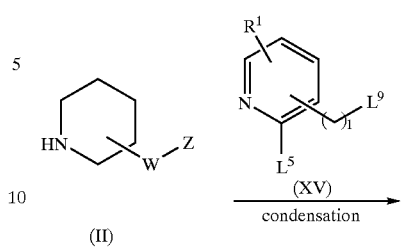

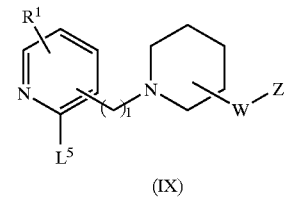

In the formula, $R^1$, 1, W and $L^5$ have the same meanings as defined above; and $L^9$ indicates a leaving group (for example, a halogen atom, tosylate etc.) or an aldehyde group. The pyridylpiperidine derivative (IX) which is the raw material for the "reaction 13" can be produced by condensing the piperidine derivative (II) and the pyridine derivative (XV) in a solvent by reductive amination reaction, or by condensing them in the presence of a base. The present reaction can be carried out under the similar condition as in the "reaction 1". The commercially available pyridine derivative (XV) used is bought, and the derivatives which are not commercially available can be easily prepared from a known raw material according to a conventional method to be used.

Production process 22

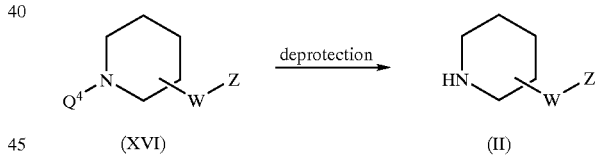

In the formula, W and Z each have the same meanings as defined above; and $Q^4$ indicates a group conventionally used for protecting an amino group. The piperidine derivative (II) can be produced by carrying out the deprotection of the piperidine derivative (XVI) which has a protecting group. The deprotection can be carried out under the condition of the deprotection conventionally used. For example, when $Q^4$ is benzyloxycarbonyl group, it can be carried out by a catalytic reduction method using palladium carbon as a catalyst in an organic solvent, and when $Q^4$ is tert-butyloxycarbonyl group, it can be carried out by interacting an appropriate acid such as hydrochloric acid, sulfuric acid and trifluoroacetic acid in an organic solvent or a mix solvent of water and an organic solvent. Further, when $Q^4$ is benzyl group, it can be carried out by interacting 1-chloroethyl chloroformate and methanol in order in an appropriate organic solvent (for example, halogenated solvents such as dichloromethane).

Production process 23

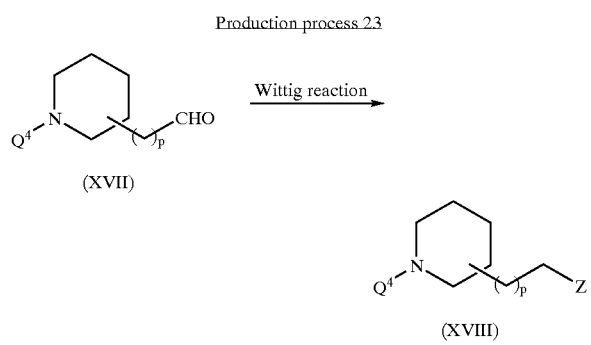

In the formula, Z and $Q^4$ have the same meanings as defined above; and p indicates a number of either of 0 or 1. The piperidinealdehyde derivative (XVIII) which is a raw material in the above-mentioned "reaction 22" can be produced by carrying out the catalytic hydrogenation of the olefin derivative prepared by reacting Wittig reagent to the piperidinealdehyde derivative (XVII) in the presence of a base. The Wittig reaction can be carried out according to the condition of the above-mentioned "reaction 2". The commercially available Wittig reagent is bought, and the reagent which is not commercially available can be easily prepared according to a conventional method to be used. The catalytic hydrogenation in the present reaction can be carried out according to the condition of the above-mentioned "reaction 4".

Production process 24

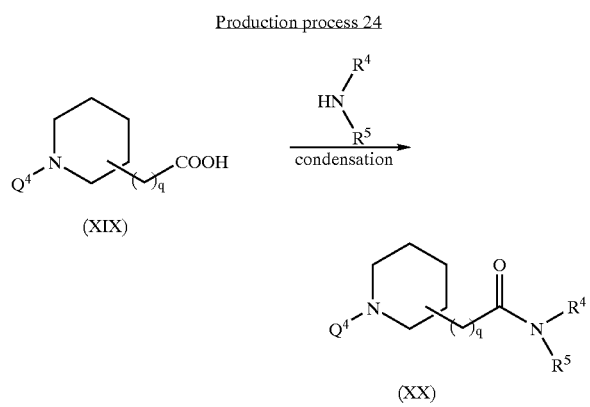

In the formula, $R^4$, $R^5$ and $Q^4$ have the same meanings as defined above; and q indicates an integer of 1 to 2. The amide derivative (XX) which is the raw material for production of the compound according to the present invention can be produced by carrying out the conventional condensation reaction of the carboxylic acid derivative (XIX) and an amine represented by the formula $NH(R^4)R^5$ in an organic solvent. The present reaction can be carried out according to the condition of the above-mentioned "reaction 11".

Production process 25

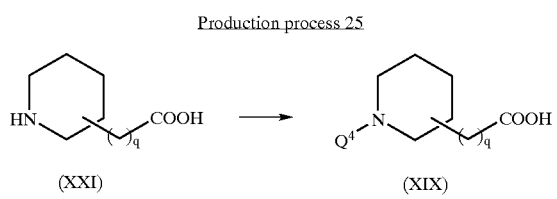

In the formula, $Q^4$ and q have the same meanings as defined above. The carboxylic acid derivative (XIX) as the raw material of the above-mentioned "reaction 24" can be produced by protecting the nitrogen atom of the piperidine derivative (XXI) by an appropriate group. The present reaction can be carried out according to the condition conventionally used for the protection of an amino group. For example, when $Q^4$ is tert-butoxycarbonyl group (Boc), di-tert-butyl dicarbonate is preferable as a reagent for adding Boc. The amount of the reagent used is 1 to 5 equivalents to a raw material. The reaction of adding Boc can be carried out in a mix solvent of water and organic solvents such as tert-butanol in the presence of a base, and the reaction temperature is generally from 0 to 80° C., and preferably from 0 to 25° C.

Production process 26

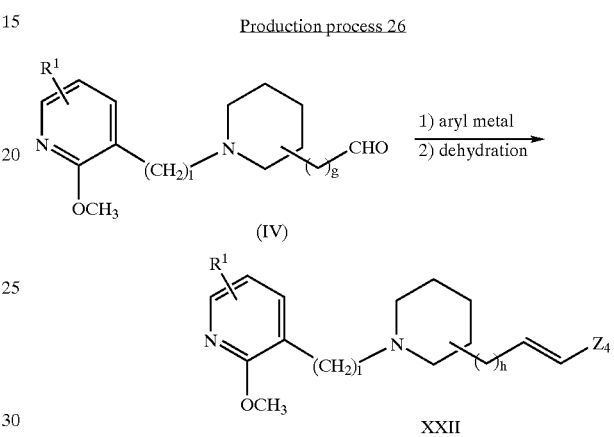

In the formula, $R^1$, l, g, h and $Z^4$ have the same meanings as defined above; and $Z^4$ indicates a 5- to 14-membered aromatic group which may be substituted. The compound (XXII) according to the present invention can be produced by carrying out the 1,2-addition of an aryl metal to the aldehyde derivative (IV) to give an alcohol intermediate and dehydrating it. The commercially available aryl metal used for the 1,2-addition is bought, and the aryl metals which are not commercially available can be prepared according to a conventional method to be used. The amount of the aryl metal used is 1 to 5 equivalents to a raw material. The solvent used is not specifically limited so far as it does not inhibit the reaction and dissolves a starting substance to an extent. For example, ethers such as tetrahydrofuran (THF), dioxane, ether and diethylene glycol dimethyl ether, and additionally, toluene, benzene etc. are preferable. The reaction temperature is conventionally from −78 to 0° C. As the dehydrating agent used for dehydration reaction, acids such as p-toluenesulfonic acid, camphorsulfonic acid, methanesulfonic acid, trifluoroacetic acid, phosphoric acid, polyphosphoric acid, hydrochloric acid, hydrobromic acid, nitric acid and sulfuric acid, and acid chlorides such as phosphorous oxychloride and thionyl chloride are preferable. When an acid chloride is used as the dehydrating agent, a good result can be also obtained by coexisting bases such as pyridine, triethylamine and diisopropylethylamine in the reaction system. The reaction can be carried out without a solvent or in an appropriate solvent. The solvent used is not specifically limited so far as it does not inhibit the reaction and dissolves a starting substance to an extent. For example, halogenated hydrocarbons such as dichlolomethane, chloroform and dichloroethane, and additionally, toluene, benzene etc. are preferable. The reaction temperature is generally from −20° C. to a reflux temperature of the solvent, and preferably from 0 to 120° C.

Production process 27

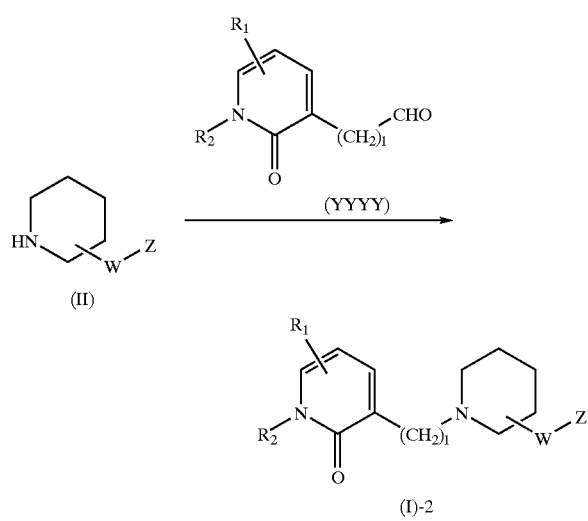

In the formula, $R^1$, $R^2$, W, Z and l have the same meanings as defined above. The compound (I)-2 according to the present invention can be produced by condensing the piperidine derivative (II) and the pyridine derivative (YYYY) in a solvent by reductive amination. The solvent used is not specifically limited so far as it does not inhibit the reaction and dissolves a starting substance to an extent. For example, ethers such as tetrahydrofuran (THF), dioxane and diethylene glycol dimethyl ether, halogenated carbons such as dichloromethane, chloroform and dichloroethane, and additionally, ethyl acetate, dimethylformamide (DMF), dimethyl sulfoxide (DMSO), 1-methylpyrrolidone, acetonitrile etc. are preferable. As the reducing agent, for example, metal hydrides such as sodium borohydride and triacetoxy sodium boronhydride can be used. Further, a catalytic reduction method conventionally used can be carried out. The amount of the reducing agent used is 1 to 5 equivalents to a raw material. The reaction temperature is generally from –50° C. to a reflux temperature of the solvent, and preferably about 0 to about 25° C.

Production process 28

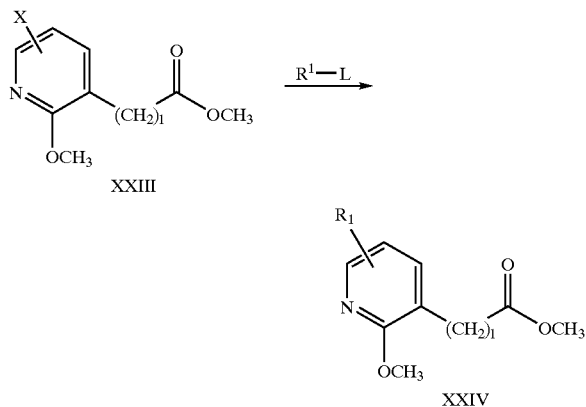

In the formula, $R^1$ and l have the same meanings as defined above; X indicates a leaving group (for example, a halogen atom, triflate etc.); and, $R^1$—L indicates an aryl metal compound or an alkyl metal compound. Examples of the aryl metal compound or alkyl metal compound used in the present reaction include, for example, aryl boric acid, aryltributyltin, alkyl boric acid, alkyltributyltin, alkoxyborane derivatives, alkylborane derivatives etc. conventionally used. The amount of the aryl metal compound or alkyl metal compound used is generally 1 to 5 equivalents to a raw material, and preferably about 2 equivalents. As the catalyst used, for example, tetrakis(triphenylphosphine)palladium, dichlorobis(triphenylphosphine)palladium(II) etc. are listed. The amount of the catalyst used is about 0.05 mol % to a raw material. The solvent used is not specifically limited so far as it does not inhibit the reaction and dissolves a starting substance to an extent. For example, tetrahydrofuran (THF), dioxane, diethylene glycol dimethyl ether, toluene, benzene, dimethylformamide (DMF), 1-methylpyrrolidone etc. are preferable. When an aryl boric acid or an alkyl boric acid is used as the aryl metal compound or alkyl metal compound, it is preferable to coexist bases such as potassium carbonate, cesium carbonate and sodium carbonate, or an aqueous solution thereof. The reaction temperature is generally from room temperature to a reflux temperature of the solvent, and preferably from 80 to 130° C.

Production process 29

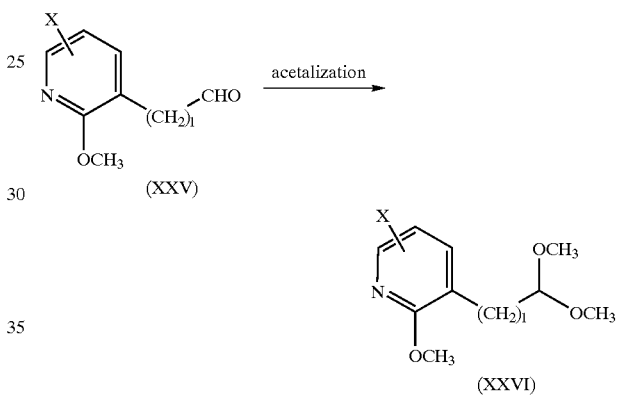

In the formula, $R^1$ and l have the same meanings as defined above; and X indicates a leaving group (for example, a halogen atom, triflate etc.). The compound (XXVI) can be produced from the aldehyde derivative (XXV) under the condition for acetalization conventionally used. For example, it can be obtained by interacting trimethyl orthoformate, dimethoxypropane etc. in an organic solvent in the presence of a catalyst (for example, p-toluenesulfonic acid) or montmorillonite K-10.

Production process 30

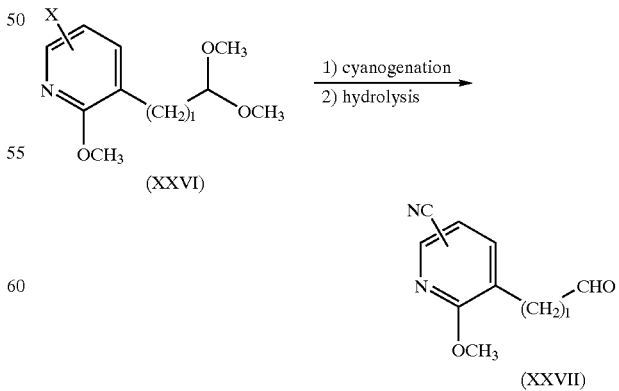

In the formula, $R^1$ and l have the same meanings as defined above, and X indicates a leaving group (for example, a halogen atom, triflate etc.). The compound (XXVII) can be obtained by reacting a cyan compound with the acetal derivative (XXVI) in the presence of cuprous iodide and a catalyst, and then hydrolyzing the acetal. As the cyanide compound used, for example, sodium cyanide, potassium cyanide, zinc cyanide etc. are mentioned. The amount of the cyanide compound used is conventionally 1 to 5 equivalents to a raw material, and preferably about 2 equivalents. As the catalyst used, for example, tetrakis(triphenylphosphine) palladium, dichlorobis(triphenylphosphine)palladium(II) etc. are mentioned. The amount of the catalyst used is about 0.001 to 0.1 mol % based on a raw material. The solvent used is not specifically limited so far as it does not inhibit the reaction and dissolves a starting substance to an extent. For example, tetrahydrofuran (THF), dioxane, diethylene glycol dimethyl ether, toluene, benzene, dimethylformamide (DMF), 1-methylpyrrolidone, acetonitrile, propionitrile, and the like are preferable. The reaction temperature is conventionally from room temperature to a reflux temperature of the solvent, and preferably from 80 to 140° C.

The hydrolysis reaction can be carried out under the condition for hydrolysis conventionally used. For example, it can be carried out by interacting an appropriate acid such as hydrochloric acid, sulfuric acid, acetic acid and trifluoroacetic acid in an organic solvent or a mix solvent of water and an organic solvent.

Production process 31

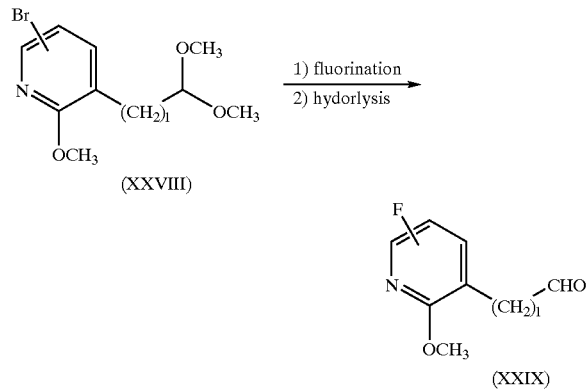

(XXVIII)

(XXIX)

In the formula, l has the same meaning as defined above. The compound (XXIX) according to the present invention can be produced by reacting the acetal derivative (XXVIII) with an organometallic reagent to be metalated, reacting it with a fluorinating agent and then hydrolyzing the acetal. The metalation reaction can be carried out under the condition for metalation conventionally used. As the organometallic reagent used for the metalation, for example, n-butyllithium, sec-butyllithium, tert-butyllithium, phenyllithium etc. are listed. As the fluorinating agent, for example, N-fluoroimides such as N-fluorobenzenesulfonimide, or N-fluoropyridinium derivatives such as N-fluoro-4-methyl pyridinium-2-sulfonate are listed. The amount of the fluorinating agent used is conventionally 1 to 2 equivalents based on a raw material. The solvent used is not specifically limited so far as it does not inhibit the reaction and dissolves a starting substance to an extent. For example, ethers such as tetrahydrofuran (THF), dioxane, ether and diethylene glycol dimethyl ether are preferable. The reaction temperature is conventionally from −78 to 0° C., and preferably from −78 to −40° C.

The hydrolysis reaction can be carried out under the condition for hydrolysis conventionally used. For example, it can be carried out by interacting an appropriate acid such as hydrochloric acid, sulfuric acid, acetic acid and trifluoroacetic acid in an organic solvent or a mix solvent of water and an organic solvent.

Production process 32

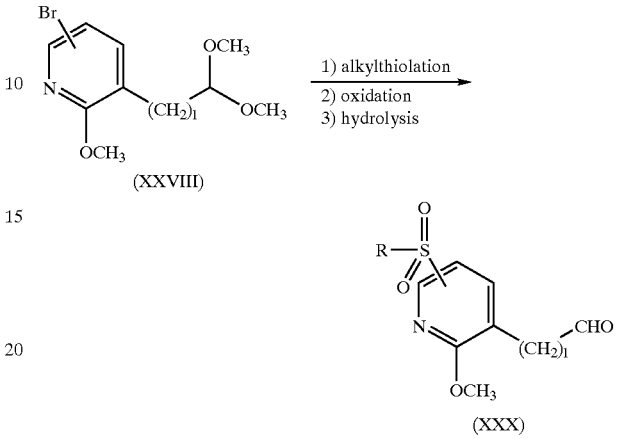

(XXVIII)

(XXX)

In the formula, l has the same meaning as defined above; and R indicates an aralkyl group. The compound (XXX) according to the present invention can be produced by reacting the acetal derivative (XXVIII) with an organometallic reagent to be metalated, reacting it with an organic sulfur compound, oxydizing the aralkylthio group and then hydrolyzing the acetal. The metalation reaction can be carried out under the conventional condition for metalation. As the organometallic reagent used for the metalation, for example, n-butyllithium, sec-butyllithium, tert-butyllithium, phenyllithium etc. may be proposed. As the organic sulfur compound used for alkylthiolation, for example, disufides such as dimethyl disulfide and diphenyl disulfide, sulfenylchlorides such as phenylsulfenylchloride, etc. may be proposed. The amount of the organic sulfur compound used is conventionally 1 to 2 equivalents based on a raw material. The solvent used is not specifically limited so far as it does not inhibit the reaction and dissolves a starting substance to an extent. For example, ethers such as tetrahydrofuran (THF), dioxane, ether, diethylene glycol dimethyl ether etc. are preferable. The reaction temperature is conventionally from −78 to 0° C., and preferably from −78 to −40° C.

The oxidation reaction of the aralkylthio group to an aralkylsulfonyl group can be carried out under the condition of oxidation which is conventionally used. For example, it can be carried out by interacting an inorganic peroxide such as hydrogen peroxide, or an organic peroxide such as m-chloroperbenzoic acid in a halogenated hydrocarbon solvent such as dichloromethane. It is preferable in the present reaction to coexist bases such as sodium bicarbonate, sodium carbonate and potassium carbonate.

The subsequent hydrolysis reaction can be carried out under the condition for hydrolysis which is conventionally used. For example, it can be carried out by interacting an appropriate acid such as hydrochloric acid, sulfuric acid, acetic acid and trifluoroacetic acid in an organic solvent or a mix solvent of water and an organic solvent.

The production process of the compound (I) according to the present invention has been described above, but the raw material compound in the production of the compound of the present invention may form a salt and a hydrate, and is not specifically limited unless the reaction is inhibited. Further, when the compound (I) according to the present invention is obtained as a free form, the above-mentioned compound (I) can be converted into a form of a salt. Further, various kinds of isomers provided for the compound (I) according to the present invention (for example, geometrical isomer, optical isomer based on asymmetric carbon, stereo isomer, tautomer etc.) can be purified and isolated by using conventional separating procedures (for example, recrystallization, diastereomeric salt method, enzyme fractionation method, various kinds of chromatography).

The compound represented by the above formula (I), a salt thereof or a hydrate of them can be formulated by a conventional method, and examples of a preferable preparation include tablets, powders, fine granules, granules, coated tablets, capsules, syrups, troches, inhalants, suppository, injections, ointment, eye ointments, eye drops, nasal drops, eardrops, poultices, lotions etc. For preparations, fillers, binders, disintegrants, lubricants, colorants, and flavoring agents conventionally used, if necessary, stabilizers, emulsifiers, absorption accelerators, surfactants, pH regulators, antiseptics, antioxidants etc. can be used. Ingredients which are conventionally used for raw materials of pharmaceutical preparations can be formulated by a normal method. As these ingredients, for example, animal and vegetable oils such as soy bean oil, tallow and synthetic glyceride; hydrocarons such as liquid paraffin, squalane and solid paraffin; ester oils such as octyldodecyl myristate and isopropyl myristate; higher alcohols such as cetostearyl alcohol and behenic alcohol; silicone resins; silicone oils; surfactants such as polyoxyethylene fatty acid ester, sorbitan fatty acid ester, glycerin fatty acid ester, polyoxyethylene sorbitan fatty acid ester, polyoxyethylene-hardened castor oil and polyoxyethylene-polyoxypropylene block copolymer; water-soluble polymers such as hydroxy ethyl cellulose, polyacrylic acid, carboxyvinyl polymer, polyethylene glycol, polyvinyl pyrrolidone and methyl cellulose; lower alcohol such as ethanol and isopropanol; polyvalent alcohols such as glycerin, propylene glycol, dipropylene glycol and sorbitol; sugars such as glucose and dextrose; inorganic powders such as silicic anhydride, aluminum magnesium silicate and aluminum silicate; purified water etc. may be proposed. Specifically, as fillers, for example, lactose, corn starch, white sugar, glucolse, mannitol, sorbit, crystalline cellulose, silicon dioxide etc.; as binders, for example, polyvinyl alcohol, polyvinyl ether, methyl cellulose, ethyl cellulose, gum arabic, tragacanth, gelatin, shellac, hydroxypropyl cellulose, hydroxypropylmethyl cellulose, polyvinyl pyrrolidone, polypropylene glycol-polyoxyethylene block copolymer, meglumine, calcium citrate, dextrin, pectin and the like; as disintegrants, for example, starch, agar, gelatin powder, crystalline cellulose, calcium carbonate, sodium bicarbonate, calcium citrate, dextrin, pectin, carboxymethyl cellulose calcium etc.; as lublicants, for example, magnesium stearate, talc, polyethylene glycol, silica, hardened vegetable oil etc.; as colorants, any colorant which is permitted to be added to pharmaceuticals; as flavoring agents, cocoa powder, menthol, aroma powder, peppermint oil, borneol, cinnamon powder etc.; and as antioxidants, which are permitted to be added to pharmaceuticals such as ascorbic acid and α-tocopherol are used, respectively.

For example, (1) oral preparations are made as powders, fine granules, granules, tablets, coated tablets, capsules etc. according to a conventional method after adding fillers, and further, if necessary, binders, disintegrants, lubricants, colorants, flavoring agents etc. to the compound according to the present invention, a salt thereof or a hydrate of them. (2) In case of tablets and granules, sugar coating and gelatin coating, and additionally, if necessary, appropriate coating are allowed to be carried out. (3) In case of syrups, preparations for injection, eye drops and the like, pH regulators, resolving aids, isotonizing agents etc., and if necessary, solubilizer, stabilizers, buffers, suspending agents, antioxidants etc. are added and formulated according to a conventional method. In case of the preparations, a freeze-dry product can be also made, and preparations for injection can be administered intravenously, subcutaneous, or in a muscle. Preferable examples of the suspending agent include methyl cellulose, polysorbate 80, hydroxyethyl cellulose, gum arabic, gum tragacanth powder, carboxymethyl cellulose sodium, polyoxyethylene sorbitan monolaurate etc.; preferable examples of the solubilizer include polyoxyethylene hardened castor oil, polysorbate 80, nicotinamide, polyoxyethylene sorbitan monolaurate etc.; preferable examples of the stabilizer include sodium sulfite, meta sodium sulfite, ether etc.; preferable examples of the preservative include methyl p-hydroxybenzoate, ethyl p-hydroxybenzoate, sorbic acid, phenol, cresol, chlorocresol etc. (4) Further, in case of external preparations, preparation process is not specifically limited, and the preparation can be produced by a conventional method. As the raw material of a base preparatiaon used, various raw materials which are conventionally used for pharmaceuticals, quasidrug, cosmetics etc. can be used. For example, raw materials such as animal and vegetable oils, a mineral oil, an ester oil, waxes, higher alcohols, fatty acids, a silicone oil, a surfactant, phosphatides, alcohols, polyvalent alcohols, water-soluble polymers, clay minerals, purified water etc. may be proposed. According to requirement, pH controller, an antioxidant, a chelating agent, antiseptic and fungicide, a coloring agent, flavors etc. can be added. Further, if necessary, ingredients having differential derivation action, blood flow accelerator, antibacterial, antiphlogistine, cell activator, vitamins, amino acids, a humectant, keratolysis medicine etc. can be formulated. The dose of the pharmaceuticals according to the present invention is different according to the extent of symptom, age, sexuality, body weight, administration form, modality of salt, the difference of sensitiveness for medicine, the specific modality of affection etc., but in case of an adult, approximately 30 µg to 1000 mg per day for oral administration, preferably 100 µg to 500 mg, and more preferably 100 µg to 100 mg is in general administered at one time or several times. Approximately 1 to 3000 µg/kg for injection administration, and preferably 3 to 1000 µg/kg is in general administered at one time or several times.

The compound represented by the above formula (I) or a salt thereof or a hydrate of them has an excellent $Na^+$ channel inhibitory action, and is useful as an $Na^+$ channel inhibitor. Accordingly, the compound represented by the above formula (I), a salt thereof or a hydrate of them and the pharmaceutical composition containing thereof can exhibit an excellent treating or preventing effect on a disease against which the $Na^+$ channel inhibitory action is useful for therapy and prevention, and are effective as an agent for treating or preventing, for example, arrhythmia (in addition, the removal of patient's stress caused by an attack of atrial fibrillation, for example, palpitation, chest discomfort, heart failure, thrombus in left mitral, thromboembolism, seizure etc.), various nuralgias (for example, diabetic neuralgia, HIV neuralgia, postherpetic neuralgia, trigeminal neuralgia, stump pain, postspinal injury pain, thalamic pain, poststroke pain etc.) and an analgesic.

EXAMPLES

Examples are shown below as the best embodiments of the compound according to the present invention, but these Reference Examples, Examples (further, a pharmacologically acceptable salt thereof or a hydrate of them and the pharmaceutical containing thereof) and Test Examples are only illustrative, and the compound according to the present invention is not limited to specific examples below at any case. Those skilled in the art can add various variations to not only Examples shown below, but also the Scope of Claim of the specification of the present application to carry out the present invention to maximum limit. Further, such variations are included in the Scope of Claim of the specification of the present application.

Reference Example 1

1-[(2-Methoxy-3-pyridyl)methyl]-4-piperidinemethanol 10 g of 4-piperidinemethanol, 13 g of 3-(chloromethyl)-2-methoxypyridine and 24 g of potassium carbonate were suspended in 80 ml of N,N-dimethylformamide, and the mixture was stirred at room temperature for 12 hours. Water was added to the reaction solution, the mixture was extracted with ethyl acetate. The organic layer was washed with brine, and then the layer was dried over anhydrous magnesium sulfate. The solvent was evaporated, to give 16.1 g of the title compound as a pale brown oil.

$^1$H-NMR (400 MHz, CDCl$_3$) δ 1.26–1.38 (2H, m), 1.52 (1H, m), 1.68–1.76 (2H, m), 2.01–2.09 (2H, m), 2.90–2.96 (2H, m), 3.49 (2H, s), 3.50 (2H, d, J=7.5 Hz), 3.95 (3H, s), 6.87 (1H, dd, J=7.2, 5.0 Hz), 7.65 (1H, dd, J=7.2, 1.9 Hz), 8.05 (1H, dd, J=5.0, 1.9 Hz).

Reference Example 2

1-[(2-Methoxy-3-pyridyl)methyl]-4-piperidinecarboxaldehyde 16.1 g of 1-[(2-methoxy-3-pyridyl)methyl]-4-piperidinemethanol and 38 ml of triethylamine were suspended in 60 ml of dimethyl sulfoxide, a mixed solution of 21.7 g of a sulfur trioxide-pyridine complex and 100 ml of dimethyl sulfoxide was added dropwise thereto, and the mixture was stirred at room temperature for one hour. Water was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate), to give 10.9 g of the title compound as a pale yellow oil.

$^1$H-NMR (400 MHz, CDCl$_3$) δ 1.66–1.76 (2H, m), 1.87–1.94 (2H, m), 2.15–2.30 (3H, m), 2.82–2.88 (2H, m), 3.50 (2H, s), 3.95 (3H, s), 6.87 (1H, dd, J=7.2, 5.0 Hz), 7.63 (1H, dd, J=7.2, 2.0 Hz), 8.06 (1H, dd, J=5.0, 2.0 Hz), 9.66 (1H, d, J=1.1 Hz).

Reference Example 3

1-Benzyl-4-(2,3-methylenedioxyphenethyl)piperidine 20.3 g of 4-(1-benzyl)piperidinecarboxaldehyde and 48.0 g of (2,3-methylenedioxybenzyl)triphenylphosphonium bromide and 12.0 g of potassium tert-butoxide were suspended in 200 ml of N,N-dimethylformamide, and the mixture was stirred at room temperature for one hour. Water was added to the reaction solution, and the mixture was extracted with ethyl acetate. The organic layer was washed with brine and then dried over anhydrous magnesium sulfate. The solvent was evaporated, and the crude product was purified and separated by NH form silica gel column chromatography (ethyl acetate:hexane=1:4). The resulting product and 2.03 g of 10% palladium-carbon powder (water-containing product) were suspended in 200 ml of ethanol. After replacing the atmosphere of a container with hydrogen, the mixture was stirred at room temperature under ordinary atmosphere for two hours. The reaction solution was filtered, and the filtrate was evaporated, to give 20.3 g of the title compound as a colorless oil.

$^1$H-NMR (400 MHz, CDCl$_3$) δ 1.24–1.36 (3H, m), 1.52–1.59 (2H, m), 1.68–1.75 (2H, m), 1.88–1.96 (2H, m), 2.84–2.91 (2H, m), 3.48 (2H, s), 5.91 (2H, s), 6.63–6.69 (2H, m), 6.74 (1H, dd, J=7.8, 7.8 Hz), 7.24 (1H, m), 7.29–7.33 (4H, m).

Reference Example 4

4-(2,3-Methylenedioxyphenethyl)piperidine 20.3 g of 1-benzyl-4-(2,3-methylenedioxyphenethyl)piperidine was dissolved in 10 ml of 1,2-dichloroethane, 7 ml of 1-chloroethyl chloroformate was added thereto under ice-cooling, and the mixture was heated under reflux for 30 minutes. The solvent was evaporated, the resulting residue was dissolved in 100 ml of methanol, and the mixture was heated under reflux for one hour. The solvent was removed, the resulting residue was basified by adding a 5N aqueous sodium hydroxide, and the mixture was extracted with ethyl acetate. The organic layer was washed with brine, and then dried over anhydrous magnesium sulfate. The solvent was evaporated, and the crude product was purified by NH form silica gel column chromatography (ethyl acetate), to give 13.1 g of the title compound as a pale yellow oil.

$^1$H-NMR (400 MHz, CDCl$_3$) δ 1.08–1.20 (2H, m), 1.39 (1H, m), 1.52–1.59 (2H, m), 1.70–1.78 (2H, m), 2.53–2.62 (4H, m), 3.03–3.10 (2H, m), 5.93 (2H, s), 6.64–6.70 (2H, m), 6.76 (1H, dd, J=7.8, 7.8 Hz).

Reference Example 5

3-Methylthio-2-thiophenecarboxaldehyde 4.44 g of 3-bromo-2-thiophenecarboxaldehyde and 1.63 g of sodium thiomethoxide were dissolved in 20 ml of N,N-dimethylformamide, and the mixture was stirred for 3 hours under ice-cooling. Ethyl acetate was added to the reaction solution. The mixture was washed with water and brine, and then dried over anhydrous magnesium sulfate. The solvent was evaporated, and the resulting crude product was purified by silica gel column chromatography (ethyl acetate:hexane=1:9), to give 3.36 g of the title compound as a yellow oil.

$^1$H-NMR (400 MHz, CDCl$_3$) δ 2.59 (3H, s), 7.10 (1H, d, J=5.1 Hz), 7.73 (1H, dd, J=5.1, 0.9 Hz), 10.0 (1H, d, J=0.9 Hz).

Reference Example 6

3-Methylthio-2-thiophenemethanol 3.36 g of 3-methylthio-2-thiophenecarboxaldehyde and 802 mg of sodium borohydride were suspended in 20 ml of methanol, and the mixture was stirred at room temperature for one hour. The solvent was evaporated, water was added to the residue, and the mixture was extracted with ethyl acetate. The organic layer was washed with brine, and then the layer was dried on anhydrous magnesium sulfate. The solvent was evaporated, and the resulting crude product was purified by silica gel column chromatography (ethyl acetate:hexane=1:5), to give 3.16 g of the title compound as a colorless oil.

¹H-NMR (400 MHz, CDCl₃) δ 2.05 (1H, t, J=4.8 Hz), 2.42 (3H, s), 4.87 (1H, d, J=4.8 Hz), 7.03 (1H, d, J=5.3 Hz), 7.27 (1H, d, J=5.3 Hz).

Reference Example 7

[(3-Methylthio-2-thienyl)methyl) triphenylphosphonium chloride 6.26 g of 3-methylthio-2-thiophenemethanol was dissolved in 40 ml of dichloromethane, 2.85 ml of thionyl chloride was added dropwise thereinto under ice-cooling, and the mixture was further stirred for 30 minutes under ice-cooling. The reaction solution was washed with an aqueous saturated sodium bicarbonate, and then dried over anhydrous magnesium sulfate. The solvent was evaporated, the resulting crude product and 15.4 g of triphenylphosphine were dissolved in 120 ml of toluene, and the mixture was heated under reflux for 20 hours. The resulting crystals were collected by filtration, washed with ethyl acetate and air-dried, to give 14.3 g of the title compound as colorless crystals.

¹H-NMR (400 MHz, CDCl₃) δ 2.07 (3H, s), 5.85 (2H, d, J=13.2 Hz), 6.92 (1H, d, J=5.3 Hz), 7.24 (1H, dd, J=5.3, 2.4 Hz), 7.63–7.70 (6H, m), 7.72–7.83 (9H, m).

Reference Example 8

1-tert-Butoxycarbonyl-4-[2-(3-methylsulfonyl-2-thienyl)ethyl]piperidine 14.4 g of [(3-methylthio-2-thienyl)methyl] triphenylphosphonium chloride and 3.67 g of potassium tert-butoxide were dissolved in 120 ml of N,N-dimethylformamide. Under rice-cooling, a mixed solution of 6.97 g of 1-tert-butoxycarbonyl-4-piperidinecarboxaldehyde and 30 ml of N,N-dimethylformamide was added thereto, and the mixture was stirred at room temperature for one hour. Water was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate:hexane=1:10). The resulting product was dissolved in 40 ml of chloroform, 3.59 g of 3-chloroperbenzoic acid was added thereto under ice-cooling, and the mixture was stirred at room temperature for one hour. An aqueous saturated sodium thiosulfate was added to the reaction mixture, to separate the organic layer. The organic layer was washed with a 1N aqueous sodium hydroxide and brine, and then dried over anhydrous magnesium sulfate. The solvent was evaporated, and the crude product was purified by silica gel column chromatography (ethyl acetate:hexane=1:3). The resulting product and 3.0 g of 10% palladium-carbon powder (water-containing product) were suspended in 150 ml of ethanol. After replacing the atmosphere of a container with hydrogen, the mixture was stirred at room temperature under normal pressure for 4 hours. The reaction solution was filtered, and then the solvent of the filtrate was evaporated, to give 11.1 g of the title compound as a pale yellow oil.

¹H-NMR (400 MHz, CDCl₃) δ 1.10–1.22 (2H, m), 1.46 (9H, s), 1.58–1.64 (2H, m), 1.66–1.77 (3H, m), 2.63–2.75 (2H, m), 3.06 (3H, s), 3.18–3.24 (2H, m), 4.10 (2H, br s), 7.19 (1H, dd, J=5.5, 0.4 Hz), 7.31 (1H, d, J=5.5 Hz).

Reference Example 9

4-[2-(3-Methylsulfonyl-2-thienyl)ethyl]piperidine hydrochloride 11.1 g of 1-tert-butoxycarbonyl-4-[2-(3-methylsulfonyl-2-thienyl)ethyl]piperidine was dissolved in 100 ml of ethyl acetate, 100 ml of an ethyl acetate solution of 4N hydrochloric acid was added thereto, and the mixture was further stirred at room temperature for 2 hours. The resulting crystals were collected by filtration, washed with ethyl acetate, and air-dried, to give 7.92 g of the title compound as colorless crystals.

¹H-NMR (400 MHz, DMSO-d₆) δ 1.30–1.42 (2H, m), 1.48–1.65 (3H, m), 1.82–1.88 (2H, m), 2.76–2.88 (2H, m), 3.12–3.18 (2H, m), 3.20 (3H, s), 3.20–3.28 (2H, m), 7.31 (1H, d, J=5.5 Hz), 7.57 (1H, d, J=5.5 Hz).

Reference Example 10

1-[(2-Methoxy-3-pyridyl)methyl]-4-(2,2-dibromovinyl)piperidine 3.0 g of 1-[(2-methoxy-3-piridyl)methyl]-4-piperidine acetaldehyde, 5.4 ml of triethylamine, 20.1 g of triphenylphosphine and 12.9 g of carbon tetrabromide were dissolved in 77 ml of dichloroethane at 0° C., and the mixture was stirred for one hour. Dichloromethane was added to the reaction solution, the mixture was washed with an aqueous saturated sodium bicarbonate, and then it was dried over anhydrous magnesium sulfate. The solvent was evaporated, and the crude product was purified by NH form silica gel column chromatography (hexane:ethyl acetate= 20:1), to give 2.9 g of the title compound as a yellow oil.

¹H-NMR (400 MHz, CDCl₃) δ 1.44–1.60 (2H, m), 1.67–1.78 (2H, m), 2.07–2.20 (2H, m), 2.31 (1H, m), 2.84–2.94 (2H, m), 3.52 (2H, s), 3.95 (3H, s), 6.27 (1H, d, J=9.1 Hz), 6.88 (1H, dd, J=7.0, 5.0 Hz), 7.65 (1H, dd, J=7.0, 1.5 Hz), 8.07 (1H, dd, J=5.0, 1,5 Hz).

Reference Example 11

1-[(2-Methoxy-3-piridyl)methyl]-4-(1-ethynyl) piperidine 2.9 g of 1-[(2-methoxy-3-piridyl)methyl]-4-(2,2-dibromovinyl)piperidine was dissolved in 25 ml of tetrahydrofuran, and 12.3 ml of a 1.50 M n-butyllithium hexane solution was added dropwise at −78° C. After completing the dropwise addition, the mixture was further stirred at −78° C. for one hour. An aqueous saturated ammonium chloride was added to the reaction solution, and the mixture was extracted with ethyl acetate. The organic layer was washed with brine, and then the dried over anhydrous magnesium sulfate. The solvent was evaporated, to give the title compound as a yellow oil (quantitatively).

¹H-NMR (400 MHz, CDCl₃) δ 1.66–1.77 (2H, m), 1.83–1.92 (2H, m), 2.07 (1H, d, J=4.0 Hz), 2.17–2.29 (2H, m), 2.41 (1H, m), 2.71–2.80 (2H, m), 3.48 (2H, s), 3.95 (3H, s), 6.87 (1H, dd, J=7.4, 5.0 Hz), 7.64 (1H, dd, J=7.4, 1.8 Hz), 8.05 (1H, dd, J=5.0, 1,8 Hz).

Reference Example 12

1-[(Ethoxymethoxy)methyl)-3,4-methylenedioxybenzene 4.56 g of piperonyl alcohol and 1.20 g of 60% sodium hydride were suspended in 30 ml of N,N-dimethylformamide. After stirring for 30 minutes under ice-cooling, 2.28 ml of chloromethyl ethyl ether was added thereto, and the mixture was stirred at room temperature for one hour. Ethyl acetate was added to the reaction solution. The mixture was washed with water and brine, and then dried over anhydrous magnesium sulfate. The solvent was evaporated, and the crude product was purified by silica gel column chromatography (ethyl acetate:hexane=1:20), to give 4.98 g of the title compound as a colorless oil.

$^1$H-NMR (400 MHz, CDCl$_3$) δ 1.24 (3H, t, J=7.1 Hz), 3.64 (2H, q, J=7.1 Hz), 4.50 (2H, s), 4.73 (2H, s), 5.95 (2H, s), 6.78 (1H, d, J=7.9 Hz), 6.81 (1H, dd, J=7.9, 1.6 Hz), 6.86 (1H, dd, J=1.6 Hz).

Reference Example 13

1-[(Ethoxymethoxy)methyl]-2-(methylthio)-3,4-methylenedioxybenzene 1.05 g of 1-[(ethoxymethoxy)methyl]-3,4-methylenedioxybenzene was dissolved in 10 ml of diethyl ether, 2 ml of a 2.52 M n-butyllithium hexane solution was added thereto at 0° C., and the mixture was stirred for 2 hours, and then 471 mg of methyldisulfide was added dropwise at −70° C. After completing the dropwise addition, the mixture was further stirred at room temperature for 12 hours. A 1N aqueous sodium hydroxide was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate:hexane=1:20), to give 561 mg of the title compound as a colorless oil.

$^1$H-NMR (400 MHz, CDCl$_3$) δ 1.25 (3H, t, J=7.1 Hz), 2.44 (3H, s), 3.66 (2H, q, J=7.1 Hz), 4.68 (2H, s), 4.76 (2H, s), 6.03 (2H, s), 6.73 (1H, d, J=7.9 Hz), 6.92 (1H, d, J=7.9 Hz).

Reference Example 14

1-((Ethoxymethoxy)methyl]-2-(methylsulfonyl)-3,4-methylenedioxybenzene 1.73 g of 1-[(ethoxymethoxy)methyl]-2-(methylthio)-3,4-methylenedioxybenzene was dissolved in 70 ml of chloroform. Under ice-cooling, 3.33 g of 3-chloroperbenzoic acid was added thereto, and the mixture was stirred at room temperature for 12 hours. The solvent was evaporated, and the residue was purified by NH form silica gel column chromatography (ethyl acetate:hexane=1:3), to give 1.87 g of the title compound as a colorless oil.

$^1$H-NMR (400 MHz, CDCl$_3$) δ 1.25 (3H, t, J=7.1 Hz), 3.24 (3H, s), 3.64 (2H, q, J=7.1 Hz), 4.77 (2H, s), 4.94 (2H, s), 6.15 (2H, s), 6.97 (1H, d, J=8.1 Hz), 7.05 (1H, d, J=8.1 Hz).

Reference Example 15

[2-(Methylsulfonyl)-3,4-methylenedioxyphenyl]methanol 571 mg of 1-[(ethoxymethoxy)methyl)-2-(methylsulfonyl)-3,4-methylenedioxybenzene was dissolved in 2 ml of dichloromethane, 2 ml of trifluoroacetic acid was added, and the mixture was stirred at room temperature for 30 minutes. The solvent was evaporated, and the residue was purified by silica gel column chromatography (ethyl acetate:hexane=1:2), to give 308 mg of the title compound as a colorless oil.

$^1$H-NMR (400 MHz, CDCl$_3$) δ 3.28 (3H, s), 4.82 (2H, s), 6.18 (2H, s), 6.94 (1H, d, J=7.9 Hz), 6.98 (1H, d, J=7.9 Hz).

Reference Example 16

1-(Bromomethyl)-2-(methylsufonyl)-3,4-methylenedioxybenzene 907 mg of [2-(methylsulfonyl)-3,4-methylenedioxyphenyl]methanol, 1.31 g of carbon tetrabromide and 1.03 g of triphenylphosphine were dissolved in 5 ml of dichloromethane, and the mixture was stirred at room temperature for 30 minutes. The solvent was evaporated, and the residue was purified by silica gel column chromatography (ethyl acetate:hexane=1:3), to give 1.10 g of the title compound as a colorless oil.

$^1$H-NMR (400 MHz, CDCl$_3$) δ 3.31 (3H, s), 5.04 (2H, s), 6.19 (2H, s), 6.96 (1H, d, J=8.1 Hz), 6.99 (1H, d, J=8.1 Hz).

Reference Example 17

[2-(Methylsulfonyl)-3,4-methylenedioxybenzyl] triphosphonium bromide 1.10 g of 1-(Bromomethyl)-2-(methylsufonyl)-3,4-methylenedioxybenzene and 1.48 g of triphenylphosphine were dissolved in 20 ml of toluene, and the mixture was heated under reflux for 12 hours. The resulting crystals were collected by filtration, washed with ether and air-dried, to give 1.90 g of the title compound as colorless crystals.

$^1$H-NMR (400 MHz, CDCl$_3$) δ 3.02 (3H, s), 5.90 (2H, d, J=14.5 Hz), 6.15 (2H, s), 6.96 (1H, dd, J=8.1, 0.9 Hz), 7.30 (1H, dd, J=8.1, 3.3 Hz), 7.62–7.70 (12H, m), 7.75–7.83 (3H, m).

Reference Example 18

1-[(2-Methoxy-3-pyridyl)methyl]-4-[2-[2-[[[(trifluoromethyl)sulfonyl]oxy]-3-pyridyl]ethyl] piperidine 110 mg of 1-[(2-methoxy-3-pyridyl)methyl]-4-[2-(2-oxo-1,2-dihydro-3-pyridinyl)ethyl]piperidine, 382 mg of N-phenyltrifluoromethane sulfonimide, 311 mg of triethylamine and 13 mg of dimethylaminopyridine were dissolved in 5 ml of tetrahydrofuran, and the mixture was stirred at room temperature for 20 hours. The solvent was evaporated, and the residue was purified and separated by NH form silica gel column chromatography (ethyl acetate:hexane=1:9), to give 151 mg of the title compound as a colorless oil.

$^1$H-NMR (400 MHz, CDCl$_3$) δ 1.27–1.40 (3H, m), 1.50–1.62 (2H, m), 1.67–1.76 (2H, m), 1.98–2.08 (2H, m), 2.65–2.72 (2H, m), 2.87–2.94 (2H, m), 3.48 (2H, s), 3.95 (3H, s), 6.87 (1H, dd, J=7.6, 5.2 Hz), 7.29 (1H, dd, J=7.6, 4.8 Hz), 7.64 (1H, dd, J=7.6, 2.0 Hz), 7.70 (1H, dd, J=7.6, 2.0 Hz), 8.05 (1H, dd, J=5.2, 2.0 Hz), 8.21 (1H, dd, J=4.8, 2.0 Hz).

Reference Example 19

1-[(6-Bromo-2-pyridyl)methyl]-4-(2,3-methylenedioxyphenethyl)piperidine 636 mg of the title compound as a pale yellow oil was obtained from 457 mg of 4-(2,3-methylenedioxyphenethyl)piperidine obtained in Reference Example 4, and 409 mg of 6-bromo-2-pyridinecarboxaldehyde in the same manner as in Example 29 described later.

$^1$H-NMR (400 MHz, CDCl$_3$) δ 1.26–1.38 (3H, m), 1.52–1.62 (2H, m), 1.70–1.78 (2H, m), 2.02–2.10 (2H, m), 2.56–2.62 (2H, m), 2.83–2.90 (2H, m), 3.62 (2H, s), 5.92 (2H, s), 6.65 (1H, dd, J=7.6, 1.2 Hz), 6.68 (1H, dd, J=7.6, 1.2 Hz), 6.75 (1H, dd, J=7.6, 7.6 Hz), 7.34 (1H, d, J=7.6 Hz), 7.44 (1H, d, J=7.6 Hz), 7.51 (1H, dd, J=7.6, 7.6 Hz).

Reference Example 20

1-[(2-Chloro-3-pyridyl)methyl]-4-(2,3-methylenedioxyphenethyl)piperidine 673 mg of the title compound as a colorless oil was obtained from 505 mg of 4-(2,3-methylenedioxyphenethyl)

piperidine obtained in Reference Example 4, and 464 mg of 2-chloro-3-pyridinecarboxaldehyde in the same manner as in Example 29 described later.

$^1$H-NMR (400 MHz, CDCl$_3$) δ 1.26–1.38 (3H, m), 1.55–1.62 (2H, m), 1.70–1.80 (2H, m), 2.06–2.16 (2H, m), 2.56–2.62 (2H, m), 2.84–2.91 (2H, m), 3.59 (2H, s), 5.92 (2H, s), 6.66 (1H, dd, J=7.8, 1.0 Hz), 6.68 (1H, dd, J=7.8, 1.0 Hz), 6.76 (1H, dd, J=7.8, 7.8 Hz), 7.23 (1H, dd, J=7.2, 5.0 Hz), 7.87 (1H, dd, J=7.2, 2.0 Hz), 8.27 (1H, dd, J=5.0, 2.0 Hz).

Reference Example 21

1-[(2-Methoxy-3-pyridyl)methyl]-4-piperidineethanol 8.2 g of 4-piperidineethanol, 10.0 g of 3-(chloromethyl)-2-methoxypyridine and 17.5 g of potassium carbonate were suspended in 65 ml of N,N-dimethylformamide, and the mixture was stirred at room temperature for 12 hours. Water was added to the reaction solution, and the mixture was extracted with ethyl acetate. The organic layer was washed with brine, and then dried over anhydrous magnesium sulfate. The solvent was evaporated, to give the title compound as a yellow oil (quantitatively).

$^1$H-NMR (400 MHz, CDCl$_3$) δ 1.26–1.72 (7H, m), 2.00–2.10 (2H, m), 2.86–2.94 (2H, m), 3.49 (2H, s), 3.70 (2H, t, J=6.7 Hz), 3.95 (3H, s), 6.87 (1H, dd, J=7.0, 5.0 Hz), 7.65 (1H, dd, J=7.0, 1.9 Hz), 8.05 (1H, dd, J=5.0, 1.9 Hz).

Reference Example 22

1-[(2-Methoxy-3-pyridyl)methyl]-4-piperidineacetaldehyde 12.0 g of the title compound was obtained as a yellow oil from 17.4 g of 1-[(2-methoxy-3-pyridyl)methyl]-4-piperidineethanol in the same manner as in Reference Example 30.

$^1$H-NMR (400 MHz, CDCl$_3$) δ 1.30–1.43 (2H, m), 1.65–1.76 (2H, m), 1.91(1H, s), 2.02–2.17 (2H, m), 2.83–2.94 (2H, m), 3.49 (2H, s), 3.94 (3H, s), 6.86 (1H, dd, J=7.1, 4.9 Hz), 7.63 (1H, dd, J=7.1, 1.9 Hz), 8.05 (1H, dd, J=4.9, 1,9 Hz), 9.78 (1H, t, J=2.0 Hz).

Reference Example 23

1-[(2-Methoxy-3-pyridyl)methyl]-4-piperidone 4.0 g of 4-piperidone hydrochloride, 4.1 g of 3-(chloromethyl)-2-methoxypyridine and 12.6 g of potassium carbonate were suspended in 26 ml of N,N-dimethylformamide, and the mixture was stirred at room temperature for 15 hours. Water was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate), to give 5.5 g of the title compound as a yellow oil.

$^1$H-NMR (400 MHz, CDCl$_3$) δ 2.45–2.52 (4H, m), 2.77–2.85 (4H, m), 3.64 (2H, s), 3.96 (3H, s), 6.90 (1H, dd, J=7.1, 4.9 Hz), 7.70 (1H, dd, J=7.1, 2.0 Hz), 8.09 (1H, dd, J=4.9, 2.0 Hz).

Reference Example 24

Ethyl 2-[1-[(2-methoxy-3-pyridyl)methyl]hexahydro-4-pyridinylidene]acetate

Under ice-cooling, a mixed solution of 2.2 ml of triethyl phosphonoacetate and 18 ml of tetrahydrofuran was added dropwise into a suspension of 0.40 g of 60% sodium hydride (oil suspension) and 18 ml of tetrahydrofuran. After stirring for 5 minutes, a mixed solution of 2.0 g of 1-[(2-methoxy-3-pyridyl)methyl]-4-piperidone and 9 ml of tetrahydrofuran was added dropwise thereinto. After completing the dropwise addition, the mixture was further stirred under ice-cooling for 30 minutes. Water was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate:hexane=1:1), to give 2.6 g of the title compound as a pale yellow oil.

$^1$H-NMR (400 MHz, CDCl$_3$) δ 1.28 (3H, t, J=6.9 Hz), 2.32–2.38 (2H, m), 2.54–2.62 (4H, m), 2.97–3.05 (2H, m), 3.53 (2H, s), 3.95 (3H, s), 4.14 (2H, q, J=6.9 Hz), 5.64 (1H, s), 6.88 (1H, dd, J=7.2, 4.9 Hz), 7.67 (1H, dd, J=7.2, 2.1 Hz), 8.07 (1H, dd, J=4.9, 2.1 Hz).

Reference Example 25

Ethyl 2-[1-[(2-methoxy-3-pyridyl)methyl]-4-piperidyl]acetate 2.6 g of ethyl 2-[1-[(2-methoxy-3-pyridyl)methyl)hexahydro-4-pyridinylidene]acetate and 380 mg of 10% palladium-carbon powder (water-containing product) were suspended in 20 ml of ethyl acetate. After replacing the atmosphere of a container with hydrogen, the mixture was stirred at room temperature under normal pressure for one hour. The reaction solution was filtered, and the filtrate was evaporated, to give the title compound as a yellow oil (quantitatively).

$^1$H-NMR (400 MHz, CDCl$_3$) δ 1.25 (3H, t, J=7.1 Hz), 1.28–1.41 (2H, m), 1.65–1.86 (3H, m), 2.02–2.12 (2H, m), 2.23 (2H, d, J=7.0 Hz), 2.84–2.92 (2H, m), 3.48 (2H, s), 3.94 (3H, s), 4.12 (2H, q, J=7.1 Hz), 6.86 (1H, dd, J=7.2, 5.0 Hz), 7.65 (1H, dd, J=7.2, 2.0 Hz), 8.06 (1H, dd, J=5.0, 2.0 Hz).

Reference Example 26

N-(tert-Butoxycarbonyl)-4-[2-[2-(methylsulfonyl)phenyl]-2-oxoethyl]piperidine 2.0 g of N-(tert-butoxycarbonyl)-4-[2-hydroxy-2-[2-(methylthio)phenyl]ethylethyl]piperidine was obtained from 2.2 g of 2-bromothioanisol, 6.9 ml of a 1.53 M n-butyllithium hexane solution and 2.0 g of N-(tert-butoxycarbonyl)-4-piperidineacetaldehyde in the same manner as in Example 71 described later. Then, 2.0 g of N-(tert-butoxycarbonyl)-4-[2-[2-(methylthio)phenyl]ethyl-2-oxoethyl]piperidine was obtained as a pale yellow oil in the same manner as in Reference Example 30. The resulting product and 2.7 g of 3-chloroperbenzoic acid were dissolved in 15 ml of tetrahydrofuran, and the mixture was stirred at room temperature for 2 hours. An aqueous sodium thiosulfate and an aqueous sodium hydroxide were added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate:hexane=1:1), to give 1.8 g of the title compound as a yellow oil.

$^1$H-NMR (400 MHz, CDCl$_3$) δ 1.14–1.29 (2H, m), 1.46 (9H, s), 1.78–1.88 (2H, m), 2.22 (1H, m), 2.73–2.86 (2H, m), 2.87 (2H, d, J=6.6 Hz), 3.25 (3H, s), 3.96–4.24 (2H, s), 7.40 (1H, d, J=7.5 Hz), 7.62 (1H, dd, J=7.8, 7.5 Hz), 7.70 (1H, dd, J=7.5, 7.5 Hz), 8.07 (1H, d, J=7.8 Hz).

Reference Example 27

Methyl 3-[1-[(2-methoxy-3-pyridyl)methyl]-4-piperidine]propanoate 2.0 g of 1-[(2-methoxy-3-pyridyl)methyl]-4-piperidinecarboxaldehyde obtained in Reference Example 2, 1.6 ml of trimethyl phosphonoacetate and 60% sodium hydride were suspended in 30 ml of tetrahydrofuran, and the mixture was stirred at room temperature for one hour. Ethyl acetate was added to the reaction solution, and the mixture was washed with a 1N aqueous sodium hydroxide and brine, and then dried over anhydrous magnesium sulfate. The solvent was evaporated, and the resulting crude product and 400 mg of 10% palladium-carbon powder (water-containing product) were suspended in 100 ml of ethanol. After replacing the atmosphere of a container with hydrogen, the mixture was stirred at room temperature under normal pressure for 20 hours. The reaction solution was filtered, and the filtrate was evaporated, to give 2.20 g of the title compound as a pale brown oil.

$^1$H-NMR (400 MHz, CDCl$_3$) δ 1.20–1.35 (3H, m), 1.55–1.70 (4H, m), 1.96–2.06 (2H, m), 2.33 (2H, t, J=7.8 Hz), 2.84–2.93 (2H, m), 3.48 (2H, s), 3.67 (3H, s), 3.94 (3H, s), 6.86 (1H, dd, J=7.2, 4.8 Hz), 7.63 (1H, dd, J=7.2, 2.0 Hz), 8.05 (1H, dd, J=4.8, 2.0 Hz).

Reference Example 28

3-[1-[(2-Methoxy-3-pyridyl)methyl]-4-piperidyl]propanal 2.20 g of methyl 3-[1-[(2-methoxy-3-pyridyl)methyl]-4-piperidine]-propanoate was conventionally reduced by using lithium aluminum hydride. The resulting product was treated in the same manner as in Reference Example 30, to give 1.29 g of the title compound as a pale yellow oil.

$^1$H-NMR (400 MHz, CDCl$_3$) δ 1.22–1.34 (3H, m), 1.56–1.70 (4H, m), 1.97–2.06 (2H, m), 2.45 (2H, td, J=7.6, 7.6, 1.8 Hz), 2.85–2.93 (2H, m), 3.48 (2H, s), 3.94 (3H, s), 6.86 (1H, dd, J=7.0, 5.0 Hz), 7.63 (1H, dd, J=7.0, 2.0 Hz), 8.05 (1H, dd, J=5.0, 2.0 Hz), 9.77 (1H, t, J=1.8 Hz).

Reference Example 29

2-[1-[(2-Methoxy-3-pyridyl)methyl]-2-piperidyl]-1-ethanol 15.6 g of 2-methoxynicotinic aldehyde, 14 g of 2-piperidineethanol, 30 g of sodium triacetoxyborohydride, 6.6 ml of acetic acid and 200 ml of tetrahydrofuran were stirred at room temperature for one hour. A diluted sodium hydroxide solution was added thereto, and the mixture was extracted with ethyl acetate and dried over anhydrous magnesium sulfate. The drying agent was filtered off, and the solvent was evaporated. The residue was purified by silica gel column chromatography (ethyl acetate, subsequently, ethyl acetate:methanol=2:1).

$^1$H-NMR (400 MHz, CDCl$_3$) δ :1.35–1.84 (8H, m), 1.93–2.04 (1H, m), 2.05–2.34 (1H, m), 2.76–2.85 (1H, m), 2.95–3.02 (1H, m), 3.59 (1H, d, J=16.0 Hz), 3.65–3.73 (1H, m), 3.84–3.92 (1H, m), 3.97 (3H, s), 4.02 (1H, d, J=16.0 Hz), 6.85 (1H, dd, J=6.8 Hz, 6.8 Hz), 7.58 (1H, d, J=6.8 Hz), 8.06 (1H, d, J=6.8 Hz).

Reference Example 30

2-[1-[(2-Methoxy-3-pyridyl)methyl]-2-piperidyl]acetaldehyde

A solution of 4.2 g of pyridine-sulfurtrioxide complex dissolved in dimethyl sulfoxide (DMSO) was added dropwise into a solution of 3 g of 2-[1-[(2-methoxy-3-pyridyl)methyl]-2-piperidyl]-1-ethanol and 7.3 ml of triethylamine dissolved in 15 ml of DMSO, while keeping the bulk temperature at 20° C. or less. After completing the dropwise addition, the mixture was stirred at room temperature for one hour. An aqueous sodium bicarbonate was added thereto, and the mixture was extracted with ethyl acetate. After drying over sodium sulfate, the solvent was evaporated. The residue was purified by silica gel chromatography (methanol), to give 2.5 g of a red brown oil.

$^1$H-NMR (400 MHz, CDCl$_3$) δ: 1.36–1.83 (6H, m), 2.18–2.26 (1H, m), 2.59–2.69 (2H, m), 2.70–2.79 (1H, m), 2.98–3.05 (1H, m), 3.37 (1H, d, J=16.0 Hz), 3.76 (1H, d, J=16.0 Hz), 3.95 (3H, s), 6.86 (1H, dd, J=6.8 Hz, 6.8 Hz), 7.63 (1H, d, J=6.8 Hz), 8.05 (1H, d, J=6.8 Hz), 9.83 (1H, s).

Reference Example 31

1-[(2-Methoxy-3-pyridyl)methyl]-2-piperidinecarboxaldehyde

1-[(2-Methoxy-3-pyridyl)methyl]-2-piperidinecarboxaldehyde was produced according to the method of Reference Example 30 using 2-piperidinemethanol in place of 2-piperidineethanol.

$^1$H-NMR (400 MHz, CDCl$_3$) δ: 1.29–1.38 (1H, m), 1.46–1.80 (5H, m), 2.05–2.14 (1H, m), 2.86–2.97 (2H, m), 3.50 (1H, d, J=16.0 Hz), 3.62 (1H, d, J=16.0 Hz), 3.94 (3H, s), 6.88 (1H, dd, J=6.8, 6.8 Hz), 7.64 (1H, dd, J=6.8, 2.0 Hz), 8.08 (1H, dd, J=6.8, 2.0 Hz), 9.60 (1H, s).

Reference Example 32

Ethyl 2-(2-piperidyl)acetate 50 ml of ethyl 2-(2-pyridyl)acetate, 18.7 ml of acetic acid, 5 g of Pd—C (water-containing product) and 200 ml of ethanol were charged in an auto clave, and the mixture was stirred at 70° C. for 9 hours at a hydrogen pressure of 56 kg/cm$^2$. The Pd—C was filtered off and ethanol was evaporated, to give 72.3 g of white crystals.

$^1$H-NMR (400 MHz, CDCl$_3$) δ: 1.12 (3H, t, J=7.2 Hz), 1.40–1.86 (6H, m), 1.96 (3H, s), 2.54 (1H, dd, J=16.4 Hz, 7.2 Hz), 2.70–2.89 (2H, m), 3.10–3.20 (1H, m), 3.12–3.30 (1H, m), 4.13 (2H, q, J=7.2 Hz), 8.39 (2H, s).

Reference Example 33

Ethyl 2-[1-[(2-methoxy-3-pyridyl)methyl]-2-piperidyl]acetate 25 g of ethyl 2-(2-pyridyl)acetate, 15.6 g of 2-methoxynicotinic aldehyde, 30 g of sodium triacetoxyborohydride, 6.6 ml of acetic acid and 200 ml of THF were stirred at room temperature overnight. A diluted sodium hydroxide was added thereto, and the mixture was extracted with ethyl acetate. After drying over anhydrous magnesium sulfate, the solvent was evaporated. The residue was purified by silica gel chromatography (hexane:ethyl acetate=2:1), to give 2.8 g of a colorless oil.

$^1$H-NMR (400 MHz, CDCl$_3$), δ: 1.12 (3H, t, J=7.2 Hz), 1.40–1.80 (6H, m), 2.22–2.32 (1H, m), 2.42 (1H, dd, J=16.4 Hz, 7.2 Hz), 2.62–2.73 (2H, m), 2.98–3.05 (1H, m), 3.41 (1H, d, J=15.6 Hz), 3.70 (1H, d, J=15.6 Hz), 2.95 (3H, s), 4.12 (2H, q, J=7.2 Hz), 6.86 (1H, dd, J=7.6 Hz, 4.8 Hz), 7.69 (1H, dd, J=7.6 Hz, 2.0 Hz), 8.02 (1H, dd, J=4.8 Hz, 2.0 Hz).

Reference Example 34

2-[1-[(2-Methoxy-3-pyridyl)methyl]-2-piperidyl]acetic acid 2.8 g of ethyl 2-[1-[(2-methoxy-3-pyridyl)methyl]-2-piperidyl]acetate, 20 ml of a 2N aqueous sodium hydroxide and 20 ml of methanol were stirred at 70° C. for 1.5 hours. 8 ml of a 5N aqueous hydrochloric acid was added thereto, and the solvent was evaporated. Ethanol was added to the residue and sodium chloride was filtered off. Ethanol was evaporated, to give 2.9 g of a colorless oil.

$^1$H-NMR (400 MHz, CDCl$_3$) δ: 1.35–1.80 (6H, m), 2.25–2.40 (2H, m), 2.60–2.70 (2H, m), 2.92–3.00 (1H, m), 3.49 (1H, d, J=15.6 Hz), 3.77 (1H, d, J=15.6 Hz), 3.90 (3H, s), 7.00 (1H, dd, J=7.6 Hz, 4.8 Hz), 7.70 (1H, dd, J=7.6 Hz, 2.0 Hz), 8.08 (1H, d, J=4.8 Hz, 2.0 Hz).

Reference Example 35

2-[(2R)-1-(tert-Butoxycarbonyl)hexahydro-2-pyridinyl]acetic acid 29.3 g of 2-[(2R)hexahydro-2-pyridinyl]acetic acid, 8 g of sodium hydroxide, 44.7 g of di-tert-butyl bicarbonate, 240 ml of water and 180 ml of tert-butanol were stirred at room temperature overnight. The reaction solution was washed with ethyl acetate. The aqueous layer was adjusted to pH 1.5 by an aqueous potassium hydrogensulfate, and then extracted with ethyl acetate. The organic layer was dried over anhydrous sodium sulfate, and then ethyl acetate was evaporated, to give 18.6 g the objective compound as white crystals.

$^1$H-NMR (400 MHz, CDCl$_3$) δ: 1.35–1.75 (15H, m), 2.52–2.66 (2H, m), 2.73–2.84 (1H, m), 3.97–4.06 (1H, m), 4.67–4.75 (1H, m).

Reference Example 36 tert-Butyl (2R)-2-[2-di(2-propynylamino)-2-oxoethyl]hexahydro-1-pyridinecarboxylate 7.4 g of 2-[(2R)-1-(tert-butoxycarbonyl)hexahydro-2-pyridinyl]acetic acid, 2.7 g of dipropargylamine, 7.2 g of WSC (1-ethyl-3-(3-dimethylaminopropyl)carbodiimide hydrochloride), 2.0 g of HOBt (1-hydroxy-1H-benzotriazole) and 50 ml of DMF were stirred at room temperature for 2 hours. Brine was added thereto. The mixture was extracted with ethyl acetate, and dried over anhydrous sodium sulfate. The anhydrous sodium sulfate was filtered off, and the solvent was evaporated. The residue was purified by silica gel chromatography (hexane:ethyl acetate=4:1, subsequently, 2:1), to give 7.7 g of the objective product as a yellow oil.

$^1$H-NMR (400 MHz, CDCl$_3$) δ: 1.36–1.75 (15H, m), 2.22 (1H, s), 2.30 (1H, s), 2.50–2.60 (1H, m), 2.73–2.85 (2H, m), 3.93–4.05 (1H, m), 4.18–4.30 (2H, m), 4.30–4.45 (2H, m), 4.58–4.65 (1H, m).

Reference Example 37

N1,N1-Di(2-propynyl)-2-[(2R)hexahydro-2-pyridinyl]acetamide 7.7 g of tert-butyl (2R)-2-[2-di(2-propynylamino)-2-oxoethyl]hexahydro-1-pyridinecarboxylate, 100 ml of a 5N aqueous hydrochloric acid and 50 ml of methyl alcohol were stirred at room temperature for one hour. 110 ml of a 5N aqueous sodium hydroxide was added thereto. Then, the mixture was extracted with ethyl acetate and dried over anhydrous sodium sulfate. After removing the anhydrous sodium sulfate, then, the organic solvent was evaporated, to give 4.4 g of the objective product as an oil.

[α]$_D$=−23.4° (C=0.74, MeOH, 28° C.).

$^1$H-NMR (400 MHz, CDCl$_3$) δ: 1.15–1.50 (3H, m), 1.56–1.63 (2H, m), 1.72–1.80 (1H, m), 2.21 (1H, s), 2.28 (1H, s), 2.40–2.48 (2H, m), 2.63–2.72 (1H, m), 2.93–3.03 (2H, m), 4.10–4.39 (4H, m).

Reference Example 38

1-[(2-Methoxy-3-pyridyl)methyl]-2-piperidinecarboxaldehyde 17 g of sodium triacetoxyborohydride was added to a reaction solution of 8.7 g of 2-methoxynicotinic aldehyde, 5.8 g of 2-piperidinemethanol, 3 ml of acetic acid and 100 ml of tetrahydrofuran (THF) at room temperature, and the mixture was stirred overnight. A diluted sodium hydroxide was added thereto, and the mixture was extracted with ethyl acetate. The solvent was evaporated, and the residue was purified by silica gel chromatography (hexane:ethyl acetate= 1:1, subsequently, ethyl acetate, and subsequently, ethyl acetate:methanol=4:1), to give 5.4 g of an oil. A solution of 8.0 g of pyridine-sulfur trioxide complex dissolved in DMSO, while keeping the bulk temperature at 20° C. or less, was added dropwise into a solution of 5.4 g of the resulting oil, 14 ml of triethylamine and 20 ml of DMSO under stirring. After stirring at room temperature for 3 hours, a cooled sodium bicarbonate was added thereto, and the mixture was extracted with ethyl acetate. The solvent was evaporated, and the residue was purified by silica gel chromatography (hexane:ethyl acetate=4:1, subsequently, 3:2, and subsequently, 2:1), to give 2.7 g of a yellow oil.

$^1$H-NMR (400 MHz, CDCl$_3$) δ: 1.28–1.80 (6H, m), 2.05–2.14 (1H, m), 2.85–2.96 (2H, m), 3.50 (1H, d, J=14.8 Hz), 3.62 (1H, d, J=14.8 Hz), 3.94 (3H, s), 6.85 (1H, dd, J=6.8 Hz, 6.8 Hz), 7.65 (1H, d, J=6.8 Hz), 8.07 (1H, d, J=6.8 Hz), 9.60 (1H, s).

Reference Example 39

Ethyl (E)-3-[1-(2-methoxy-3-pyridyl)methyl]-2-piperidyl]-2-propenoate 2.4 g of potassium tert-butoxide was added under stirring at room temperature to a solution of 4.2 ml of triethyl phosphonoacetate dissolved in 40 ml of THF. After 10 minutes, a solution of 5 g of 1-[(2-Methoxy-3-pyridyl) methyl]-2-piperidinecarboxaldehyde dissolved in THF was added thereto under stirring at room temperature. After stirring for one hour as it was, water was added thereto and the mixture was extracted with ethyl acetate. After drying over anhydrous magnesium sulfate, the solvent was evaporated. The residue was purified by silica gel chromatography (hexane:ethyl acetate=4:1, subsequently, 2:1), to give 3.4 g of an oil.

$^1$H-NMR (400 MHz, CDCl$_3$) δ: 1.27 (3H, t, J=7.2 Hz), 1.28–1.80 (6H, m), 1.94–2.02 (1H, m), 2.82–2.97 (2H, m), 3.19 (1H, d, J=14.8 Hz), 3.70 (1H, d, J=14.8 Hz), 3.94 (3H, s), 4.19 (2H, q, J=7.2 Hz), 5.98 (1H, d, J=16.0 Hz), 6.85 (1H, dd, J=6.8 Hz, 6.8 Hz), 6.96 (1H, dd, J=16.0 Hz, 7.0 Hz), 7.67 (1H, d, J=6.8 Hz), 8.02 (1H, d, J=6.8 Hz).

Reference Example 40

Ethyl 3-[1-[(2-methoxy-3-pyridyl)methyl]-2-piperidyl]propanoate 3.4 g of Ethyl (E)-3-[1-(2-methoxy-3-pyridyl)methyl]-2-piperidyl]-2-propenoate was dissolved in ethanol, 1 g of Pd—C (water-containing product) was added thereto, and the mixture was catalytically hydrogenated overnight under normal pressure. The catalyst was filtered off, and the solvent was evaporated. The residue was purified by silica gel chromatography (hexane:ethyl acetate=3:1), to give 1.58 g of a colorless oil.

$^1$H-NMR (400 MHz, CDCl$_3$) δ: 1.03 (3H, t, J=7.2 Hz), 1.30–1.73 (6H, m), 1.88–1.95 (2H, m), 2.09–2.17 (1H, m), 2.23–2.45 (3H, m), 2.75–2.80 (1H, m), 3.26 (1H, d, J=14.8 Hz), 3.83 (1H, d, J=14.8 Hz), 3.95 (3H, s), 4.10 (2H, q, J=7.2 Hz), 6.84 (1H, dd, J=6.8 Hz, 6.8 Hz), 7.67 (1H, d, J=6.8 Hz), 8.02 (1H, d, J=6.8 Hz).

Reference Example 41

(2-Methoxy-3-pyridyl)methyl cyanide 4 g of (2-methoxy-3-pyridyl)methyl chloride, 2.5 g of sodium cyanide and 10 ml of DMF were stirred under heating for 10 minutes. Water was added thereto, and the mixture was extracted with ethyl acetate and dried over anhydrous magnesium sulfate. The drying agent was removed, and the solvent was evaporated. The residue was purified by silica gel chromatography (hexane:ethyl acetate=3:1), to give 2.5 g of a colorless oil.

$^1$H-NMR (400 MHz, CDCl$_3$) δ: 3.65 (2H, s), 3.99 (3H, s), 6.93 (1H, dd, J=6.8 Hz), 7.66 (1H, d, J=6.8 Hz), 8.15 (1H, d, J=6.8 Hz).

Reference Example 42

2-(2-Methoxy-3-pyridyl)acetic acid 2.2 g of (2-methoxy-3-pyridyl)methyl cyanide, 35 ml of a 1N aqueous sodium hydroxide and 35 ml of methanol were stirred under heating at 100° C. for 1.5 hours. The mixture was cooled to room temperature, and then, 35 ml of a 5N aqueous hydrochloric acid was added thereto, and the solvent was evaporated. Ethanol was added to the residue and a solid was filtered off. Ethanol was evaporated, and ethanol was added again to the residue and a solid was filtered off. Ethanol was evaporated, to give 2.4 g of white crystals.

$^1$H-NMR (400 Hz, DMSO-d6) δ: 3.53 (2H, s), 3.86 (3H, s), 6.95 (1H, dd, J=6.8 Hz, 6.8 Hz), 7.60 (1H, di J=6.8 Hz), 8.07 (1H, d, J=6.8 Hz).

Reference Example 43

2-(2-Methoxy-3-pyridyl)ethanol 2.4 g of (2-methoxy-3-pyridyl)acetic acid, 550 mg of lithium aluminum hydride and 20 ml of THF were stirred at room temperature for 0.5 hour. 0.27 ml of water, 3.9 ml of a 3.8N aqueous sodium hydroxide and 0.78 ml of water were successively added thereto, and the resulting solid was filtered off. The filtrate was evaporated, and the residue was purified by silica gel chromatography (hexane:ethyl acetate=2:1, subsequently 1:1), to give 1.2 g of a yellow oil.

$^1$H-NMR (400 MHz, CDCl$_3$) δ: 2.83 (3H, t, J=7.2 Hz), 3.84 (2H, q, J=7.2 Hz), 3.97 (3H, s), 6.83 (1H, dd, J=6.8 Hz, 6.8 Hz), 7.42 (1H, d, J=6.8 Hz), 8.03 (1H, d, J=6.8 Hz).

Reference Example 44

2-(2-Methoxy-3-pyridyl)acetaldehyde

A solution of 2.7 g of pyridine-sulfur trioxide complex dissolved in DMSO was added dropwise at 20° C. or less to a solution of 1.2 g of 2-(2-methoxy-3-pyridyl)ethanol and 4.8 ml of triethylamine dissolved in DMSO. After stirring for 0.5 hour, a cooled sodium bicarbonate was added thereto, and the mixture was extracted with ethyl acetate. After drying over sodium sulfate, the solvent was evaporated. The residue was purified by silica gel chromatography (hexane:ethyl acetate=4:1), to give 200 mg of a yellow oil.

$^1$H-NMR (400 MHz, CDCl$_3$) δ: 3.60 (2H, s), 3.95 (3H, s), 6.85 (1H, dd, J=6.8 Hz, 6.8 Hz), 7.40 (1H, d, J=6.8 Hz), 8.10 (1H, d, J=6.8 Hz), 9.70 (1H, s).

Reference Example 45

[[(2-(Cyclohexylmethyloxy)phenyl)methyl] triphenylphosphonium chloride

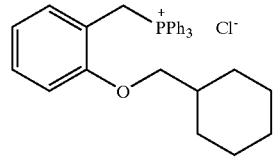

3.06 g of 2-(cyclohexylmethyloxy)benzyl alcohol was dissolved in 30 ml of toluene, 1.52 ml of thionyl chloride and 5 drops of N,N-dimethylformamide were added thereto and the mixture was stirred for 70 minutes under ice-cooling. An aqueous sodium carbonate was added to the reaction solution, and the mixture was extracted with ethyl acetate. The organic layer was washed with water and brine, and then dried over anhydrous magnesium sulfate. The solution was filtered through alumina, and the solvent was evaporated, to give a slight yellow oil. The oil was dissolved in 3 ml of acetonitrile, 3.65 g of triphenylphosphine was added thereto, and the mixture was stirred at 110° C. for one hour and 45 minutes. Ethyl acetate was added to the reaction solution and the product was collected by filtration, to give 6.51 g of the title compound as a white powder.

$^1$H-NMR (400 MHz, CDCl$_3$) δ 0.75–0.89 (2H, m), 1.06–1.38 (4H, m), 1.51–1.58 (2H, m), 1.64–1.84 (3H, m), 3.21 (2H, d, J=6.4 Hz), 5.34 (2H, d, J=14.0 Hz), 6.59 (1H, d, J=8.0 Hz), 6.80 (1H, dt, J=8.0, 0.8 Hz), 7.22 (1H, m), 7.32 (1H, m), 7.58–7.68 (12H, m), 7.73–7.81 (3H, m).

Reference Example 46

Methyl 5-methyl-2-methoxy-3-pyridinecarboxylate

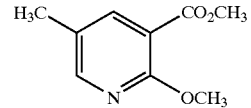

1.2 g of methyl 5-bromo-2-methoxy-3-pyridinecarboxylate was dissolved in 20 ml of N,N-dimethylformamide, 440 mg of methylboric acid, 4.79 g of anhydrous cesium carbonate, and 564 mg of tetrakis (triphenylphosphine)palladium were added thereto, and the mixture was stirred at 120° C. for 2 hours under a nitrogen atmosphere. Ice-water was added to the reaction solution, and the mixture was extracted with ethyl acetate. The organic layer was washed with water and brine, and then dried over anhydrous magnesium sulfate. The solvent was evaporated, and the crude product was purified by silica gel column chromatography (hexane:ethyl acetate=20:1), to give 461 mg of the title compound as a colorless oil.

$^1$H-NMR (400 MHz, CDCl$_3$) δ 2.29 (3H, s), 3.90 (3H, s), 4.02 (3H, s), 7.99 (1H, d, J=2.4 Hz), 8.12 (1H, d, J=2.4 Hz).

Reference Example 47

Methyl 5-phenyl-2-methoxy-3-pyridinecarboxylate

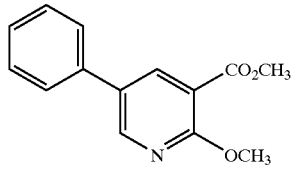

The title compound was obtained from a corresponding raw material in accordance with the method of Reference Example 46.

$^1$H-NMR (400 MHz, CDCl$_3$) δ 3.94 (3H, s), 4.10 (3H, s), 7.38 (1H, m), 7.44–7.50 (2H, m), 7.54–7.58 (2H, m), 8.39 (1H, d, J=2.8 Hz), 8.54 (1H, d, J=2.8 Hz).

Reference Example 48

Methyl 5-(3-pyridinyl)-2-methoxy-3-pyridinecarboxylate

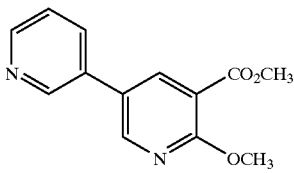

The title compound was obtained from a corresponding raw material in accordance with the method of Reference Example 46.

$^1$H-NMR (400 MHz, CDCl$_3$) δ 3.95 (3H, s), 4.11 (3H, s), 7.41 (1H, ddd, J=8.0, 4.8, 1.2 Hz), 7.86 (1H, ddd, J=8.0, 2.4, 1.6 Hz), 8.39 (1H, d, J=2.8 Hz), 8.55 (1H, d, J=2.8 Hz), 8.64 (1H, dd, J=4.8, 1.6 Hz), 8.83 (1H, dd, J=2.4, 1.2 Hz).

Reference Example 49

Methyl 5-(4-pyridinyl)-2-methoxy-3-pyridinecarboxylate

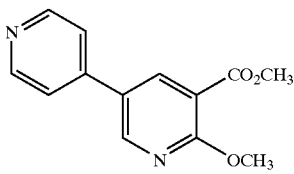

The title compound was obtained from a corresponding raw material in accordance with the method of Reference Example 46.

$^1$H-NMR (400 MHz, CDCl$_3$) δ 3.95 (3H, s), 4.12 (3H, s), 7.47–7.53 (2H, m), 8.44 (1H, d, J=2.8 Hz), 8.61 (1H, d, J=2.8 Hz), 8.67–8.73 (2H, m).

Reference Example 50

6-Methyl-2-methoxy-3-pyridinemethanol

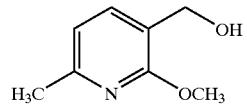

0.9 g of lithium aluminum hydride was suspended in 60 ml of tetrahydrofuran, and a solution of 4.41 g of 6-methyl 2-methoxy-3-pyridinecarboxylate dissolved in 20 ml of tetrahydrofuran was added dropwise there into under ice-cooling and stirring. After stirring for 30 minutes, 0.9 ml of water, 0.9 ml of a 15% aqueous sodium hydroxide and 2.7 ml of water were successively added thereto. Celite and anhydrous magnesium sulfate were added thereto, followed by stirring at room temperature. After filtering the reaction solution, the solvent was evaporated, to give 3.78 g of the title compound as a white solid.

$^1$H-NMR (400 MHz, CDCl$_3$) δ 2.26 (1H, m), 2.44 (3H, s), 3.98 (3H, s), 4.60 (2H, d, J=5.2 Hz), 6.71 (1H, d, J=7.2 Hz), 7.42 (1H, d, J=7.2 Hz).

Reference Example 51

5-Chloro-2-methoxy-3-pyridinemethanol

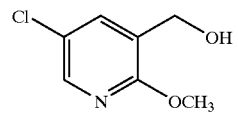

The title compound was obtained from a corresponding raw material in accordance with the method of Reference Example 50.

$^1$H-NMR (400 MHz, CDCl$_3$) δ 3.97 (3H, s), 4.63 (2H, s), 7.59–7.65 (1H, m), 8.03 (1H, d, J=2.4 Hz).

Reference Example 52

5-Bromo-2-methoxy-3-pyridinemethanol

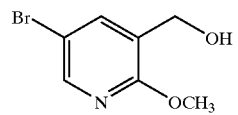

The title compound was obtained from a corresponding raw material in accordance with the method of Reference Example 50.

$^1$H-NMR (400 MHz, CDCl$_3$) δ 3.96 (3H, s), 4.63 (2H, s), 7.73 (1H, d, J=2.4 Hz), 8.13 (1H, d, J=2.4 Hz).

Reference Example 53

5-Methyl-2-methoxy-3-pyridinemethanol

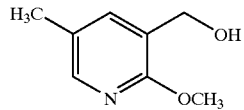

The title compound was obtained from a corresponding raw material in accordance with the method of Reference Example 50.

$^1$H-NMR (400 MHz, CDCl$_3$) δ 2.25 (3H, s), 3.97 (3H, s), 4.26 (2H, s), 7.40 (1H, d, J=2.4 Hz), 7.89 (1H, d, J=2.4 Hz).

Reference Example 54

5-Phenyl-2-methoxy-3-pyridinemethanol

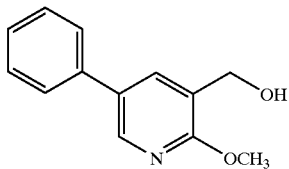

The title compound was obtained from a corresponding raw material in accordance with the method of Reference Example 50.

$^1$H-NMR (400 MHz, CDCl$_3$) δ 4.04 (3H, s), 4.72 (2H, s), 7.36 (1H, m), 7.42–7.48 (2H, m), 7.52–7.56 (2H, m), 7.82 (1H, d, J=2.4 Hz), 8.32 (1H, d, J=2.4 Hz).

Reference Example 55

5-(3-Pyridinyl)-2-methoxy-3-pyridinemethanol

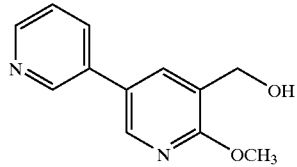

The title compound was obtained from a corresponding raw material in accordance with the method of Reference Example 50.

$^1$H-NMR (400 MHz, CDCl$_3$) δ 4.05 (3H, s), 4.74 (2H, s), 7.39 (1H, ddd, J=8.0, 4.8, 0.4 Hz), 7.85–7.88 (2H, m), 8.32 (1H, d, J=2.4 Hz), 8.61 (1H, dd, J=4.8, 1.6 Hz), 8.11 (1H, dd, J=2.4, 0.4 Hz).

Reference Example 56

5-(4-Pyridinyl)-2-methoxy-3-pyridinemethanol

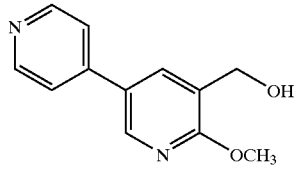

The title compound was obtained from a corresponding raw material in accordance with the method of Reference Example 50.

$^1$H-NMR (400 MHz, CDCl$_3$) δ 2.38 (1H, s), 4.06 (3H, s), 4.75 (2H, s), 7.47–7.50 (2H, m), 7.91 (1H, m), 8.40 (1H, d, J=2.4 Hz), 8.64–8.68 (2H, m).

Reference Example 57

6-Methyl-2-methoxy-3-(chloromethyl)pyridine

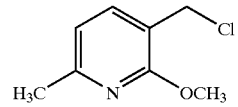

3.78 g of 6-methyl-2-methoxy-3-pyridinemethanol was dissolved in 60 ml of carbon tetrachloride, 6.48 g of triphenylphosphine was added thereto, and the mixture was heated under reflux for 6 hours 30 minutes. The solvent was evaporated, n-hexane was added to the residue, and the insoluble matters were filtered off. The filtrate was evaporated, and the crude product was purified by silica gel chromatography (n-hexane:ethyl acetate=100:1), to give 2.29 g of the title compound as a colorless oil.

$^1$H-NMR (400 MHz, CDCl$_3$) δ 2.45 (3H, s), 3.98 (3H, s), 4.58 (2H, s), 6.72 (1H, d, J=7.2 Hz), 7.50 (1H, d, J=7.2 Hz).

Reference Example 58

5-Chloro-2-methoxy-3-(chloromethyl)pyridine

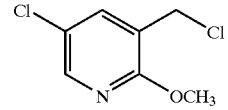

The title compound was obtained from a corresponding raw material in accordance with the method of Reference Example 57.

$^1$H-NMR (400 MHz, CDCl$_3$) δ 3.98 (3H, s), 4.55 (2H, s), 7.63–7.68 (1H, m), 8.07 (1H, d, J=2.4 Hz).

Reference Example 59

5-Bromo-2-methoxy-3-(chloromethyl)pyridine

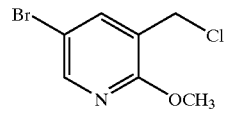

The title compound was obtained from a corresponding raw material in accordance with the method of Reference Example 57.

$^1$H-NMR (400 MHz, CDCl$_3$) δ 3.98 (3H, s), 4.54 (2H, s), 7.78 (1H, d, J=2.4 Hz), 8.12 (1H, d, J=2.4 Hz).

Reference Example 60

5-Methyl-2-methoxy-3-(chloromethyl)pyridine

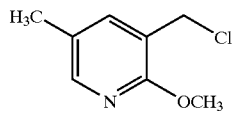

The title compound was obtained from a corresponding raw material in accordance with the method of Reference Example 57.

$^1$H-NMR (400 MHz, CDCl$_3$) δ 2.26 (3H, s), 3.97 (3H, s), 4.58 (2H, s), 7.48 (1H, d, J=2.0 Hz), 7.93 (1H, d, J=2.0 Hz).

Reference Example 61

5-Phenyl-2-methoxy-3-(chloromethyl)pyridine

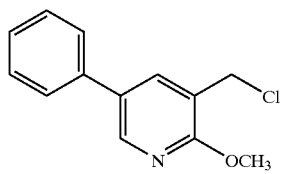

The title compound was obtained from a corresponding raw material in accordance with the method of Reference Example 57.

$^1$H-NMR (400 MHz, CDCl$_3$) δ 4.05 (3H, s), 4.66 (2H, s), 7.37 (1H, m), 7.43–7.48 (2H, m), 7.52–7.56 (2H, m), 7.88 (1H, d, J=2.4 Hz), 8.36 (1H, d, J=2.4 Hz).

Reference Example 62

5-(4-Pyridinyl)-2-methoxy-3-pyridinecarboxaldehyde

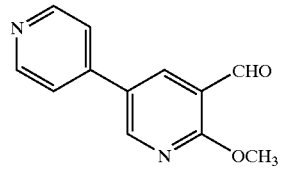

321 mg of 5-(4-pyridinyl)-2-methoxy-3-pyridinemethanol was dissolved in 10 ml of chloroform, 1.6 g of manganese dioxide was added thereto, and the mixture was stirred at room temperature for 14 hours. After filtering through Celite, the filtrate was evaporated. The crude product was purified by silica gel chromatography (toluene:ethyl acetate=3:1), to give 329 mg of the title compound as a white powder.

$^1$H-NMR (400 MHz, CDCl$_3$) δ 4.17 (3H, s), 7.48–7.56 (2H, m), 8.40 (1H, d, J=2.8 Hz), 8.66–8.76 (3H, m), 10.45 (1H, s).

Reference Example 63

5-(3-Pyridinyl)-2-methoxy-3-pyridinecarboxaldehyde

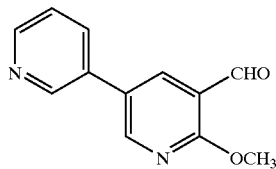

The title compound was obtained from a corresponding raw material in accordance with the method of Reference Example 62.

$^1$H-NMR (400 MHz, CDCl$_3$) δ 4.15 (3H, s), 7.41 (1H, ddd, J=0.8, 4.8, 8.0 Hz), 7.87 (1H, ddd, J=8.0, 2.4, 1.6 Hz), 8.33 (1H, d, J=2.4 Hz), 8.63 (1H, d, J=2.4 Hz), 8.65 (1H, dd, J=4.8, 1.6 Hz), 8.84 (1H, dd, J=2.4, 0.8 Hz), 10.44 (1H, s).

Reference Example 64

5-Bromo-2-methoxy-3-pyridinecarboxaldehyde dimethyl acetal

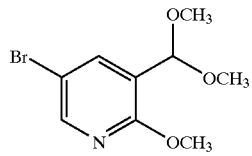

2.58 g of 5-bromo-2-methoxy-3-pyridinecarboxaldehyde was dissolved in 30 ml of dichloromethane, a mixture of 9 ml of trimethyl orthoformate and montmorillonite K-10 (3 g) was added thereto, and the mixture was stirred at room temperature for 2 hours. After filtering the reaction solution, the filtrate was evaporated. To the residue was added ethyl acetate, followed by filtering through alumina. The filtrate was evaporated, to give 3.09 g of the title compound as a yellow oil.

$^1$H-NMR (400 MHz, CDCl$_3$) δ 3.36 (6H, s), 3.96 (3H, s), 5.51 (1H, s), 7.90 (1H, dd, J=2.4, 0.4 Hz), 8.18 (1H, d, J=2.4 Hz).

Reference Example 65

5-(Methylsulfonyl)-2-methoxy-3-pyridinecarboxaldehyde dimethyl acetal

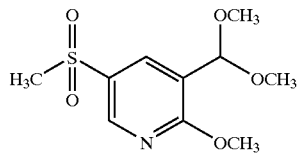

20 ml of tetrahydrofuran was cooled to −78° C., 4.17 ml of n-butyllithium (1.6 M, hexane solution) was added thereto, and the mixture was stirred. A solution of 1.59 g of 5-bromo-2-methoxy-3-pyridinecarboxaldehyde dimethyl acetal dissolved in 5 ml of tetrahydrofuran was added dropwise thereinto. After 30 minutes, 0.66 ml of dimethyldisulfide was added dropwise thereinto, and the mixture was further stirred for 1.5 hours. water was added to the reaction solution, and the mixture was extracted with ethyl acetate. The organic layer was washed with water and brine, and then dried over anhydrous magnesium sulfate. The solvent was evaporated, to give a pale yellow oil. The oil was dissolved in 30 ml of dichloromethane, 5.12 g of sodium bicarbonate and 2.32 g of m-chloroperbenzoic acid were added thereto, and the mixture was stirred for 30 minutes under ice-cooling. An aqueous sodium thiosulfate was added to the reaction solution, and the mixture was extracted with ethyl acetate. The organic layer was washed with water, a 1N aqueous sodium hydroxide and brine, and then dried over anhydrous magnesium sulfate. The solvent was evaporated, and the crude product was purified by silica gel column chromatography (n-hexane:ethyl acetate=2:1), to give 0.81 g of the title compound as a white solid.

$^1$H-NMR (400 MHz, CDCl$_3$) δ 3.08 (3H, s), 3.38 (6H, s), 4.08 (3H, s), 5.51 (1H, s), 8.29 (1H, dd, J=2.8, 0.8 Hz), 8.71 (1H, d, J=2.8 Hz).

Reference Example 66

5-(Methylsulfonyl)-2-methoxy-3-pyridinecarboxaldehyde

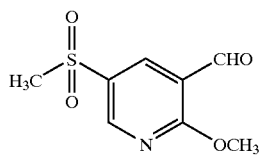

0.81 g of 5-(methylsulfonyl)-2-methoxy-3-pyridinecarboxaldehyde dimethyl acetal was dissolved in 8 ml of acetone, 2 ml of 5N-hydrochloric acid was added thereto, and the mixture was stirred at room temperature for 30 minutes. An aqueous sodium carbonate was added to the reaction solution, and the mixture was extracted with ethyl acetate. The organic layer was washed with water and brine, and then dried over anhydrous magnesium sulfate. The solvent was evaporated, n-hexane was added to the residue and the resulting product was collected by filtration, to give 0.62 g of the title compound as a white powder.

$^1$H-NMR (400 MHz, CDCl$_3$) δ 3.11 (3H, s), 4.12 (3H, s), 8.58 (1H, d, J=2.8 Hz), 8.93 (1H, d, J=2.8 Hz), 10.38 (1H, s).

Reference Example 67

5-Fluoro-2-methoxy-3-pyridinecarboxaldehyde

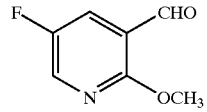

20 ml of tetrahydrofuran was cooled to −78° C., 2.41 ml of n-butyllithium (2.6 M, hexane solution) was added thereto, and the mixture was stirred. A solution of 1.50 g of 5-bromo-2-methoxy-3-pyridinecarboxaldehyde dimethyl acetal dissolved in 5 ml of tetrahydrofuran was added dropwise thereinto. After 25 minutes, a solution of 2.16 g of N-fluorobenzenesulfonimide dissolved in 20 ml of tetrahydrofuran was added dropwise thereinto over 20 minutes and the mixture was further stirred for 55 minutes. To the reaction mixture were added brine and 20 ml of 2N-hydrochloric acid, followed by stirring at room temperature. After 40 minutes, a diluted ammonia was added to the reaction solution, and the mixture was extracted with ethyl acetate. The organic layer was washed with water and brine, and then dried over anhydrous magnesium sulfate. The solvent was evaporated, to give a yellow oil. The oil was dissolved in 16 ml of acetone, 4 ml of 5N-hydrochloric acid was added thereto, and the mixture was left for 30 minutes at room temperature. An aqueous potassium carbonate was added to the reaction solution, and the mixture was extracted with ethyl acetate. The organic layer was washed with water and brine, and then dried over anhydrous magnesium sulfate. The solvent was evaporated, and the crude product was purified by silica gel column chromatography (n-hexane:ethyl acetate=15:1), to give 234 mg of the title compound as a slight yellow solid.

$^1$H-NMR (400 MHz, CDCl$_3$) δ 4.07 (3H, s), 7.84 (1H, dd, J=3.2, 7.6 Hz), 8.24 (1H, d, J=3.2 Hz), 10.33 (1H, d, J=2.8 Hz).

Reference Example 68

5-Cyano-2-methoxy-3-pyridinecarboxaldehyde

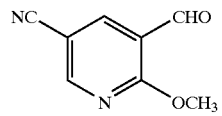

2.00 g of 5-bromo-2-methoxy-3-pyridinecarboxaldehyde dimethyl acetal was dissolved in 25 ml of propionitrile. To the mixture were added 449 mg of sodium cyanide, 152 mg of cuprous iodide and 462 mg of tetrakis (triphenylphosphine)palladium, followed by stirring at 100° C. for 45 minutes in nitrogen atmosphere. A diluted ammonia was added to the reaction solution, and the mixture was extracted with ethyl acetate. The organic layer was washed with water and brine, and then dried over anhydrous magnesium sulfate. The solvent was evaporated, to give an oil. The oil was dissolved in 16 ml of acetone, 4 ml of 5N-hydrochloric acid was added thereto, and the mixture was left for 30 minutes at room temperature. An aqueous sodium carbonate aqueous solution was added to the reaction solution, and the mixture was extracted with ethyl acetate. The organic layer was washed with water and brine, and then dried over anhydrous magnesium sulfate. The solvent was evaporated, and the crude product was purified by silica gel column chromatography (toluene:ethyl acetate= 1:1), to give 843 mg of the title compound as white crystals.

$^1$H-NMR (400 MHz, CDCl$_3$) δ 4.17 (3H, s), 8.34 (1H, d, J=2.4 Hz), 8.67 (1H, d, J=2.4 Hz), 10.33 (1H, s).

Reference Example 69

1-(Benzyloxycarbonyl)-4-[(E)-2-[2-(cyclohexylmethyloxy)phenyl]-1-ethenyl]piperidine

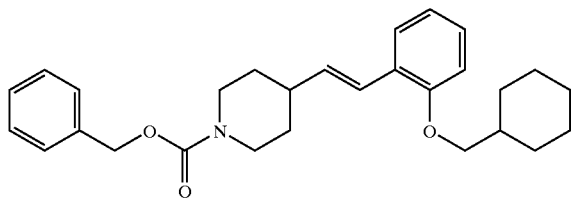

1.75 g of [[2-(cyclohexylmethyloxy)phenyl]methyl] triphenylphosphonium chloride was dissolved in 10 ml of dimethyl sulfoxide, 144 mg of 60% sodium hydride was added thereto, and the mixture was stirred at 70° C. After leaving to cool to room temperature, a solution of 800 mg of 1-(benzyloxycarbonyl)-4-piperidinecarboxaldehyde dissolved in 3 ml of tetrahydrofuran was added dropwise thereinto and the mixture was stirred at room temperature for one hour. Water was added to the reaction solution, and the mixture was extracted with ethyl acetate. The organic layer was washed with 1N-hydrochloric acid, an aqueous saturated sodium bicarbonate and brine, and then dried over anhydrous magnesium sulfate. The solvent was evaporated, and the crude product was purified by silica gel column chromatography (n-hexane:ethyl acetate=10:1), to give 554 mg of the title compound as a colorless oil.

$^1$H-NMR (400 MHz, CDCl$_3$) δ 0.98–1.50 (7H, m), 1.63–1.92 (8H, m), 2.34 (3/4H, m), 2.66 (1/4H, m), 2.73–2.97 (2H, m), 3.66 (1/2H, d, J=6.0 Hz), 3.68 (3/2H, d, J=6.0 Hz), 4.20 (2H, m), 5.13 (1/2H, s), 5.14 (3/2H, s), 5.46 (1/4H, dd, J=11.6, 10.0 Hz), 6.15 (3/4H, dd, J=16.0, 6.4 Hz), 6.50 (1/4H, d, J=11.6 Hz), 6.72 (3/4H, d, J=16.0 Hz), 6.81–6.94 (2H, m), 7.14–7.41 (7H, m).

Reference Example 70

(2-Cyclohexylmethyloxy)bromobenzene

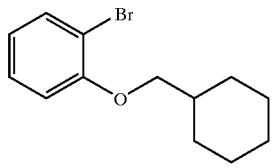

5.00 ml of 2-bromophenol was dissolved in 90 ml of N,N-dimethylformamide, 7.21 ml of (bromomethyl)cyclohexane and 7.15 g of potassium carbonate were added thereto, and the mixture was stirred at 100° C. for 5 hours. Water was added to the reaction solution, and the mixture was extracted with n-hexane. The organic layer was washed with water, 5N-sodium hydroxide and brine, and then dried over anhydrous magnesium sulfate. The mixture was filtered through alumina, and the solvent was evaporated, to give 10.47 g of the title compound as a slight yellow oil.

$^1$H-NMR (400 MHz, CDCl$_3$) δ 1.04–1.38 (5H, m), 1.67–1.95 (6H, m), 3.81 (2H, d, J=6.0 Hz), 6.80 (1H, dt, J=7.6, 1.2 Hz), 6.87 (1H, dd, J=8.0, 1.2 Hz), 7.23 (1H, ddd, J=8.0, 7.6, 2.0 Hz), 7.52 (1H, d, J=7.6, 2.0 Hz).

Reference Example 71

1-Benzyl-4-[2-hydroxy-2-[(2-cyclohexylmethyloxy)phenyl]ethyl]piperidine

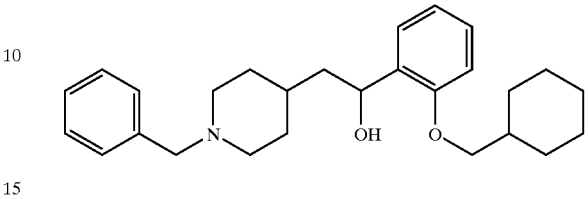

10 ml of tetrahydrofuran was cooled to −78° C., 5.11 ml of n-butyllithium (1.6 M, hexane solution) was added thereto, and the mixture was stirred. A solution of 2.000 g of (2-cyclohexylmethyloxy)bromobenzene dissolved in 5 ml of tetrahydrofuran was added dropwise thereinto. After one hour, a solution of 1.93 g of 1-benzyl-4-piperidineacetaldehyde dissolved in 5 ml of tetrahydrofuran was added dropwise thereinto, and the mixture was further stirred for one hour. Water was added to the reaction solution, and the mixture was extracted with ethyl acetate. The organic layer was washed with water and brine, and then dried over anhydrous magnesium sulfate. The solvent was evaporated, and the crude product was purified by NH form silica gel column chromatography (n-hexane:ethyl acetate= 4:1), to give 2.986 g of the title compound as a colorless oil.

$^1$H-NMR (400 MHz, CDCl$_3$) δ 1.03–1.44 (7H, m), 1.47–1.90 (1H, m), 1.92–2.02 (2H, m), 2.83–2.92 (2H, m), 3.50 (2H, s), 3.76 (1H, dd, J=8.8, 6.0 Hz), 3.82 (1H, dd, J=8.8, 5.6 Hz), 4.99 (1H, dd, J=9.2, 7.6, Hz), 6.84 (1H, dd, J=8.0, 0.8 Hz), 6.93 (1H, dt, J=7.6, 1.2 Hz), 7.18–7.34 (7H, m).

Reference Example 72

1-Benzyl-4-[(E)-2-[(2-dyclohexylmethyloxy)phenyl]-1-ethenyl]piperidine

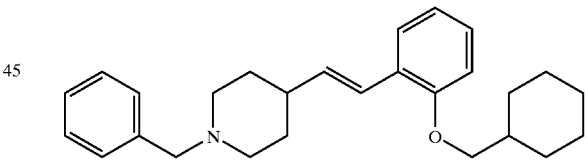

2.986 g of 1-Benzyl-4-[2-hydroxy-2-[(2-cyclohexylmethyloxy)phenyl]ethyl]piperidine was dissolved in 70 ml of toluene. To the mixture was added 1.38 g of p-toluenesulfonic acid, followed by heating under reflux for one hour. An aqueous saturated sodium hydrogencarbonate was added to the reaction solution, and the mixture was extracted with ethyl acetate. The organic layer was washed with water and brine, and then dried over anhydrous magnesium sulfate. The solvent was evaporated, to give 2.848 g of the title compound as a slight yellow oil.

$^1$H-NMR (400 MHz, CDCl$_3$) δ 1.02–1.42 (5H, m), 1.48–1.92 (10H, m), 2.01–2.10 (2H, m), 2.16 (1H, m), 2.89–2.96 (2H, m), 3.53 (2H, s), 3.76 (2H, d, J=6.4 Hz), 6.19 (1H, dd, J=16.0, 7.2 Hz), 6.70 (1H, d, J=16.0 Hz), 6.82 (1H, dd, J=8.8, 0.8 Hz), 6.87 (1H, dt, J=8.8, 0.8 Hz), 7.14 (1H, dt, J=8.8, 0.8 Hz), 7.22–7.36 (5H, m), 7.40 (1H, dd, J=8.8, 0.8 Hz).

Reference Example 73

1-Benzyl-4-[2-[(2-cyclohexylmethyloxy)phenyl]-1-ethynyl]piperidine

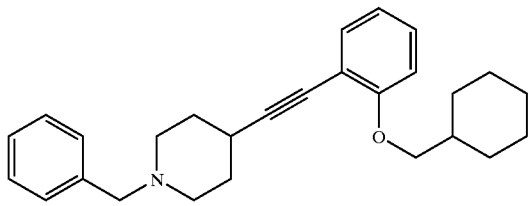

1.19 g of 1-benzyl-4-ethynylpiperidine was dissolved in 20 ml of N,N-dimethylformamide, 1.774 g of (2-cyclohexylmethyloxy)bromobenzene, 114 mg of cuprous iodide, 0.92 ml of triethylamine and 347 mg of tetrakis (triphenylphosphine)palladium were added thereto, and the mixture was stirred at 100° C. for 3.5 hours under anitrogen atmosphere. Ice-water and a diluted ammonia were added to the reaction solution, and the mixture was extracted with ethyl acetate. The organic layer was washed with water and brine, and then dried over anhydrous magnesium sulfate. After filtering through alumina and silica gel, the solvent was evaporated, and the crude product was purified by silica gel column chromatography (n-hexane:ethyl acetate=10:1), to give 316 mg of the title compound as a slight yellow oil.

$^1$H-NMR (400 MHz, CDCl$_3$) δ 1.05–1.36 (5H, m), 1.64–1.98 (10H, m), 2.22–2.34 (2H, m), 2.64–2.81 (3H, m), 3.52 (2H, s), 3.80 (2H, d, J=6.0 Hz), 6.82 (1H, dd, J=8.4, 1.2 Hz), 6.84 (1H, dt, J=8.4, 1.2 Hz), 7.18–7.36 (7H, m).

Reference Example 74

1-(Vinyloxycarbonyl)-4-[(E)-2-[(2-cyclohexylmethyloxy)phenyl]-1-ethenyl]piperidine

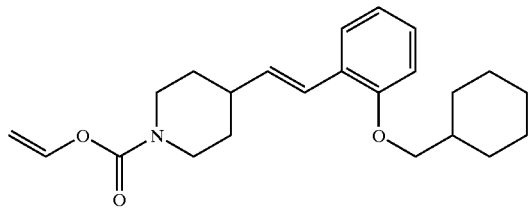

2.848 g of 1-benzyl-4-[(E)-2-[(2-cyclohexylmethyloxy)phenyl]-1-ethenyl]piperidine was dissolved in 15 ml of 1,2-dichloroethane, 0.93 ml of vinyl chloroformate was added thereto, and the mixture was stirred at room temperature for 50 minutes and heated under reflux for one hour. The solvent was evaporated, and the crude product was purified by silica gel column chromatography (n-hexane:ethyl acetate=50:1), to give 2.026 g of the title compound as a colorless oil.

$^1$H-NMR (400 MHz, CDCl$_3$) δ 1.03–1.52 (7H, m), 1.67–1.92 (8H, m), 2.37 (1H, m), 2.84–3.03 (2H, m), 3.78 (2H, d, J=6.4 Hz), 4.16–4.27 (2H, m), 4.45 (1H, dd, J=6.4, 1.6 Hz), 4.78 (1H, dd, J=13.2, 1.6 Hz), 6.15 (1H, dd, J=16.0, 6.8 Hz), 6.73 (1H, d, J=16.0 Hz), 6.84 (1H, dd, J=8.4, 1.2 Hz), 6.88 (1H, dt, J=8.4, 1.2 Hz), 7.17 (1H, dt, J=8.4, 1.2 Hz), 7.24 (1H, dd, J=13.2, 6.4 Hz), 7.39 (1H, dd, J=8.4, 1.2 Hz).

Reference Example 75

1-(Vinyloxycarbonyl)-4-[(E)-2-(2-fluorophenyl)-1-ethenyl)piperidine

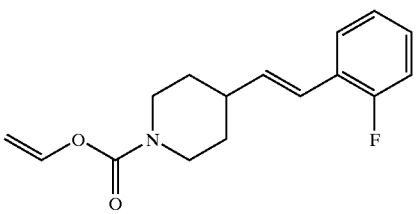

The title compound was obtained from a corresponding raw material in accordance with the method of Reference Example 74.

$^1$H-NMR (400 MHz, CDCl$_3$) δ 1.39–1.52 (2H, m), 1.83 (2H, br d, J=15.6 Hz), 2.37 (1H, m), 2.83–3.01 (2H, m), 4.09–4.29 (2H, m), 4.46 (1H, dd, J=6.4, 1.6 Hz), 4.78 (1H, dd, J=10.4, 1.6 Hz), 6.21 (1H, dd, J=16.0, 6.8 Hz), 6.56 (1H, d, J=16.0 Hz), 7.02 (1H, ddd, J=10.8, 8.4, 1.2 Hz), 7.08 (1H, dt, J=8.0, 1.2 Hz), 7.15–7.26 (2H, m), 7.42 (1H, dt, J=8.0, 1.2 Hz).

Reference Example 76

1-(Vinyloxycarbonyl)-4-[2-[(2-cyclohexylmethyloxy)phenyl]-1-ethynyl]piperidine

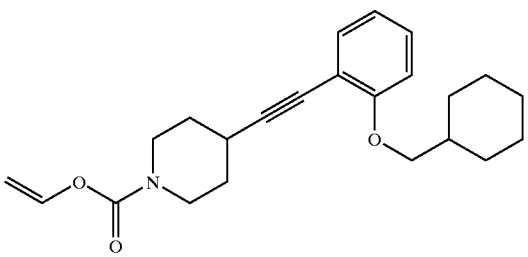

The title compound was obtained from a corresponding raw material in accordance with the method of Reference Example 74.

$^1$H-NMR (400 MHz, CDCl$_3$) δ 1.03–1.35 (5H, m), 1.65–1.93 (10H, m), 2.98 (1H, m), 3.56–3.64 (2H, m), 3.67–3.79 (2H, m), 3.79 (2H, d, J=6.4 Hz), 4.45 (1H, dd, J=6.4, 1.6 Hz), 4.78 (1H, dd, J=11.6, 1.6 Hz), 6.83 (1H, dd, J=8.0, 1.2 Hz), 6.86 (1H, dt, J=8.0, 1.2 Hz), 7.21–7.27 (2H, m), 7.34 (1H, dd, J=11.6, 1.6 Hz).

Reference Example 77

1-(Vinyloxycarbonyl)-4-[(E)-2-(2-chlorophenyl)-1-ethenyl]piperidine

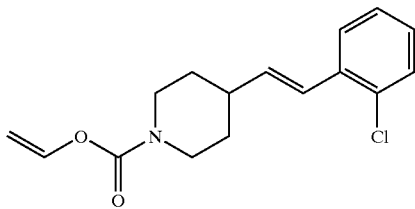

The title compound was obtained from a corresponding raw material in accordance with the method of Reference Example 74.

¹H-NMR (400 MHz, CDCl₃) δ 1.40–1.54 (2H, m), 1.85 (2H, br d, J=13.2 Hz), 2.41 (1H, m), 2.83–3.02 (2H, m), 4.19–4.29 (2H, m), 4.46 (1H, dd, J=6.0, 1.6 Hz), 4.79 (1H, dd, J=14.4, 1.6 Hz), 6.12 (1H, dd, J=16.0, 7.2 Hz), 6.56 (1H, dd, J=16.0, 0.8 Hz), 7.13–7.28 (3H, m), 7.34 (1H, dd, J=7.6, 1.2 Hz), 7.50 (1H, dd, J=7.6, 2.0 Hz).

Reference Example 78

1-(Vinyloxycarbonyl)-4-[(E)-2-(2-methylphenyl)-1-ethenyl]piperidine

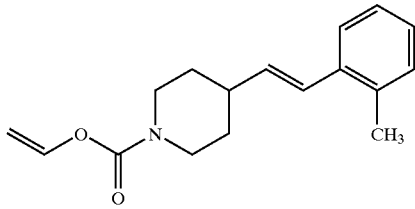

The title compound was obtained from a corresponding raw material in accordance with the method of Reference Example 74.

¹H-NMR (400 MHz, CDCl₃) δ 1.39–1.53 (2H, m), 1.84 (2H, br d, J=12.8 Hz), 2.33 (3H, s), 2.36 (1H, m), 2.83–3.02 (2H, m), 4.19–4.29 (2H, m), 4.45 (1H, dd, J=6.4, 1.6 Hz), 4.78 (1H, dd, J=14.0, 1.6 Hz), 6.01 (1H, dd, J=16.0, 7.2 Hz), 6.60 (1H, dd, J=16.0, 0.8 Hz), 7.10–7.19 (3H, m), 7.34 (1H, dd, J=14.0, 6.4 Hz), 7.40 (1H, d, J=8.0 Hz).

Reference Example 79

4-[2-[(Cyclohexylmethyloxy)phenyl]piperidine

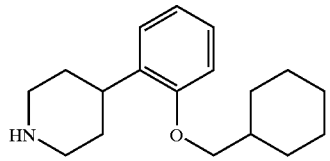

398 mg of 1-benzyl-4-[2-[(2-cyclohexylmethyloxy)phenyl]-3,4-dehydropiperidine was dissolved in 10 ml of ethanol, 150 mg of 20% palladium hydroxide-carbon powder (water-containing product) was added thereto, and the mixture was stirred at room temperature under normal pressure overnight under hydrogen atmosphere. Ethyl acetate was added to the reaction solution, and the mixture was filtered. The filtrate was evaporated, to give 315 mg of the title compound as a slight yellow oil.

¹H-NMR (400 MHz, CDCl₃) δ 1.05–1.38 (5H, m), 1.54–1.92 (10H, m), 2.74–2.82 (2H, m), 3.10 (1H, tt, J=12.0, 3.2 Hz), 3.16–3.23 (2H, m), 3.76 (2H, d, J=6.0 Hz), 6.83 (1H, dd, J=8.0, 1.2 Hz), 6.91 (1H, dt, J=8.0, 1.2 Hz), 7.15 (1H, dt, J=8.0, 1.2 Hz), 7.19 (1H, dd, J=8.0, 1.2 Hz).

Reference Example 80

4-[2-[2-(Cyclohexylmethyloxy)phenyl]ethyl]piperidine

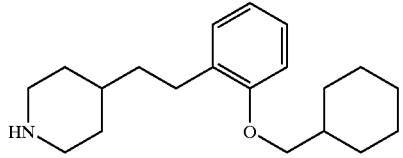

554 mg of 1-(benzyloxycarbonyl)-4-[(E)-2-[(2-cyclohexylmethyloxy)phenyl]-1-ethenyl]piperidine was dissolved in 10 ml of ethanol, 250 mg of 10% palladium-carbon powder (water-containing product) was added thereto, and the mixture was stirred at room temperature under normal pressure overnight under a hydrogen atmosphere. The reaction solution was filtered and the filtrate was evaporated, to give 379 mg of the title compound as a colorless oil.

¹H-NMR (400 MHz, CDCl₃) δ 1.05–1.76 (8H, m), 1.67–1.96 (10H, m), 2.56–2.67 (4H, m), 3.06–3.13 (2H, m), 3.75 (2H, d, J=5.6 Hz), 6.81 (1H, d, J=8.0 Hz), 6.85 (1H, dt, J=8.0, 1.2 Hz), 7.09–7.16 (2H, m).

Reference Example 81

4-[2-[2-(Isobutyloxy)phenyl]ethyl]piperidine

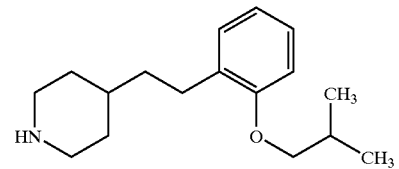

The title compound was obtained from a corresponding raw material in accordance with the method of Reference Example 80.

¹H-NMR (400 MHz, CDCl₃) δ 1.05 (6H, d, J=6.8 Hz), 1.12–1.24 (2H, m), 1.42 (1H, m), 1.48–1.56 (2H, m), 1.73–1.81 (2H, m), 2.10 (1H, m), 2.56–2.67 (4H, m), 3.06–3.14 (2H, m), 3.72 (2H, d, J=6.4 Hz), 6.80 (1H, d, J=8.0 Hz), 6.86 (1H, dt, J=1.2, 7.6 Hz), 7.09–7.17 (2H, m).

Reference Example 82

4-[[2-(2-Phenylethyl)phenyl]ethyl]piperidine

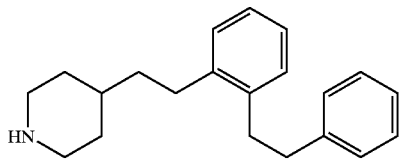

The title compound was obtained from a corresponding raw material in accordance with the method of Reference Example 80.

$^1$H-NMR (400 MHz, CDCl$_3$) δ 1.13–1.26 (2H, m), 1.39–1.55 (3H, m), 1.72–1.79 (2H, m), 2.56–2.66 (4H, m), 2.84–2.94 (4H, m), 3.06–3.14 (2H, m), 7.12–7.33 (9H, m).

Reference Example 83

[2-[2-[(cyclohexylmethyl)amino]phenyl]ethyl]piperidine

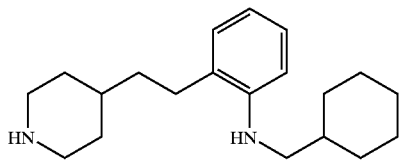

The title compound was obtained from a corresponding raw material in accordance with the method of Reference Example 80.

$^1$H-NMR (400 MHz, CDCl$_3$) δ 0.95–1.08 (2H, m), 1.12–1.34 (5H, m), 1.40–1.86 (7H, m), 1.87–2.04 (4H, m), 2.43–2.50 (2H, m), 2.62 (2H, dt, J=12.0, 2.4 Hz), 2.98 (2H, d, J=6.8 Hz), 3.08–3.14 (2H, m), 3.61 (1H, m), 4.22 (2H, m), 6.61 (1H, dd, J=1.2, 7.6 Hz), 6.65 (1H, dt, J=7.6, 1.2 Hz), 7.02 (1H, dd, J=7.6, 1.2 Hz), 7.11 (1H, dt, J=7.6, 1.2 Hz).

Reference Example 84

[2-[2-[N-(Cyclohexylmethyl)-N-methylamino]phenyl]ethyl]piperidine

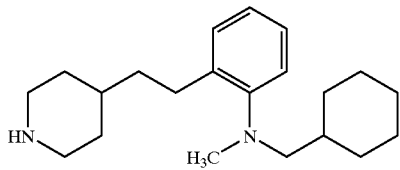

The title compound was obtained from a corresponding raw material in accordance with the method of Reference Example 80.

$^1$H-NMR (400 MHz, CDCl$_3$) δ 0.95–1.08 (2H, m), 1.12–1.34 (5H, m), 1.401.86 (8H, m), 1.87–2.04 (4H, m), 2.43–2.50 (2H, m), 2.62 (2H, dt, J=12.0, 2.4 Hz), 2.98 (2H, d, J=6.8 Hz), 3.08–3.14 (2H, m), 3.61 (1H, m), 6.61 (1H, dd, J=1.2, 7.6 Hz), 6.65 (1H, dt, J=7.6, 1.2 Hz), 7.02 (1H, dd, J=7.6, 1.2 Hz), 7.11 (1H, dt, J=7.6, 1.2 Hz).

Reference Example 85

4-[[2-(Cyclohexylethyl)phenoxy]methyl]piperidine

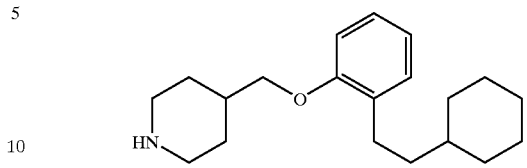

1.138 g of 1-(tert-butoxycarbonyl)-4-[[(2-cyclohexylethyl)phenoxy]methyl]piperidine was dissolved in 3 ml of dichloromethane, 3 ml of trifluoroacetic acid was added thereto, and the mixture was left at room temperature for one hour 30 minutes. An aqueous sodium carbonate was added to the reaction solution, and the mixture was extracted with ethyl acetate. The organic layer was washed with water and brine, and then dried over anhydrous magnesium sulfate. The solvent was evaporated, and to the residue was added n-hexane, to give 899 mg of the title compound as a white powder.

$^1$H-NMR (400 MHz, CDCl$_3$) δ 0.86–0.97 (2H, m), 1.091.22 (4H, m), 1.40–1.48 (2H, m), 1.61–1.80 (7H, m), 2.05–2.20 (3H, m), 2.56–2.63 (2H, m), 2.96 (2H, dt, J=12.8, 2.4 Hz), 3.50 (2H, br d, J=11.6 Hz), 3.84 (2H, d, J=6.4 Hz), 6.78 (1H, d, J=8.0 Hz), 6.89 (1H, dt, J=7.6, 0.8 Hz), 7.16 (1H, d, J=7.6 Hz), 7.15 (1H, dd, J=7.6, 0.8 Hz).

Reference Example 86

4-[(E)-2-[2-(Cyclohexylmethyloxy)phenyl]-1-ethenyl]piperidine

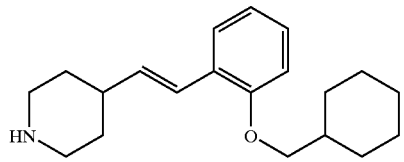

2.026 g of 1-(vinyloxycarbonyl)-4-[(E)-2-[(2-cyclohexylmethyloxy)phenyl]-1-ethenyl]piperidine was suspended in 20 ml of a 10% hydrogen chloride-methanol solution, and the mixture was stirred for 20 minutes under ice-cooling. After stirring for 15 minutes at room temperature, the mixture was heated under reflux for one hour 10 minutes. The solvent was evaporated, and to the residue was added an aqueous saturated sodium bicarbonate. The mixture was extracted with ethyl acetate. The organic layer was washed with water and brine, and then dried over anhydrous magnesium sulfate. The solvent was evaporated, and to the residue was added n-heptane. The insoluble matters were filtered off, and the filtrate was evaporated, to give 1.556 g of the title compound as a colorless oil.

$^1$H-NMR (400 MHz, CDCl$_3$) δ 1.03–1.46 (6H, m), 1.66–1.93 (9H, m), 2.28 (1H, m), 2.68 (2H, dt, J=2.4, 12.0 Hz), 3.12 (2H, dt, J=12.0, 3.2 Hz), 3.77 (2H, d, J=6.0 Hz), 6.18 (1H, dd, J=16.0 Hz), 6.70 (1H, d, J=16.0 Hz), 6.82 (1H, dd, J=7.6, 0.8 Hz), 6.88 (1H, dt, J=7.6, 0.8 Hz), 7.15 (1H, dt, J=7.6, 0.8 Hz), 7.41 (1H, dd, J=7.6, 0.8 Hz).

Reference Example 87

4-[(E)-2-(2-fluorophenyl)-1-ethenyl]piperidine

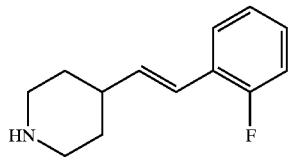

904 mg of 1-(vinyloxycarbonyl)-4-[(E)-2-(2-fluorophenyl)-1-ethenyl]piperidine was suspended in 5 ml of a 10% hydrogen chloride-methanol solution. After stirring for 15 minutes at room temperature, the mixture was heated at 70° C. for one hour. The solvent was evaporated, and water and ethyl acetate were added to the residue, to separate the aqueous layer. The aqueous layer was basified with a diluted ammonia, and extracted with ethyl acetate. The organic layer was washed with water and brine, and then dried over anhydrous magnesium sulfate. The solvent was evaporated, to give 660 mg of the title compound as a colorless oil.

$^1$H-NMR (400 MHz, CDCl$_3$) δ 1.34–1.47 (2H, m), 1.75–1.84 (2H, m), 2.29 (1H, m), 2.64–2.73 (2H, m), 3.13 (2H, br d, J=12.4 Hz), 6.24 (1H, dd, J=16.0, 6.4 Hz), 6.54 (1H, d, J=16.0 Hz), 6.97–7.11 (2H, m), 7.16 (1H, m), 7.44 (1H, m).

Reference Example 88

4-[(E)-2-(2-Chlorophenyl)-1-ethenyl]piperidine

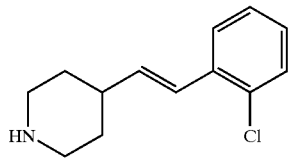

The title compound was obtained from a corresponding raw material in accordance with the method of Reference Example 87.

$^1$H-NMR (400 MHz, CDCl$_3$) δ 1.34–1.46 (2H, m), 1.75–1.86 (2H, m), 2.31 (1H, m), 2.68 (2H, dt, J=8.4, 2.8 Hz), 3.12 (2H, dt, J=11.6, 3.2 Hz), 6.15 (1H, dd, J=16.0, 6.8 Hz), 6.75 (1H, dd, J=16.0, 0.8 Hz), 7.13 (1H, dt, J=8.0, 2.0 Hz), 7.20 (1H, dd, J=8.0, 1.6 Hz), 7.33 (1H, dd, J=8.0, 1.6 Hz), 7.51 (1H, dd, J=8.0, 2.0 Hz).

Reference Example 89

4-[(E)-2-(2-Methylphenyl)-1-ethenyl]piperidine

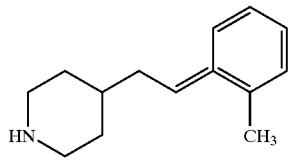

The title compound was obtained from a corresponding raw material in accordance with the method of Reference Example 87.

$^1$H-NMR (400 MHz, CDCl$_3$) δ 1.34–1.47 (2H, m), 1.75–1.84 (4H, m), 2.29 (1H, m), 2.64–2.73 (2H, m), 3.13 (2H, br d, J=12.4 Hz), 6.24 (1H, dd, J=16.0, 6.4 Hz), 6.54 (1H, d, J=16.0 Hz), 6.97–7.11 (2H, m), 7.16 (1H, m), 7.41–7.48 (2H, m).

Reference Example 90

4-[2-(2-Cyclohexylmethyloxy)phenyl]-1-ethynyl]piperidine

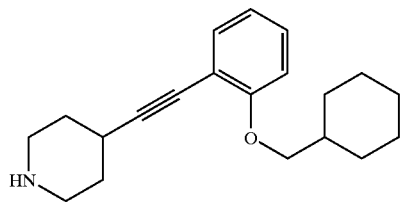

The title compound was obtained from a corresponding raw material in accordance with the method of Reference Example 87.

$^1$H-NMR (400 MHz, CDCl$_3$) δ 1.03–1.42 (5H, m), 1.64–1.96 (10H, m), 2.74 (2H, ddd, J=3.2, 8.4, 12.0 Hz), 2.81 (1H, m), 3.10–3.17 (2H, m), 3.80 (2H, d, J=6.4 Hz), 6.82 (1H, dd, J=8.4, 2.0 Hz), 6.85 (1H, dt, J=8.4, 1.2 Hz), 7.21 (1H, ddd, J=8.4, 7.6, 2.0 Hz), 7.35 (1H, dt, J=7.6, 1.2 Hz).

Example 1

1-[(2-Methoxy-3-pyridyl)methyl]-4-[2-(methylsulfonyl)phenethyl]piperidine 3.90 g of 1-[(2-methoxy-3-pyridyl)methyl]-4-piperidinecarboxaldehyde, 8.92 g of (2-methylsulfonylbenzyl)triphenylphosphonium chloride and 1.96 g of potassium tert-butoxide were suspended in 80 ml of N,N-dimethylformamide, and the mixture was stirred for 3 hours at room temperature. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane= 1:4). The resulting product and 440 mg of 10% palladium-carbon powder (water-containing product) were suspended in 80 ml of ethanol. After replacing the atmosphere of a container with hydrogen, the mixture was stirred at room temperature under normal pressure for 30 minutes. The reaction solution was filtered, and the filtrate was evaporated, to give 4.05 g of the title compound as a colorless oil.

$^1$H-NMR (400 MHz, CDCl$_3$) δ 1.30–1.44 (3H, m), 1.61–1.68 (2H, m), 1.74–1.81 (2H, m), 2.02–2.10 (2H, m), 2.88–2.96 (2H, m), 3.00–3.08 (2H, m), 3.08 (3H, s), 3.49 (2H, s), 3.95 (3H, s), 6.87 (1H, dd, J=7.1, 5.0 Hz), 7.33–7.42 (2H, m), 7.55 (1H, ddd, J=7.7, 7.7, 1.3 Hz), 7.65 (1H, dd, J=7.1, 1.8 Hz), 8.00–8.08 (2H, m).

Example 2

1-[(2-Methoxy-3-pyridyl)methyl]-4-(3,4-(methylenedioxyphenethyl)piperidine

The title compound was obtained from a corresponding raw material in accordance with the method of Example 1.

¹H-NMR (400 MHz, CDCl₃) δ 1.22–1.37 (3H, m), 1.47–1.58 (2H, m), 1.64–1.77 (2H, m), 1.96–2.07 (2H, m), 2.50–2.59 (2H, m), 2.84–2.94 (2H, m), 3.48 (2H, s), 3.94 (3H, s), 5.91 (2H, s), 6.61 (1H, dd, J=7.8, 1.6 Hz), 6.67 (1H, d, J=1.6 Hz), 6.72 (1H, d, J=7.8 Hz), 6.87 (1H, dd, J=7.2, 5.2 Hz), 7.64 (1H, dd, J=7.2, 1.8 Hz), 8.05 (1H, dd, J=5.2, 1.8 Hz).

Example 3

1-[(2-Methoxy-3-pyridyl)methyl]-4-phenethylpiperidine

The title compound was obtained from a corresponding raw material in accordance with the method of Example 1.

¹H-NMR (400 MHz, CDCl₃) δ 1.24–1.39 (3H, m), 1.52–1.61 (2H, m), 1.68–1.77 (2H, m), 1.96–2.07 (2H, m), 2.58–2.66 (2H, m), 2.85–2.93 (2H, m), 3.48 (2H, s), 3.94 (3H, s), 6.86 (1H, dd, J=7.1, 4.9 Hz), 7.14–7.21 (3H, m), 7.23–7.31 (2H, m), 7.65 (1H, dd, J=7.1, 1.8 Hz), 8.05 (1H, dd, J=4.9, 1.8 Hz).

Example 4

1-[(2-Methoxy-3-pyridyl)methyl]-4-(2-hydroxyphenethyl)piperidine

The title compound was obtained from a corresponding raw material in accordance with the method of Example 1.
¹H-NMR (400 MHz, CDCl₃) δ 1.28–1.42 (3H, m), 1.46–1.54 (2H, m), 1.69–1.77 (2H, m), 2.00–2.10 (2H, m), 2.57–2.63 (2H, m), 2.73–3.00 (2H, m), 3.55 (2H, s), 3.90 (3H, s), 6.58 (1H, dd, J=7.5, 1.1 Hz), 6.79 (1H, ddd, J=7.5, 7.5, 1.1 Hz), 6.86 (1H, dd, J=7.2, 5.1 Hz), 7.00 (1H, ddd, J=7.5, 7.5, 1.6 Hz), 7.07 (1H, dd, J=7.5, 1.6 Hz), 7.62 (1H, dd, J=7.2, 1.9 Hz), 8.07 (1H, dd, J=5.1, 1.9 Hz).

Example 5

1-[(2-Methoxy-3-pyridyl)methyl]-4-(3-fluorophenethyl)piperidine

The title compound was obtained from a corresponding raw material in accordance with the method of Example 1.

¹H-NMR (400 MHz, CDCl₃) δ 1.21–1.40 (3H, m), 1.51–1.61 (2H, m), 1.65–1.77 (2H, m), 1.95–2.08 (2H, m), 2.57–2.66 (2H, m), 2.85–2.94 (2H, m), 3.48 (2H, s), 3.95 (3H, s), 6.83–6.91 (2H, m), 6.87 (1H, dd, J=7.1, 4.9 Hz), 6.94 (1H, m), 7.18–7.26 (1H, m), 7.64 (1H, dd, J=7.1, 2.0 Hz), 8.05 (1H, dd, J=4.9, 2.0 Hz).

Example 6

1-[(2-Methoxy-3-pyridyl)methyl]-4-(2-trifluoromethylphenethyl)piperidine

The title compound was obtained from a corresponding raw material in accordance with the method of Example 1.

¹H-NMR (400 MHz, CDCl₃) δ 1.27–1.42 (3H, m), 1.51–1.61 (2H, m), 1.69–1.80 (2H, m), 1.99–2.11 (2H, m), 2.73–2.82 (2H, m), 2.87–2.95 (2H, m), 3.49 (2H, s), 3.95 (3H, s), 6.87 (1H, dd, J=7.1, 4.9 Hz), 7.26 (1H, dd, J=7.7, 7.6 Hz), 7.31 (1H, d, J=7.5 Hz), 7.45 (1H, dd, J=7.6, 7.5 Hz), 7.60 (1H, d, J=7.7 Hz), 7.65 (1H, dd, J=7.1, 1.9 Hz), 8.05 (1H, dd, J=4.9, 1.9 Hz).

Example 7

1-[(2-Methoxy-3-pyridyl)methyl]-4-[2-(1-pyrazolo)phenethyl]piperidine

The title compound was obtained from a corresponding raw material in accordance with the method of Example 1.

¹H-NMR (400 MHz, CDCl₃) δ 1.10–1.23 (3H, m), 1.32–1.39 (2H, m), 1.49–1.57 (2H, m), 1.90–1.99 (2H, m), 2.52–2.59 (2H, m), 2.78–2.85 (2H, m), 3.44 (2H, s), 3.93 (3H, s), 6.42 (1H, dd, J=2.0, 2.0 Hz), 6.85 (1H, dd, J=7.2, 4.8 Hz), 7.24–7.38 (4H, m), 7.56 (1H, d, J=2.0 Hz), 7.61 (1H, dd, J=7.2, 2.0 Hz), 7.70 (1H, d, J=2.0 Hz), 8.04 (1H, dd, J=4.8, 2.0 Hz).

Example 8

1-[(2-Methoxy-3-pyridyl)methyl]-4-[2-(4-acetylpiperazino)phenethyl]piperidine

The title compound was obtained from a corresponding raw material in accordance with the method of Example 1.

¹H-NMR (400 MHz, CDCl₃) δ 1.26–1.39 (3H, m), 1.52–1.61 (2H, m), 1.71–1.79 (2H, m), 1.97–2.07 (2H, m), 2.14 (3H, s), 2.65–2.72 (2H, m), 2.81–2.94 (6H, m), 3.48 (2H, s), 3.55–3.61 (2H, m), 3.70–3.78 (2H, m), 3.95 (3H, s), 6.87 (1H, dd, J=7.2, 4.8 Hz), 7.04 (1H, d, J=7.6 Hz), 7.07 (1H, dd, J=7.6, 7.2 Hz), 7.17 (1H, dd, J=7.6, 7.2 Hz), 7.21 (1H, d, J=7.6 Hz), 7.64 (1H, dd, J=7.2, 1.6 Hz), 8.05 (1H, dd, J=4.8, 1.6 Hz).

Example 9

1-[(2-Methoxy-3-pyridyl)methyl]-4-[6-(methylsulfonyl)-2,3-methylenedioxyphenethyl]piperidine The title compound was obtained from a corresponding raw material in accordance with the method of Example 1.
¹H-NMR (400 MHz, CDCl₃) δ 1.30–1.42 (3H, m), 1.56–1.66 (2H, m), 1.73–1.81 (2H, m), 2.02–2.10 (2H, m), 2.88–2.99 (4H, m), 3.04 (3H, s), 3.49 (2H, s), 3.95 (3H, s), 6.08 (2H, s), 6.78 (1H, d, J=8.3 Hz), 6.87 (1H, dd, J=7.2, 5.0 Hz), 7.62 (1H, d, J=8.3 Hz), 7.66 (1H, dd, J=7.2, 1.8 Hz), 8.05 (1H, dd, J=5.0, 1.8 Hz).

Example 10

1-[(2-Methoxy-3-pyridyl)methyl]-4-[2-(2-thienyl)ethyl]piperidine

The title compound was obtained from a corresponding raw material in accordance with the method of Example 1.

¹H-NMR (400 MHz, CDCl₃) δ 1.24–1.38 (3H, m), 1.59–1.75 (4H, m), 1.95–2.06 (2H, m), 2.80–2.93 (4H, m), 3.47 (2H, s), 3.94 (3H, s), 6.77 (1H, d, J=3.5 Hz), 6.85 (1H, dd, J=7.1, 4.9 Hz), 6.90 (1H, dd, J=5.1, 3.5 Hz), 7.09 (1H, d, J=5.1 Hz), 7.64 (1H, dd, J=7.1, 1.8 Hz), 8.04 (1H, dd, J=4.9, 1.8 Hz).

Example 11

1-[(2-Methoxy-3-pyridyl)methyl]-4-[2-(3-methoxy-2-thienyl)ethyl]piperidine

The title compound was obtained from a corresponding raw material in accordance with the method of Example 1.

¹H-NMR (400 MHz, CDCl₃) δ 1.24–1.37 (3H, m), 1.52–1.59 (2H, m), 1.67–1.77 (2H, m), 1.96–2.07 (2H, m), 2.67–2.74 (2H, m), 2.85–2.92 (2H, m), 3.47 (2H, s), 3.80 (3H, s), 3.94 (3H, s), 6.80 (1H, d, J=5.5 Hz), 6.86 (1H, dd, J=7.1, 4.9 Hz), 6.98 (1H, d, J=5.5 Hz), 7.64 (1H, dd, J=7.1, 1.8 Hz), 8.04 (1H, dd, J=4.9, 1.8 Hz).

Example 12

1-[(2-Methoxy-3-pyridyl)methyl]-4-[2-(3-cyano-2-thienyl)ethyl]piperidine

The title compound was obtained from a corresponding raw material in accordance with the method of Example 1.

¹H-NMR (400 MHz, CDCl₃) δ 1.30–1.40 (3H, m), 1.62–1.77 (4H, m), 1.98–2.09 (2H, m), 2.87–2.95 (2H, m), 2.99–3.06 (2H, m), 3.49 (2H, s), 3.95 (3H, s), 6.87 (1H, dd, J=7.1, 4.9 Hz), 7.11 (1H, d, J=5.3 Hz), 7.17 (1H, d, J=5.3 Hz), 7.64 (1H, dd, J=7.1, 1.8 Hz), 8.05 (1H, dd, J=4.9, 1.8 Hz).

Example 13

1-[(2-Methoxy-3-pyridyl)methyl]-4-[2-(3-phenyl-2-thienyl)ethyl]piperidine

The title compound was obtained from a corresponding raw material in accordance with the method of Example 1.

¹H-NMR (400 MHz, CDCl₃) δ 1.21–1.31 (3H, m), 1.55–1.69 (4H, m), 1.91–2.01 (2H, m), 2.80–2.92 (4H, m), 3.46 (2H, s), 3.94 (3H, s), 6.86 (1H, dd, J=7.1, 4.9 Hz), 7.00 (1H, d, J=5.2 Hz), 7.15 (1H, d, J=5.2 Hz), 7.27–7.43 (5H, m), 7.62 (1H, dd, J=7.1, 2.0 Hz), 8.04 (1H, dd, J=4.9, 2.0 Hz).

Example 14

1-[(2-Methoxy-3-pyridyl)methyl]-4-[2-(3-thienyl)ethyl]piperidine

The title compound was obtained from a corresponding raw material in accordance with the method of Example 1.

¹H-NMR (400 MHz, CDCl₃) δ 1.25–1.38 (3H, m), 1.54–1.64 (2H, m), 1.66–1.76 (2H, m), 1.96–2.07 (2H, m), 2.62–2.68 (2H, m), 2.85–2.94 (2H, m), 3.48 (2H, s), 3.94 (3H, s), 6.87 (1H, dd, J=7.2, 5.2 Hz), 6.90–6.95 (2H, m), 7.24 (1H, dd, J=5.2, 3.0 Hz), 7.64 (1H, dd, J=7.2, 2.0 Hz), 8.05 (1H, dd, J=5.2, 2.0 Hz).

Example 15

1-[(2-Methoxy-3-pyridyl)methyl]-4-[2-(2-methanesulfonyl-3-thienyl)ethyl]piperidine The title compound was obtained from a corresponding raw material in accordance with the method of Example 1.

¹H-NMR (400 MHz, CDCl₃) δ 1.27–1.41 (3H, m), 1.56–1.66 (2H, m), 1.68–1.80 (2H, m), 1.97–2.10 (2H, m), 2.85–2.99 (4H, m), 3.14 (3H, s), 3.48 (2H, s), 3.95 (3H, s), 6.86 (1H, dd, J=7.1, 4.9 Hz), 7.01 (1H, d, J=5.0 Hz), 7.56 (1H, d, J=5.0 Hz), 7.64 (1H, dd, J=7.1, 1.8 Hz), 8.05 (1H, dd, J=4.9, 1.8 Hz).

Example 16

1-[(2-Methoxy-3-pyridyl)methyl]-4-[2-(benzo[b]thiophen-2-yl)ethyl]piperidine The title compound was obtained from a corresponding raw material in accordance with the method of Example 1.

¹H-NMR (400 MHz, CDCl₃) δ 1.27–1.41 (3H, m), 1.65–1.78 (4H, m), 1.96–2.07 (2H, m), 2.85–2.97 (4H, m), 3.48 (2H, s), 3.94 (3H, s), 6.86 (1H, dd, J=7.3, 5.1 Hz), 6.99 (1H, s), 7.24 (1H, dd, J=7.5, 7.1 Hz), 7.30 (1H, dd, J=7.9, 7.1 Hz), 7.64 (1H, dd, J=7.3, 2.0 Hz), 7.66 (1H, d, J=7.5 Hz), 7.75 (1H, d, J=7.9 Hz), 8.05 (1H, dd, J=5.1, 2.0 Hz).

Example 17

1-[(2-Methoxy-3-pyridyl)methyl]-4-[2-(2-methylsulfonyl-3-pyridyl)ethyl]piperidine The title compound was obtained from a corresponding raw material in accordance with the method of Example 1.

¹H-NMR (400 MHz, CDCl₃) δ 1.30–1.40 (3H, m), 1.60–1.68 (2H, m), 2.02–2.10 (2H, m), 2.88–2.95 (2H, m), 3.08–3.14 (2H, m), 3.37 (3H, m), 3.50 (2H, s), 3.95 (3H, s), 6.87 (1H, dd, J=7.2, 4.8 Hz), 7.43 (1H, dd, J=7.8, 4.8 Hz), 7.66 (1H, dd, J=7.2, 1.8 Hz), 7.71 (1H, dd, J=7.8, 1.8 Hz), 8.05 (1H, dd, J=4.8, 1.8 Hz), 8.41 (1H, dd, J=4.8, 1.8 Hz).

Example 18

1-[(2-Methoxy-3-pyridyl)methyl]-4-[2-(2-n-butyl-3-pyridyl)ethyl]piperidine

The title compound was obtained from a corresponding raw material in accordance with the method of Example 1.

¹H-NMR (400 MHz, CDCl₃) δ 0.96 (3H, t, J=7.3 Hz), 1.30–1.48 (5H, m), 1.48–1.56 (2H, m), 1.63–1.80 (4H, m), 2.00–2.11 (2H, m), 2.57–2.66 (2H, m), 2.77 (2H, t, J=8.1 Hz), 2.88–2.97 (2H, m), 3.50 (2H, s), 3.95 (3H, s), 6.87 (1H, dd, J=7.2, 5.0 Hz), 7.03 (1H, dd, J=7.6, 4.8 Hz), 7.39 (1H, dd, J=7.2, 1.8 Hz), 7.65 (1H, dd, J=7.6, 1.8 Hz), 8.06 (1H, dd, J=5.0, 1.8 Hz), 8.37 (1H, dd, J=4.8, 1.8 Hz).

Example 19

1-[(2-Methoxy-3-pyridyl)methyl]-4-[2-(3-pyridyl)ethyl]piperidine

The title compound was obtained from a corresponding raw material in accordance with the method of Example 1.

¹H-NMR (400 MHz, CDCl₃) δ 1.24–1.40 (3H, m), 1.54–1.62 (2H, m), 1.67–1.76 (2H, m), 1.98–2.08 (2H, m), 2.6–2.66 (2H, m), 2.87–2.96 (2H, m), 3.49 (2H, s), 3.95 (3H, s), 6.87 (1H, dd, J=8.0, 5.0 Hz), 7.20 (1H, dd, J=8.0, 5.0 Hz), 7.49 (1H, ddd, J=8.0, 2.0, 2.0 Hz), 7.65 (1H, d, J=8.0 Hz), 8.06 (1H, dd, J=5.0, 2.0 Hz), 8.42–8.46 (2H, m).

Example 20

1-[(2-Methoxy-3-pyridyl)methyl]-4-[2-(2-phenoxy-3-pyridyl)ethyl]piperidine

The title compound was obtained from a corresponding raw material in accordance with the method of Example 1.

¹H-NMR (400 MHz, CDCl₃) δ 1.28–1.40 (3H, m), 1.55–1.68 (2H, m), 1.70–1.80 (2H, m), 1.98–2.08 (2H, m), 2.70–2.77 (2H, m), 2.86–2.94 (2H, m), 3.48 (2H, s), 3.94 (3H, s), 6.86 (1H, dd, J=7.1, 5.0 Hz), 6.93 (1H, dd, J=7.1, 5.0 Hz), 7.07–7.11 (2H, m), 7.17 (1H, m), 7.36–7.42 (2H, m), 7.52 (1H, dd, J=7.1, 2.0 Hz), 7.64 (1H, dd, J=7.1, 2.0 Hz), 8.00 (1H, dd, J=5.0, 2.0 Hz), 8.05 (1H, dd, J=5.0, 2.0 Hz).

Example 21

1-[(2-Methoxy-3-pyridyl)methyl]-4-[2-(5-methoxy-2-pyridyl)ethyl]piperidine 310 mg of the title compound was obtained as a colorless oil from 300 mg of 1-[(2-methoxy-3-pyridyl)methyl]-4-piperidinecarboxaldehyde obtained in Reference Example 2 and 592 mg of [(5-methoxy-2-pyridyl)methyl]triphenylphosphonium chloride in the same manner as in Example 1.

¹H-NMR (400 MHz, CDCl₃) δ 1.24–1.41 (3H, m), 1.59–1.68 (2H, m), 1.71–1.83 (2H, m), 1.97–2.08 (2H, m), 2.79–2.94 (4H, m), 3.49 (2H, s), 3.82 (3H, m), 3.95 (3H, s), 6.87 (1H, dd, J=7.1, 4.9 Hz), 7.09 (1H, d, J=2.9 Hz), 7.09 (1H, d, J=2.9 Hz), 7.65 (1H, dd, J=7.1, 1.8 Hz), 8.05 (1H, dd, J=4.9, 1.8 Hz), 8.11 (1H, dd, J=2.9, 2.9 Hz).

Example 22

1-[(2-Methoxy-3-pyridyl)methyl]-4-[2-(4-methoxyphenyl)-3-pyridyl)ethyl]piperidine The title compound was obtained from a corresponding raw material in accordance with the method of Example 1.

$^1$H-NMR (400 MHz, CDCl$_3$) δ 1.11–1.23 (3H, m), 1.41–1.49 (2H, m), 1.51–1.59 (2H, m), 1.90–1.99 (2H, m), 2.62–2.69 (2H, m), 2.78–2.88 (2H, m), 3.44 (2H, s), 3.85 (3H, s), 3.93 (3H, s), 6.85 (1H, dd, J=7.2, 4.8 Hz), 6.96 (2H, d, J=8.4 Hz), 7.17 (1H, dd, J=8.0, 4.8 Hz), 7.40 (2H, d, J=8.4 Hz), 7.57 (1H, dd, J=8.0, 1.6 Hz), 7.61 (1H, dd, J=7.2, 2.0 Hz), 8.04 (1H, dd, J=4.8, 2.0 Hz), 8.49 (1H, dd, J=4.8, 1.6 Hz).

Example 23

1-[(2-Methoxy-3-pyridyl)methyl]-4-[2-(1,3-thiazol-2-yl)ethyl]piperidine

The title compound was obtained from a corresponding raw material in accordance with the method of Example 1.

$^1$H-NMR (400 MHz, CDCl$_3$) δ 1.29–1.40 (3H, m), 1.69–1.81 (4H, m), 1.97–2.07 (2H, m), 2.85–2.93 (2H, m), 3.01–3.08 (2H, m), 3.48 (2H, s), 3.94 (3H, s), 6.86 (1H, dd, J=7.3, 5.1 Hz), 7.18 (1H, d, J=3.5 Hz), 7.64 (1H, dd, J=7.3, 2.0 Hz), 7.66 (1H, d, J=3.5 Hz), 8.05 (1H, dd, J=5.1, 2.0 Hz).

Example 24

1-[(2-Methoxy-3-pyridyl)methyl]-4-[2-(2-(1-morpholino)-3-pyridyl)ethyl]piperidine The title compound was obtained from a corresponding raw material in accordance with the method of Example 1.

$^1$H-NMR (400 MHz, CDCl$_3$) δ 1.27–1.39 (3H, m), 1.56–1.64 (2H, m), 1.70–1.78 (2H, m), 1.99–2.07 (2H, m), 2.60–2.66 (2H, m), 2.86–2.94 (2H, m), 3.10 (4H, t, J=4.7 Hz), 3.49 (2H, s), 3.85 (4H, J=A4.7 Hz), 3.95 (3H, s), 6.87 (1H, dd, J=7.4, 4.8 Hz), 6.93 (1H, dd, J=7.4, 4.8 Hz), 7.46 (1H, dd, J=7.4, 1.9 Hz), 7.64 (1H, dd, J=7.4, 1.9 Hz), 8.06 (1H, dd, J=4.8, 1.9 Hz), 8.18 (1H, dd, J=4.8, 1.9 Hz).

Example 25

1-[(2-Methoxy-3-pyridyl)methyl]-4-(2-aminophenethyl)piperidine 255 mg of the title compound was obtained as colorless crystals from 310 mg of 1-(2-methoxy-3-pyridyl)methyl]-4-piperidinecarboxaldehyde obtained in Reference Example 2 and 767 mg of (2-nitrobenzyl)triphenylphosphonium bromide in the same manner as in Example 1.

$^1$H-NMR (400 MHz, CDCl$_3$) δ 1.30–1.40 (3H, m), 1.52–1.66 (2H, m), 1.72–1.82 (2H, m), 2.00–2.10 (2H, m), 2.46–2.54 (2H, m), 2.87–2.96 (2H, m), 3.49 (2H, s), 3.59 (2H, br s), 3.95 (3H, s), 6.68 (1H, dd, J=8.3, 1.1 Hz), 6.73 (1H, dd, J=7.4, 1.1 Hz), 6.87 (1H, dd, J=7.1, 4.9 Hz), 7.01–7.06 (2H, m), 7.65 (1H, dd, J=7.1, 1.8 Hz), 8.05 (1H, dd, J=4.9, 1.8 Hz).

Example 26

1-[(2-Methoxy-3-pyridyl)methyl]-4-[(2-methylsulfonylamino)phenethyl]piperidine 255 mg of 1-[(2-methoxy-3-pyridyl)methyl]-4-(2-aminophenethyl)piperidine, 110 mg of methylsulfonyl chloride and 0.13 ml of pyridine were dissolved in 5 ml of tetrahydrofuran, and the mixture were stirred at room temperature for 3 hours. The reaction mixture was basified by adding a 1N aqueous sodium hydroxide thereto, and then extracted with ethyl acetate. The organic layer was washed with brine, and then dried over anhydrous magnesium sulfate. The solvent was evaporated, and the crude product was purified by NH form silica gel chromatography (ethyl acetate:hexane=1:1), to give 286 mg of the title compound as a colorless oil.

$^1$H-NMR (400 MHz, CDCl$_3$) δ 1.30–1.41 (3H, m), 1.50–1.60 (2H, m), 1.68–1.78 (2H, m), 2.00–2.09 (2H, m), 2.61–2.68 (2H, m), 2.88–2.95 (2H, m), 3.03 (3H, s), 3.49 (2H, s), 3.95 (3H, s), 6.87 (1H, dd, J=7.3, 5.0 Hz), 7.15–7.26 (3H, m), 7.45 (1H, m), 7.65 (1H, dd, J=7.3, 1.9 Hz), 8.05 (1H, dd, J=5.0, 1.9 Hz).

Example 27

1-[(2-Methoxy-3-pyridyl)methyl]-4-[2-(2-chloro-6-methyl-3-pyridyl)ethyl)piperidine 445 mg of the title compound was obtained as a colorless oil from 500 mg of 1-[(2-methoxy-3-pyridyl)methyl]-4-piperidinecarboxaldehyde obtained in Reference Example 2 and 1.01 g of [(2-chloro-6-methyl-3-pyridyl)methyl]triphenylphosphonium chloride in accordance with the method of Example 1.

$^1$H-NMR (400 MHz, CDCl$_3$) δ 1.28–1.39 (3H, m), 1.50–1.59 (2H, m), 1.70–1.78 (2H, m), 1.98–2.07 (2H, m), 2.49 (3H, s), 2.63–2.71 (2H, m), 2.86–2.95 (2H, m), 3.49 (2H, s), 3.95 (3H, s), 6.87 (1H, dd, J=7.1, 4.9 Hz), 7.01 (1H, d, J=7.9 Hz), 7.41 (1H, d, J=7.9 Hz), 7.65 (1H, dd, J=7.1, 2.0 Hz), 8.05 (1H, dd, J=4.9, 2.0 Hz).

Example 28

1-[(2-Methoxy-3-pyridyl)methyl]-4-[2-(6-chloro-3-pyridyl)ethyl]piperidine 600 mg of the title compound was obtained as a colorless oil from 504 mg of 1-[(2-methoxy-3-pyridyl)methyl]-4-piperidinecarboxaldehyde obtained in Reference Example 2 and 1.01 g of [(6-chloro-3-pyridyl)methyl]triphenylphosphonium chloride in accordance with the method of Example 1.

$^1$H-NMR (400 MHz, CDCl$_3$) δ 1.23–1.38 (3H, m), 1.50–1.59 (2H, m), 1.66–1.74 (2H, m), 1.96–2.06 (2H, m), 2.57–2.65 (2H, m), 2.85–2.94 (2H, m), 3.48 (2H, s), 3.94 (3H, s), 6.86 (1H, dd, J=7.1, 5.0 Hz), 7.24 (1H, d, J=8.3 Hz), 7.46 (1H, dd, J=8.3, 2.4 Hz), 7.63 (1H, dd, J=7.1, 1.9 Hz), 8.05 (1H, dd, J=5.0, 1.9 Hz), 8.20 (1H, d, J=2.4 Hz).

Example 29

1-[(2-Methoxy-3-pyridyl)methyl]-4-[(E)-2-(2-pyridyl)-1-ethenyl]piperidine 488 mg of 1-[(2-methoxy-3-pyridyl)methyl]-4-piperidinecarboxaldehyde obtained in Reference Example 2, 1.07 g of (2-pyridylmethyl)triphenylphosphonium chloride and 561 mg of potassium tert-butoxide were suspended in 10 ml of N,N-dimethylformamide, and the mixture was stirred for 1 hour at room temperature. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:9), to give 453 mg of the title compound as a colorless oil.

$^1$H-NMR (400 MHz, CDCl$_3$) δ 1.55–1.70 (3H, m), 1.75–1.85 (2H, m), 2.08–2.20 (2H, m), 2.91–3.00 (2H, m), 3.53 (2H, s), 3.96 (3H, s), 6.48 (1H, dd, J=15.8, 1.3 Hz), 6.71 (1H, dd, J=15.8, 6.9 Hz), 6.88 (1H, dd, J=7.2, 5.0 Hz), 7.10 (1H, ddd, J=7.6, 4.8, 1.1 Hz), 7.25 (1H, m), 7.60 (1H, ddd, J=7.6, 7.6, 1.8 Hz), 7.67 (1H, dd, J=7.2, 1.9 Hz), 8.06 (1H, dd, J=5.0, 1.9 Hz), 8.53 (1H, m).

Example 30

1-[(2-Methoxy-3-pyridyl)methyl]-4-[2-(2-pyridyl)ethyl]piperidine 332 mg of 1-[(2-methoxy-3-pyridyl)methyl]-4-[(E)-2-(2-pyridyl)-1-ethenyl]piperidine obtained in Example 29 and 79 mg of 10% palladium-carbon powder (water-containing product) were suspended in 5 ml of ethanol. After replacing the atmosphere of a container with hydrogen, the mixture was stirred at normal temperature under normal pressure for 30 minutes. The reaction solution was filtered, and the filtrate was evaproated, to give 234 mg of the title compound as a colorless oil.

$^1$H-NMR (400 MHz, CDCl$_3$) δ 1.28–1.41 (3H, m), 1.62–1.78 (4H, m), 1.98–2.09 (2H, m), 2.76–2.84 (2H, m), 2.86–2.95 (2H, m), 3.49 (2H, s), 3.94 (3H, s), 6.87 (1H, dd, J=7.5, 5.0 Hz), 7.10 (1H, ddd, J=7.5, 5.0, 1.2 Hz), 7.14 (1H, d, J=7.5 Hz), 7.58 (1H, ddd, J=7.5, 7.5, 2.0 Hz), 7.65 (1H, dd, J=7.5, 2.0 Hz), 8.05 (1H, dd, J=5.0, 2.0 Hz), 8.52 (1H, m).

Example 31

1-[(2-Methoxy-3-pyridyl)methyl]-4-[(E)-(2,3-methylenedioxyphenyl)-1-ethenyl]piperidine 324 mg of the title compound was obtained as a colorless oil from 784 mg of 1-[(2-methoxy-3-pyridyl)methyl]-4-piperidinecarboxaldehyde obtained in Reference Example 2 and 1.76 g of (3,4-methylenedioxybenzyl)triphenylphosphonium chloride in the same manner as in Example 29.

$^1$H-NMR (400 MHz, CDCl$_3$) δ 1.48–1.62 (3H, m), 1.70–1.79 (2H, m), 2.06–2.18 (2H, m), 2.90–2.99 (2H, m), 3.52 (2H, s), 3.96 (3H, s), 5.94 (2H, s), 6.00 (1H, dd, J=15.8, 7.2 Hz), 6.29 (1H, d, J=15.8 Hz), 6.70–6.79 (2H, m), 6.83–6.92 (2H, m), 7.67 (1H, dd, J=7.0, 1.8 Hz), 8.06 (1H, dd, J=5.2, 1.8 Hz).

Example 32

1-[(2-Methoxy-3-pyridyl)methyl]-4-[2-(2-choro-3-pyridyl)ethyl]piperidine 2.35 g of 1-[(2-methoxy-3-pyridyl)methyl]-4-piperidinecarboxaldehyde obtained in Reference Example 2, 4.68 g of [(2-chloro-3-pyridyl)methyl]triphenylphosphonium chloride and 1.24 g of potassium tert-butoxide were suspended in 50 ml of N,N-dimethylformamide, and the mixture was stirred for 1 hour at room temperature. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:19). The resulting product and 330 mg of platinum oxide were suspended in a mixed solvent of 20 ml of ethanol and 40 ml of tetrahydrofuran. After replacing the atmosphere of a container with hydrogen, the mixture was stirred at room temperature under normal pressure for 20 hours. The reaction solution was filtered, and the filtrate was evaporated. Then, the crude product was purified by NH form silica gel column chromatography (ethyl acetate:hexane=1:19), to give 1.89 g of the title compound as a colorless oil.

$^1$H-NMR (400 MHz, CDCl$_3$) δ 1.28–1.44 (3H, m), 1.54–1.62 (2H, m), 1.70–1.81 (2H, m), 2.00–2.12 (2H, m), 2.70–2.77 (2H, m), 2.88–2.98 (2H, m), 3.51 (2H, s), 3.95 (3H, s), 6.88 (1H, dd, J=7.4, 5.2 Hz), 7.17 (1H, dd, J=7.4, 5.0 Hz), 7.53 (1H, dd, J=7.4, 2.0 Hz), 7.66 (1H, dd, J=5.2, 2.0 Hz), 8.06 (1H, dd, J=5.2, 2.0 Hz), 8.24 (1H, dd, J=5.0, 2.0 Hz).

Example 33

1-[(2-Methoxy-3-pyridyl)methyl]-4-[2-[4-(methylsulfonyl)-3-(1,3-thiazol-2-yl)-2-thienyl]ethyl]piperidine 250 mg of 1-[(2-methoxy-3-pyridyl)methyl]-4-piperidinecarboxaldehyde obtained in Reference Example 2, 680 mg of [[4-(methylsulfonyl)-3-bromo-2-thienyl]methyl]triphenylphosphonium bromide and 258 mg of potassium tert-butoxide were suspended in 5 ml of N,N-dimethylformamide, and the mixture was stirred for 1 hour at room temperature. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:4). The resulting product, 408 mg of 2-(tributylstannyl)thiazole and 39 mg of tetrakis(triphenylphosphine)palladium were suspended in 5 ml of toluene, and the mixture was heated under reflux for 8 hours under nitrogen flow. The solvent was evaporated, and then the residue was purified by silica gel column chromatography (ethyl acetate). The resulting product and 300 mg of 10% palladium-carbon powder (water-containing product) were suspended in 10 ml of ethanol. After replacing the atmosphere of a container with hydrogen, the mixture was stirred at room temperature under normal pressure for 3 hours. The reaction solution was filtered, and the filtrate was evaporated, to give 230 mg of the title compound as a colorless oil.

$^1$H-NMR (400 MHz, CDCl$_3$) δ 1.18–1.32 (3H, m), 1.54–1.65 (4H, m), 1.92–2.02 (2H, m), 2.76–2.90 (4H, m), 3.24 (3H, s), 3.44 (2H, s), 3.95 (3H, s), 6.87 (1H, dd, J=7.4, 5.0 Hz), 7.55 (1H, d, J=3.4 Hz), 7.65 (1H, dd, J=7.4, 2.0 Hz), 7.94 (1H, d, J=3.4 Hz), 8.05 (1H, dd, J=5.0, 2.0 Hz), 8.10 (1H, s).

Example 34

1-[(2-Methoxy-3-pyridyl)methyl]-4-[2-[3-(1,3-thiazol-2-yl)-2-thienyl]ethyl]piperidine 230 mg of the title compound was obtained as a colorless oil from 400 mg of 1-[(2-methoxy-3-pyridyl)methyl]-4-piperidinecarboxaldehyde obtained in Reference Example 2 and 974 mg of [(3-bromo-2-thienyl)methyl]triphenylphosphonium bromide in accordance with the method of Example 33.

$^1$H-NMR (400 MHz, CDCl$_3$) δ 1.29–1.43 (3H, m), 1.65–1.78 (4H, m), 1.98–2.09 (2H, m), 2.87–2.95 (2H, m), 3.21–3.27 (2H, m), 3.50 (2H, s), 3.95 (3H, s), 6.87 (1H, dd, J=7.5, 4.9 Hz), 7.13 (1H, d, J=5.2 Hz), 7.29 (1H, d, J=3.4 Hz), 7.40 (1H, d, J=5.2 Hz), 7.66 (1H, dd, J=7.5, 2.0 Hz), 7.83 (1H, d, J=3.4 Hz), 8.05 (1H, dd, J=4.9, 2.0 Hz).

Example 35

1-[(2-Methoxy-3-pyridyl)methyl]-4-[2-(1,3-thiazol-2-yl)phenethyl]piperidine 233 mg of the title compound was obtained as a colorless oil from 293 mg of 1-[(2-methoxy-3-pyridyl)methyl]-4- piperidinecarboxaldehyde obtained in Reference Example 2 and (2-bromobenzyl)triphenylphosphonium bromide in accordance with the method of Example 33.

$^1$H-NMR (400 MHz, CDCl$_3$) δ 1.15–1.28 (3H, m), 1.42–1.50 (2H, m), 1.56–1.66 (2H, m), 1.93–2.02 (2H, m), 2.80–2.89 (2H, m), 2.91–2.98 (2H, m), 3.45 (2H, s), 3.94 (3H, s), 6.85 (1H, dd, J=6.8, 4.8 Hz), 7.26 (1H, dd, J=7.6, 7.6 Hz), 7.30 (1H, d, J=7.6 Hz), 7.35 (1H, dd, J=7.6, 7.6 Hz), 7.39 (1H, d, J=3.2 Hz), 7.57 (1H, d, J=7.6 Hz), 7.62 (1H, dd, J=6.8, 2.0 Hz), 7.88 (1H, d, J=3.2 Hz), 8.04 (1H, dd, J=4.8, 2.0 Hz).

Example 36

1-[(2-Methoxy-3-pyridyl)methyl]-4-(2,3-methylenedioxyphenethyl)piperidine 591 mg of 4-(2,3-methylenedioxphenethyl)piperidine, 404 mg of 3-(chloromethyl)-2-methoxypyridine and 415 mg of potassium carbonate were suspended in 5 ml of N,N-dimethylformamide, and the mixture was stirred for 12 hours at room temperature. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane= 1:9), to give 809 mg of the title compound as a pale yellow oil.

$^1$H-NMR (400 MHz, CDCl$_3$) δ 1.24–1.38 (3H, m), 1.53–1.61 (2H, m), 1.68–1.78 (2H, m), 1.97–2.06 (2H, m), 2.56–2.62 (2H, m), 2.85–2.92 (2H, m), 3.48 (2H, s), 3.94 (3H, s), 5.92 (2H, s), 6.63–6.70 (2H, m), 6.75 (1H, dd, J=7.7, 7.7 Hz), 6.86 (1H, dd, J=7.1.5.0 Hz), 7.64 (1H, dd, J=7.1, 1.9 Hz), 8.05 (1H, dd, J=5.0, 1.9 Hz).

Example 37

1-[(2-Methoxy-3-pyridyl)methyl]-4-(2-cyanophenethyl)piperidine $^1$H-NMR (400 MHz, CDCl$_3$) δ 1.30–1.42 (3H, m), 1.57–1.65 (2H, m), 1.72–1.80 (2H, m), 1.98–2.09 (2H, m), 2.81–2.95 (4H, m), 3.48 (2H, s), 3.95 (3H, s), 6.87 (1H, dd, J=7.3, 5.1 Hz), 7.27 (1H, ddd, J=7.7, 7.7, 0.9 Hz), 7.31 (1H, dd, J=7.7, 1.5 Hz), 7.50 (1H, ddd, J=7.7, 7.7, 1.5 Hz), 7.60 (1H, dd, J=7.7, 0.9 Hz), 7.65 (1H, dd, J=7.3, 2.0 Hz), 8.05 (1H, dd, J=5.1, 2.0 Hz).

Example 38

1-[(2-Methoxy-3-pyridyl)methyl]-4-(3-cyanophenethyl)piperidine $^1$H-NMR (400 MHz, CDCl$_3$) δ 1.23–1.39 (3H, m), 1.52–1.61 (2H, m), 1.66–1.78 (2H, m), 1.97–2.07 (2H, m), 2.61–2.70 (2H, m), 2.86–2.94 (2H, m), 3.48 (2H, s), 3.95 (3H, s), 6.87 (1H, dd, J=7.3, 5.1 Hz), 7.33–7.50 (4H, m), 7.64 (1H, dd, J=7.3, 1.8 Hz), 8.05 (1H, dd, J=5.1, 1.8 Hz).

Example 39

1-[(2-Methoxy-3-pyridyl)methyl]-4-(4-phenylphenethyl)piperidine $^1$H-NMR (400 MHz, CDCl$_3$) δ 1.28–1.40 (3H, m), 1.57–1.64 (2H, m), 1.70–1.80 (2H, m), 2.00–2.08 (2H, m), 2.64–2.70 (2H, m), 2.86–2.94 (2H, m), 3.49 (2H, s), 3.95 (3H, s), 6.87 (1H, dd, J=7.2, 5.0 Hz), 7.22–7.27 (2H, m), 7.32 (1H, m), 7.40–7.45 (2H, m), 7.49–7.53 (2H, m), 7.56–7.60 (2H, m), 7.65 (1H, dd, J=7.2, 1.8 Hz), 8.05 (1H, dd, J=5.0, 1.8 Hz).

Example 40

1-[(2-Methoxy-3-pyridyl)methyl]-4-(2-phenylphenethyl)piperidine 181 mg of 4-(2-phenylphenethyl)piperidine synthesized from the corresponding raw material in the same manner as in the above-mentioned process, 150 mg of 2-methoxy-3-pyridinecarboxaldehyde and 226 mg of sodium triacetoxy borohydride were suspended in 5 ml of tetrahydrofuran, and the mixture was stirred for 20 hours at room temperature. The reaction mixture was basified by adding a 1N aqueous sodium hydroxide thereto, and then extracted with ethyl acetate. The organic layer was washed with brine, and then dried over anhydrous magnesium sulfate. The solvent was evaporated, and the crude product was purified by NH form silica gel column chromatography (ethyl acetate:hexane= 1:19), to give 213 mg of the title compound as a colorless oil.

$^1$H-NMR (400 MHz, CDCl$_3$) δ 1.07–1.20 (3H, m), 1.37–1.45 (2H, m), 1.45–1.53 (2H, m), 1.87–1.97 (2H, m), 2.55–2.62 (2H, m), 2.75–2.83 (2H, m), 3.43 (2H, s), 3.93 (3H, s), 6.85 (1H, dd, J=7.6, 5.0 Hz), 7.18–7.42 (9H, m), 7.60 (1H, dd, J=7.6, 2.0 Hz), 8.04 (1H, dd, J=5.0, 2.0 Hz).

Example 41

1-[(2-Methoxy-3-pyridyl)methyl]-4-(2-methylthiophenethyl)piperidine $^1$H-NMR (400 MHz, CDCl$_3$) δ 1.30–1.42 (3H, m), 1.52–1.62 (2H, m), 1.71–1.82 (2H, m), 2.02–2.13 (2H, m), 2.46 (3H, s), 2.68–2.74 (2H, m), 2.87–2.97 (2H, m), 3.51 (2H, s), 3.95 (3H, s), 6.87 (1H, dd, J=7.2, 5.2 Hz), 7.04–7.14 (2H, m), 7.16–7.21 (2H, m), 7.66 (1H, dd, J=7.2, 2.0 Hz), 8.05 (1H, dd, J=5.2, 2.0 Hz).

Example 42

1-[(2-Methoxy-3-pyridyl)methyl]-4-(2-methoxyphenethyl)piperidine $^1$H-NMR (400 MHz, CDCl$_3$) δ 1.23–1.38 (3H, m), 1.48–1.57 (2H, m), 1.70–1.79 (2H, m), 1.97–2.07 (2H, m), 2.57–2.65 (2H, m), 2.85–2.93 (2H, m), 3.48 (2H, s), 3.81 (3H, s), 3.94 (3H, s), 6.84 (1H, dd, J=8.0, 1.2 Hz), 6.86 (1H, dd, J=7.2, 5.0 Hz), 6.88 (1H, ddd, J=7.6, 7.6, 1.2 Hz), 7.12 (1H, dd, J=7.6, 1.6 Hz), 7.17 (1H, ddd, J=8.0, 7.6, 1.6 Hz), 7.65 (1H, dd, J=7.2, 2.0 Hz), 8.05 (1H, dd, J=5.0, 2.0 Hz).

Example 43

1-[(2-Methoxy-3-pyridyl)methyl]-4-[2-(3-methylsulfonyl-2-thienyl)ethyl]piperidine 4.41 g of 4-[2-(3-methylsulfonyl-2-thienyl)ethyl] piperidine hydrochloride, 2.36 g of 3-(chloromethyl)-2-methoxypyridine and 5.90 g of potassium carbonate were suspended in 30 ml of N,N-dimethylformamide, and the mixture was stirred for 12 hours at room temperature. Water was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate:hexane=1:3), to give 809 mg of the title compound as a colorless oil (quantitatively).

¹H-NMR (400 MHz, CDCl₃) δ 1.28–1.42 (3H, m), 1.66–1.78 (4H, m), 2.00–2.09 (2H, m), 2.88–2.94 (2H, m), 3.06 (3H, s), 3.17–3.23 (2H, m), 3.49 (2H, s), 3.94 (3H, s), 6.87 (1H, dd, J=7.2, 5.0 Hz), 7.18 (1H, d, J=5.4 Hz), 7.30 (1H, d, J=5.4 Hz), 7.64 (1H, dd, J=7.2, 1.9 Hz), 8.05 (1H, dd, J=5.0, 1.9 Hz).

Example 44

1-[(2-Methoxy-3-pyridyl)methyl]-4-[2-[3-(methylsulfonyl)-2-thienyl]-1-ethynyl]piperidine 500 mg of 1-[(2-methoxy-3-pyridyl)methyl]-4-(1-ethynyl)piperidine, 530 mg of 2-bromo-3-(methylsulfonyl)thiophene, 21 mg of anhydrous cupric iodide and 127 mg of tetrakis(triphenylphosphine)palladium were suspended in a mixed solvent of 2.2 ml of triethylamine and 2.2 ml of N,N-dimethylformamide, and the mixture was stirred at 100° C. for 2 hours under nitrogen flow. Ethyl acetate was added to the reaction solution, and the resulting precipitates were filtered off. Then, water was added to the filtrate, and the mixture was extracted with ethyl acetate. The solvent was evaporated, and then the crude product was purified by silica gel column chromatography (ethyl acetate), to give 450 mg of the title compound as a colorless oil.

¹H-NMR (400 MHz, CDCl₃) δ 1.77–1.89 (2H, m), 1.93–2.03 (2H, m), 2.25–2.37 (2H, m), 2.70–2.84 (3H, m), 3.19 (3H, m), 3.51 (2H, s), 3.95 (3H, s), 6.87 (1H, dd, J=7.2, 5.0 Hz), 7.21 (1H, d, J=7.1 Hz), 7.38 (1H, d, J=7.1 Hz), 7.65 (1H, dd, J=7.2, 2.0 Hz), 8.06 (1H, dd, J=5.0, 2.0 Hz).

Example 45

1-[(2-Methoxy-3-pyridyl)methyl]-4-[2-[3-(methylsulfonyl)-2-thienyl]ethyl]piperidine 450 mg of 1-[(2-methoxy-3-pyridyl)methyl]-4-[2-[3-(methylsulfonyl)-2-thienyl]-1-ethynyl]piperidine and 250 mg of 10% palladium-carbon powder (water-containing product) were suspended in 10 ml of ethanol. After replacing the atmosphere of a container with hydrogen, the mixture was stirred at room temperature under normal pressure for 8 hours. The reaction solution was filtered, and the filtrate was evaporated, to give the title compound as a yellow oil (quantitatively).

The NMR spectrum Data of the title compound were agreed with those of the compound of Example 43.

Example 46

1-[(2-Methoxy-3-pyridyl)methyl]-4-[2-(methylsulfonyl)-3,4-methylenedioxyphenethyl]piperidine 800 mg of 1-[(2-methoxy-3-pyridyl)methyl]-4-piperidinecarboxaldehyde, 1.90 g of [2-(methylsulfonyl)-3,4-methylenedioxybenzyl]triphenylphosphonium bromide and 384 mg of potassium tert-butoxide were suspended in 10 ml of N,N-dimethylformamide, and the mixture was stirred for 1 hour at room temperature. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:4). The resulting product and 400 mg of 10% palladium-carbon powder (water-containing product) were suspended in 40 ml of ethanol. After replacing the atmosphere of a container with hydrogen, the mixture was stirred at room temperature under normal pressure for 30 minutes. The reaction solution was filtered, and the filtrate was evaporated, to give the title compound as a colorless oil (quantitatively).

¹H-NMR (400 MHz, CDCl₃) δ 1.30–1.40 (3H, m), 1.52–1.60 (2H, m), 1.68–1.78 (2H, m), 2.00–2.09 (2H, m), 2.86–2.93 (2H, m), 2.96–3.02 (2H, m), 3.21 (3H, s), 3.49 (2H, s), 3.95 (3H, s), 6.12 (2H, s), 6.75 (1H, d, J=8.1 Hz), 6.86 (1H, dd, J=7.1, 5.0 Hz), 6.93 (1H, d, J=8.1 Hz), 7.64 (1H, dd, J=7.1, 1.9 Hz), 8.05 (1H, dd, J=5.0, 1.9 Hz).

Example 47

1-[(2-Methoxy-3-pyridyl)methyl]-4-[2-(2-oxo-1,2-dihydro-3-pyridinyl)ethyl]piperidine 500 mg of 1-[(2-methoxy-3-pyridyl)methyl]-4-piperidinecarboxaldehyde obtained in Reference Example 2, 905 mg of [(2-chloro-3-pyridyl)methyl]triphenylphosphonium chloride and 340 mg of potassium tert-butoxide were suspended in 15 ml of N,N-dimethylformamide, and the mixture was stirred for 1 hour at room temperature. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane= 1:19). The resulting product was added to a solution in which 116 mg of benzyl alcohol and 35 mg of 60% oil-suspended sodium hydride were dissolved in 5 ml of N,N-dimethylformamide and stirred for 1 hour at room temperature, and the mixture was stirred at 120° C. for 2 hours. water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:19). The resulting product and 50 mg of 5% palladium-carbon powder (water-containing product) were suspended in 20 ml of methanol. After replacing the atmosphere of a container with hydrogen, the mixture was stirred at room temperature under normal pressure for 3 hours. The reaction solution was filtered, and after the filtrate was evaporated, it was washed with ethyl acetate, to give 130 mg of the title compound as colorless crystals.

¹H-NMR (400 MHz, CDCl₃) δ 1.24–1.39 (3H, m), 1.49–1.59 (2H, m), 1.70–1.80 (2H, m), 1.97–2.09 (2H, m), 2.50–2.58 (2H, m), 2.84–2.93 (2H, m), 3.48 (2H, s), 3.94 (3H, s), 6.20 (1H, dd, J=6.8, 6.8 Hz), 6.86 (1H, dd, J=7.2, 4.8 Hz), 7.20 (1H, dd, J=6.8, 2.0 Hz), 7.26 (1H, dd, J=6.8, 2.0 Hz), 7.64 (1H, dd, J=4.8, 2.0 Hz), 8.04 (1H, dd, J=4.8, 2.0 Hz).

Example 48

1-[(2-Methoxy-3-pyridyl)methyl]-4-[2-[2-(1,3-thiazol-2-yl)-3-pyridyl]ethyl]piperidine 150 mg of 1-[(2-methoxy-3-pyridyl)methyl]-4-[2-[2-[((trifluoromethyl)sulfonyl]oxy]-3-pyridyl]ethyl]piperidine, 180 mg of 2-(tributylstannyl)thiazole and 20 mg of tetrakis(triphenylphosphine)palladium were suspended in 4 ml of toluene, and the mixture was heated under reflux for 2 hours under nitrogen flow. The solvent was evaporated, and the residue was purified by NH form silica gel column chromatography (ethyl acetate:hexane=1:4), to give 39 mg of the title compound as a colorless oil.

¹H-NMR (400 MHz, CDCl₃) δ 1.28–1.41 (3H, m), 1.52–1.62 (2H, m), 1.72–1.78 (2H, m), 1.99–2.09 (2H, m), 2.86–2.94 (2H, m), 3.27–3.34 (2H, m), 3.49 (2H, s), 3.95 (3H, s), 6.87 (1H, dd, J=7.2, 5.0 Hz), 7.23 (1H, dd, J=8.0, 4.8 Hz), 7.40 (1H, d, J=3.4 Hz), 7.61 (1H, dd, J=8.0, 1.6 Hz), 7.65 (1H, dd, J=7.2, 2.0 Hz), 7.91 (1H, d, J=3.4 Hz), 8.05 (1H, dd, J=5.0, 2.0 Hz), 8.47 (1H, dd, J=4.8, 1.6 Hz).

Example 49

1-[(2-Methoxy-3-pyridyl)methyl]-4-[2-[1-(4-hydroxy)piperidino]-3-pyridyl)ethyl]piperidine 269 mg of 1-[(2-methoxy-3-pyridyl)methyl]-4-[2-[2-[[(trifluoromethyl)sulfonyl]oxy]-3-pyridyl]ethyl]piperidine obtained in Reference Example 18, 178 mg of 4-hydroxypiperidine and 243 mg of potassium carbonate were suspended in 5 ml of N,N-dimethylformamide, and the mixture was stirred at 130° C. for 3 hours. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:1), to give 70 mg of the title compound as a colorless oil.

¹H-NMR (400 MHz, CDCl₃) δ 1.26–1.40 (3H, m), 1.54–1.80 (6H, m), 1.98–2.08 (4H, m), 2.58–2.64 (2H, m), 2.84–2.95 (4H, m), 3.25–3.33 (2H, m), 3.49 (2H, s), 3.84 (1H, m), 3.95 (3H, s), 6.85–6.92 (2H, m), 7.44 (1H, dd, J=7.2, 1.9 Hz), 7.64 (1H, d, J=7.2 Hz), 8.06 (1H, dd, J=4.9, 1.9 Hz), 8.15 (1H, dd, J=4.9, 1.9 Hz).

Example 50

1-[(2-Methoxy-3-pyridyl)methyl]-4-[2-[2-(3-cyanopropoxy)-3-pyridyl]ethyl]piperidine 200 mg of 1-[(2-methoxy-3-pyridyl)methyl]-4-[2-(2-oxo-1,2-dihydro-3-pyridinyl)ethyl]piperidine obtained in Example 47, 95 mg of γ-bromobutyronitrile and 169 mg of potassium carbonate were suspended in 5 ml of N,N-dimethylformamide, and the mixture was stirred at 60° C. for 4 hours. Ethyl acetate was added thereto, the resulting salt was filtered off, and the solvent was evaporated. The crude product was purified by NH form silica gel column chromatography (ethyl acetate:hexane=1:4), to give 77 mg of the title compound as a colorless oil.

¹H-NMR (400 MHz, CDCl₃) δ 1.23–1.39 (3H, m), 1.47–1.56 (2H, m), 1.68–1.77 (2H, m), 1.97–2.07 (2H, m), 2.11–2.21 (2H, m), 2.51–2.61 (4H, m), 2.86–2.93 (2H, m), 3.49 (2H, s), 3.95 (3H, s), 4.40–4.45 (2H, m), 6.82 (1H, dd, J=7.2, 5.0 Hz), 6.87 (1H, dd, J=7.2, 4.8 Hz), 7.38 (1H, dd, J=7.2, 2.0 Hz), 7.64 (1H, dd, J=7.2, 2.0 Hz), 7.97 (1H, dd, J=5.0, 2.0 Hz), 8.05 (1H, dd, J=4.8, 2.0 Hz).

Example 51

1-[(2-Methoxy-3-pyridyl)methyl]-4-[2-[1-(2-fluorobenzyl)-2-oxo-1,2-dihydro-3-pyridinyl]ethyl]piperidine 87 mg of the title compound was obtained as a colorless oil from 100 mg of 1-[(2-methoxy-3-pyridyl)methyl]-4-[2-(2-oxo-1,2-dihydro-3-pyridinyl)ethyl]piperidine obtained in Example 47 and 61 mg of 2-fluorobenzyl bromide in the same manner as in Example 50.

¹H-NMR (400 MHz, CDCl₃) δ 1.24–1.36 (3H, m), 1.47–1.56 (2H, m), 1.68–1.78 (2H, m), 1.97–2.06 (2H, m), 2.51–2.58 (2H, m), 2.84–2.92 (2H, m), 3.47 (2H, s), 3.94 (3H, s), 5.17 (2H, s), 6.08–6.13 (1H, m), 6.86 (1H, dd, J=7.2, 5.2 Hz), 7.03–7.16 (3H, m), 7.24–7.31 (2H, m), 7.40–7.46 (1H, m), 7.64 (1H, dd, J=7.2, 2.0 Hz), 8.04 (1H, dd, J=5.2, 2.0 Hz).

Example 52

1-[(2-Benzyloxy-3-pyridyl)methyl]-4-(2,3-methylenedioxyphenethyl)piperidine 369 mg of the title compound was obtained as a colorless oil from 478 mg of 1-[(2-chloro-3-pyridyl)methyl]-4-(2,3-methylenedioxyphenethyl)piperidine in the same manner as in Example 120 described later.

¹H-NMR (400 MHz, CDCl₃) δ 1.24–1.36 (3H, m), 1.54–1.62 (2H, m), 1.69–1.77 (2H, m), 1.98–2.07 (2H, m), 2.56–2.63 (2H, m), 2.86–2.92 (2H, m), 3.53 (2H, s), 5.41 (2H, s), 5.92 (2H, s), 6.66 (1H, dd, J=7.8, 1.0 Hz), 6.68 (1H, dd, J=7.8, 1.0 Hz), 6.75 (1H, dd, J=7.8, 7.8 Hz), 6.89 (1H, dd, J=7.2, 5.0 Hz), 7.32 (1H, m), 7.35–7.41 (2H, m), 7.45–7.50 (2H, m), 7.68 (1H, dd, J=7.2, 2.0 Hz), 8.06 (1H, dd, J=5.0, 2.0 Hz).

Example 53

1-[(2-Methoxy-3-pyridyl)methyl]-4-[2-hydroxy-2-(2-thienyl)ethyl]piperidine 48.4 ml of a 1.0M (2-thienyl)lithium in tetrahydrofuran was dissolved in 40 ml of tetrahydrofuran at −78° C., and a mixed solution of 10.0 g of 1-[(2-methoxy-3-pyridyl)methyl]-4-piperidineacetaldehyde obtained in Reference Example 24 and 40 ml of tetrahydrofuran was added dropwise thereinto. After completion of the dropwise addition, the mixture was further stirred at −78° C. for 20 minutes. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:3), to give 12.1 g of the title compound as a yellow oil.

¹H-NMR (400 MHz, CDCl₃) δ 1.27–1.55 (3H, m), 1.65–2.08 (6H, m), 2.83–2.90 (2H, m), 3.47 (2H, s), 3.94 (3H, s), 5.03 (1H, dd, J=8.3, 5.6), 6.86 (1H, dd, J=7.1, 4.9 Hz), 6.94–6.99 (2H, m), 7.25 (1H, m), 7.63 (1H, dd, J=7.1, 2.0 Hz), 8.04 (1H, dd, J=4.9, 2.0 Hz).

Example 54

1-[(2-Methoxy-3-pyridyl)methyl]-4-[2-oxo-2-(2-thienyl)ethyl]piperidine 12.0 g of 1-[(2-methoxy-3-pyridyl)methyl]-4-[2-hydroxy-2-(2-thienyl)ethyl]piperidine and 30.2 ml of triethylamine were dissolved in 72 ml of dimethyl sulfoxide, and a mix solution of 17.2 g of sulfur trioxide-pyridine complex and 90 ml of dimethyl sulfoxide was added dropwise thereinto under ice-cooling. After completion of the dropwise addition, the mixture was further stirred at room temperature for 30 minutes. An aqueous sodium bicarbonate was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate:hexane=1:1), to give 9.6 g of the title compound as a pale yellow oil.

¹H-NMR (400 MHz, CDCl₃) δ 1.34–1.48 (2H, m), 1.69–1.80 (2H, m), 1.94–2.15 (3H, m), 2.82 (2H, d, J=7.0 Hz), 2.84–2.93 (2H, m), 3.49 (2H, s), 3.94 (3H, s), 6.86 (1H, dd, J=7.3, 5.0 Hz), 7.13 (1H, dd, J=4.9, 3.9 Hz), 7.63 (1H, dd, J=4.9, 1.3 Hz), 7.64 (1H, dd, J=7.3, 1.9 Hz), 7.70 (1H, dd, J=3.9, 1.3 Hz), 8.05 (1H, dd, J=5.0, 1.9 Hz).

Example 55

N1-Methoxy,N1-methyl-2-[1-[(2-methoxy-3-pyridyl)methyl]-4-piperidyl]acetamide 2.6 g of ethyl 2-[1-[(2-methoxy-3-pyridyl)methyl]-4-(piperidyl)acetate and 1.3 g of N,O-dimethylhydroxylamine hydrochloride were suspended in 18 ml of tetrahydrofuran, and 13.2 ml of a 2 M chloroisopropylmagnesium diethyl ether solution was added dropwise thereinto at −23° C. After completion of the dropwise addition, the mixture was further stirred at room temperature for 30 minutes. An aqueous saturated ammonium chloride was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane= 1:2), to give 2.3 g of the title compound as a yellow oil.

¹H-NMR (400 MHz, CDCl₃) δ 1.29–1.42 (2H, m), 1.69–1.78 (2H, m), 1.88 (1H, m), 2.05–2.15 (2H, m), 2.32–2.40 (2H, m), 2.85–2.94 (2H, m), 3.18 (3H, s), 3.49 (2H, s), 3.67 (3H, s), 3.95 (3H, s), 6.86 (1H, dd, J=7.2, 5.0 Hz), 7.64 (1H, dd, J=7.2, 1.9 Hz), 8.05 (1H, dd, J=5.0, 1.9 Hz).

Example 56

1-[(2-Methoxy-3-pyridyl)methyl]-4-[2-oxo-2-(2-thienyl)ethyl]piperidine 0.50 g of N1-methoxy,N1-ethyl-2-[1-[(2-methoxy-3-pyridyl)methyl]-4-piperidyl]acetamide obtained in Example 55 was dissolved in 3 ml of tetrahydrofuran and 1.8 ml of a 1.0M (2-thienyl)-lithium in tetrahydrofuran was added dropwise thereinto at −78° C. After completion of the dropwise addition, the mixture was further stirred at −78° C. for 1 hour. An aqueous saturated ammonium chloride was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate), to give 0.22 g of the title compound as a pale yellow oil. The NMR spectrum data of the title compound were agreed with those of Example 54.

¹H-NMR (400 MHz, CDCl₃) δ 1.34–1.48 (2H, m), 1.69–1.80 (2H, m), 1.94–2.15 (3H, m), 2.82 (2H, d, J=7.0 Hz), 2.84–2.93 (2H, m), 3.49 (2H, s), 3.94 (3H, s), 6.86 (1H, dd, J=7.3, 5.0 Hz), 7.13 (1H, dd, J=4.9, 3.9 Hz), 7.63 (1H, dd, J=4.9, 1.3 Hz), 7.64 (1H, dd, J=7.3, 1.9 Hz), 7.70 (1H, dd, J=3.9, 1.3 Hz), 8.05 (1H, dd, J=5.0, 1.9 Hz).

Example 57

1-[(2-Methoxy-3-pyridyl)methyl]-4-(2-hydroxy-2-phenylethyl)piperidine 2.2 g of the title compound was obtained as a yellow oil from 2.0 g of 1-[(2-methoxy-3-pyridyl)methyl]-4-piperidineacetaldehyde obtained in Reference Example and 10.0 ml of a 0.97M phenyllithium cyclohexane/diethyl ether in the same manner as in Example 53.

¹H-NMR (400 MHz, CDCl₃) δ 1.24–1.60 (4H, m), 1.64–1.82 (3H, m), 1.96–2.07 (2H, m), 2.82–2.91 (2H, m), 3.46 (2H, s), 3.92 (3H, s), 4.71–4.78 (1H, m), 6.84 (1H, dd, J=7.1, 4.9 Hz), 7.23–7.37 (5H, m), 7.62 (1H, dd, J=7.1, 2.0 Hz), 8.03 (1H, dd, J=4.9, 2.0 Hz).

Example 58

1-[(2-Methoxy-3-pyridyl)methyl]-4-(2-oxo-2-phenylethyl)piperidine 2.2 g of 1-[(2-methoxy-3-pyridyl)methyl]-4-(2-hydroxy-2-phenylethyl)piperidine and 8.6 g of manganese dioxide were suspended in 35 ml of toluene, and the mixture was heated under reflux for 2 hours. The reaction solution was filtered, and the filtrate was evaporated. Then, the residue was purified and separated by silica gel column chromatography (ethyl acetate), to give 1.54 g of the title compound as a pale yellow oil.

¹H-NMR (400 MHz, CDCl₃) δ 1.32–1.47 (2H, m), 1.70–1.80 (2H, m), 1.92–2.17 (3H, m), 2.83–2.94 (4H, m), 3.49 (2H, s), 3.94 (3H, s), 6.86 (1H, dd, J=7.3, 5.1 Hz), 7.42–7.49 (3H, m), 7.52–7.59 (1H, m), 7.64 (1H, dd, J=7.3, 2.0 Hz), 7.92–7.98 (2H, m), 8.05 (1H, dd, J=5.1, 2.0 Hz).

Example 59

1-[(2-Methoxy-3-pyridyl)methyl]-4-[2-(2-chlorophenyl)-2-hydroxyethyl]piperidine 1.0 g of 2-bromochlorobenzene was dissolved in 11 ml of tetrahydrofuran and 10.0 ml of a 1.54 M n-butyllithium in hexane was added dropwise thereinto at −78° C. After stirring for 20 minutes, a mixed solution of 1.0 g of 1-[(2-methoxy-3-pyridyl)methyl]-4-piperidineacetaldehyde obtained in Reference Example 22 and 4 ml of tetrahydrofuran was added dropwise thereinto. After completion of the dropwise addition, the mixture was further stirred at −78° C. for 10 minutes. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:3), to give 0.90 g of the title compound as a yellow oil.

¹H-NMR (400 MHz, CDCl₃) δ 1.32–1.45 (2H, m), 1.52–1.95 (5H, m), 2.83–2.97 (2H, m), 3.49 (2H, s), 3.95 (3H, s), 5.19–5.27 (1H, m), 6.86 (1H, dd, J=7.2, 5.0 Hz), 7.19 (1H, ddd, J=7.6, 7.6, 1.6 Hz), 7.28 (1H, dd, J=7.6, 1.6 Hz), 7.31 (1H, ddd, J=7.6, 7.6, 1.6 Hz), 7.57 (1H, dd, J=7.6, 1.6 Hz), 7.65 (1H, dd, J=7.2, 2.0 Hz), 8.04 (1H, dd, J=5.0, 2.0 Hz).

Example 60

1-[(2-Methoxy-3-pyridyl)methyl]-4-[2-(2-chlorophenyl)-2-oxoethyl]piperidine 720 mg of the title compound was obtained as a pale yellow oil from 900 mg of 1-[(2-methoxy-3-pyridyl)methyl]-4-[2-(2-chlorophenyl)-2-hydroxyethyl]piperidine in the same manner as in Example 54.

¹H-NMR (400 MHz, CDCl₃) δ 1.32–1.46 (2H, m), 1.71–1.80 (2H, m), 1.93–2.16 (3H, m), 2.84–2.93 (4H, m), 3.50 (2H, s), 3.94 (3H, s), 6.86 (1H, dd, J=7.2, 5.0 Hz), 7.26–7.44 (4H, m), 7.64 (1H, d, J=7.2, 1.8 Hz), 8.05 (1H, d, J=5.0, 1.8 Hz).

Example 61

1-[(2-Methoxy-3-pyridyl)methyl]-4-[2-(2-chloro-3-pyridyl)-2-hydroxyethyl]piperidine 0.26 ml of 2-chloropyridine, 2.9 ml of a 0.97M phenyllithium cyclohexane/diethyl ether and 0.039 ml of diisopropylamine were dissolved in 9 ml of tetrahydrofuran, and the mixture was stirred at −45° C. for 1 hour. A mixed solution of 500 mg of 1-[(2-methoxy-3-pyridyl)methyl]-4-piperidineacetaldehyde obtained in Reference Example 22 and 2 ml of tetrahydrofuran was added dropwise thereinto, and the mixture was further stirred at −45° C. for 20 minutes. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:2), to give 420 mg of the title compound as a yellow oil.

$^1$H-NMR (400 MHz, CDCl$_3$) δ 1.33–1.47 (2H, m), 1.55–1.95 (5H, m), 2.01–2.14 (2H, m), 2.83–2.97 (2H, m), 3.49 (2H, s), 3.94 (3H, s), 5.12–5.20 (1H, m), 6.86 (1H, dd, J=7.3, 5.0 Hz), 7.28 (1H, dd, J=7.7, 5.0 Hz), 7.65 (1H, dd, J=7.3, 2.0 Hz), 7.94 (1H, dd, J=7.7, 1.9 Hz), 8.05 (1H, dd, J=5.0, 1.9 Hz), 8.29 (1H, dd, J=5.0, 2.0 Hz).

Example 62

1-[(2-Methoxy-3-pyridyl)methyl]-4-[2-(2-chloro-3-pyridyl)-2-oxoethyl]piperidine 463 mg of the title compound was obtained as a pale yellow oil from 610 mg of 1-[(2-methoxy-3-pyridyl)methyl]-4-[2-(2-chloro-3-pyridyl)-2-hydroxyethyl]piperidine in accordance with the method of Example 54.

$^1$H-NMR (400 MHz, CDCl$_3$) δ 1.33–1.47 (2H, m), 1.70–1.79 (2H, m), 1.93–2.17 (3H, m), 2.84–2.97 (4H, m), 3.50 (2H, s), 3.95 (3H, s), 6.86 (1H, dd, J=7.1, 4.9 Hz), 7.33 (1H, dd, J=7.7, 4.9 Hz), 7.63 (1H, dd, J=7.1, 1.8 Hz), 7.77 (1H, dd, J=7.7, 1.9 Hz), 8.05 (1H, d, J=4.9, 1.9 Hz), 8.48 (1H, dd, J=4.9, 1.8 Hz).

Example 63

1-[(2-Methoxy-3-pyridyl)methyl]-4-[2-oxo-2-(2-trifluoroacetylaminophenyl)ethyl]piperidine 482 mg of 2-bromo-N-(trifluoroacetyl)aniline was dissolved in a mixed solvent of 1.8 ml of tetrahydrofuran and 1.8 ml of diethyl ether, and a 1.14M methyllithium diethyl ether solution was added dropwise thereinto at 0° C. After stirring for 10 minutes, the mixture was slowly charged by a cannular to a solution of 2.4 ml of 1.51 M tert-butyllithium and 4 ml of a diethyl ether solution cooled at −78° C. The mixture was stirred for 1 hour. Then, a mixed solution of 500 mg of N1-methoxy,N1-ethyl-2-[1-(2-methoxy-3-pyridyl)methyl]-4-piperidyl]acetamide obtained in Example 55 and 2 ml of tetrahydrofuran was added dropwise thereinto, and the mixture was further stirred for 20 minutes. Water was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate), to give 150 mg of the above compound as a yellow oil.

$^1$H-NMR (400 MHz, CDCl$_3$) δ 1.35–1.48 (2H, m), 1.70–1.80 (2H, m), 1.94–2.18 (3H, m), 2.87–2.95 (2H, m), 2.98 (2H, d, J=6.4 Hz), 3.51 (2H, s), 3.95 (3H, s), 6.87 (1H, dd, J=7.2, 4.9 Hz), 7.29 (1H, dd, J=8.6, 7.7 Hz), 7.62 (1H, dd, J=7.2, 1.9 Hz), 7.64 (1H, dd, J=8.1, 7.7 Hz), 8.00 (1H, d, J=8.1 Hz), 8.06 (1H, dd, J=4.9, 1.9 Hz), 8.70 (1H, d, J=8.6 Hz).

Example 64

1-[(2-Methoxy-3-pyridyl)methyl]-4-[2-(2-aminophenyl)-2-oxoethyl]piperidine 150 mg of 1-[(2-methoxy-3-pyridyl)methyl]-4-[2-oxo-2-(2-trifluoroacetylaminophenyl)ethyl]piperidine obtained in Example 63 and 141 mg of potassium carbonate were suspended in a mixed solvent of 3 ml of methanol and 3 ml of water, and the mixture was stirred at room temperature for one hour. The reaction solution was extracted with ethyl acetate, and the organic layer was washed with brine, and then dried over anhydrous magnesium sulfate. The solvent was evaporated, to give the title compound as a yellow oil (quantitatively).

$^1$H-NMR (400 MHz, CDCl$_3$) δ 1.33–1.47 (2H, m), 1.70–1.79 (2H, m), 1.92.03 (1H, m), 2.06–2.17 (2H, m), 2.82–2.94 (4H, m), 3.50 (2H, s), 3.94 (3H, s), 6.64 (1H, dd, J=8.0, 7.0 Hz), 6.65 (1H, d, J=7.2 Hz), 6.86 (1H, dd, J=7.2, 5.0 Hz), 7.26 (1H, ddd, J=8.0, 7.2, 1.5 Hz), 7.64 (1H, dd, J=7.2, 1.8 Hz), 7.73 (1H, dd, J=7.0, 1.5 Hz), 8.05 (1H, dd, J=5.0, 1.8 Hz).

Example 65

1-[(2-Methoxy-3-pyridyl)methyl]-4-[2-(2-methylsulfonylaminophenyl)-2-oxoethyl]piperidine 120 mg of 1-[(2-methoxy-3-pyridyl)methyl]-4-[2-(2-aminophenyl)-2-oxoethyl]piperidine obtained in Example 64, 0.1 ml of triethylamine and 0.041 ml of methanesulfonyl chloride were dissolved in 2 ml of dichloromethane, and the mixture was stirred for 2 hours under ice-cooling. An aqueous sodium bicarbonate was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate), to give 90 mg of the title compound as a yellow oil.

$^1$H-NMR (400 MHz, CDCl$_3$) δ 1.36–1.47 (2H, m), 1.76–1.85 (2H, m), 1.99–2.22 (3H, m), 2.83–2.96 (4H, m), 3.50 (3H, s), 3.52 (2H, s), 3.95 (3H, s), 6.86 (1 H, dd, J=7.3, 5.0 Hz), 7.40 (1H, dd, J=5.9, 3.4 Hz), 7.54 (1H, d, J=3.4 Hz), 7.56 (1H, d, J=3.4 Hz), 7.65 (1H, dd, J=7.3, 1.9 Hz), 7.67 (1H, dd, J=5.9, 3.4 Hz), 8.05 (1H, dd, J=5.0, 1.9 Hz).

Example 66

1-[(2-Methoxy-3-pyridyl)methyl]-4-[2-[2-(methylsulfonyl)phenyl]-2-oxoethyl]piperidine 953 mg of N-(tert-butoxycarbonyl)-4-[2-[2-(methylsulfonylphenyl)-2-oxoethyl]piperidine and 19.2 ml of a 4 M hydrogen chloride ethyl acetate solution were dissolved in 15 ml of ethyl acetate, and the mixture was stirred at room temperature for 4 hours. The solvent was evaporated, and the residue was recrystallized from ethyl acetate, to give 800 mg of 4-[2-(2-methylsulfonylphenyl)-2-oxoethyl]piperidine hydrochloride. Then, the product was suspended in 400 mg of 3-(chloromethyl)-2-methoxypyridine, 1.0 g of potassium carbonate and 15 ml of N,N-dimethylformamide, and the mixture was stirred at room temperature for 12 hours. Water was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate), to give 1.07 g of the title compound as a pale yellow oil (quantitatively).

$^1$H-NMR (400 MHz, CDCl$_3$) δ 1.33–1.47 (2H, m), 1.80–1.89 (2H, m), 2.02–2.20 (3H, m), 2.85–2.95 (4H, m), 3.25 (3H, s), 3.50 (2H, s), 3.95 (3H, s), 6.86 (1H, dd, J=7.1, 4.9 Hz), 7.41 (1H, d, J=7.5 Hz), 7.61 (1H, dd, J=7.9, 7.5 Hz), 7.64 (1H, d, J=7.1, 1.8 Hz), 7.69 (1H, dd, J=7.5, 7.5 Hz), 8.05 (1H, dd, J=4.9, 1.8 Hz), 8.07 (1H, d, J=7.9 Hz).

Example 67

1-[(2-Methoxy-3-pyridyl)methyl]-4-[2-(2-methoxyphenyl)-2-oxoethyl]piperidine 2.4 g of 1-[(2-methoxy-3-pyridyl)methyl]-4-[2-hydroxy-2-(2-methoxyphenyl}ethyl]piperidine was obtained in accordance with the method of Example 59 from 2.1 g of 2-bromoanisole, 7.4 ml of a 1.54 M n-butyllithium hexane solution and 2.0 g of 1-[(2-methoxy-3-pyridyl)methyl]-4-piperidineacetaldehyde obtained in Reference Example 22. Then, the product was treated by the same manner as in Example 54, to give 0.93 g of the title compound as a yellow oil.

$^1$H-NMR (400 MHz, CDCl$_3$) δ 1.29–1.43 (2H, m), 1.65–1.77 (2H, m), 1.89–2.15 (3H, m), 2.81–2.95 (4H, m), 3.48 (2H, s), 3.89 (3H, s), 3.94 (3H, s), 6.86 (1H, dd, J=7.1, 4.9 Hz), 6.95 (1H, d, J=8.4 Hz), 6.99 (1H, dd, J=7.5, 7.5 Hz), 7.44 (1H, ddd, J=8.4, 7.5, 1.5 Hz), 7.61 (1H, dd, J=7.5, 1.5 Hz), 7.63 (1H, dd, J=7.1, 1.8 Hz), 8.04 (1H, dd, J=4.9, 1.8 Hz).

Example 68

1-[(2-Methoxy-3-pyridyl)methyl]-4-[2-(2-cyclopropylmethoxyphenyl)-2-oxoethyl]piperidine $^1$H-NMR (400 MHz, CDCl$_3$) δ 0.32–0.39 (2H, m), 0.62–0.70 (2H, m), 1.22–1.47 (3H, m), 1.69–1.80 (2H, m), 1.92–2.19 (3H, m), 2.70–2.96 (2H, m), 3.01 (2H, d, J=6.9 Hz), 3.50 (2H, s), 3.88 (2H, d, J=6.5 Hz), 3.94 (3H, s), 6.86 (1H, dd, J=7.1, 4.9 Hz), 6.88 (1H, d, J=8.4 Hz), 6.97 (1H, dd, J=7.5, 7.4 Hz), 7.40 (1H, ddd, J=8.4, 7.4, 1.8 Hz), 7.64 (1H, dd, J=7.5, 1.8 Hz), 7.65 (1H, dd, J=7.1, 1.8 Hz), 8.05 (1H, dd, J=4.9, 1.8 Hz).

Example 69

1-[(2-Methoxy-3-pyridyl)methyl]-4-[2-oxo-2-(2-trifluoromethylphenyl)ethyl]piperidine $^1$H-NMR (400 MHz, CDCl$_3$) δ 1.29–1.43 (2H, m), 1.73–1.83 (2H, m), 1.96–2.18 (3H, m), 2.79 (2H, d, J=6.6 Hz), 2.85–2.94 (2H, m), 3.50 (2H, s), 3.95 (3H, s), 6.86 (1H, dd, J=7.2, 4.9 Hz), 7.39 (1H, d, J=7.5 Hz), 7.54 (1H, dd, J=7.5, 7.5 Hz), 7.60 (1H, dd, J=7.5, 7.5 Hz), 7.63 (1H, dd, J=7.2, 1.8, Hz), 7.71 (1H, d, J=7.5 Hz), 8.05 (1H, dd, J=4.9, 1.8 Hz).

Example 70

1-[(2-Methoxy-3-pyridyl)methyl]-4-[2-oxo-2-(3-thienyl)ethyl]piperidine $^1$H-NMR (400 MHz, CDCl$_3$) δ 1.33–1.46 (2H, m), 1.68–1.80 (2H, m), 1.92–2.15 (3H, m), 2.78–2.94 (4H, m), 3.49 (2H, s), 3.94 (3H, s), 6.86 (1H, dd, J=7.1, 4.9 Hz), 7.31 (1H, dd, J=5.1, 2.9 Hz), 7.54 (1H, dd, J=5.1, 1.3 Hz), 7.63 (1H, dd, J=7.1, 1.8 Hz), 8.03 (1H, dd, J=2.9, 1.3 Hz), 8.05 (1H, dd, J=4.9, 1.8 Hz).

Example 71

1-[(2-Methoxy-3-pyridyl)methyl]-4-[2-oxo-2-(1,3-thiazol-2-yl)ethyl]piperidine $^1$H-NMR (400 MHz, CDCl$_3$) δ 1.37–1.51 (2H, m), 1.71–1.80 (2H, m), 1.97–2.16 (3H, m), 2.85–2.93 (2H, m), 3.10 (2H, d, J=6.8 Hz), 3.49 (2H, s), 3.94 (3H, s), 6.86 (1H, dd, J=7.1, 5.0 Hz), 7.64 (1H, dd, J=7.1, 1.8 Hz), 7.67 (1H, d, J=3.0 Hz), 8.00 (1H, dd, J=3.0 Hz), 8.05 (1H, dd, J=5.0, 1.8 Hz).

Example 72

1-[(2-Methoxy-3-pyridyl)methyl]-4-[2-(3,4-methylenedioxyphenyl)-2-oxoethyl]piperidine $^1$H-NMR (400 MHz, CDCl$_3$) δ 1.38–1.43 (2H, m), 1.68–1.76 (2H, m), 2.09 (1H, m), 2.80 (2H, d, J=6.8 Hz), 2.84–2.92 (2H, m), 3.48 (2H, s), 3.94 (3H, s), 6.04 (2H, s), 6.85 (1H, d, J=8.2 Hz), 6.86 (1H, dd, J=7.2, 4.9 Hz), 7.43 (1H, d, J=1.8 Hz), 7.55 (1H, d, J=8.2, 1.8 Hz), 7.63 (1H, d, J=7.2, 1.8 Hz), 8.05 (1H, dd, J=4.9, 1.8 Hz).

Example 73

1-[(2-Methoxy-3-pyridyl)methyl]-4-[2-(3-bromo-2-thienyl)-2-oxoethyl]piperidine $^1$H-NMR (400 MHz, CDCl$_3$) δ 1.34–1.48 (2H, m), 1.72–1.82 (2H, m), 1.95–2.17 (3H, m), 2.84–2.99 (4H, m), 3.49 (2H, s) 3.94 (3H, s), 6.86 (1H, dd, J=7.3, 5.1 Hz), 7.11 (1H, d, J=5.1 Hz), 7.50 (1H, d, J=5.1 Hz), 7.64 (1H, dd, J=7.3, 2.0 Hz), 8.05 (1H, dd, J=5.1, 2.0 Hz).

Example 74

1-[(2-Methoxy-3-pyridyl)methyl]-4-[2-oxo-2-[3-(1,3-thiazol-2-yl)-2-thienyl]ethyl]piperidine 300 mg of 1-[(2-methoxy-3-pyridyl)methyl]-4-[2-(3-bromo-2-thienyl)-2-oxoethyl]piperidine obtained in Example 73, 438 mg of 2-(tributylstannyl)thiazole and 42 mg of tetrakis(triphenylphosphine)palladium were suspended in 4 ml of toluene, and the mixture was heated under reflux for 2 hours under nitrogen flow. The solvent was evaporated, and the residue was purified by silica gel column chromatography (ethyl acetate), to give 300 mg of the title compound as a colorless oil.

$^1$H-NMR (400 MHz, CDCl$_3$) δ 1.29–1.43 (2H, m), 1.66–1.96 (2H, m), 1.94–2.14 (3H, m), 2.76–2.91 (4H, m), 3.48 (2H, s), 3.94 (3H, s), 6.85 (1H, dd, J=7.3, 5.1 Hz), 7.46 (1H, d, J=3.3 Hz), 7.53 (1H, d, J=5.2 Hz), 7.62 (1H, dd, J=7.3, 2.0 Hz), 7.82 (1H, d, J=5.2 Hz), 7.93 (1H, d, J=3.3 Hz), 8.05 (1H, dd, J=5.1, 2.0 Hz).

Example 75

1-[(2-Methoxy-3-pyridyl)methyl]-4-[2-oxo-2-(3-phenyl-2-thienyl)ethyl]piperidine 290 mg of 1-[(2-methoxy-3-pyridyl)methyl]-4-[2-(3-bromo-2-thienyl)-2-oxoethyl]piperidine obtained in Example 73, 173 mg of phenylboric acid and 42 mg of tetrakis(triphenylphosphine)palladium were suspended in 5.6 ml of toluene, 1.4 ml of methanol and 2.8 ml of 2 M sodium carbonate, and the mixture was heated under reflux for 3 hours under nitrogen flow. Water was added to the reaction solution, and the mixture was extracted with ethyl acetate. The organic layer was washed with brine, and then dried over anhydrous magnesium sulfate. The solvent was evaporated, and the crude product was purified by silica gel column chromatography (ethyl acetate), to give 290 mg of the title compound as a yellow oil.

$^1$H-NMR (400 MHz, CDCl$_3$) δ 1.09–1.24 (2H, m), 1.48–1.59 (2H, m), 1.83 (1H, m), 1.98–2.11 (2H, m), 2.42 (2H, d, J=6.8 Hz), 2.75–2.87 (2H, m), 3.42 (2H, s), 6.30 (1H, dd, J=7.5, 6.0 Hz), 7.06 (1H, d, J=4.9 Hz), 7.33 (1H, d, J=6.0 Hz), 7.34–7.46 (5H, m), 7.48 (1H, d, J=7.5 Hz), 7.54 (1H, d, J=4.9 Hz).

Example 76

1-[(2-Methoxy-3-pyridyl)methyl]-4-(3-phenylpropyl)piperidine 214 mg of the title compound was obtained as a colorless oil from 332 mg of 1-[(2-methoxy-3-pyridyl)methyl]-4- piperidineacetaldehyde obtained in Reference Example 22 and 491 mg of benzyltriphenylphosphonium chloride in accordance with the method of Example 46.

$^1$H-NMR (400 MHz, CDCl$_3$) δ 1.30–1.42 (5H, m), 1.57–1.70 (4H, m), 1.76–2.06 (2H, m), 2.59 (2H, t, J=7.7 Hz), 2.84–2.91 (2H, m), 3.47 (2H, s), 3.94 (3H, s), 6.86 (1H, dd, J=7.2, 5.0 Hz), 7.14–7.20 (3H, m), 7.24–7.30 (2H, m), 7.64 (1H, dd, J=7.2, 1.9 Hz), 8.04 (1H, dd, J=5.0, 1.9 Hz).

Example 77

1-[(2-Methoxy-3-pyridyl)methyl]-4-(3-(2-thienyl)propyl)piperidine 206 mg of the title compound was obtained as a pale brown oil from 261 mg of 1-[(2-methoxy-3-pyridyl)methyl]-4-piperidineacetoaldehyde which was obtained in Reference Example 22 and 499 mg of (2-thienylmethyl)triphenylphosphonium chloride.

$^1$H-NMR (400 MHz, CDCl$_3$) δ 1.20–1.35 (5H, m), 1.62–1.74 (4H, m), 1.76–2.06 (2H, m), 2.81 (2H, t, J=7.6 Hz), 2.84–2.92 (2H, m), 3.48 (2H, s), 3.94 (3H, s), 6.77 (1H, dd, J=3.4, 1.1 Hz), 6.86 (1H, dd, J=7.2, 5.0 Hz), 6.91 (1H, dd, J=5.1, 3.4 Hz), 7.10 (1H, dd, J=5.1, 1.1 Hz), 7.64 (1H, dd, J=7.2, 2.0 Hz), 8.04 (1H, dd, J=5.0, 2.0 Hz).

Example 78

1-[(2-Methoxy-3-pyridyl)methyl]-4-benzylpiperidine 472 mg of the title compound was obtained as a pale yellow oil from 292 mg of 4-benzylpiperidine in accordance with the method of Example 43.

$^1$H-NMR (400 MHz, CDCl$_3$) δ 1.28–1.40 (2H, m), 1.53 (1H, m), 1.58–1.68 (2H, m), 1.95–2.04 (2H, m), 2.54 (2H, d, J=7.0 Hz), 2.84–2.91 (2H, m), 3.47 (2H, s), 3.93 (3H, s), 6.86 (1H, dd, J=7.2, 5.0 Hz), 7.12–7.21 (3H, m), 7.24–7.30 (2H, m), 7.63 (1H, dd, J=7.2, 2.0 Hz), 8.04 (1H, dd, J=5.0, 2.0 Hz).

Example 79

1-[(2-Methoxy-3-pyridyl)methyl]-4-(4-phenylbutyl)piperidine 150 mg of the title compound was obtained as a colorless oil from 220 mg of 3-[1-[(2-methoxy-3-pyridyl)methyl]-4-pyperidyl]propanal obtained in Reference Example 28 and 407 mg of benzyltriphenylphosphonium chloride in accordance with the method of Example 46. $^1$H-NMR (400 MHz, CDCl$_3$) δ 1.18–1.38 (7H, m), 1.55–1.70 (4H, m), 1.96–2.06 (2H, m), 2.60 (2H, t, J=7.7 Hz), 2.84–2.93 (2H, m), 3.48 (2H, s), 3.94 (3H, s), 6.86 (1H, dd, J=7.2, 5.0 Hz), 7.14–7.20 (3H, m), 7.24–7.30 (2H, m), 7.64 (1H, dd, J=7.2, 1.8 Hz), 8.05 (1H, dd, J=5.0, 1.8 Hz).

Example 80

1-[(2-Methoxy-3-pyridyl)methyl]-4-[oxo(2-thienyl)methyl)piperidine 101 mg of the title compound was obtained as colorless crystals from 210 mg of 4-[oxo(2-thienyl)methyl]piperidine in accordance with the method of Example 43.

$^1$H-NMR (400 MHz, CDCl$_3$) δ 1.82–1.98 (4H, m), 2.14–2.23 (2H, m), 2.94–3.03 (2H, m), 3.09 (1H, m), 3.52 (2H, s), 3.95 (3H, s), 6.87 (1H, dd, J=7.2, 5.0 Hz), 7.12 (1H, dd, J=5.0, 3.8 Hz), 7.62 (1H, dd, J=5.0, 1.0 Hz), 7.67 (1H, dd, J=7.2, 1.8 Hz), 7.72 (1H, dd, J=3.8, 1.0 Hz), 8.05 (1H, dd, J=5.0, 1.8 Hz).

Example 81

1-[(2-Methoxy-3-pyridyl)methyl]-4-piperidinecarboxamide 832 mg of the title compound was obtained as colorless crystals from 496 mg of isonipecotamide in accordance with the method of Example 43.

$^1$H-NMR (400 MHz, CDCl$_3$) δ 1.73–1.91 (4H, m), 2.04–2.22 (3H, m), 2.90–2.98 (2H, m), 3.49 (2H, s), 3.95 (3H, s), 5.35 (1H, br s), 5.47 (1H, br s), 6.87 (1H, dd, J=7.2, 5.0 Hz), 7.65 (1H, dd, J=7.2, 1.9 Hz), 8.06 (1H, dd, J=5.0, 1.9 Hz).

Example 82

N4-(2-Phenyl)benzyl-1-[(2-methoxy-3-pyridyl)methyl]-4-piperidinecarboxamide 212 mg of 1-[(2-methoxy-3-pyridyl)methyl]-4-piperidinecarboxamide, 0.16 ml of 2-(bromomethyl)biphenyl and 46 mg of 60% sodium hydride were suspended in 5 ml of N,N-dimethylformamide, and-the mixture was stirred for 2 hours at room temperature. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (ethyl acetate:hexane=1:3), to give 92 mg of the title compound as colorless crystals.

$^1$H-NMR (400 MHz, CDCl$_3$) δ 1.60–1.78 (4H, m), 1.96–2.08 (3H, m), 2.86–2.94 (2H, m), 3.47 (2H, s), 3.94 (3H, s), 4.43 (2H, d, J=5.5 Hz), 5.48 (1H, t, J=5.5 Hz), 6.87 (1H, dd, J=7.2, 5.0 Hz), 7.24–7.45 (9H, m), 7.63 (1H, dd, J=7.2, 1.9 Hz), 8.05 (1H, dd, J=5.0, 1.9 Hz).

Example 83

1-[(2-Methoxy-3-pyridyl)methyl]-4-[[(2-bromo-3-pyridyl)oxy]methyl]piperidine 1.18 g of 1-[(2-methoxy-3-pyridyl)methyl]-4-piperidinemethanol obtained in Reference Example 1 and 0.87 g of 2-bromo-3-hydroxypyridine were dissolved in 50 ml of tetrahydrofuran. Under cooling at 10° C., 1.12 g of diisopropyl azodicarboxylate and 1.44 g of triphenylphosphine were added thereto, and the mixture was stirred at room temperature for 20 hours. The solvent was evaporated, and the residue was purified by silica gel column chromatography (dichloromethane-methanol), to give 550 mg of the title compound as a colorless oil.

$^1$H-NMR (400 MHz, CDCl$_3$) δ 1 1 401.52 (2H, m), 1.84–1.98 (3H, m), 2.08–2.17 (2H, m), 2.92–3.01 (2H, m), 3.53 (2H, s), 3.87 (2H, d, J=6.4 Hz), 3.96 (3H, s), 6.88 (1H, dd, J=6.8, 4.8 Hz), 7.11 (1H, dd, J=8.0, 1.6 Hz), 7.19 (1H, dd, J=8.0, 4.8 Hz), 7.65 (1H, dd, J=6.8, 2.0 Hz), 7.97 (1H, dd, J=4.8, 1.6 Hz), 8.06 (1H, dd, J=4.8, 2.0 Hz).

Example 84

1-[(2-Methoxy-3-pyridyl)methyl]-4-[[[2-(1,3-thiazol-2-yl)-3-pyridyl]oxy]methyl]piperidine 238 mg of the title compound was obtained as a colorless oil from 250 mg of 1-[(2-methoxy-3-pyridyl)methyl]-4-[[(2-bromo-3-pyridyl)oxy]methyl]piperidine in accordance with the method of Reference Example 33.

$^1$H-NMR (400 MHz, CDCl$_3$) δ 1.44–1.59 (2H, m), 1.92–2.20 (5H, m), 2.93–3.02 (2H, m), 3.54 (2H, s), 3.96

(3H, s), 4.04 (2H, d, J=6.4 Hz), 6.88 (1H, dd, J=7.2, 4.8 Hz), 7.31 (1H, dd, J=8.4, 4.4 Hz), 7.37 (1H, dd, J=8.4, 1.2 Hz), 7.48 (1H, d, J=3.2 Hz), 7.66 (1H, dd, J=7.2, 1.6 Hz), 8.04 (1H, d, J=3.2 Hz), 8.06 (1H, dd, J=4.8, 1.6 Hz), 8.39 (1H, dd, J=4.4, 1.2 Hz).

Example 85

1-[(2-Methoxy-3-pyridyl)methyl]-4-[2-cyano-2-(3,4-methylenedioxyphenyl)ethyl]piperidine 227 mg of the title compound was obtained as a colorless oil from 200 mg of 4-[2-cyano-2-(3,4-methylenedioxyphenyl)ethyl]piperidine in accordance with the method of Reference Example 33.

$^1$H-NMR (400 MHz, CDCl$_3$) δ 1.26–1.40 (2H, m), 1.43–1.56 (1H, m), 1.63–1.80 (3H, m), 1.86–1.96 (1H, m), 2.00–2.10 (2H, m), 2.84–2.93 (2H, m), 3.48 (2H, s), 3.71–3.77 (1H, m), 3.94 (3H, s), 5.98 (2H, s), 6.73–6.80 (3H, m), 6.86 (1H, dd, J=7.2, 4.8 Hz), 7.62 (1H, dd, J=7.2, 2.0 Hz), 8.05 (1H, dd, J=4.8, 2.0 Hz).

Example 86

1-[(2-Methoxy-3-pyridyl)methyl]-4-[2-cyano-2-(2-methoxyphenyl)ethyl]piperidine 191 mg of the title compound was obtained as a colorless oil from 242 mg of 4-[2-cyano-2-(2-methoxyphenyl)ethyl]piperidine in accordance with the method of Example 80.

$^1$H-NMR (400 MHz, CDCl$_3$) δ 1.26–1.40 (2H, m), 1.52–1.74 (3H, m), 1.80–1.91 (2H, m), 2.01–2.12 (2H, m), 2.83–2.95 (2H, m), 3.48 (2H, s), 3.84 (3H, s), 3.95 (3H, s), 4.22–4.28 (1H, m), 6.86 (1H, dd, J=7.2, 5.2 Hz), 6.88 (1H, d, J=8.0 Hz), 6.98 (1H, dd, J=8.0, 7.6 Hz), 7.29 (1H, dd, J=8.0, 7.6 Hz), 7.40 (1H, d, J=8.0 Hz), 7.62 (1H, dd, J=7.2, 2.0 Hz), 8.05 (1H, dd, J=5.2, 2.0 Hz).

Example 87

1-[(2-Oxo-1,2-dihydro-3-pyridinyl)methyl]-4-[2-(methylsulfonyl)phenethyl]piperidine 479 mg of 1-[(2-methoxy-3-pyridyl)methyl]-4-[2-(methylsulfonyl)phenethyl]piperidine obtained in Example 1 and 2 ml of thionyl chloride were dissolved in 50 ml of ethanol, and the mixture was heated under reflux for 2 hours. The reaction mixture was basified by adding a 1N aqueous sodium hydroxide thereto, and the mixture was extracted with dichloromethane. The organic layer was washed with brine, and then dried over anhydrous magnesium sulfate. The solvent was evaporated, and the resulting crude product was purified by silica gel column chromatography (ethyl acetate), to give 368 mg of the title compound as white crystals.

$^1$H-NMR (400 MHz, CDCl$_3$) δ 1.32–1.48 (3H, m), 1.62–1.68 (2H, m), 1.75–1.82 (2H, m), 2.06–2.16 (2H, m), 2.91–2.99 (2H, m), 3.02–3.07 (2H, m), 3.08 (3H, s), 3.48 (2H, s), 6.33 (1H, dd, J=6.5, 6.5 Hz), 7.35–7.40 (3H, m), 7.53–7.58 (2H, m), 8.03 (1H, dd, J=8.3.1.4 Hz).

Example 88

1-[(2-Oxo-1,2-dihydro-3-pyridinyl)methyl]-4-(3,4-methylenedioxyphenethyl)piperidine $^1$H-NMR (400 MHz, CDCl$_3$) δ 1.25–1.38 (3H, m), 1.49–1.57 (2H, m), 1.68–1.77 (2H, m), 2.02–2.12 (2H, m), 2.52–2.58 (2H, m), 2.88–2.96 (2H, m), 3.47 (2H, s), 5.92 (2H, s), 6.34 (1H, dd, J=6.6, 6.6 Hz), 6.61 (1H, dd, J=7.9, 1.7 Hz), 6.67 (1H, d, J=1.7 Hz), 6.72 (1H, d, J=7.9 Hz), 7.36 (1H, d, J=6.6 Hz), 7.53 (1H, d, J=6.6 Hz).

Example 89

1-[(2-Oxo-1,2-dihydro-3-pyridinyl)methyl]-4-phenethylpiperidine $^1$H-NMR (400 MHz, CDCl$_3$) δ 1.26–1.40 (3H, m), 1.53–1.62 (2H, m), 1.69–1.79 (2H, m), 2.01–2.13 (2H, m), 2.58–2.67 (2H, m), 2.88–2.97 (2H, m), 3.47 (2H, s), 6.33 (1H, dd, J=6.6, 6.6 Hz), 7.14–7.21 (3H, s), 7.24–7.31 (2H, s), 7.36 (1H, d, J=6.6 Hz), 7.54 (1H, d, J=6.6 Hz).

Example 90

1-[(2-Oxo-1,2-dihydro-3-pyridinyl)methyl]-4-(2-hydroxyphenethyl)piperidine $^1$H-NMR (400 MHz, DMSO-d6) δ 1.12–1.24 (3H, m), 1.40–1.48 (2H, m), 1.64–1.71 (2H, m), 1.87–1.96 (2H, m), 2.48–2.55 (2H, m), 2.75–2.82 (2H, m), 3.22 (2H, s), 6.16 (1H, dd, J=6.6, 6.6 Hz), 6.69 (1H, ddd, J=7.5, 7.5, 1.2 Hz), 6.75 (1H, dd, J=7.5, 1.2 Hz), 6.96 (1H, ddd, J=7.5, 7.5, 1.7 Hz), 7.02 (1H, dd, J=7.5, 1.7 Hz), 7.24 (1H, dd, J=6.6, 2.2 Hz), 7.37 (1H, dd, J=6.6, 2.2 Hz).

Example 91

1-[(2-oxo-1,2-dihydro-3-pyridinyl)methyl]-4-(3-fluorophenethyl)piperidine $^1$H-NMR (400 MHz, CDCl$_3$) δ 1.24–1.40 (3H, m), 1.52–1.61 (2H, m), 1.68–1.77 (2H, m), 2.02–2.12 (2H, m), 2.58–2.66 (2H, m), 2.88–2.97 (2H, m), 3.47 (2H, s), 6.33 (1H, dd, J=6.8, 6.8 Hz), 6.83–6.91 (2H, m), 6.94 (1H, m), 7.19–7.26 (1H, m), 7.36 (1H, d, J=6.8 Hz), 7.54 (1H, d, J=6.8 Hz).

Example 92

1-[(2-Oxo-1,2-dihydro-3-pyridinyl)methyl]-4-(2-trifluoromethylphenethyl)piperidine $^1$H-NMR (400 MHz, CDCl$_3$) δ 1.29–1.45 (3H, m), 1.51–1.61 (2H, m), 1.70–1.81 (2H, m), 2.04–2.16 (2H, m), 2.73–2.82 (2H, m), 2.89–2.99 (2H, m), 3.49 (2H, s), 6.34 (1H, dd, J=6.8, 6.8 Hz), 7.26 (1H, dd, J=7.7, 7.6 Hz), 7.31 (1H, d, J=7.5 Hz), 7.36 (1H, d, J=6.8 Hz), 7.45 (1H, dd, J=7.6, 7.5 Hz), 7.54 (1H, d, J=6.8 Hz), 7.60 (1H, d, J=7.7 Hz).

Example 93

1-[(2-Oxo-1,2-dihydro-3-pyridinyl)methyl]-4-[2-(1-pyrazolo)phenethyl]piperidine $^1$H-NMR (400 MHz, CDCl$_3$) δ 1.12–1.24 (3H, m), 1.31–1.40 (2H, m), 1.50–1.59 (2H, m), 1.94–2.04 (2H, m), 2.51–2.59 (2H, m), 2.81–2.89 (2H, m), 3.42 (2H, s), 6.30 (1H, dd, J=6.4, 6.4 Hz), 6.42 (1H, dd, J=2.4, 2.0 Hz), 7.23–7.38 (5H, m), 7.52 (1H, d, J=6.4 Hz), 7.56 (1H, d, J=2.4 Hz), 7.70 (1H, d, J=2.0 Hz).

Example 94

1-[(2-Oxo-1,2-dihydro-3-pyridinyl)methyl]-4-[2-(4-acetylpiperazino)phenethyl]piperidine $^1$H-NMR (400 MHz, CDCl$_3$) δ 1.27–1.40 (3H, m), 1.53–1.61 (2H, m), 1.73–1.81 (2H, m), 2.03–2.12 (2H, m), 2.13 (3H, s), 2.65–2.72 (2H, m), 2.81–2.97 (6H, m), 3.46 (2H, s), 3.55–3.61 (2H, m), 3.68–3.77 (2H, m), 6.34 (1H, dd, J=6.4, 6.4 Hz), 7.04 (1H, d, J=7.6 Hz), 7.07 (1H, dd, J=7.6, 7.6 Hz), 7.17 (1H, dd, J=7.6, 7.6 Hz), 7.21 (1H, d, J=7.6 Hz), 7.36 (1H, d, J=6.4 Hz), 7.51 (1H, d, J=6.4 Hz).

Example 95

1-[(2-Oxo-1,2-dihydro-3-pyridinyl)methyl]-4-[6-(methylsulfonyl)-2,3-methylenedioxyphenethyl]piperidine $^1$H-NMR (400 MHz, CDCl$_3$) δ 1.32–1.44 (3H, m), 1.58–1.67 (2H, m), 1.74–1.84 (2H, m), 2.06–2.15 (2H, m), 2.90–2.98 (4H, m), 3.05 (3H, s), 3.49 (2H, s), 6.09 (2H, s), 6.34 (1H, dd, J=6.5, 6.5 Hz), 6.78 (1H, d, J=8.4 Hz), 7.37 (1H, d, J=6.5 Hz), 7.54 (1H, d, J=6.5 Hz), 7.62 (1H, d, J=8.4 Hz).

Example 96

1-[(2-Oxo-1,2-dihydro-3-pyridinyl)methyl]-4-[2-(2-thienyl)ethyl]piperidine $^1$H-NMR (400 MHz, CDCl$_3$) δ 1.27–1.40 (3H, m), 1.60–1.77 (4H, m), 2.02–2.12 (2H, m), 2.81–2.97 (4H, m), 3.47 (2H, s), 6.33 (1H, dd, J=6.9, 6.9 Hz), 6.78 (1H, d, J=3.5 Hz), 6.91 (1H, dd, J=5.1, 3.5 Hz), 7.11 (1H, d, J=5.1 Hz), 7.36 (1H, d, J=6.9 Hz), 7.52 (1H, d, J=6.9 Hz).

Example 97

1-[(2-Oxo-1,2-dihydro-3-pyridinyl)methyl]-4-[2-(3-methoxy-2-thienyl)ethyl]piperidine $^1$H-NMR (400 MHz, CDCl$_3$) δ 1.25–1.38 (3H, m), 1.52–1.61 (2H, m), 1.70–1.79 (2H, m), 2.01–2.12 (2H, m), 2.67–2.75 (2H, m), 2.87–2.96 (2H, m), 3.46 (2H, s), 3.81 (3H, s), 6.33 (1H, dd, J=6.4, 6.4 Hz), 6.81 (1H, d, J=5.2 Hz), 6.99 (1H, d, J=5.2 Hz), 7.36 (1H, d, J=6.4 Hz), 7.54 (1H, d, J=6.4 Hz).

Example 98

1-[(2-Oxo-1,2-dihydro-3-pyridinyl)methyl]-4-[2-(3-cyano-2-thienyl)ethyl]piperidine $^1$H-NMR (400 MHz, CDCl$_3$) δ 1.31–1.42 (3H, m), 1.63–1.81 (4H, m), 2.03–2.15 (2H, m), 2.90–2.99 (2H, m), 3.00–3.07 (2H, m), 3.48 (2H, s), 6.33 (1H, dd, J=6.5, 6.5 Hz), 7.11 (1H, d, J=5.3 Hz), 7.17 (1H, d, J=5.3 Hz), 7.35 (1H, d, J=6.5 Hz), 7.53 (1H, d, J=6.5 Hz).

Example 99

1-[(2-Oxo-1,2-dihydro-3-pyridinyl)methyl]-4-[2-(3-phenyl-2-thienyl)ethyl]piperidine $^1$H-NMR (400 MHz, CDCl$_3$) δ 1.20–1.33 (3H, m), 1.56–1.66 (4H, m), 1.96–2.07 (2H, m), 2.83–2.92 (4H, m), 3.44 (2H, s), 6.32 (1H, dd, J=6.4, 6.4 Hz), 7.00 (1H, d, J=5.2 Hz), 7.15 (1H, d, J=5.2 Hz), 7.27–7.43 (6H, m), 7.52 (1H, d, J=6.4 Hz).

Example 100

1-[(2-Oxo-1,2-dihydro-3-pyridinyl)methyl]-4-[2-(3-thienyl)ethyl]piperidine $^1$H-NMR (400 MHz, CDCl$_3$) δ 1.26–1.38 (3H, m), 1.55–1.62 (2H, m), 1.66–1.78 (2H, m), 2.01–2.12 (2H, m), 2.62–2.68 (2H, m), 2.88–2.96 (2H, m), 3.47 (2H, s), 6.34 (1H, dd, J=6.4 Hz), 6.91–6.95 (2H, m), 7.24 (2H, dd, J=4.8, 2.8 Hz), 7.34 (1H, d, J=6.4 Hz), 7.52 (1H, d, J=6.4 Hz).

Example 101

1-[(2-Oxo-1,2-dihydro-3-pyridinyl)methyl]-4-[2-[2-(methylsulfonyl)-3-thienyl]ethyl]piperidine $^1$H-NMR (400 MHz, CDCl$_3$) δ 1.34–1.46 (3H, m), 1.57–1.66 (2H, m), 1.73–1.82 (2H, m), 2.10–2.22 (2H, m), 2.92–3.03 (4H, m), 3.14 (3H, s), 3.54 (2H, s), 6.34 (1H, dd, J=6.6, 6.6 Hz), 7.01 (1H, d, J=5.0 Hz), 7.36 (1H, d, J=6.6 Hz), 7.54 (1H, d, J=6.6 Hz), 7.57 (1H, d, J=5.0 Hz).

Example 102

1-[(2-Oxo-1,2-dihydro-3-pyridinyl)methyl]-4-[2-(benzo[b]thiophen-2-yl)ethyl]piperidine $^1$H-NMR (400 MHz, CDCl$_3$) δ 1.29–1.43 (3H, m), 1.66–1.80 (4H, m), 2.02–2.13 (2H, m), 2.89–2.97 (4H, m), 3.47 (2H, s), 6.33 (1H, dd, J=6.4, 6.4 Hz), 7.00 (1H, s), 7.24 (1H, dd, J=7.2, 7.1 Hz), 7.30 (1H, dd, J=7.6, 7.1 Hz), 7.36 (1H, d, J=6.4 Hz), 7.53 (1H, d, J=6.4 Hz), 7.66 (1H, d, J=7.2 Hz), 7.76 (1H, d, J=7.6 Hz).

Example 103

1-[(2-Oxo-1,2-dihydro-3-pyridinyl)methyl]-4-[2-[2-(methylsulfonyl)-3-pyridyl]ethyl]piperidine $^1$H-NMR (400 MHz, CDCl$_3$) δ 1.32–1.46 (3H, m), 1.62–1.70 (2H, m), 1.74–1.83 (2H, m), 2.06–2.17 (2H, m), 2.91–2.99 (2H, m), 3.07–3.15 (2H, m), 3.37 (3H, s), 3.49 (2H, s), 6.34 (1H, dd, J=6.6, 6.6 Hz), 7.37 (1H, d, J=6.6 Hz), 7.43 (1H, dd, J=7.8, 4.6 Hz), 7.56 (1H, d, J=6.6 Hz), 7.72 (1H, dd, J=7.8, 1.6), 8.42 (1H, dd, J=4.8, 1.6 Hz).

Example 104

1-[(2-Oxo-1,2-dihydro-3-pyridinyl)methyl]-4-[2-(2-n-butyl-3-pyridyl)ethyl]piperidine $^1$H-NMR (400 MHz, CDCl$_3$) δ 0.96 (3H, t, J=7.3 Hz), 1.34–1.49 (5H, m), 1.49–1.60 (2H, m), 1.63–1.80 (4H, m), 2.06–2.17 (2H, m), 2.59–2.66 (2H, m), 2.77 (2H, t, J=8.1 Hz), 2.92–3.00 (2H, m), 3.50 (2H, s), 6.34 (1H, dd, J=6.4, 6.4 Hz), 7.04 (1H, dd, J=7.6, 4.8 Hz), 7.33–7.42 (2H, m), 7.53 (1H, d, J=6.4 Hz), 8.37 (1H, dd, J=4.8, 1.8 Hz).

Example 105

1-[(2-Oxo-1,2-dihydro-3-pyridinyl)methyl]-4-[2-(3-pyridyl)ethyl]piperidine $^1$H-NMR (400 MHz, CDCl$_3$) δ 1.28–1.40 (3H, m), 1.56–1.62 (2H, m), 1.70–1.78 (2H, m), 2.04–2.12 (2H, m), 2.60–2.66 (2H, m), 2.90–2.97 (2H, m), 3.47 (2H, s), 6.33 (1H, dd, J=6.6, 6.6 Hz), 7.21 (1H, dd, J=7.8, 4.8 Hz), 7.36 (1H, d, J=6.6 Hz), 7.49 (1H, ddd, J=7.8, 2.0, 2.0 Hz), 7.54 (1H, d, J=6.6 Hz), 8.42–8.46 (2H, m).

Example 106

1-[(2-Oxo-1,2-dihydro-3-pyridinyl)methyl]-4-[2-(2-phenoxy-3-pyridyl)ethyl]piperidine $^1$H-NMR (400 MHz, CDCl$_3$) δ 1.32–1.40 (3H, m), 1.6–1.68 (2H, m), 1.72–1.82 (2H, m), 2.04–2.12 (2H, m), 2.70–2.77 (2H, m), 2.90–2.97 (2H, m), 3.47 (2H, s), 6.33

(1H, dd, J=6.4, 6.4 Hz), 6.94 (1H, dd, J=7.2, 5.0 Hz), 7.07–7.12 (2H, m), 7.17 (1H, m), 7.33–7.42 (3H, m), 7.50–7.55 (2H, m), 8.00 (1H, dd, J=5.0, 1.8 Hz).

Example 107

1-[(2-Oxo-1,2-dihydro-3-pyridinyl)methyl]-4-[2-(5-methoxy-2-pyridyl)ethyl]piperidine $^1$H-NMR (400 MHz, CDCl$_3$) δ 1.30–1.44 (3H, m), 1.61–1.70 (2H, m), 1.74–1.84 (2H, m), 2.05–2.16 (2H, m), 2.80–2.87 (2H, m), 2.91–2.99 (2H, m), 3.49 (2H, s), 3.83 (3H, m), 6.34 (1H, dd, J=6.4, 6.4 Hz), 7.09 (1H, d, J=2.8 Hz), 7.09 (1H, d, J=2.8 Hz), 7.37 (1H, d, J=6.4 Hz), 7.57 (1H, d, J=6.4 Hz), 8.11 (1H, dd, J=2.8, 2.8 Hz).

Example 108

1-[(2-Oxo-1,2-dihydro-3-pyridinyl)methyl]-4-[[2-(4-methoxyphenyl)-3-pyridyl]ethyl]piperidine $^1$H-NMR (400 MHz, CDCl$_3$) δ 1.13–1.29 (3H, m), 1.41–1.50 (2H, m), 1.52–1.62 (2H, m), 1.96–2.09 (2H, m), 2.62–2.70 (2H, m), 2.81–2.93 (2H, m), 3.45 (2H, s), 3.85 (3H, s), 6.31 (1H, dd, J=6.4, 6.4 Hz), 6.96 (2H, d, J=8.8 Hz), 7.18 (1H, dd, J=7.8, 4.8 Hz), 7.33 (1H, d, J=6.4 Hz), 7.40 (2H, d, J=8.8 Hz), 7.55 (1H, d, J=6.4 Hz), 7.57 (1H, dd, J=7.8, 1.6 Hz), 8.50 (1H, dd, J=4.8, 1.6 Hz).

Example 109

1-[(2-Oxo-1,2-dihydro-3-pyridinyl)methyl]-4-[2-(1,3-thiazol-2-yl)ethyl]piperidine $^1$H-NMR (400 MHz, CDCl$_3$) δ 1.29–1.42 (3H, m), 1.69–1.83 (4H, m), 2.03–2.13 (2H, m), 2.89–2.97 (2H, m), 3.02–3.10 (2H, m), 3.47 (2H, s), 6.33 (1H, dd, J=6.6, 6.6 Hz), 7.19 (1H, d, J=3.3 Hz), 7.35 (1H, d, J=6.6 Hz), 7.53 (1H, d, J=6.6 Hz), 7.67 (1H, d, J=3.3 Hz).

Example 110

1-[(2-Oxo-1,2-dihydro-3-pyridinyl)methyl]-4-[2-[2-(1-morpholino)-3-pyridyl]ethyl]piperidine $^1$H-NMR (400 MHz, CDCl$_3$) δ 1.30–1.42 (3H, m), 1.56–1.64 (2H, m), 1.72–1.80 (2H, m), 2.04–2.12 (2H, m), 2.60–2.66 (2H, m), 2.72–2.78 (2H, m), 3.10 (4H, t, J=4.7 Hz), 3.48 (2H, s), 3.85 (4H, t, J=4.7 Hz), 6.34 (1H, dd, J=6.6, 6.6 Hz), 6.93 (1H, dd, J=7.4, 4.8 Hz), 7.36 (1H, d, J=6.6 Hz), 7.47 (1H, dd, J=7.4, 1.9 Hz), 7, 54 (1H, m), 8.19 (1H, dd, J=4.8, 1.9 Hz).

Example 111

1-[(2-Oxo-1,2-dihydro-3-pyridinyl)methyl]-4-[2-[(methylsulfonyl)amino]phenethyl]piperidine 155 mg of the title compound was obtained as colorless crystals from 286 mg of 1-[(2-methoxy-3-pyridyl)methyl]-4-[(2-methylsulfonylamino)phenethyl]piperidine obtained in Example 26, in the same manner as in Example 87.

$^1$H-NMR (400 MHz, CDCl$_3$) δ 1.31–1.40 (3H, m), 1.52–1.60 (2H, m), 1.72–1.80 (2H, m), 2.04–2.13 (2H, m), 2.64–2.71 (2H, m), 2.90–2.97 (2H, m), 3.03 (3H, s), 3.47 (2H, s), 6.33 (1H, dd, J=6.6, 6.6 Hz), 7.15–7.28 (3H, m), 7.34 (1H, d, J=6.6 Hz), 7.45 (1H, m), 7.54 (1H, m).

Example 112

1-[(2-Oxo-1,2-dihydro-3-pyridinyl)methyl]-4-[2-(2-methoxy-6-methyl-3-pyridyl)ethyl]piperidine 1-[(2-Oxo-1,2-dihydro-3-pyridinyl)methyl]-4-[2-(2-chloro-6-methyl-3-pyridyl)ethyl]piperidine was obtained in the same manner as in Example 87 from 275 mg of 1-[(2-methoxy-3-pyridyl)methyl]-4-[2-(2-chloro-6-methyl-3-pyridyl)ethyl]piperidine obtained in Example 27. Then, the product was dissolved in 5 ml of a 28% aqueous sodium methoxide, and the mixture was heated under reflux for 3 hours. Water was added to the reaction solution, and the mixture was extracted with ethyl acetate. The extract was washed with brine, and then dried over anhydrous magnesium sulfate. The solvent was evaporated, to give 80 mg of the title compound as white crystals.

$^1$H-NMR (400 MHz, CDCl$_3$) δ 1.21–1.39 (3H, m), 1.45–1.55 (2H, m), 1.68–1.78 (2H, m), 1.97–2.08 (2H, m), 2.41 (3H, s), 2.48–2.56 (2H, m), 2.85–2.95 (2H, m), 3.49 (2H, s), 3.92 (3H, s), 3.95 (3H, s), 6.35 (1H, dd, J=6.6, 6.6 Hz), 6.63 (1H, d, J=7.3 Hz), 7.23 (1H, d, J=7.3 Hz), 7.37 (1H, d, J=6.6 Hz), 7.53 (1H, d, J=6.6 Hz).

Example 113

1-[(2-Oxo-1,2-dihydro-3-pyridinyl)methyl]-4-[2-(6-methoxy-3-pyridyl)ethyl]piperidine 86 mg of the title compound was obtained as colorless crystals from 300 mg of 1-[(2-methoxy-3-pyridyl)methyl]-4-[2-(6-choro-3-pyridyl)ethyl]piperidine obtained in Example 28, in accordance with the method of Example 112.

$^1$H-NMR (400 MHz, CDCl$_3$) δ 1.24–1.44 (3H, m), 1.47–1.59 (2H, m), 1.67–1.78 (2H, m), 2.04–2.17 (2H, m), 2.51–2.58 (2H, m), 2.90–3.01 (2H, m), 3.51 (2H, s), 3.92 (3H, m), 6.35 (1H, dd, J=6.6, 6.6 Hz), 6.68 (1H, d, J=8.3 Hz), 7.36 (1H, d, J=6.6 Hz), 7.39 (1H, d, J=8.3, 2.4 Hz), 7.55 (1H, d, J=6.6 Hz), 7.95 (1H, d, J=2.4 Hz).

Example 114

1-[(2-Oxo-1,2-dihydro-3-pyridinyl)methyl]-4-[(E)-2-(2-pyridyl)-1-ethenyl]piperidine 110 mg of the title compound was obtained as colorless crystals from 121 mg of 1-[(2-methoxy-3-pyridyl)methyl]-4-[(E)-2-(2-pyridyl)-1-ethenyl]piperidine obtained in Example 29, in accordance with the method of Example 87.

$^1$H-NMR (400 MHz, CDCl$_3$) δ 1.57–1.72 (3H, m), 1.77–1.88 (2H, m), 2.15–2.28 (2H, m), 2.95–3.05 (2H, m), 3.52 (2H, s), 6.35 (1H, dd, J=6.6, 6.6 Hz), 6.49 (1H, d, J=15.9 Hz), 6.73 (1H, dd, J=15.9, 7.0 Hz), 7.11 (1H, dd, J=7.5, 5.0 Hz), 7.25 (1H, d, J=7.5 Hz), 7.37 (1H, d, J=6.6 Hz), 7.56–7.65 (2H, m), 8.54 (1H, m).

Example 115

1-[(2-Oxo-1,2-dihydro-3-pyridinyl)methyl]-4-[2-(2-pyridyl)ethyl]piperidine 128 mg of the title compound was obtained as colorless crystals from 150 mg of 1-[(2-methoxy-3-pyridyl)methyl]-4-[2-(2-pyridyl)ethyl]piperidine obtained in Example 30, in accordance with the method of Example 114.

$^1$H-NMR (400 MHz, CDCl$_3$) δ 1.28–1.42 (3H, m), 1.64–1.82 (4H, m), 2.03–2.15 (2H, m), 2.77–2.85 (2H, m), 2.90–2.99 (2H, m), 3.48 (2H, s), 6.33 (1H, dd, J=6.6, 6.6 Hz), 7.10 (1H, ddd, J=7.8, 4.4, 1.2 Hz), 7.14 (1H, d, J=7.8 Hz), 7.36 (1H, d, J=6.6 Hz), 7.53–7.62 (2H, m), 7.52 (1H, dd, J=4.4, 1.2 Hz).

Example 116

1-[(2-Oxo-1,2-dihydro-3-pyridinyl)methyl)-4-[(E)-2-(2,3-methylenedioxyphenyl)-1-ethenyl]piperidine 64 mg of the title compound was obtained as colorless crystals from 99 mg of 1-[(2-methoxy-3-pyridyl)methyl]-4-

[(E)-(2,3-methylenedioxyphenyl)-1-ethenyl]piperidine obtained in Example 31, in accordance with the method of Example 114.

$^1$H-NM (400 MHz, CDCl$_3$) δ 1.501.64 (3H, m), 1.70–1.83 (2H, m), 2.12–2.24 (2H, m), 2.94–3.02 (2H, m), 3.51 (2H, s), 5.94 (2H, s), 6.01 (1H, dd, J=15.8, 7.0 Hz), 6.29 (1H, d, J=15.8 Hz), 6.34 (1H, dd, J=6.8, 6.8 Hz), 6.74 (1H, d, J=8.1 Hz), 6.77 (1H, dd, J=8.1, 1.4 Hz), 6.90 (1H, d, J=1.4 Hz), 7.35 (1H, d, J=6.8 Hz), 7.56 (1H, d, J=6.8 Hz).

Example 117

1-[(2-Oxo-1,2-dihydro-3-pyridinyl)methyl]-4-[2-(2-chloro-3-pyridyl)ethyl]piperidine 1.15 g of the title compound was obtained as colorless crystals from 1.37 g of 1-[(2-methoxy-3-pyridyl)methyl]-4-[2-(2-chloro-3-pyridyl)ethyl]piperidine obtained in Example 32, in accordance with the method of Example 87.

$^1$H-NMR (400 MHz, CDCl$_3$) δ 1.32–1.44 (3H, m), 1.54–1.64 (2H, m), 1.72–1.84 (2H, m), 2.07–2.18 (2H, m), 2.69–2.78 (2H, m), 2.92–3.01 (2H, m), 3.51 (2H, s), 6.34 (1H, dd, J=6.6, 6.6 Hz), 7.18 (1H, dd, J=7.2, 4.8 Hz), 7.37 (1H, d, J=6.4 Hz), 7.54 (1H, dd, J=7.2, 1.8 Hz), 7.57 (1H, d, J=6.4 Hz), 8.25 (1H, dd, J=4.8, 1.8 Hz).

Example 118

1-[(2-Oxo-1,2-dihydro-3-pyridinyl)methyl]-4-[2-(2-methoxy-3-pyridyl)ethyl]piperidine 192 mg of the title compound was obtained as colorless crystals from 220 mg of 1-[(2-oxo-1,2-dihydro-3-pyridinyl)methyl]-4-[2-(2-chloro-3-pyridyl)ethyl]piperidine obtained in Example 117, in accordance with the method of Example 112.

$^1$H-NMR (400 MHz, CDCl$_3$) δ 1.28–1.40 (3H, m), 1.49–1.57 (2H, m), 1.72–1.80 (2H, m), 2.03–2.13 (2H, m), 2.54–2.60 (2H, m), 2.89–2.98 (2H, m), 3.48 (2H, s), 3.94 (3H, s), 6.33 (1H, dd, J=6.6 Hz), 6.80 (1H, dd, J=7.2, 5.0 Hz), 7.34–7.39 (2H, m), 7.57 (1H, d, J=6.6 Hz), 8.01 (1H, dd, J=5.2, 1.8 Hz).

Example 119

1-[(2-Oxo-1,2-dihydro-3-pyridinyl)methyl]-4-[2-(2-methylthio-3-pyridyl)ethyl]piperidine 168 mg of 1-[(2-oxo-1,2-dihydro-3-pyridinyl)methyl]-4-(2-(2-chloro-3-pyridyl)ethyl]piperidine obtained in Example 117 and 354 mg of sodium thiomethoxide were suspended in 5 ml of 1-methyl-2-pyrrolidinone, and the mixture was stirred at 150° C. for 2 hours. Water was added to the reaction solution, and the mixture was extracted with ethyl acetate. The organic layer was washed with brine, and then dried over anhydrous magnesium sulfate. The solvent was evaporated, and the crude product was purified by NH form silica gel column chromatography (methanol:ethyl acetate=1:19), to give 20 mg of the title compound as colorless crystals.

$^1$H-NMR (400 MHz, CDCl$_3$) δ 1.30–1.44 (3H, m), 1.54–1.64 (2H, m), 1.72–1.83 (2H, m), 2.05–2.16 (2H, m), 2.57 (3H, s), 2.57–2.66 (2H, m), 2.90–3.00 (2H, m), 3.49 (2H, s), 6.34 (1H, dd, J=6.6 Hz), 6.94 (1H, dd, J=7.4, 4.8 Hz), 7.31 (1H, dd, J=7.4, 1.9 Hz), 7.36 (1H, d, J=6.6 Hz), 7.56 (1H, d, J=6.6 Hz), 8.32 (1H, dd, J=4.8, 1.9 Hz).

Example 120

1-[(2-Oxo-1,2-dihydro-3-pyridinyl)methyl]-4-[2-[(2-methoxyethoxy)-3-pyridyl]ethyl]piperidine 183 mg of 1-[(2-oxo-1,2-dihydro-3-pyridinyl)methyl]-4-[2-(2-chloro-3-pyridyl)ethyl]piperidine obtained in Example 117 and 226 mg of oil-dispersed 60% sodium hydride were suspended in 3 ml of 2-methoxyethanol, and the mixture was stirred at 150° C. for 2 hours. Water was added to the reaction solution, and the mixture was extracted with dichloromethane. The organic layer was washed with brine, and then dried over anhydrous magnesium sulfate. The solvent was evaporated, and the crude product was purified by NH form silica gel column chromatography (methanol:ethyl acetate=1:19), to give 135 mg of the title compound as colorless crystals.

$^1$H-NMR (400 MHz, CDCl$_3$) δ 1.28–1.42 (3H, m), 1.50–1.60 (2H, m), 1.72–1.82 (2H, m), 2.03–2.15 (2H, m), 2.56–2.65 (2H, m), 2.893.00 (2H, m), 3.43 (3H, s), 3.48 (2H, s), 3.76 (2H, t, J=4.8 Hz), 4.48 (2H, t, J=4.8 Hz), 6.34 (1H, dd, J=6.6 Hz), 6.80 (1H, dd, J=7.2, 4.8 Hz), 7.34–7.41 (2H, m), 7.56 (1H, d, J=6.6 Hz), 7.97 (1H, dd, J=4.8, 1.8 Hz).

Example 121

1-[(2-Oxo-1,2-dihydro-3-pyridinyl)methyl]-4-[2-(2-cyclopropylmethoxy)-3-pyridyl]ethyl]piperidine 179 mg of 1-[(2-oxo-1,2-dihydro-3-pyridinyl)methyl]-4-[2-(2-chloro-3-pyridyl)ethyl]piperidine obtained in Example 117, 0.44 ml of cyclopropanemethanol and 246 mg of oil-dispersed 60% sodium hydride were suspended in 5 ml of 1-methyl-pyrrolidinone, and the mixture was stirred at 150° C. for 1 hour. Water was added to the reaction solution, and the mixture was extracted with dichloromethane. The organic layer was washed with brine, and then dried over anhydrous magnesium sulfate. The solvent was evaporated, and the crude product was purified by NH form silica gel column chromatography (methanol:ethyl acetate=1:19), to give 147 mg of the title compound as colorless crystals.

$^1$H-NMR (400 MHz, CDCl$_3$) δ 0.31–0.70 (2H, m), 0.54–0.60 (2H, m), 1.22–1.42 (4H, m), 1.52–1.60 (2H, m), 1.74–1.82 (2H, m), 2.05–2.14 (2H, m), 2.56–2.64 (2H, m), 2.90–2.99 (2H, m), 3.48 (2H, s), 4.14 (2H, d, J=7.0 Hz), 6.34 (1H, dd, J=6.6, 6.6 Hz), 6.78 (1H, dd, J=7.2, 5.0 Hz), 7.32–7.42 (2H, m), 7.55 (1H, d, J=6.6 Hz), 7.96 (1H, dd, J=5.0, 1.9 Hz).

Example 122

1-[(2-Oxo-1,2-dihydro-3-pyridinyl)methyl]-4-[2-(2-trifluoroethoxy)-3-pyridyl]ethyl]piperidine 373 mg of the title compound was obtained as colorless crystals from 404 mg of 1-[(2-oxo-1,2-dihydro-3-pyridinyl)methyl]-4-[2-(2-chloro-3-pyridyl)ethyl]piperidine obtained in Example 117 and 0.88 ml of trifluoroethanol, in accordance with the method of Example 120.

$^1$H-NMR (400 MHz, CDCl$_3$) δ 1.25–1.40 (3H, m), 1.50–1.58 (2H, m), 1.70–1.80 (2H, m), 2.02–2.14 (2H, m), 2.56–2.64 (2H, m), 2.89–2.98 (2H, m), 3.48 (2H, s), 4.76 (2H, q, J=8.4 Hz), 6.34 (1H, dd, J=6.6, 6.6 Hz), 6.90 (1H, dd, J=7.2, 5.0 Hz), 7.36 (1H, d, J=6.6 Hz), 7.44 (1H, dd, J=7.2, 2.0 Hz), 7.55 (1H, d, J=6.6 Hz), 7.98 (1H, dd, J=5.0, 2.0 Hz).

Example 123

1-[(2-Oxo-1,2-dihydro-3-pyridinyl)methyl]-4-[2-(2-hydroxyethoxy)-3-pyridyl]ethyl]piperidine 72 mg of the title compound was obtained as colorless crystals from 213 mg of 1-[(2-oxo-1,2-dihydro-3-pyridinyl)methyl]-4-[2-(2-chloro-3-pyridyl)ethyl]piperidine obtained in Example 117 and 395 mg of ethylene glycol, in accordance with the method of Example 121.

¹H-NMR (400 MHz, CDCl₃) δ 1.27–1.41 (3H, m), 1.50–1.59 (2H, m), 1.70–1.79 (2H, m), 2.03–2.13 (2H, m), 2.56–2.63 (2H, m), 2.90–2.97 (2H, m), 3.47 (2H, s), 3.92–3.97 (2H, m), 4.47–4.52 (2H, m), 6.33 (1H, dd, J=6.6, 6.6 Hz), 6.85 (1H, dd, J=7.2, 5.0 Hz), 7.36 (1H, d, J=6.6 Hz), 7.42 (1H, dd, J=7.2, 1.8 Hz), 7.55 (1H, m), 7.95 (1H, dd, J=5.0, 1.8 Hz).

Example 124

1-[(2-Oxo-1,2-dihydro-3-pyridinyl)methyl]-4-[2-[2-(N,N-dimethylamino)ethoxy-3-pyridyl]ethyl]piperidine 220 mg of the title compound was obtained as colorless crystals from 254 mg of 1-[(2-oxo-1,2-dihydro-3-pyridinyl)methyl]-4-[2-(2-chloro-3-pyridyl)ethyl]piperidine obtained in Example 117 and 0.77 ml of N,N-dimethylaminoethanol, in accordance with the method of Example 121.

¹H-NMR (400 MHz, CDCl₃) δ 1.25–1.40 (3H, m), 1.50–1.58 (2H, m), 1.72–1.80 (2H, m), 2.04–2.13 (2H, m), 2.36 (6H, s), 2.53–2.61 (2H, m), 2.76 (2H, t, J=5.8 Hz), 2.90–2.98 (2H, m), 3.48 (2H, s), 4.44 (2H, t, J=5.8 Hz), 6.35 (1H, dd, J=6.4, 6.4 Hz), 6.80 (1H, dd, J=7.2, 5.2 Hz), 7.34–7.40 (2H, m), 7.54 (1H, d, J=6.4 Hz), 7.99 (1H, dd, J=5.0, 2.0 Hz).

Example 125

1-[(2-Oxo-1,2-dihydro-3-pyridinyl)methyl]-4-[2-[4-(methylsulfonyl)-3-(1,3-thiazol-2-yl)-2-thienyl]ethyl]piperidine 90 mg of the title compound was obtained as colorless crystals from 230 mg of 1-[(2-methoxy-3-pyridyl)methyl]-4-[2-[4-(methylsulfonyl)-3-(1,3-thiazol-2-yl)-2-thienyl]ethyl]piperidine obtained in Example 33, in accordance with the method of Example 87.

¹H-NMR (400 MHz, CDCl₃) δ 1.18–1.33 (3H, m), 1.54–1.65 (4H, m), 1.97–2.09 (2H, m), 2.76–2.94 (4H, m), 3.24 (3H, s), 3.44 (2H, s), 6.31 (1H, dd, J=6.7, 6.7 Hz), 7.34 (1H, d, J=6.7 Hz), 7.52 (1H, d, J=6.7 Hz), 7.55 (1H, d, J=3.4 Hz), 7.94 (1H, d, J=3.4 Hz), 8.10 (1H, s).

Example 126

1-[(2-Oxo-1,2-dihydro-3-pyridinyl)methyl]-4-[2-[3-(1,3-thiazol-2-yl)-2-thienyl]ethyl]piperidine 156 mg of the title compound was obtained as colorless crystals from 230 mg of 1-[(2-methoxy-3-pyridyl)methyl]-4-[2-[3-(1,3-thiazol-2-yl)-2-thienyl]ethyl]piperidine obtained in Example 34, in accordance with the method of Example 87.

¹H-NMR (400 MHz, CDCl₃) δ 1.30–1.45 (3H, m), 1.65–1.81 (4H, m), 2.05–2.16 (2H, m), 2.90–2.99 (2H, m), 3.21–3.29 (2H, m), 3.49 (2H, s), 6.34 (1H, dd, J=6.8, 6.8 Hz), 7.13 (1H, d, J=5.2 Hz), 7.29 (1H, d, J=3.4 Hz), 7.36 (1H, d, J=6.8 Hz), 7.40 (1H, d, J=5.2 Hz), 7.54 (1H, d, J=6.8 Hz), 7.83 (1H, d, J=3.4 Hz).

Example 127

1-[(2-Oxo-1,2-dihydro-3-pyridinyl)methyl]-4-[2-(1,3-thiazol-2-yl)phenethyl]piperidine 171 mg of the title compound was obtained as colorless crystals from 233 mg of 1-[(2-methoxy-3-pyridyl)methyl]-4-[2-(1,3-thiazol-2-yl)phenethyl]piperidine obtained in Example 35, in accordance with the method of Example 87.

¹H-NMR (400 MHz, CDCl₃) δ 1.18–1.33 (3H, m), 1.43–1.52 (2H, m), 1.58–1.69 (2H, m), 1.98–2.09 (2H, m), 2.82–2.98 (4H, m), 3.45 (2H, s), 6.33 (1H, dd, J=6.6, 6.6 Hz), 7.26 (1H, dd, J=7.6, 7.6 Hz), 7.30 (1H, d, J=7.6 Hz), 7.36 (1H, dd, J=7.6, 7.6 Hz), 7.36 (1H, d, J=6.6 Hz), 7.39 (1H, d, J=3.2 Hz), 7.51 (1H, d, J=6.6 Hz), 7.57 (1H, d, J=7.6 Hz), 7.89 (1H, d, J=3.2 Hz).

Example 128

1-[(2-Oxo-1,2-dihydro-3-pyridinyl)methyl]-4-(2,3-methylenedioxyphenethyl)piperidine ¹H-NMR (400 MHz, CDCl₃) δ 1.24–1.40 (3H, m), 1.54–1.62 (2H, m), 1.70–1.80 (2H, m), 2.02–2.12 (2H, m), 2.56–2.63 (2H, m), 2.88–2.96 (2H, m), 3.46 (2H, s), 5.92 (2H, s), 6.33 (1H, dd, J=6.5 Hz), 6.64–6.70 (2H, m), 6.75 (1H, dd, J=7.8, 7.8 Hz), 7.36 (1H, d, J=6.5 Hz), 7.54 (1H, d, J=6.5 Hz).

Example 129

1-[(2-Oxo-1,2-dihydro-3-pyridinyl)methyl]-4-(2-cyanophenethyl)piperidine

¹H-NMR (400 MHz, CDCl₃) δ 1.31–1.45 (3H, m), 1.57–1.67 (2H, m), 1.72–1.82 (2H, m), 2.03–2.15 (2H, m), 2.81–2.99 (4H, m), 3.47 (2H, s), 6.32 (1H, dd, J=6.9, 6.3 Hz), 7.27 (1H, dd, J=7.6, 7.6 Hz), 7.32 (1H, d, J=7.6 Hz), 7.36 (1H, d, J=6.3 Hz), 7.50 (1H, dd, J=7.6, 7.6 Hz), 7.58 (1H, d, J=6.9 Hz), 7.60 (1H, d, J=7.6 Hz).

Example 130

1-[(2-Oxo-1,2-dihydro-3-pyridinyl)methyl]-4-(3-cyanophenethyl)piperidine

¹H-NMR (400 MHz, CDCl₃) δ 1.24–1.41 (3H, m), 1.52–1.62 (2H, m), 1.68–1.77 (2H, m), 2.01–2.13 (2H, m), 2.62–2.71 (2H, m), 2.89–2.99 (2H, m), 3.47 (2H, s), 6.32 (1H, dd, J=6.6, 6.6 Hz), 7.36–7.50 (4H, m), 7.36 (1H, d, J=6.6 Hz), 7.57 (1H, d, J=6.6 Hz).

Example 131

1-[(2-Oxo-1,2-dihydro-3-pyridinyl)methyl]-4-(4-phenylphenethyl)piperidine

¹H-NMR (400 MHz, CDCl₃) δ 1.32–1.42 (3H, m), 1.58–1.65 (2H, m), 1.73–1.81 (2H, m), 2.05–2.14 (2H, m), 2.64–2.70 (2H, m), 2.91–2.98 (2H, m), 3.48 (2H, s), 6.34 (1H, dd, J=6.4, 6.4 Hz), 7.23–7.28 (2H, m), 7.32 (1H, m), 7.3i (1H, d, J=6.4 Hz), 7.40–7.45 (2H, m), 7.49–7.60 (5H, m).

Example 132

1-[(2-Oxo-1,2-dihydro-3-pyridinyl)methyl]-4-(2-phenylphenethyl)piperidine

¹H-NMR (400 MHz, CDCl₃) δ 1.10–1.20 (3H, m), 1.37–1.45 (2H, m), 1.46–1.54 (2H, m), 1.94–2.03 (2H, m), 2.56–2.62 (2H, m), 2.79–2.86 (2H, m), 3.43 (2H, s), 6.32 (1H, dd, J=6.4, 6.4 Hz), 7.18–7.42 (10H, m), 7.48 (1H, d, J=6.4 Hz).

Example 133

1-[(2-Oxo-1,2-dihydro-3-pyridinyl)methyl]-4-(2-methylphenethyl)piperidine

¹H-NMR (400 MHz, CDCl₃) δ 1.32–1.43 (3H, m), 1.53–1.62 (2H, m), 1.73–1.84 (2H, m), 2.06–2.17 (2H, m), 2.46 (3H, s), 2.67–2.75 (2H, m), 2.90–3.00 (2H, m), 3.49 (2H, s), 6.34 (1H, dd, J=6.6 Hz), 7.06–7.16 (2H, m), 7.18–7.21 (2H, m), 7.37 (1H, d, J=6.6 Hz), 7.57 (1H, d, J=6.6 Hz).

Example 134

1-[(2-Oxo-1,2-dihydro-3-pyridinyl)methyl]-4-(2-methoxyphenethyl)piperidine $^1$H-NMR (400 MHz, CDCl$_3$) δ 1.25–1.40 (3H, m), 1.48–1.57 (2H, m), 1.72–1.82 (2H, m), 2.02–2.14 (2H, m), 2.58–2.66 (2H, m), 2.88–2.97 (2H, m), 3.48 (2H, s), 3.81 (3H, s), 6.35 (1H, dd, J=6.6, 6.6 Hz), 6.84 (1H, d, J=8.2 Hz), 6.88 (1H, dd, J=7.6, 7.6 Hz), 7.12 (1H, dd, J=7.6, 2.0 Hz), 7.17 (1H, ddd, J=8.2, 7.6, 2.0 Hz), 7.38 (1H, d, J=6.6 Hz), 7.53 (1H, d, J=6.6 Hz).

Example 135

1-[(2-Oxo-1,2-dihydro-3-pyridinyl)methyl]-4-[2-(3-methylsulfonyl-2-thienyl)ethyl]piperidine 6.09 g of 1-[(2-methoxy-3-pyridyl)methyl]-4-[2-(3-methylsulfonyl-2-thienyl)ethyl]piperidine obtained in Example 43 and 2 ml of thionyl chloride were dissolved in 50 ml of ethanol, and the mixture was heated under reflux for 2 hours. The reaction mixture was basified by adding a 1N aqueous sodium hydroxide thereto, and then extracted with dichloromethane. The organic layer was washed with brine, and then dried over anhydrous magnesium sulfate. The solvent was evaporated, and the resulting crude product was purified by NH form silica gel column chromatography (ethyl acetate), to give 4.89 g of the title compound as colorless crystals.

$^1$H-NMR (400 MHz, CDCl$_3$) δ 1.30–1.44 (3H, m), 1.67–1.80 (4H, m), 2.04–2.13 (2H, m), 2.90–2.97 (2H, m), 3.06 (3H, s), 3.18–3.24 (2H, m), 3.46 (2H, s), 6.32 (1H, dd, J=6.6, 6.6 Hz), 7.18 (1H, d, J=5.5 Hz), 7.31 (1H, d, J=5.5 Hz), 7.36 (1H, dd, J=6.6, 2.0 Hz), 7.56 (1H, dd, J=6.6, 2.0 Hz).

Example 136

1-[(2-Oxo-1,2-dihydro-3-pyridinyl)methyl]-4-[2-(methylsulfonyl)-3,4-methylenedioxyphenethyl]piperidine 875 mg of the title compound was obtained as colorless crystals from 1.45 g of 1-[(2-methoxy-3-pyridyl)methyl]-4-[2-(methylsulfonyl)-3,4-methylenedioxyphenethyl]piperidine obtained in Example 46, in accordance with the method of Example 135.

$^1$H-NMR (400 MHz, CDCl$_3$) δ 1.30–1.42 (3H, m), 1.52–1.60 (2H, m), 1.72–1.80 (2H, m), 2.07–2.16 (2H, m), 2.90–2.96 (2H, m), 2.96–3.02 (2H, m), 3.21 (3H, s), 3.48 (2H, s), 6.12 (2H, s), 6.34 (1H, dd, J=6.5, 6.5 Hz), 6.75 (1H, d, J=8.1 Hz), 6.93 (1H, d, J=8.1 Hz), 7.37 (1H, d, J=6.5 Hz), 7.53 (1H, d, J=6.5 Hz).

Example 137

1-[(2-Oxo-1,2-dihydro-3-pyridinyl)methyl]-4-[2-[2-(1,3-thiazol-2-yl)-3-pyridyl]ethyl]piperidine $^1$H-NMR (400 MHz, CDCl$_3$) δ 1.32–1.46 (3H, m), 1.54–1.63 (2H, m), 1.73–1.82 (2H, m), 2.06–2.16 (2H, m), 2.90–2.98 (2H, m), 3.27–3.34 (2H, m), 3.49 (2H, s), 6.34 (1H, dd, J=6.4, 6.4 Hz), 7.23 (1H, dd, J=7.6, 4.4 Hz), 7.37 (1H, d, J=6.4 Hz), 7.40 (1H, d, J=3.6 Hz), 7.56 (1H, d, J=6.4 Hz), 7.61 (1H, dd, J=7.6, 1.6 Hz), 7.91 (1H, d, J=3.6 Hz), 8.47 (1H, dd, J=4.4, 1.6 Hz).

Example 138

1-[(2-Oxo-1,2-dihydro-3-pyridinyl)methyl]-4-[2-[1-(4-hydroxy)piperidino]-3-pyridyl]ethyl]piperidine 49 mg of the title compound was obtained as a colorless oil from 70 mg of 1-[(2-methoxy-3-pyridyl)methyl]-4-[2-[1-(4-hydroxy)piperidino]-3-pyridyl)ethyl]piperidine obtained in Example 49 in accordance with the method of Example 135.

$^1$H-NMR (400 MHz, CDCl$_3$) δ 1.26–1.42 (3H, m), 1.54–1.62 (2H, m), 1.64–1.82 (4H, m), 1.96–2.14 (4H, m), 2.58–2.65 (2H, m), 2.84–2.99 (4H, m), 3.25–3.34 (2H, m), 3.48 (2H, s), 3.84 (1H, m), 6.33 (1H, dd, J=6.6, 6.6 Hz), 6.90 (1H, dd, J=7.4, 4.9 Hz), 7.37 (1H, d, J=6.6 Hz), 7.44 (1H, dd, J=7.4.1.9 Hz), 7.55 (1H, d, J=6.6 Hz), 8.15 (1H, dd, J=4.9, 1.9 Hz).

Example 139

1-[(2-Oxo-1,2-dihydro-3-pyridinyl)methyl]-4-[2-[2-(3-cyanopropoxy)-3-pyridyl]ethyl]piperidine $^1$H-NMR (400 MHz, CDCl$_3$) δ 1.27–1.40 (31H, m), 1.48–1.57 (2H, m), 1.70–1.81 (2H, m), 2.03–2.20 (4H, m), 2.51–2.61 (4H, m), 2.89–2.97 (2H, m), 3.47 (2H, s), 4.40–4.47 (2H, m), 6.33 (1H, dd, J=6.4, 6.4 Hz), 6.82 (1H, dd, J=7.2, 5.2 Hz), 7.35 (1H, d, J=6.4 Hz), 7.38 (1H, dd, J=7.2, 2.0 Hz), 7.55 (1H, d, J=6.4 Hz), 7.97 (1H, dd, J=5.2, 2.0 Hz).

Example 140

1-[(2-Oxo-1,2-dihydro-3-pyridinyl)methyl]-4-[2-[1-(2-fluorobenzyl)-2-oxo-1,2-dihydro-3-pyridinyl]ethyl]piperidine $^1$H-NMR (400 MHz, CDCl$_3$) δ 1.28–1.41 (3H, m), 1.48–1.57 (2H, m), 1.71–1.82 (2H, m), 2.01–2.15 (2H, m), 2.52–2.58 (2H, m), 2.88–2.98 (2H, m), 3.49 (2H, s), 5.17 (2H, s), 6.08–6.13 (1H, m), 6.34 (1H, dd, J=6.4, 6.4 Hz), 7.03–7.17 (3H, m), 7.24–7.31 (2H, m), 7.36 (1H, d, J=6.4 Hz), 7.40–7.46 (1H, m), 7.55 (1H, d, J=6.4 Hz).

Example 141

1-[(2-Oxo-1,2-dihydro-3-pyridinyl)methyl]-4-[2-oxo-2-(2-thienyl)ethyl]piperidine 9.6 g of 1-[(2-methoxy-3-pyridyl)methyl]-4-[2-oxo-2-(2-thienyl)ethyl]piperidine obtained in Example 54 and 8.5 ml of thionyl chloride were dissolved in 60 ml of ethanol, and the mixture was heated under reflux for 3 hours. The solvent was evaporated, and then the residue was dissolved in chloroform and a 1N aqueous sodium hydroxide. The organic layer was separated, washed with brine, and then dried over anhydrous magnesium sulfate. The solvent was evaporated, and the crude product was recrystallized from ethanol, to give 9.0 g of the title compound as colorless crystals.

$^1$H-NMR (400 MHz, CDCl$_3$) δ 1.36–1.49 (2H, m), 1.72–1.81 (2H, m), 2.03 (1H, m), 2.09–2.20 (2H, m), 2.82 (2H, d, J=7.0 Hz), 2.87–2.96 (2H, m), 3.47 (2H, s), 6.32 (1H, dd, J=6.6, 6.6 Hz), 7.13 (1H, dd, J=4.9, 3.9 Hz), 7.35 (1H, d, J=6.6 Hz), 7.54 (1H, d, J=6.6 Hz), 7.63 (1H, dd, J=4.9, 1.1 Hz), 7.70 (1H, dd, J=3.9, 1.1 Hz).

Example 142

1-[(2-Oxo-1,2-dihydro-3-pyridinyl)methyl]-4-(2-oxo-2-phenylethyl)piperidine $^1$H-NMR (400 MHz, CDCl$_3$) δ 1.35–1.49 (2H, m), 1.72–1.82 (2H, m), 1.97–2.22 (3H, m), 2.87–2.97 (3H, m), 3.48 (2H, s), 6.32 (1H, dd, J=6.6, 6.6 Hz), 7.36 (1H, d, J=6.6 Hz), 7.46 (1H, dd, J=8.0, 8.0 Hz), 7.55 (1H, d, J=6.6 Hz), 7.56 (1H, dd, J=8.0, 8.0 Hz), 7.95 (1H, d, J=8.0 Hz).

Example 143

1-[(2-Oxo-1,2-dihydro-3-pyridinyl)methyl]-4-[2-(2-chlorophenyl)-2-oxoethyl]piperidine $^1$H-NMR (400 MHz, CDCl$_3$) δ 1.33–1.47 (2H, m), 1.72–1.82 (2H, m), 2.01 (1H, m), 2.09–2.21 (2H, m), 2.85–2.96 (4H, m), 3.47 (2H, s), 6.32 (1H, dd, J=6.8, 6.8 Hz), 7.29–7.34 (1H, m), 7.35 (1H, d, J=6.8 Hz), 7.35–7.44 (3H, m), 7.54 (1H, d, J=6.8 Hz).

Example 144

1-[(2-Oxo-1,2-dihydro-3-pyridinyl)methyl]-4-[2-(2-methoxyphenyl)-2-oxoethyl]piperidine $^1$H-NMR (400 MHz, CDCl$_3$) δ 1.32–1.46 (2H, m), 1.69–1.79 (2H, m), 1.99 (1H, m), 2.09–2.20 (2H, m), 2.86–2.96 (3H, m), 3.48 (2H, s), 3.89 (3H, s), 6.33 (1H, dd, J=7.0, 5.8 Hz), 6.99 (1H, dd, J=7.5, 7.2 Hz), 6.95 (1H, d, J=8.4 Hz), 7.37 (1H, d, J=5.8 Hz), 7.44 (1H, ddd, J=8.4, 7.2, 1.8 Hz), 7.53 (1H, d, J=7.0 Hz), 7.62 (1H, dd, J=7.5, 1.8 Hz).

Example 145

1-[(2-Oxo-1,2-dihydro-3-pyridinyl)methyl]-4-[2-(2-methylsulfonylphenyl)-2-oxoethyl]piperidine $^1$H-NMR (400 MHz, CDCl$_3$) δ 1.35–1.49 (2H, m), 1.81–1.91 (2H, m), 2.05–2.25 (3H, m), 2.85–2.99 (4H, m), 3.25 (3H, s), 3.49 (2H, s), 6.32 (1H, dd, J=6.6, 6.2 Hz), 7.36 (1H, d, J=6.2 Hz), 7.41 (1H, d, J=7.5 Hz), 7.55 (1H, d, J=6.6 Hz), 7.61 (1H, dd, J=7.7, 7.5 Hz), 7.69 (1H, dd, J=7.5, 7.5 Hz), 8.07 (1H, d, J=7.7 Hz).

Example 146

1-[(2-Oxo-1,2-dihydro-3-pyridinyl)methyl]-4-[2-(2-cyclopropylmethoxyphenyl)-2-oxoethyl]piperidine $^1$H-NMR (400 MHz, CDCl$_3$) δ 0.32–0.38 (2H, m), 0.63–0.70 (2H, m), 1.24–1.46 (3H, m), 1.70–1.80 (2H, m), 2.02 (1H, m), 2.08–2.19 (2H, m), 2.86–2.94 (2H, m), 3.02 (2H, d, J=6.8 Hz), 3.47 (2H, s), 3.89 (2H, d, J=7.2 Hz), 6.32 (1H, dd, J=6.9, 5.9 Hz), 6.88 (1H, d, J=8.2 Hz), 6.97 (1H, dd, J=7.7, 7.4 Hz), 7.36 (1H, d, J=5.9 Hz), 7.41 (1H, dd, J=8.2, 7.4 Hz), 7.53 (1H, d, J=6.9 Hz), 7.65 (1H, d, J=7.7 Hz).

Example 147

1-[(2-Oxo-1,2-dihydro-3-pyridinyl)methyl]-4-[2-oxo-2-(2-trifluoromethylphenyl)ethyl]piperidine $^1$H-NMR (400 MHz, CDCl$_3$) δ 1.31–1.45 (2H, m), 1.75–1.85 (2H, m), 1.95–2.24 (3H, m), 2.80 (2H, d, J=6.6 Hz), 2.88–2.98 (2H, m), 3.48 (2H, s), 6.32 (1H, dd, J=7.1, 6.2 Hz), 7.36 (1H, d, J=6.2 Hz), 7.40 (1H, d, J=7.3 Hz), 7.54 (1H, d, J=7.1 Hz), 7.55 (1H, dd, J=7.8, 7.1 Hz), 7.60 (1H, dd, J=7.8, 7.3 Hz), 7.71 (1H, d, J=7.1 Hz).

Example 148

1-[(2-Oxo-1,2-dihydro-3-pyridinyl)methyl]-4-[2-oxo-2-(3-thienyl)ethyl]piperidine $^1$H-NMR (400 MHz, CDCl$_3$) δ 1.34–1.48 (2H, m), 1.71–1.81 (2H, m), 2.02 (1H, m), 2.09–2.21 (2H, m), 2.80 (2H, d, J=6.8 Hz), 2.88–2.97 (2H, m), 3.47 (2H, s), 6.32 (1H, dd, J=6.8, 6.8 Hz), 7.31 (1H, dd, J=5.1, 2.9 Hz), 7.36 (1H, d, J=6.8 Hz), 7.54 (1H, d, J=6.8 Hz), 7.545 (1H, d, J=5.1 Hz), 8.04 (1H, d, J=2.9 Hz).

Example 149

1-[(2-Oxo-1,2-dihydro-3-pyridinyl)methyl]-4-[2-oxo-2-(1,3-thiazol-2-yl)ethyl]piperidine $^1$H-NMR (400 MHz, CDCl$_3$) δ 1.39–1.52 (2H, m), 1.73–1.82 (2H, m), 2.01–2.21 (3H, m), 2.87–2.96 (2H, m), 3.11 (2H, d, J=6.8 Hz), 3.47 (2H, s), 6.32 (1H, dd, J=6.6, 6.6 Hz), 7.34 (1H, d, J=6.6 Hz), 7.54 (1H, d, J=6.6 Hz), 7.67 (1H, d, J=3.1 Hz), 8.00 (1H, dd, J=3.1 Hz).

Example 150

1-[(2-Oxo-1,2-dihydro-3-pyridinyl)methyl]-4-[2-(3,4-methylenedioxyphenyl)-2-oxoethyl]piperidine $^1$H-NMR (400 MHz, CDCl$_3$) δ 1.34–1.45 (2H, m), 1.71–1.80 (2H, m), 2.01 (1H, m), 2.10–2.20 (2H, m), 2.81 (2H, d, J=6.8 Hz), 2.88–2.96 (2H, m), 3.47 (2H, s), 6.04 (2H, s), 6.33 (1H, dd, J=6.5, 6.5 Hz), 6.85 (1H, d, J=8.2 Hz), 7.36 (1H, d, J=6.5 Hz), 7.43 (1H, d, J=1.7 Hz), 7.52 (1H, d, J=6.5 Hz), 7.55 (1H, dd, J=8.2, 1.7 Hz).

Example 151

1-[(2-Oxo-1,2-dihydro-3-pyridinyl)methyl]-4-[2-oxo-2-[3-(1,3-thiazol-2-yl)-2-thienyl]ethyl]piperidine $^1$H-NMR (400 MHz, CDCl$_3$) δ 1.31–1.45 (2H, m), 1.69–1.78 (2H, m), 1.96–2.19 (3H, m), 2.80 (2H, d, J=6.8 Hz), 2.85–2.94 (2H, m), 3.46 (2H, s), 6.31 (1H, dd, J=6.9, 5.9 Hz), 7.35 (1H, d, J=5.9 Hz), 7.47 (1H, d, J=3.3 Hz), 7.52 (1H, d, J=6.9 Hz), 7.54 (1H, d, J=5.2 Hz), 7.82 (1H, d, J=5.2 Hz), 7.93 (1H, d, J=3.3 Hz).

Example 152

1-[(2-Oxo-1,2-dihydro-3-pyridinyl)methyl]-4-[2-oxo-2-(3-phenyl-2-thienyl)ethyl]piperidine $^1$H-NMR (400 MHz, CDCl$_3$) δ 1.09–1.24 (2H, m), 1.48–1.59 (2H, m), 1.83 (1H, m), 1.98–2.11 (2H, m), 2.42 (2H, d, J=6.8 Hz), 2.75–2.87 (2H, m), 3.42 (2H, s), 6.30 (1H, dd, J=7.5, 6.0 Hz), 7.06 (1H, d, J=4.9 Hz), 7.33 (1H, d, J=6.0 Hz), 7.34–7.46 (5H, m), 7.48 (1H, d, J=7.5 Hz), 7.54 (1H, d, J=4.9 Hz).

Example 153

1-[(2-Oxo-1,2-dihydro-3-pyridinyl)methyl]-4-[2-(2-chloro-3-pyridinyl)-2-oxoethyl]piperidine In acetonitrile (4 ml) were dissolved 100 mg of 1-[(2-methoxy-3-pyridyl)methyl]-4-[2-(2-chloro-3-pyridyl)-2-oxoethyl)piperidine obtained in Example 62 and 0.35 ml of a 4 M hydrogen chloride ethyl acetate solution, followed by heating under reflux for 1 hour. The solvent was evaporated, and then the residue was dissolved in ethyl acetate and a 1N sodium hydroxide aqueous solution. The organic layer was separated, washed with brine, and then dried over anhydrous magnesium sulfate. The solvent was evaporated, and the crude product was recrystallized from ethanol, to give 46 mg of the title compound as colorless crystals.

$^1$H-NMR (400 MHz, CDCl$_3$) δ 1.34–1.48 (2H, m), 1.71–1.81 (2H, m), 2.02 (1H, m), 2.09–2.21 (2H, m), 2.87–2.98 (4H, m), 3.47 (2H, s), 6.31 (1H, dd, J=6.6, 6.6 Hz), 7.33 (1H, dd, J=7.5, 4.8 Hz), 7.35 (1H, d, J=6.6 Hz), 7.54 (1H, d, J=6.6 Hz), 7.77 (1H, dd, J=7.5, 1.9 Hz), 8.48 (1H, dd, J=4.8, 1.9 Hz).

Example 154

1-[(2-Oxo-1,2-dihydro-3-pyridinyl)methyl]-4-[2-(2-methylsulfonylaminophenyl)-2-oxoethyl]piperidine In acetonitrile (4 ml) were dissolved 90 mg of 1-[(2-methoxy-3-pyridyl)methyl]-4-[2-(2-methanesulfonylaminophenyl)-2-oxoethyl]piperidine obtained in Example 65 and 0.30 ml of concentrated hydrochloric acid, followed by heating under reflux for 5 hours. The solvent was evaporated, and then the residue was dissolved in ethyl acetate and an aqueous 1N sodium hydroxide. The organic layer was separated, washed with brine, and then dried over anhydrous magnesium sulfate. The solvent was evaporated, and the crude product was recrystallized from ethanol, to give 45 mg of the title compound as colorless crystals.

$^1$H-NMR (400 MHz, CDCl$_3$) δ 1.33–1.47 (2H, m), 1.75–1.89 (2H, m), 2.01–2.25 (3H, m), 2.83–2.98 (4H, m), 3.50 (5H, m), 6.33 (1H, dd, J=6.6, 6.6 Hz), 7.36 (1H, d, J=6.6 Hz), 7.40 (1H, dd, J=5.6, 3.2 Hz), 7.52 (1H, d, J=6.6 Hz), 7.55 (1H, d, J=3.2 Hz), 7.57 (1H, dd, J=3.4 Hz), 7.67 (1H, dd, J=5.6, 3.4 Hz).

Example 155

1-[(2-Oxo-1.2-dihydro-3-pyridinyl)methyl]-4-(3-phenylpropyl)piperidine 161 mg of the title compound was obtained as colorless crystals from 214 mg of 1-[(2-methoxy-3-pyridyl)methyl]-4-(3-phenylpropyl)piperidine obtained in Example 76, in accordance with the method of Example 141.

$^1$H-NMR (400 MHz, CDCl$_3$) δ 1.22–1.34 (5H, m), 1.58–1.72 (4H, m), 2.00–2.10 (2H, m), 2.59 (2H, t, J=7.8 Hz), 2.86–2.94 (2H, m), 3.45 (2H, s), 6.32 (1H, dd, J=6.6, 6.6 Hz), 7.14–7.20 (3H, m), 7.24–7.30 (2H, m), 7.36 (1H, d, J=6.6 Hz), 7.53 (1H, m).

Example 156

1-[(2-Oxo-1,2-dihydro-3-pyridinyl)methyl]-4-benzylpiperidine 365 mg of the title compound was obtained as colorless crystals from 472 mg of 1-[(2-methoxy-3-pyridyl)methyl]-4-benzylpiperidine obtained in Example 78, in accordance with the method of Example 141.

$^1$H-NMR (400 MHz, CDCl$_3$) δ 1.30–1.42 (2H, m), 1.56 (1H, m), 1.60–1.68 (2H, m), 2.02–2.10 (2H, m), 2.55 (2H, d, J=7.0 Hz), 2.89–2.96 (2H, m), 3.46 (2H, s), 6.32 (1H, dd, J=6.6, 6.6 Hz), 7.12–7.21 (3H, m), 7.24–7.30 (2H, m), 7.35 (1H, d, J=6.6 Hz), 7.54 (1H, d, J=6.6 Hz).

Example 157

1-[(2-Oxo-1,2-dihydro-3-pyridinyl)methyl]-4-(4-phenylbutyl)piperidine 105 mg of the title compound was obtained as colorless crystals from 150 mg of 1-[(2-methoxy-3-pyridyl)methyl]-4-(4-phenylbutyl)piperidine obtained in Example 79, in accordance with the method of Example 141.

$^1$H-NMR (400 MHz, CDCl$_3$) δ 1.20–1.40 (7H, m), 1.56–1.70 (4H, m), 2.02–2.12 (2H, m), 2.60 (2H, t, J=7.7 Hz), 2.88–2.96 (2H, m), 3.47 (2H, s), 6.33 (1H, dd, J=6.5, 6.5 Hz), 7.14–7.20 (3H, m), 7.24–7.30 (2H, m), 7.37 (1H, d, J=6.5 Hz), 7.54 (1H, d, J=6.5 Hz).

Example 158

1-[(2-Oxo-1,2-dihydro-3-pyridinyl)methyl]-4-[oxo(2-thienyl)methyl]piperidine 101 mg of the title compound was obtained as colorless crystals from 273 mg of 1-[(2-methoxy-3-pyridyl)methyl]-4-[oxo(2-thienyl)methyl)piperidine obtained in Example 80, in accordance with the method of Example 172.

$^1$H-NMR (400 MHz, CDCl$_3$) δ 1.86–2.02 (4H, m), 2.20–2.30 (2H, m), 3.00–3.07 (2H, m), 3.13 (1H, m), 3.52 (2H, s), 6.33 (1H, dd, J=6.6, 6.6 Hz), 7.14 (1H, dd, J=5.0, 4.0 Hz), 7.33 (1H, dd, J=6.6, 2.0 Hz), 7.61 (1H, m), 7.64 (1H, dd, J=5.0, 1.0 Hz), 7.74 (1H, dd, J=4.0, 1.0 Hz).

Example 159

1-[(2-Oxo-1,2-dihydro-3-pyridinyl)methyl]-4-(3-oxo-3-phenylpropyl)piperidine 414 mg of 1-[(2-methoxy-3-pyridyl)methyl]-4-piperidinecarboxaldehyde obtained in Reference Example 2, 0.46 ml of diethyl (2-oxo-2-phenylethyl)phosphonate and 78 mg of oil-suspended 60% sodium hydride were suspended in 8 ml of tetrahydrofuran, followed by stirring at room temperature for 1 hour. Ethyl acetate was added to the reaction solution, the mixture was washed with a 1N sodium hydroxide aqueous solution and brine, and then dried over anhydrous magnesium sulfate. The solvent was evaporated, and the resulting crude product and 160 mg of 10% palladium-carbon powder (water-containing product) were suspended in 10 ml of ethanol. After the atmosphere of a container was replaced with hydrogen, the mixture was stirred at room temperature under normal pressure for 4 hours. The reaction solution was filtered, and the filtrate was evaporated. The resulting crude product and purified by silica gel column chromatography (methanol:ethyl acetate=1:9). In ethanol (2 ml) were dissolved the resulting product and 0.15 ml of thionyl chloride, followed by heating under reflux for 2 hours. The mixture was basified by adding a 1N sodium hydroxide aqueous solution thereto, and then extracted with dichloromethane. The organic layer was washed with brine, and then dried over anhydrous magnesium sulfate. The solvent was evaporated, and the resulting crude product and purified by NH form silica gel column chromatography (ethyl acetate), to give 104 mg of the title compound as colorless crystals.

$^1$H-NMR (400 MHz, CDCl$_3$) δ 1.30–1.42 (3H, m), 1.67–1.78 (4H, m), 2.04–2.14 (2H, m), 2.90–2.97 (2H, m), 3.00 (2H, t, J=7.5 Hz), 3.46 (2H, 8), 6.32 (1H, dd, J=6.6, 6.6 Hz), 7.36 (1H, d, J=6.6 Hz), 7.44–7.49 (2H, m), 7.53–7.59 (2H, m), 7.96–7.99 (2H, m).

Example 160

N4-(2-Phenyl)benzyl-1-[(2-oxo-1,2-dihydro-3-pyridinyl)methyl]-4-piperidinecarboxamide 47 mg of the title compound was obtained as colorless crystals from 92 mg of N4-(2-phenyl)benzyl-1-[(2-methoxy-3-pyridyl)methyl]-4-piperidinecarboxamide obtained in Example 82, in accordance with the method of Example 141.

$^1$H-NMR (400 MHz, DMSO-d6) δ 1.52–1.68 (4H, m), 1.90–1.98 (2H, m), 2.14 (1H, m), 2.78–2.85 (2H, m), 3.23

(2H, 9), 4.17 (2H, d, J=5.8 Hz), 6.17 (1H, dd, J=6.7, 6.7 Hz), 7.19–7.27 (2H, m), 7.29–7.40 (7H, m), 7.41–7.47 (2H, m), 8.18 (1H, t, J=5.8 Hz).

Example 161

1-[(2-Oxo-1,2-dihydro-3-pyridinyl)methyl]-4-[[[2-(1,3-thiazol-2-yl)-3-pyridyl]oxy]methyl]piperidine 200 mg of the title compound was obtained as colorless crystals from 238 mg of 1-[(2-methoxy-3-pyridyl)methyl]-4-[[[2-(1,3-thiazol-2-yl)-3-pyridyl]oxy]methyl]piperidine obtained in Example 84, in accordance with the method of Example 141.

$^1$H-NMR (400 MHz, CDCl$_3$) δ 1.47–1.61 (2H, m), 1.93–2.26 (5H, m), 2.97–3.06 (2H, m), 3.52 (2H, s), 4.04 (2H, d, J=6.4 Hz), 6.32 (1H, dd, J=6.4, 6.4 Hz), 7.30 (1H, dd, J=8.4, 4.4 Hz), 7.35 (1H, d, J=6.4 Hz), 7.36 (1H, dd, J=8.4, 1.2 Hz), 7.48 (1H, d, J=3.0 Hz), 7.57 (1H, d, J=6.4 Hz), 8.03 (1H, d, J=3.0 Hz), 8.40 (1H, dd, J=4.4, 1.2 Hz).

Example 162

1-[(2-Oxo-1,2-dihydro-3-pyridinyl)methyl]-4-[2-cyano-2-(3,4-methylenedioxyphenyl)ethyl]piperidine 183 mg of the title compound was obtained as colorless crystals from 227 mg of 1-[(2-methoxy-3-pyridyl)methyl]-4-[2-cyano-2-(3,4-methylenedioxyphenyl)ethyl]piperidine obtained in Example 85, in accordance with the method of Example 141.

$^1$H-NMR (400 MHz, CDCl$_3$) δ 1.27–1.42 (2H, m), 1.45–1.58 (1H, m), 1.63–1.79 (3H, m), 1.85–1.95 (1H, m), 2.04–2.15 (2H, m), 2.88–2.97 (2H, m), 3.47 (2H, s), 3.70–3.77 (1H, m), 5.97 (2H, s), 6.30 (1H, dd, J=6.4, 6.4 Hz), 6.72–6.81 (3H, m), 7.34 (1H, d, J=6.4 Hz), 7.54 (1H, d, J=6.4 Hz).

Example 163

1-[(2-Oxo-1,2-dihydro-3-pyridinyl)methyl]-4-[2-cyano-2-(2-methoxyphenyl)ethyl]piperidine dihydrochloride In ethanol (2 ml) was dissolved 191 mg of 1-[(2-methoxy-3-pyridyl)methyl]-4-[2-cyano-2-(2-methoxyphenyl)ethyl]piperidine obtained in Example 86. To the mixture was added 0.3 ml of a 4N hydrogen chloride ethyl acetate solution, followed by heating under reflux for 2 hours. The solvent was evaporated, to give 199 mg of the title compound as colorless crystals.

$^1$H-NMR (400 MHz, DMSO-d$_6$) δ 1.43–1.67 (4H, m), 1.80–1.96 (3H, m), 2.87–2.99 (2H, m), 3.28–3.37 (2H, m), 3.81 (3H, s), 4.00 (2H, s), 4.27–4.33 (1H, m), 6.27 (1H, dd, J=6.4, 6.4 Hz), 6.98 (1H, dd, J=7.6, 7.6 Hz), 7.06 (1H, d, J=8.0 Hz), 7.32 (1H, d, J=6.4 Hz), 7.35 (1H, dd, J=8.0, 7.6 Hz), 7.51 (1H, d, J=6.4 Hz), 7.77 (1H, d, J=7.6 Hz).

Example 164

1-[(6-Methoxy-2-pyridyl)methyl]-4-(3,4-methylenedioxyphenethyl)piperidine $^1$H-NMR (400 MHz, CDCl$_3$) δ 1.24–1.38 (3H, m), 1.47–1.56 (2H, m), 1.66–1.74 (2H, m), 2.01–2.10 (2H, m), 2.50–2.57 (2H, m), 2.90–2.98 (2H, m), 3.56 (2H, s), 3.91 (3H, s), 5.91 (2H, s), 6.58 (1H, d, J=8.2 Hz), 6.61 (1H, dd, J=7.9, 1.6 Hz), 6.66 (1H, d, J=1.6 Hz), 6.72 (1H, d, J=7.9 Hz), 6.98 (1H, d, J=7.2 Hz), 7.52 (1H, dd, J=8.2, 7.2 Hz).

Example 165

1-[(6-Methoxy-2-pyridyl)methyl]-4-[2-(3-thienyl)ethyl]piperidine $^1$H-NMR (400 MHz, CDCl$_3$) δ 1.26–1.39 (3H, m), 1.54–1.63 (2H, m), 1.68–1.77 (2H, m), 2.01–2.11 (2H, m), 2.61–2.69 (2H, m), 2.71–2.79 (2H, m), 3.57 (2H, s), 3.92 (3H, s), 6.59 (1H, d, J=8.2 Hz), 6.92 (1H, d, J=2.9 Hz), 6.93 (1H, d, J=7.7 Hz), 6.98 (1H, d, J=7.3 Hz), 7.24 (1H, dd, J=7.7, 2.9 Hz), 7.52 (1H, dd, J=8.2, 7.3 Hz).

Example 166

1-[(6-Methoxy-2-pyridyl)methyl]-4-[2-(2-methoxy-3-pyridyl)ethyl]piperidine $^1$H-NMR (400 MHz, CDCl$_3$) δ 1.23–1.40 (3H, m), 1.48–1.56 (2H, m), 1.70–1.78 .(2H, m), 2.02–2.12 (2H, m), 2.53–2.60 (2H, m), 2.92–2.99 (2H, m), 3.57 (2H, s), 3.92 (3H, s), 3.94 (3H, s), 6.59 (1H, d, J=8.2 Hz), 6.80 (1H, dd, J=7.1, 5.1 Hz), 6.99 (1H, d, J=7.1 Hz), 7.36 (1H, dd, J=7.1, 1.8 Hz), 7.52 (1H, dd, J=8.2, 7.1 Hz), 8.00 (1H, dd, J=5.1, 1.8 Hz).

Example 167

1-[(6-Methoxy-2-pyridyl)methyl]-4-(2,3-methylenedioxyphenethyl)piperidine

In a 28% sodium methoxide methanol solution (2 ml) was dissolved 218 mg of 1-[(6-bromo-2-pyridyl)methyl]-4-(2,3-methylenedioxyphenethyl)piperidine obtained in Referential Example 19, followed by heating under reflux for 1 hour. Water was added to the reaction solution, and the mixture was extracted with ethyl acetate. The extract was washed with brine, dried over anhydrous magnesium sulfate and the solvent was evaporated, to give 144 mg of the title compound as a colorless oil.

$^1$H-NMR (400 MHz, CDCl$_3$) δ 1.24–1.38 (3H, m), 1.54–1.60 (2H, m), 1.70–1.77 (2H, m), 2.02–2.10 (2H, m), 2.56–2.62 (2H, m), 2.92–2.98 (2H, m), 3.56 (2H, s), 3.91 (3H, s), 5.92 (2H, s), 6.58 (1H, d, J=8.2 Hz), 6.66 (1H, dd, J=7.8, 1.2 Hz), 6.68 (1H, dd, J=7.8, 1.2 Hz), 6.75 (1H, dd, J=7.8, 7.8 Hz), 6.98 (1H, d, J=7.4 Hz), 7.52 (1H, dd, J=8.2, 7.4 Hz).

Example 168

1-[[6-(2-Hydroxyethoxy)-2-pyridyl]methyl]-4-(2,3-methylenedioxyphenethyl)piperidine 226 mg of the title compound was obtained as colorless crystals from 320 mg of 1-[(3-bromo-2-pyridyl)methyl]-4-(2,3-methylenedioxyphenethyl)piperidine obtained in Reference Example 19, in accordance with the method of Example 123.

$^1$H-NMR (400 MHz, CDCl$_3$) δ 1.25–1.38 (3H, m), 1.54–1.61 (2H, m), 1.62–1.75 (2H, m), 1.98–2.06 (2H, m), 2.55–2.62 (2H, m), 2.85–2.92 (2H, m), 3.52 (2H, s), 3.90–3.94 (2H, m), 4.45–4.50 (2H, m), 5.92 (2H, s), 6.64–6.69 (3H, m), 6.75 (1H, dd, J=7.8, 7.8 Hz), 6.97 (1H, d, J=7.2 Hz), 7.56 (1H, dd, J=7.8, 7.2 Hz).

Example 169

1-[(6-Oxo-1,6-dihydro-2-pyridinyl)methyl]-4-(3,4-methylenedioxyphenethyl)piperidine 186 mg of 4-(3,4-methylenedioxyphenethyl)piperidine obtained in Reference Example 4, 228 mg of 6-tertbutyldimethylsilyloxy-2-pyridinecarboxaldehyde and 203 mg of sodium triacetoxyborohydride were suspended in 2 ml of tetrahydrofuran, followed by stirring at room temperature for 20 hours. An aqueous saturated sodium bicarbonate was added to the reaction solution, and the mixture was extracted with ethyl acetate. The organic layer was washed with brine, dried over anhydrous magnesium sulfate and the solvent was evaporated. The crude product was purified and separated by NH form silica gel column chromatography (ethyl acetate), to give 160 mg of the title compound as colorless crystals.

$^1$H-NMR (400 MHz, CDCl$_3$) δ 1.23–1.36 (3H, m), 1.48–1.61 (2H, m), 1.66–1.75 (2H, m), 2.03–2.13 (2H, m), 2.51–2.58 (2H, m), 2.73–2.81 (2H, m), 3.34 (2H, s), 5.92 (2H, s), 5.99 (1H, d, J=6.8 Hz), 6.43 (1H, d, J=9.3 Hz), 6.62 (1H, dd, J=7.9, 1.6 Hz), 6.67 (1H, d, J=1.6 Hz), 6.73 (1H, d, J=7.9 Hz), 7.31 (1H, dd, J=9.3, 6.8 Hz).

Example 170

1-[(6-Oxo-1,6-dihydro-2-pyridinyl)methyl]-4-[2-(3-thienyl)ethyl]piperidine

The title compound was obtained in accordance with the method of Example 169.

$^1$H-NMR (400 MHz, CDCl$_3$) δ 1.22–1.37 (3H, m), 1.53–1.63 (2H, m), 1.67–1.76 (2H, m), 2.03–2.13 (2H, m), 2.61–2.69 (2H, m), 2.74–2.82 (2H, m), 3.35 (2H, s), 5.95 (1H, d, J=6.8 Hz), 6.43 (1H, d, J=9.2 Hz), 6.92 (1H, d, J=2.9 Hz), 6.94 (1H, d, J=4.8 Hz), 7.25 (1H, dd, J=4.8, 2.9 Hz), 7.31 (1H, dd, J=9.2, 6.8 Hz).

Example 171

1-[(6-Oxo-1,6-dihydro-2-pyridinyl)methyl]-4-[2-(2-methoxy-3-pyridyl)ethyl]piperidine The title compound was obtained in accordance with the method of Example 169.

$^1$H-NMR (400 MHz, CDCl$_3$) δ 1.23–1.38 (3H, m), 1.49–1.58 (2H, m), 1.71–1.79 (2H, m), 2.04–2.14 (2H, m), 2.53–2.61 (2H, m), 2.75–2.83 (2H, m), 3.36 (2H, s), 3.95 (2H, s), 5.95 (1H, d, J=6.8 Hz), 6.43 (1H, d, J=9.3 Hz), 6.81 (1H, dd, J=7.1, 5.1 Hz), 7.32 (1H, dd, J=9.3, 6.8 Hz), 7.36 (1H, dd, J=7.1, 1.8 Hz), 8.01 (1H, dd, J=5.1, 1.8 Hz).

Example 172

1-[(6-Oxo-1,6-dihydro-2-pyridinyl)methyl]-4-(2,3-methylenedioxyphenethyl)piperidine In tert-butanol (5 ml) were suspended 316 mg of 1-[(6-bromo-2-pyridyl)methyl]-4-(2,3-methylenedioxyphenethyl)piperidine obtained in Referential Example 19 and 880 mg of potassium tert-butoxide, followed by heating under reflux for 8 hours. Water was added to the reaction solution, and the mixture was extracted with ethyl acetate. The organic layer was washed with brine, and then dried over anhydrous magnesium sulfate. The solvent was evaporated, and the crude product was separated and purified by NH form silica gel column chromatography (ethyl acetate), to give 96 mg of the title compound as colorless crystals.

$^1$H-NMR (400 MHz, CDCl$_3$) δ 1.24–1.36 (3H, m), 1.54–1.64 (2H, m), 1.71–1.78 (2H, m), 2.04–2.12 (2H, m), 2.56–2.62 (2H, m), 2.75–2.82 (2H, m), 3.35 (2H, s), 5.93 (2H, s), 5.99 (1H, d, J=6.8 Hz), 6.43 (1H, d, J=7.2 Hz), 6.66 (1H, dd, J=7.6, 1.2 Hz), 6.69 (1H, dd, J=7.6, 1.2 Hz), 6.76 (1H, dd, J=7.6, 7.6 Hz), 7.31 (1H, dd, J=7.2, 6.8 Hz).

Example 173

N1-Benzyl-2-[1-[(2-methoxy-3-pyridyl)methyl]-2-piperidinyl]acetamide 1.0 g of 2-[1-[(2-Methoxy-3-pyridyl)methyl]-2-piperidyl]acetic acid, 0.41 ml of benzylamine, 950 mg of WSC and 260 mg of HOBt were suspended in DMF, followed by stirring at room temperature for 2 hours. Water was added thereto, and the mixture was extracted with ethyl acetate. The extract was dried over sodium sulfate. The drying agent was filtered off, the solvent was evaporated and the residue was purified by silica gel column chromatography (ethyl acetate:methanol=10:1, subsequently 5:1), to give 500 mg of the title compound as white crystals.

$^1$H-NMR (400 MHz, CDCl$_3$) δ: 1.30–1.42 (2H, m), 1.52–1.85 (4H, m), 2.03–2.10 (1H, m), 2.47 (1H, dd, J=16.4, 4.8 Hz), 2.66–2.73 (1H, m), 2.76–2.85 (2H, m), 3.33 (1H, d, J=13.6 Hz), 3.86 (3H, s), 3.94 (1H, d, J=13.6 Hz), 4.30 (1H, dd, J=14.8, 5.2 Hz), 4.54 (1H, dd, J=14.8, 6.4 Hz), 6.67 (1H, dd, J=7.2, 4.8 Hz), 7.17 (1H, dd, J=7.2, 2 Hz), 7.24–7.34 (5H, m), 8.02 (1H, dd, J=4.8, 2 Hz), 8.70 (1H, bs).

Example 174

N1-(3-Fluorobenzyl)-2-[1-[(2-methoxy-3-pyridyl)methyl]-2-piperidyl]acetamide

The title compound was obtained from a corresponding raw material in accordance with the method of Example 173.

$^1$H-NMR (400 MHz, CDCl$_3$) δ: 1.30–1.45 (2H, m), 1.52–1.65 (2H, m), 1.67–1.84 (2H, m), 2.08–2.17 (1H, m), 2.51 (1H, dd, J=16.8, 5.2 Hz), 2.69–2.90 (3H, m), 3.35 (1H, d, J=13.6 Hz), 3.85 (3H, s), 3.97 (1H, d, J=13.6 Hz), 4.28 (1H, dd, J=14.8, 5.2 Hz), 4.52 (1H, dd, J=14.8, 6.4 Hz), 6.72 (1H, dd, J=7.2, 4.8 Hz), 6.90–7.08 (3H, m), 7.22–7.32 (2H, m), 8.04 (1H, dd, J=4.8, 2.0 Hz), 8.03 (1H, bs).

Example 175

N1,N1-Di(2-propynyl)-2-[(R)-1-[(2-methoxy-3-pyridyl)methyl]-2-piperidyl]acetamide 4.4 g of N1,N1-di(2-propynyl)-2-[(2R)hexahydro-2-pyridinyl]acetamide, 3.8 g of 3-(chloromethyl)-2-methoxypyridine, 16.6 g of potassium carbonate and 50 ml of DMF were stirred at room temperature overnight. Water was added thereto, and the mixture was extracted with ethyl acetate. The extract was dried over anhydrous sodium sulfate. After filtering off the anhydrous sodium sulfate, the organic solvent was evaporated. The residue was purified by silica gel column chromatography (hexane:ethyl acetate=2:1 to 1:1, subsequently ethyl acetate, and subsequently ethyl acetate:methanol=9:1), to give 640 mg of an oil.

[α]$_D$=+31.8° (C=0.99, MeOH, 28° C.).

$^1$H-NMR (400 MHz, CDCl$_3$) δ: 1.40–1.70 (5H, m), 1.75–1.85 (1H, m), 2.23 (1H, m), 2.26 (1H, m), 2.47–2.84 (1H, m), 2.51 (1H, dd, J=15.6 Hz, 8.4 Hz), 2.69–2.75 (1H, m), 2.83 (1H, dd, J=15.6 Hz, 4.0 Hz), 3.11–3.18 (1H, m), 3.42 (1H, d, J=16.0 Hz), 3.68 (1H, d, J=16.0 Hz), 3.94 (3H, s), 4.21 (2H, s), 4.33 (2H, s), 6.86 (1H, dd, J=6.8 Hz, 6.8 Hz), 7.70 (1H, dd, J=6.8 Hz, 2.0 Hz), 8.04 (1H, dd, J=6.8 Hz, 2.0 Hz).

Example 176

N1,N1-Di(2-propynyl)-3-[1-[(2-methoxy-3-pyridyl)methyl]-2-piperidyl]propanamide 500 mg of ethyl 3-[1-[(2-methoxy-3-pyridyl)methyl]-2-piperidyl]propanoate, 2 ml of a 2N aqueous sodium hydroxide and 2 ml of methanol were stirred at 60° C. for 2 hours. After cooling to room temperature, 4 ml of a 1N aqueous hydrochloric acid was added thereto and the solvent was evaporated. Ethanol was added to the residue, the insoluble matters were filtered off and the solvent was evaporated. The resulting oil (500 mg), 170 mg of dipropargylamine, 450 mg of WSC and 240 mg of HOBt were dissolved in DMF, followed by stirring under room temperature for 3 hours. Water was added thereto, and the mixture was extracted with ethyl acetate. The extract was dried over sodium sulfate, and the solvent was evaporated. The residue was purified by silica gel column chromatography (hexane:ethyl acetate=2:1 to 1:1, subsequently ethyl acetate), to give 300 mg of an oil.

$^1$H-NMR (400 MHz, CDCl$_3$) δ: 1.32–1.52 (4H, m), 1.60–1.75 (2H, m), 1.91–2.02 (2H, m), 2.10–2.25 (3H, m), 2.44–2.53 (3H, m), 2.76–2.83 (1H, m), 3.29 (1H, d, J=14.8 Hz), 3.83 (1H, d, J=14.8 Hz), 3.94 (3H, s), 4.99 (2H, s), 4.30 (2H, s), 6.83 (1H, dd, J=6.8 Hz, 6.8 Hz), 7.69 (1H, d, J=6.8 Hz), 8.02 (1H, d, J=6.8 Hz).

Example 177

N1-(3-Fluorobenzyl)-2-[1-[2-(2-methoxy-3-pyridyl) ethyl]-2-piperidyl]acetamide 200 mg of 2-(2-methoxy-3-pyridyl)acetaldehyde, 400 mg of N1-(3-fluorobenzyl)-2-(2-piperidyl)acetamide, 440 mg of sodium triacetoxyborohydride and 0.12 ml of acetic acid were suspended in THF, followed by stirring at room temperature for 1 hour. An aqueous sodium bicarbonate was added thereto, and the mixture was extracted with ethyl acetate. The extract was dried over sodium sulfate. After filtering off the drying agent, the solvent was evaporated. The residue was purified by silica gel column chromatography (ethyl acetate:methanol=8:1, subsequently 4:1), to give 370 mg of a yellow oil.

$^1$H-NMR (400 MHz, CDCl$_3$) δ: 1.28–1.75 (6H, m), 2.26–2.34 (1H, m), 2.37 (1H, dd, J=16.8 Hz, 4.4 Hz), 2.57–2.80 (5H, m), 2.93–3.00 (1H, m), 3.06–3.13 (1H, m), 3.91 (3H, s), 4.20 (1H, dd, J=15.2 Hz, 5.2 Hz), 4.46 (1H, dd, J=15.2 Hz, 6.4 Hz), 6.77 (1H, dd, J=7.2 Hz, 5.2 Hz), 6.88–6.98 (2H, m), 7.01 (1H, dd, J=7.6 Hz, 1.0 Hz), 7.22–7.30 (2H, m), 8.01 (1H, dd, J=5.2 Hz, 2.0 Hz), 8.81 (1H, bs).

Example 178

1-[(2-Oxo-1,2-dihydro-3-pyridinyl)methyl]-2-[3-(2-pyridyl)propyl]piperidine

In DMF was dissolved 2.1 g of triphenyl(2-pyridylmethyl)phosphonium dihydrochloride, followed by adding 1.4 g of potassium tert-butoxide thereto at room temperature under stirring. After 15 minutes, a solution of 1.25 g of 2-[1-[(2-methoxy-3-pyridyl)methyl]-2-piperidyl] acetaldehyde dissolved in DMF was added dropwise into the above-mentioned solution at room temperature under stirring, and the mixture was left overnight. Water was added thereto, and the mixture was extracted with ethyl acetate. The extract was dried over sodium sulfate, and the solvent was evaporated. The residue was purified by silica gel column chromatography (hexane:ethyl acetate=2:1, subsequently ethyl acetate, and subsequently ethyl acetate:methanol=4:1). 760 mg of the resulting brown oil, 0.56 ml of thionyl chloride and 10 ml of ethanol were stirred under reflux for 30 minutes. The reaction solution was cooled to room temperature, a 2N aqueous sodium hydroxide was added thereto, and the mixture was extracted with ethyl acetate. The extract was dried over sodium sulfate, and the solvent was evaporated. The residue was purified by silica gel column chromatography (hexane:ethyl acetate= 2:1, subsequently ethyl acetate, and subsequently ethyl acetate:methanol=4:1). The resulting yellow oil (350 mg) was dissolved in 10 ml of ethanol, 100 mg of 10% palladium-carbon (water-containing product) was added thereto, and the mixture was catalytically hydrogenated at normal pressure under stirring for 1.5 hours. The catalyst was filtered off and the solvent was evaporated. The residue was purified by NH-silica gel chromatography (ethyl acetate, subsequently ethyl acetate:methanol=4:1), to give 310 mg of an oil.

$^1$H-NMR (400 MHz, CDCl$_3$) δ: 1.28–1.86 (10H, m), 2.16–2.24 (1H, m), 2.40–2.48 (1H, m), 2.73–2.82 (3H, m), 3.30 (1H, d, J=16.0 Hz), 3.77 (1H, d, J=16.0 Hz), 6.33 (1H, dd, J=6.8 Hz, 6.8 Hz), 7.05–7.13 (2H, m), 7.35 (1H, d, J=6.8 Hz), 7.55 (1H, ddd, J=7.0 Hz, 7.0 Hz, 2.0 Hz), 7.63 (1H, d, J=6.8 Hz), 8.50 (1H, d, J=5 Hz).

Example 179

1-[(2-oxo-1,2-dihydro-3-pyridinyl)methyl]-2-(2-phenylethyl)piperidine

The title compound was obtained using the compound obtained in Reference Example 31, in accordance with the method of Example 178.

$^1$H-NMR (400 MHz, CDCl$_3$) δ: 1.36–1.46 (1H, m), 1.48–1.64 (3H, m), 1.66–1.98 (4H, m), 2.20–2.28 (1H, m), 2.48–2.77 (3H, m), 2.78–2.86 (1H, m), 3.34 (1H, d, J=16 Hz), 3.85 (1H, d, J=16.0 Hz), 6.32 (1H, dd, J=6.8, 6.8 Hz), 7.13–7.34 (6H, m), 7.63 (1H, d, J=6.8 Hz).

Example 180

1-[(2-oxo-1-cyclopropylmethyl-1,2-dihydro-3-pyridinyl)methyl]-2-[(3-pyridyl)propyl]piperidine 300 mg of 1-[(2-Oxo-1,2-dihydro-3-pyridinyl)methyl]-2-[3-(2-pyridyl)propyl]piperidine obtained in Example 178, 0.2 ml of (bromomethyl)cyclopropane and 610 mg of potassium carbonate were suspended in 5 ml of N,N-dimethylformamide (DMF), and the mixture were stirred at 80° C. for 4 hours. Water was added thereto, and the mixture was extracted with ethyl acetate. The extract was dried over sodium sulfate. The drying agent was filtered off, and the solvent was evaporated. The residue was purified by NH-silica gel column chromatography (hexane:ethyl acetate=2:1, subsequently 1:1, and subsequently ethyl acetate), to give 150 mg of the objective oil.

$^1$H-NMR (400 MHz, CDCl$_3$) δ: 0.36–0.42 (2H, m), 0.57–0.64 (2H, m), 1.20–1.90 (1H, m), 2.15–2.23 (1H, m), 2.39–2.47 (1H, m), 2.72–2.82 (3H, m), 3.29 (1H, d, J=16.4 Hz), 3.75 (1H, d, J=16.4 Hz), 3.81 (2H, d, J=7.2 Hz), 6.19 (1H, dd, J=6.8 Hz, 6.8 Hz), 7.05–7.14 (2H, m), 7.27 (1H, dd, J=6.8 Hz, 2 Hz), 7.50–7.58 (2H, m), 8.48–8.52 (1H, m).

Example 181

N1-Benzyl-2-[1-(2-oxo-1,2-dihydro-3-pyridinyl) methyl]-2-piperidyl]acetamide

To ethanol (5 ml) were added 250 mg of N1-benzyl-2-[1-[(2-methoxy-3-pyridyl)methyl]-2-piperidinyl]acetamide obtained in Example 173 and 0.11 ml of thionyl chloride, followed by stirring at 100° C. for 1.5 hours. The solvent was evaporated, and to the residue was added an aqueous diluted sodium hydroxide, followed by extracting with ethyl acetate. The organic layer was dried over sodium sulfate, and then evaporated, to give 180 mg of the objective oil.

$^1$H-NMR (400 MHz, CDCl$_3$) δ: 1.30–1.43 (2H, m), 1.50–1.82 (4H, m), 2.07–2.16 (1H, m), 2.50–2.60 (1H, m), 2.67–2.80 (2H, m), 2.83–2.90 (1H, m), 3.30 (1H, d, J=14.4 Hz), 3.89 (1H, d, J=14.4 Hz), 4.33 (1H, dd, J=14.8 Hz, 2.8 Hz), 4.51 (1H, dd, J=14.8 Hz, 2.0 Hz), 6.05 (1H, dd, J=6.8 Hz, 6.8 Hz), 7.06 (1H, dd, J=6.8 Hz, 2.0 Hz), 7.11 (1H, dd, J=6.8 Hz, 2.0 Hz), 7.18–7.32 (5H, m), 8.67–8.74 (1H, m).

Example 182

N1-(3-fluorobenzyl)-2-[1-(2-oxo-1,2-dihydro-3-pyridinyl)methyl]-2-piridinyl]acetamide 500 mg of N1-(3-fluorobenzyl)-2-[1-[(2-methoxy-3-pyridyl)methyl]-2-piperidyl]acetamide obtained in Example 174 and a 2N aqueous hydrochloric acid were stirred at 90° C. for 3.5 hours. After cooling to room temperature, the mixture was basified by adding a 2N aqueous sodium hydroxide thereto, and extracted with ethyl acetate. The extract was dried over sodium sulfate. The drying agent was filtered off, and the solvent was evaporated. The residue was purified by NH form silica gel column chromatography (hexane:ethyl acetate=1:1, subsequently ethyl acetate, and subsequently ethyl acetate:methanol=4:1), to give 270 mg of a colorless oil.

$^1$H-NMR (400 MHz, CDCl$_3$) δ: 1.32–1.88 (6H, m), 2.10–2.21 (1H, m), 2.52–2.63 (1H, m), 2.69–2.80 (2H, m), 2.87–2.95 (1H, m), 3.29 (1H, d, J=13.6 Hz), 3.94 (1H, d, J=13.6 Hz), 4.30 (1H, dd, J=15.2, 5.2 Hz), 4.51 (1H, dd, J=15.2, 6.4 Hz), 6.11 (1H, dd, J=6.8, 6.8 Hz), 6.85–7.10 (4H, m), 7.17–7.26 (2H, m), 8.86–8.94 (1H, m).

Example 183

N1-(2-cyclopropylethyl)-2-[1-(2-oxo-1,2-dihydro-3-pyridinyl)methyl]-2-piperidyl]acetamide 400 mg of 2-1-[(2-methoxy-3-pyridyl)methyl]-2-piperidyl]acetic acid obtained in Reference Example 34, 200 mg of 2-cyclopropylethylamine, 370 mg of WSC, 100 mg of HOBt, 0.42 ml of triethylamine and 10 ml of DMF were stirred at room temperature overnight. Water was added thereto, and the mixture was extracted with ethyl acetate. The extract was dried over anhydrous sodium sulfate, and the solvent was evaporated. 310 mg of the resulting oil was added to 0.23 ml of thionyl chloride and 5 ml of ethanol, and the mixture was stirred under reflux at room temperature for 1 hour. An aqueous diluted sodium hydroxide was added thereto, and the mixture was extracted with ethyl acetate. The extract was dried over sodium sulfate, and then the solvent was evaporated. The residue was purified by NH form silica gel column chromatography (hexane:ethyl acetate=2:1, subsequently ethyl acetate, and subsequently ethyl acetate:methanol=10:1, subsequently 4:1), to give 290 mg of a yellow oil.

$^1$H-NMR (400 MHz, CDCl$_3$) δ: −0.08–0.08 (2H, m), 0.35–0.40 (2H, m), 0.58–0.68 (1H, m), 1.30–1.80 (8H, m), 2.10–2.20 (1H, m), 2.45–2.53 (1H, s), 2.65–2.74 (2H, m), 2.88–2.95 (1H, m), 3.13–3.22 (1H, m), 3.33 (1H, d, J=14.4 Hz), 3.35–3.45 (1H, m), 3.91 (1H, d, J=14.4 Hz), 6.30 (1H, dd, J=6.8 Hz, 6.8 Hz), 7.33 (1H, dd, J=6.8 Hz, 2.0 Hz), 7.44 (1H, dd, J=6.8 Hz. 2.0 Hz).

Example 184

N1-Cyclopropylmethyl-2-[1-(2-oxo-1,2-dihydro-3-pyridinyl)methyl]-2-piperidyl]acetamide The title compound was obtained using a corresponding compound, in accordance with the method of Example 183.

$^1$H-NMR (400 MHz, CDCl$_3$) δ: 0.25–0.30 (2H, m), 0.40–0.47 (2H, m), 0.88–1.00 (1H, m), 1.30–1.80 (6H, m), 2.10–2.20 (1H, m), 2.42–2.50 (1H, m), 2.67–2.78 (2H, m), 2.903.02 (2H, m), 3.19–3.27 (1H, m), 3.34 (1H, d, J=14.4 Hz), 3.94 (1H, d, J=14.4 Hz), 6.30 (1H, dd, J=6.8 Hz, 6.8 Hz), 7.35 (1H, dd, J=6.8 Hz, 2 Hz), 7.49 (1H, dd, J=6.8 Hz, 2.0 Hz), 8.20 (1H, m).

Example 185

N1-(4-Fluorophenyl)-2-[1-(2-oxo-1,2-dihydro-3-pyridinyl)methyl]-2-piperidyl]acetamide The title compound was obtained using a corresponding compound, in accordance with the method of Example 183.

$^1$H-NMR (400 MHz, CDCl$_3$) δ: 1.30–1.84 (6H, m), 2.49 (1H, dd, J=16.4 Hz, 4.4 Hz), 2.57–2.65 (1H, m), 2.97–3.06 (2H, m), 3.11 (1H, dd, J=16.4 Hz, 4 Hz), 4.22 (1H, d, J=12.8 Hz), 6.09 (1H, dd, J=6.8 Hz, 6.8 Hz), 6.64 (1H, dd, 6.8 Hz, 2.0 Hz), 6.81–6.89 (2H, m), 7.35 (1H, dd, J=6.8 Hz, 2.0 Hz), 7.50–7.58 (2H, m), 10.68 (1H, s).

Example 186

N1-(2-Pyridylmethyl)-2-[1-(2-oxo-1,2-dihydro-3-pyridinyl)methyl]-2-piperidyl]acetamide The title compound was obtained using a corresponding compound, in accordance with the method of Example 183.

$^1$H-NMR (400 MHz, CDCl$_3$) δ: 1.30–1.80 (6H, m), 2.13–2.22 (1H, m), 2.05–2.63 (1H, m), 2.70–2.82 (2H, m), 2.88–2.95 (1H, m), 3.35 (1H, d, J=14.8 Hz, 2.0 Hz), 3.92 (1H, d, J=14.8 Hz, 2.0 Hz), 4.49 (1H, dd, J=16.0 Hz, 5.2 Hz), 4.64 (1H, dd, J=16.0 Hz, 2.0 Hz), 6.16 (1H, dd, J=6.8 Hz, 6.8 Hz), 7.12–7.17 (1H, m), 7.22 (1H, dd, 6.8 Hz, 2.0 Hz), 7.25–7.32 (1H, m), 7.45 (1H, dd, J=6.8 Hz, 2.0 Hz), 7.58–7.64 (1H, m), 8.47–8.52 (1H, m), 8.86–8.93 (1H, m).

Example 187

N1-(2-Cyclopropylethyl)-2-[1-[1-(cyclopropylmethyl)-2-oxo-1,2-dihydro-3-pyridinyl)methyl]-2-piperidyl]acetamide 300 mg of N1-(2-cyclopropylethyl)-2-[1-(2-oxo-1,2-dihydro-3-pyridinyl)methyl]-2-pyridinyl]acetamide obtained in Example 183, 0.2 ml of (bromomethyl)cyclopropane and 470 mg of potassium carbonate solution were suspended in 5 ml of N,N-dimethylformamide (DMF), and the mixture was stirred at 80° C. for 4 hours. Water was added thereto, and the mixture was extracted with ethyl acetate. The extract was dried over sodium sulfate. The drying agent was filtered off, and the solvent was evaporated. The residue was purified by NH-silica gel chromatography (hexane:ethyl acetate=2:1 subsequently 1:1, and subsequently ethyl acetate), to give 150 mg of the objective oil.

$^1$H-NMR (400 MHz, CDCl$_3$) δ: 0.02–0.08 (2H, m), 0.37–0.45 (4H, m), 0.58–0.74 (3H, m), 1.20–1.84 (9H, m), 2.02–2.21 (1H, m), 2.49–2.73 (3H, m), 2.87–2.96 (1H, m), 3.17–3.27 (1H, m), 3.33 (1H, d, J=14.4 Hz), 3.32–3.43 (1H, m), 3.81 (1H, d, J=6.8 Hz), 3.90 (1H, d, J=14.4 Hz), 6.19 (1H, dd, J=6.8 Hz, 6.8 Hz), 7.31 (1H, dd, J=6.8 Hz, 2 Hz), 7.36 (1H, dd, J=6.8 Hz, 2 Hz), 8.14–8.20 (1H, m).

Example 188

N1-(3-Fluorobenzyl)-2-[1-[[1-(cyclopropylmethyl)-2-oxo-1,2-dihydro-3-pyridinyl)methyl]-2-piperidyl]acetamide The title compound was obtained using a corresponding compound, in accordance with the method of Example 187.

¹H-NMR (400 MHz, CDCl₃) δ: 0.27–0.33 (2H, m), 0.50–0.58 (2H, m), 1.05–1.16 (1H, m), 1.30–1.85 (6H, m), 2.09–2.18 (1H, m), 2.55–2.78 (3H, m), 2.87–2.96 (1H, m), 3.27 (1H, d, J=14.6 Hz), 3.56–3.70 (2H, m), 3.98 (1H, d, J=14.6 Hz), 4.38 (1H, dd, J=15.2, 5.2 Hz), 4.57 (1H, dd, J=15.2, 6.4 Hz), 6.09 (1H, dd, J=6.8, 6.8 Hz), 7.00–7.26 (5H, m), 7.29 (1H, dd, J=6.8, 2.0 Hz), 8.98–9.06 (1H, m).

Example 189

N1-(4-Fluorophenyl)-2-[1-[[1-(cyclopropylmethyl)-2-oxo-1,2-dihydro-3-pyridinyl)methyl]-2-piperidyl]acetamide The title compound was obtained using a corresponding compound, in accordance with the method of Example 187.

¹H-NMR (400 MHz, CDCl₃) δ: 0.30–0.40 (2H, m), 0.56–0.63 (2H, m), 1.15–1.25 (1H, m), 1.30–1.87 (6 h, m), 2.16–2.24 (1H, m), 2.60–2.73 (2H, m), 2.89 (1H, dd, J=15.2, 4.0 Hz), 2.99–3.06 (1H, m), 3.35 (1H, d, J=13.6 Hz), 3.76 (2H, dd, J=7.2, 1.6 Hz), 3.99 (1H, d, J=13.6 Hz), 6.17 (1H, dd, J=6.8, 6.8 Hz), 6.93–7.00 (2H, m), 7.31 (1H, dd, J=6.8, 2.0 Hz), 7.36 (1H, dd, J=6.8, 2.0 Hz), 7.55–7.63 (2H, m), 10.49 (1H, s).

Example 190

N1-(2-Pyridylmethyl)-2-[1-[(1-benzyl-2-oxo-1,2-dihydro-3-pyridinyl)methyl]-2-piperidyl]acetamide The title compound was obtained using a corresponding compound, in accordance with the method of Example 187.

¹H-NMR (400 MHz, CDCl₃) δ: 1.33–1.80 (6H, m), 2.17–2.24 (1H, m), 2.60–2.75 (2H, m), 2.76 (1H, m), 2.40 (1H, m), 3.39 (1H, d, J=6.8 Hz), 3.92 (1H, d, J=6.8 Hz), 4.50 (1H, dd, J=16.0 Hz, 5.2 Hz), 4.64 (1H, dd, J=16.0 Hz, 6.0 Hz), 5.00 (1H, d, J=14.4 Hz), 5.07 (1H, d, J=14.4 Hz), 6.06 (1H, dd, J=6.8 Hz, 6.8 Hz), 7.10–7.35 (9H, m), 7.55 (1H, ddd, J=7.6 Hz, 7.6 Hz, 1.6 Hz), 8.48–8.52 (1H, m), 8.87–8.93 (1H, m).

Example 191

N1,N1-Di(2-propynyl)-2-[(2R)-1-[(2-oxo-1,2-dihydro-3-pyridinyl)methyl]-2-piperidyl]acetamide 640 mg of N1,N1-di(2-propynyl)-2-[(R)-1-[(2-methoxy-3-pyridyl)methyl]-2-piperidyl]acetamide obtained in Example 175 and 0.45 ml of thionyl chloride were dissolved in 20 ml of ethanol, and the mixture was heated under reflux for 1.5 hours. After cooling to room temperature, a 2N aqueous sodium hydroxide was added thereto, and the mixture was extracted with ethyl acetate. The organic layer was washed with brine and dried over anhydrous sodium sulfate. The anhydrous sodium sulfate was filtered off and ethyl acetate was evaporated. The residue was purified by silica gel chromatography (ethyl acetate:methanol=9;1), to give 530 mg of the objective oil.

[α]$_D$=+37.9° (C=0.23, MeOH, 26° C.).

¹H-NMR (400 MHz, CDCl₃) δ 1.40–1.70 (5H, m), 1.81 (1H, m), 2.22 (1H, s), 2.28 (1H, s), 2.37 (1H, m), 2.53 (1H, dd, J=15.6 Hz, 8.4 Hz), 2.75 (1H, m), 2.88 (1H, dd, J=15.6 Hz, 4.0 Hz), 3.19 (1H, m), 3.40 (1H, d, J=16.0 Hz), 3.68 (1H, d, J=16.0 Hz), 4.16–4.40 (4H, m), 6.32 (1H, t, J=6.8 Hz), 7.34 (1H, d, J=6.8 Hz), 7.60 (1H, d, J=6.8 Hz).

Example 192

N1,N1-Di(2-propynyl)-2-[(2R)-1-[(1-cyclopropylmethyl)-2-oxo-1,2-dihydro-3-pyridinyl)methyl]hexahydro-2-pyridinyl]acetamide 200 mg of N1,N1-di(2-propynyl)-2-[(2R)-1-[(2-oxo-1,2-dihydro-3-pyridinyl)methyl]-2-piperidyl]acetamide obtained in Example 175, 0.09 ml of (bromomethyl)cyclopropane and 510 mg of potassium carbonate were suspended in 10 ml of DMF, and the mixture were stirred at 80° C. for 1.5 hours. Water was added thereto, and the mixture was extracted with ethyl acetate. The extract was dried over anhydrous sodium sulfate. The anhydrous sodium sulfate was filtered off, and ethyl acetate was evaporated. The residue was purified by NH-silica gel column chromatography (hexane:ethyl acetate=2:1, subsequently 1:1), to give 100 mg of the objective oil.

¹H-NMR (400 MHz, CDCl₃) δ: 0.35–0.42 (2H, m), 0.57–0.64 (2H, m), 1.19–1.30 (1H, m), 1.40–1.85 (6H, m), 2.21 (1H, s), 2.28 (1H, s), 2.34–2.43 (1H, m), 2.50–2.60 (1H, m), 2.69–2.76 (1H, m), 2.85–2.93 (1H, m), 3.19 (1H, bs), 3.40 (1H, d, J=14.8 Hz), 3.68 (1H, d, J=14.8 Hz), 3.75–3.86 (2H, m), 4.18–4.40 (4H, m), 6.20 (1H, t, J=6.8 Hz), 7.29 (1H, d, J=6.8 Hz), 7.50 (1H, d, J=6.8 Hz).

Example 193

N1,N-Di(2-propynyl)-2-[(2R)-1-[[1-(2-methoxyethyl)-2-oxo-1,2-dihydro-3-pyridinyl)methyl]hexahydro-2-pyridinyl]acetamide The title compound was obtained using a corresponding compound, in accordance with the method of Example 192.

¹H-NMR (400 MHz, CDCl₃) δ: 1.40–1.83 (6H, m), 2.21 (1H, s), 2.28 (1H, s), 2.33–2.42 (1H, m), 2.49–2.58 (1H, m), 2.69–2.76 (1H, m), 2.83–2.90 (1H, m), 3.17 (1H, bs), 3.32 (3H, s), 3.39 (1H, d, J=15.5 Hz), 3.64–3.71 (3H, m), 4.06–4.17 (2H, m), 4.20–4.35 (4H, m), 6.16 (1H, dd, J=6.8 Hz, 6.8 Hz), 7.23 (1H, dd, J=6.8 Hz, 2 Hz), 7.49 (1H, dd, J=6.8 Hz, 2 Hz).

Example 194

N1,N1-Di(2-propynyl)-2-[(2R)-1-[[2-oxo-1-(2,2,2-trifluoroethyl)-1,2-dihydro-3-pyridinyl)methyl]hexahydro-2-pyridinyl]acetamide The title compound was obtained using a corresponding compound, in accordance with the method of Example 192.

¹H-NMR (400 MHz, CDCl₃) δ: 1.40–1.70 (5H, m), 1.75–1.85 (1H, m), 2.21 (1H, s), 2.28 (1H, s), 2.32–2.42 (1H, m), 2.52 (1H, dd, J=15.2, 8.4 Hz), 2.68–2.76 (1H, m), 2.83 (1H, dd, J=15.2, 4.0 Hz), 3.20 (1H, bs), 3.38 (1H, d, J=16.4 Hz), 3.66 (1H, d, J=16.4 Hz), 4.17–4.40 (4H, m), 4.62 (2H, q, J=8.8 Hz), 6.25 (1H, dd, J=6.6, 6.8 Hz), 7.17 (1H, d, J=6.8 Hz), 7.53 (1H, d, J=6.8 Hz).

Example 195

N1,N1-Di(2-propynyl)-2-[(2R)-1-[1-[2-(diisopropylamino)ethyl]-2-oxo-1,2-dihydro-3-pyridinyl]methyl]hexahydro-2-pyridinyl]acetamide The title compound was obtained using a corresponding compound, in accordance with the method of Example 192.

¹H-NMR (400 MHz, CDCl₃) δ 0.93 (6H, d, J=6.8 Hz), 1.40–1.65 (5H, m), 1.74–1.83 (1H, m), 2.20 (1H, s), 2.27 (1H, s), 2.30–2.38 (1H, m), 2.53 (1H, dd, J=15.2, 9.2 Hz), 2.65–2.76 (3H, m), 2.83–2.90 (1H, m), 2.92–3.02 (2H, m), 3.13–3.20 (1H, m), 3.38 (1H, d, J=15.6 Hz), 3.67 (1H, d, J=15.6 Hz), 3.80–3.92 (2H, m), 4.17–4.39 (4H, m), 6.13 (1H, dd, J=6.8, 6.8 Hz), 7.16 (1H, dd, J=6.8, 2.0 Hz), 7.46 (1H, dd, J=6.8, 2.0 Hz).

Example 196

N1,N1-Di(2-propynyl)-3-[1-[(2-oxo-1,2-dihydro-3-pyridinyl)methyl]-2-piperidyl]propanamide 300 mg of N1,N1-di(2-propynyl)-3-[1-[(2-methoxy-3-pyridyl)methyl]-2-piperidyl]propanamide obtained in Example 176, 0.4 ml of thionyl chloride and 5 ml of ethanol were stirred under reflux for 1 hour, and then the mixture was left overnight. An aqueous dilute sodium hydroxide was added thereto, and the mixture was extracted with ethyl acetate. The extract was dried over sodium sulfate. The sodium sulfate was removed, and the solvent was evaporated. The residue was purified by silica gel chromatography (hexane:ethyl acetate=3:1, subsequently ethyl acetate:methanol=9:1), to give 300 mg of a yellow oil.

$^1$H-NMR (400 MHz, CDCl$_3$) δ 1.33–1.57 (4H, m), 1.62–1.75 (2H, m), 1.87–2.00 (2H, m), 2.17–2.27 (2H, m), 2.30–2.59 (4H, m), 2.80–2.88 (1H, m), 3.31 (1H, d, J=16.0 Hz), 3.82 (1H, d, J=16.0 Hz), 4.20 (2H, s), 4.31 (2H, s), 6.31 (1H, dd, J=6.8 Hz), 7.33 (1H, d, J=6.8 Hz), 7.59 (1H, d, J=6.8 Hz).

Example 197

N1,N1-Di(2-propynyl)-3-[1-[(1-cyclopropylmethyl)-2-oxo-1,2-dihydro-3-pyridinyl)methyl]-2-piperidyl]propanamide 300 mg of N1,N1-di(2-propynyl)-3-[1-[(2-oxo-1,2-dihydro-3-pyridinyl)methyl]-2-piperidyl]propanamide, 0.1 ml of cyclopropylmethyl bromide, 620 mg of potassium carbonate and 5 ml of DMF were heated under stirring at 60° C. for 1 hour and at 80° C. for 1 hour. Water was added thereto, and the mixture was extracted with ethyl acetate. The extract was dried over magnesium sulfate. The drying agent was filtered off, and the solvent was evaporated. The residue was purified by NH-silica gel column chromatography (hexane:ethyl acetate=4:1, subsequently 2:1, and subsequently ethyl acetate), to give 150 mg of an oil.

$^1$H-NMR (400 MHz, CDCl$_3$) δ 0.35–0.75 (2H, m), 0.57–0.71 (2H, m), 1.20–1.30 (1H, m), 1.30–1.55 (4H, m), 1.61–1.75 (2H, m), 1.90–1.97 (2H, m), 2.15–2.28 (3H, m), 2.43–2.58 (3H, m), 2.80–2.87 (1H, m), 3.29 (1H, d, J=16.0 Hz), 3.79 (1H, d, J=16.0 Hz), 3.80 (2H, d, J=7.2 Hz), 4.22 (2H, s), 4.30 (2H, s), 6.17 (1H, dd, J=6.8 Hz, 6.8 Hz), 7.28 (1H, dd, J=6.8 Hz, 2.0 Hz), 7.48 (1 H, dd, J=6.8 Hz, 2.0 Hz).

Example 198

N1-(3-Fluorobenzyl)-2-[1-[2-(2-oxo-1,2-dihydro-3-pyridinyl)ethyl]-2-piperidyl]acetamide 370 mg of N1-(3-fluorobenzyl)-2-[1-[2-(2-methoxy-3-pyridyl)ethyl]-2-piperidyl]acetamide obtained in Example 177, 0.44 ml of thionyl chloride and 5 ml of ethanol were stirred at 100° C. for 2 hours. The solvent was evaporated, and to the residue was added an aqueous sodium bicarbonate. The mixture was extracted with ethyl acetate, and dried over sodium sulfate. Then the drying agent was filtered off, and the solvent was evaporated, to give 330 mg of white crystals.

$^1$H-NMR (400 MHz, CDCl$_3$) δ 1.30–1.77 (6H, m), 2.30–2.58 (3H, m), 2.69–2.80 (4H, m), 2.88–2.97 (1H, m), 3.00–3.06 (1H, m), 4.32 (1H, dd, J=15.2 Hz, 5.6 Hz), 4.48 (1H, dd, J=15.2 Hz, 6.0 Hz), 6.16 (1H, dd, J=6.8 Hz, 6.8 Hz), 6.86–6.93 (1H, m), 6.97–7.03 (1H, m), 7.04 (1H, d, J=7.6 Hz), 7.16–7.26 (3H, m), 8.80–8.86 (1H, m).

Example 199

N1-(3-Fluorobenzyl)-2-[1-[2-[1-(cyclopropylmethyl)-2-oxo-1,2-dihydro-3-pyridinyl]ethyl]-2-piperidyl]acetamide 230 mg of N1-(3-fluorobenzyl)-2-[1-[2-(2-oxo-1,2-dihydro-3-pyridinyl)ethyl]-2-piperidyl]acetamide obtained in Example 198, 0.08 ml of cyclopropylmethyl chloride, 450 mg of potassium carbonate and 5 ml of DMF were stirred at 60° C. for 1 hour. Water was added thereto, and the mixture was extracted with ethyl acetate. The extract was dried over sodium sulfate. The drying agent was filtered off, and the solvent was evaporated. The residue was purified by NH-silica gel column chromatography (hexane:ethyl acetate=1:1, subsequently ethyl acetate), to give 180 mg of a colorless oil.

$^1$H-NMR (400 MHz, CDCl$_3$) δ 0.30–0.35 (2H, m), 0.54–0.60 (2H, m), 12–1.22 (1H, m), 1.28–1.48 (6H, m), 2.32–2.40 (1H, m), 2.45–2.63 (3H, m), 2.67–2.91 (4H, m), 2.95–3.02 (1H, m), 3.65–3.77 (2H, m), 4.29 (1H, dd, J=15.2 Hz, 5.2 Hz), 4.49 (1H, dd, J=15.2 Hz, 5.6 Hz), 6.08 (1H, dd, J=6.8 Hz, 6.8 Hz), 6.87–7.11 (4H, m), 7.2–7.27 (1H, m), 8.86 (1H, bs).

Example 200

1-[(2-Oxo-1,2-dihydro-3-pyridinyl)methyl]-4-[3-(2-thienyl)propyl]piperidine 159 mg of the title compound was obtained as colorless crystals from 206 mg of 1-[(2-methoxy-3-pyridyl)methyl]-4-(3-(2-thienyl)propyl)piperidine which was obtained in Example 77.

$^1$H-NMR (400 MHz, CDCl$_3$) δ 1.20–1.36 (5H, m), 1.62–1.76 (4H, m), 2.02–2.10 (2H, m), 2.81 (2H, t, J=7.6 Hz), 2.87–2.94 (2H, m), 3.46 (2H, s), 6.33 (1H, dd, J=6.6, 6.6 Hz), 6.77 (1H, dd, J=3.3, 1.1 Hz), 6.91 (1H, dd, J=5.1, 3.3 Hz), 7.10 (1H, dd, J=5.1, 1.1 Hz), 7.36 (1H, d, J=6.6 Hz), 7.52 (1H, m).

Example 201

1-[(2-Methoxy-3-pyridinyl)methyl]-4-[(2-methoxyphenoxy)methyl]piperidine 200 mg of 2-methoxy-3-(chloromethyl)pyridine, 380 mg of 4-[(2-methoxyphenoxy)methyl]piperidine and 235 mg of potassium carbonate were added in 10 ml of acetonitrile, and the mixture were stirred at room temperature for 3 hours 15 minutes. After filtering the reaction solution, the solvent was evaporated, and the crude product was purified by silica gel column chromatography (hexane:ethyl acetate=3:2), to give 359 mg of the title compound as a colorless oil.

$^1$H-NMR (400 MHz, CDCl$_3$) δ 1.36–1.48 (2H, m), 1.84–1.97 (3H, m), 2.05–2.14 (2H, m), 2.94 (2H, br d, J=11.6 Hz), 3.51 (2H s), 3.86 (3H, s), 3.87 (2H, s), 3.95 (3H, s), 6.85–6.94 (5H, m), 7.66 (1H, dd, J=7.2, 2.0 Hz), 8.06 (1H, dd, J=5.2, 2.0 Hz).

Example 202

1-[(2-Methoxy-3-pyridinyl)methyl]-4-[(2-fluorophenoxy)methyl]piperidine

The title compound was obtained from a corresponding raw material in accordance with the method of Example 201.

$^1$H-NMR (400 MHz, CDCl$_3$) δ 1.36–1.52 (2H, m), 1.86 (3H, br d, J=8.8 Hz), 2.10 (2H, br t, J=12.0 Hz), 2.94 (2H, br d, J=8.4 Hz), 3.51 (2H, s), 3.87 (2H, d, J=6.0 Hz), 3.95 (3H, s), 6.84–6.93 (2H, m), 6.90–7.00 (1H, m), 7.04 (1H, t, J=7.6 Hz), 7.00–7.14 (1H, m), 7.66 (1H, dd, J=7.6, 2.0 Hz), 8.06 (1H, dd, J=5.2, 2.0 Hz).

Example 203

1-[(5-Chloro-2-methoxy-3-pyridinyl)methyl]-4-[(2-fluorophenoxy)methyl]piperidine The title compound was obtained from a corresponding raw material in accordance with the method of Example 201.

¹H-NMR (400 MHz, CDCl₃) δ 1.36–1.52 (2H, m), 1.87 (3H, br d, J=8.8 Hz), 2.12 (2H, br t, J=10.8 Hz), 2.92 (2H, br d, J=11.6 Hz), 3.46 (2H, s), 3.88 (2H, d, J=6.0 Hz), 3.93 (3H, s), 6.84–6.93 (1H, m), 6.95 (1H, t, J=8.0 Hz), 7.00–7.14 (2H, m), 7.64–7.70 (1H, m), 7.98 (1H, d, J=2.0 Hz).

Example 204

1-[(2-Methoxy-3-pyridinyl)methyl]-4-[(2-(cyclohexylmethyloxy)phenoxymethyl]piperidine The title compound was obtained from a corresponding raw material in accordance with the method of Example 201.

¹H-NMR (400 MHz, CDCl₃) δ 1.01–1.12 (2H, m), 1.13–1.36 (3H, m), 1.38–1.50 (2H, m), 1.64–1.94 (9H, m), 2.06–2.15 (2H, m), 2.94 (2H, br d, J=11.6 Hz), 3.51 (2H, s), 3.78 (2H, d, J=6.0 Hz), 3.84 (2H, d, J=6.0 Hz), 3.95 (3H, s), 6.84–6.92 (5H, m), 7.67 (1H, dd, J=7.2, 2.0 Hz), 8.06 (1H, dd, J=4.8, 2.0 Hz).

Example 205

1-[(5-Chloro-2-methoxy-3-pyridinyl)methyl]-4-[[2-(2-cyclohexylethyl)phenoxy]methyl]piperidine The title compound was obtained from a corresponding raw material in accordance with the method of Example 201.

¹H-NMR (400 MHz, CDCl₃) δ 0.87–0.99 (2H, m), 1.009–1.34 (4H, m), 1.42–1.54 (4H, m), 1.60–1.90 (8H, m), 2.08–2.16 (2H, m), 2.58–2.64 (2H, m), 2.96 (2H, br d, J=11.2 Hz), 3.52 (2H, s), 3.80 (2H, d, J=5.6 Hz), 3.96 (3H, s), 6.80 (1H, d, J=7.6 Hz), 6.83–6.90 (2H, m), 7.10–7.16 (2H, m), 7.68 (1H, dd, J=4.8, 2.0 Hz), B. 06 (1H, dd, J=4.8, 2.0 Hz).

Example 206

1-[(5-Chloro-2-methoxy-3-pyridinyl)methyl]-4-[2-(cyclohexylmethyloxy)phenoxymethyl]piperidine 150 mg of 5-chloro-2-methoxy-3-pyridinecarboxaldehyde and 291 mg of 4-[2-(cyclohexylmethyloxy)phenoxymethyl]piperidine were dissolved in 5 ml of 1,2-dichloroethane. To the mixture were added 0.06 ml of acetic acid and 214 mg of sodium triacetoxyborohydride, followed by stirring at room temperature overnight. An aqueous saturated sodium bicarbonate was added to the reaction solution, and then the mixture was extracted with ethyl acetate. The organic layer was washed with water and brine, and then dried over anhydrous magnesium sulfate. The solvent was evaporated, and the crude product was purified by silica gel column chromatography (n-hexane:ethyl acetate=10:1), to give 285 mg of the title compound as a pale yellow oil.

¹H-NMR (400 MHz, CDCl₃) δ 1.01–1.36 (5H, m), 1.39–1.52 (2H, m), 1.65–1.94 (9H, m), 2.08–2.16 (2H, m), 2.92 (2H, br d, J=11.6 Hz), 3.46 (2H, s), 3.78 (2H, d, J=6.4 Hz), 3.85 (2H, d, J=6.4 Hz), 3.93 (3H, s), 6.86–6.92 (4H, m), 7.67 (1H, d, J=2.4 Hz), 7.98 (1H, d, J=2.4 Hz).

Example 207

1-[(2-Methoxy-3-pyridinyl)methyl]-4-[(E)-2-[(2-cyclohexylmethyloxy)phenyl)-1-etheny]piperidine To acetonitrile (10 ml) were added 500 mg of 2-methoxy-3-(chloromethyl)pyridine, 1.04 g of 4-[(E)-2-[(2-cyclohexylmethyloxy)phenyl]-1-ethenyl]piperidine and 531 mg of potassium carbonate, followed by stirring at room temperature overnight. Ethyl acetate was added to the reaction solution, and the mixture was filtered through alumina-silica gel. Then, the solvent was evaporated, and the crude product was purified by silica gel column chromatography (hexane:ethyl acetate=8:1), to give 961 mg of the title compound as a pale yellow oil.

¹H-NMR (400 MHz, CDCl₃) δ 1.02–1.38 (5H, m), 1.52–1.92 (10H, m), 2.10–2.23 (3H, m), 2.92–2.98 (2H, m), 3.53 (2H, s), 3.77 (2H, d, J=6.0 Hz), 3.96 (3H, s), 6.19 (1H, dd, J=16.0, 7.2 Hz), 6.71 (1H, d, J=16.0 Hz), 6.80–6.92 (3H, m), 7.15 (1H, dt, J=7.2, 1.2 Hz), 7.41 (1H, dd, J=7.2, 1.6 Hz), 7.67 (1H, dd, J=7.6, 2.0 Hz), 8.06 (1H, dd, J=4.8, 2.0 Hz).

Example 208

1-[(5-Chloro-2-methoxy-3-pyridinyl)methyl]-4-[(E)-2-(2-fluorophenyl)-1-ethenyl]piperidine 200 mg of 5-chloro-2-methoxy-3-pyridinecarboxaldehyde and 263 mg of 4-[(E)-2-(2-fluorophenyl)-1-ethenyl]piperidine were dissolved in 5 ml of 1,2-dichloroethane. To the mixture were added 0.09 ml of acetic acid and 339 mg of sodium triacetoxyborohydride, followed by stirring at room temperature for 2.5 hours. The reaction solution was filtered through NH-form silica gel, and the filtrate was evaporated. Ethyl acetate was added to the residue, and the mixture was filtered through alumina, and the filtrate was evaporated. The crude product was purified by silica gel column chromatography (n-hexane:ethyl acetate=10:1), to give 245 mg of the title compound as a colorless oil.

¹H-NMR (400 MHz, CDCl₃) δ 1.53–1.69 (2H, m), 1.75–1.83 (2H, m), 2.10–2.24 (3H, m), 2.85–2.96 (2H, m), 3.47 (2H, s), 3.93 (3H, s), 6.25 (1H, dd, J=16.0, 6.8 Hz), 6.55 (1H, d, J=16.0 Hz), 7.01 (1H, ddd, J=10.8, 8.0, 1.2 Hz), 7.07 (1H, dt, J=8.0, 1.2 Hz), 7.16 (1H, m), 7.44 (1H, dt, J=8.0, 1.2 Hz), 7.68 (1H, d, J=2.4 Hz), 7.99 (1H, d, J=2.4 Hz).

Example 209

1-[(5-Cyano-2-methoxy-3-pyridinyl)methyl]-4-[(E)-2-(2-fluorophenyl)-1-ethenyl]piperidine The title compound was obtained from a corresponding raw material in accordance with the method of Example 206.

¹H-NMR (400 MHz, CDCl₃) δ 1.53–1.66 (2H, m), 1.76–1.84 (2H, m), 2.12–2.26 (3H, m), 2.85–2.92 (2H, m), 3.48 (2H, s), 4.01 (3H, s), 6.26 (1H, dd, J=16.0, 6.8 Hz), 6.56 (1H, d, J=16.0 Hz), 7.01 (1H, ddd, J=11.2, 8.4, 1.2 Hz), 7.08 (1H, dt, J=8.4, 1.2 Hz), 7.17 (1H, m), 7.45 (1H, dt, J=8.4, 1.2 Hz), 7.95 (1H, d, J=2.4 Hz), 8.37 (1H, d, J=2.4 Hz).

Example 210

1-[(5-Fluoro-2-methoxy-3-pyridinyl)methyl]-4-[(E)-2-(2-fluorophenyl)-1-ethenyl]piperidine 117 mg of 5-fluoro-2-methoxy-3-pyridinecarboxaldehyde and 291 mg of 4-[(E)-2-(2-fluorophenyl)-1-ethenyl]piperidine were dissolved in 3 ml of 1,2-dichloroethane, 0.06 ml of acetic acid and 238 mg of sodium triacetoxyborohydride were added thereto, and the mixture was stirred at room temperature overnight. An aqueous saturated sodium carbonate was added to the reaction solution, and the mixture was extracted with ethyl acetate. The organic layer was washed with water and brine, and then dried over anhydrous magnesium sulfate. The solvent was evaporated, and the crude product was purified by silica gel column chromatography (n-hexane:ethyl acetate=8:1), to give 221 mg of the title compound as a colorless oil.

$^1$H-NMR (400 MHz, CDCl$_3$) δ 1.53–1.69 (2H, m), 1.75–1.83 (2H, m), 2.11–2.25 (3H, m), 2.89–2.96 (2H, m), 3.48 (2H, s), 3.93 (3H, s), 6.26 (1H, dd, J=16.0, 6.8 Hz), 6.55 (1H, d, J=16.0 Hz), 7.01 (1H, ddd, J=10.4, 8.0, 1.2 Hz), 7.07 (1H, dt, J=8.0, 1.2 Hz), 7.16 (1H, m), 7.44 (1H, dt, J=8.0.1.2 Hz), 7.53 (1H, dd, J=8.4, 3.2 Hz), 7.87 (1H, d, J=3.2 Hz).

Example 211

1-[(5-Fluoro-2-methoxy-3-pyridinyl)methyl]-4-[(E)-2-[(2-cyclohexylmethyloxy)phenyl]-1-ethenyl]piperidine The title compound was obtained from a corresponding raw material in accordance with the method of Example 206.

$^1$H-NMR (400 MHz, CDCl$_3$) δ 1.03–1.38 (5H, m), 1.52–1.93 (10H, m), 2.12–2.24 (3H, m), 2.89–2.96 (2H, m), 3.48 (2H, s), 3.78 (2H, d, J=6.0 Hz), 3.93 (3H, s), 6.20 (1H, dd, J=16.0, 7.2 Hz), 6.72 (1H, d, J=16.0 Hz), 6.83 (1H, d, J=8.0 Hz), 6.88 (1H, dt, J=7.6, 1.6 Hz), 7.15 (1H, dt, J=7.6, 2.0 Hz), 7.41 (1H, dd, J=7.6, 1.6 Hz), 7.53 (1H, dd, J=8.4, 2.8 Hz), 7.87 (1H, d, J=2.8 Hz).

Example 212

1-[(5-Chloro-2-methoxy-3-pyridinyl)methyl]-4-[(E)-2-(2-chlorophenyl)-1-ethenyl]piperidine The title compound was obtained from a corresponding raw material in accordance with the method of Example 206.

$^1$H-NMR (400 MHz, CDCl$_3$) δ 1.54–1.66 (2H, m), 1.76–1.84 (2H, m), 2.15 (2H, dt, J=2.4, 12.0 Hz), 2.21 (1H, m), 2.89–2.96 (2H, m), 3.47 (2H, s), 3.93 (3H, s), 6.17 (1H, dd, J=16.0, 7.2 Hz), 6.77 (1H, d, J=16.0 Hz), 7.14 (1H, dt, J=8.0, 2.0 Hz), 7.20 (1H, dt, J=8.0, 2.0 Hz), 7.33 (1H, dd, J=8.0, 2.0 Hz), 7.51 (1H, dt, J=8.0, 2.0 Hz), 7.68 (1H, d, J=2.8 Hz).

Example 213

1-[(5-Chloro-2-methoxy-3-pyridinyl)methyl]-4-[(E)-2-(2-methylphenyl)-1-ethenyl]piperidine The title compound was obtained from a corresponding raw material in accordance with the method of Example 206.

$^1$H-NMR (400 MHz, CDCl$_3$) δ 1.53–1.67 (2H, m), 1.75–1.83 (2H, m), 2.10–2.24 (3H, m), 2.33 (3H, s), 2.89–2.96 (2H, m), 3.47 (2H, s), 3.93 (3H, s), 6.06 (1H, dd, J=16.0, 7.2 Hz), 6.48 (1H, dd, J=16.0, 0.8 Hz), 7.08–7.18 (3H, m), 7.41 (1H, d, J=6.8 Hz), 7.68 (1H, d, J=2.8 Hz), 7.98 (1H, d, J=2.8 Hz).

Example 214

1-[(2-Methoxy-3-pyridinyl)methyl]-4-[(E)-2-(2-methylphenyl)-1-ethenyl]piperidine In N,N-dimethylformamide (10 ml) was suspended 1.15 g of [(2-methylphenyl)methyl]triphenylphosphonium bromide. To the suspension was added 288 mg of potassium tert-butoxide, followed by stirring for 15 minutes under ice-cooling. A solution of 500 mg of 1-[(2-methoxy-3-pyridinyl)methyl]-4-piperidinecarboxaldehyde dissolved in 3 ml of N,N-dimethylformamide was added dropwise thereinto, followed by stirring at room temperature overnight. Ice-water was added to the reaction solution, and the mixture was extracted with ethyl acetate. The organic layer was washed with water and brine, and then dried over anhydrous magnesium sulfate. The solvent was evaporated, and the crude product was purified by silica gel column chromatography (n-hexane:ethyl acetate=1:1), to give 473 mg of the title compound as a pale yellow oil.

$^1$H-NMR (400 MHz, CDCl$_3$) δ 1.48–1.68 (2H, m), 1.74–1.83 (2H, m), 1.96–2.22 (3H, m), 2.19 (3/4H s), 2.32 (9/4H, s), 2.86 (1/2H, br d, J=7.6 Hz), 2.99 (3/2H, br d, J=12 Hz), 3.47 (1/2H s), 3.52 (3/2H, s), 3.93 (3/4H s), 3.96 (9/4H, s), 5.55 (1/4H, dd, J=11.6, 10.0 Hz), 6.05 (3/4H, dd, J=15.6, 7.6 Hz), 6.37 (1/4H, d, J=11.6 Hz), 6.57 (3/4H, d, J=15.6 Hz), 6.84–6.92 (1H, m), 7.00–7.20 (3H, m), 7.41 (1H, d, J=6.4 Hz), 7.63 (1/4H, dd, J=7.2, 2.0 Hz), 7.67 (3/4H, dd, J=6.8, 2.0 Hz), 8.03–8.09 (1H, m).

Example 215

1-[(2-Methoxy-3-pyridinyl)methyl]-4-[(E)-2-[3-(benzyloxy)phenyl]-1-ethenyl]piperidine The title compound was obtained from a corresponding raw material in accordance with the method of Example 214.

$^1$H-NMR (400 MHz, CDCl$_3$) δ 1.50–1.80 (4H, m), 2.02–2.20 (11/5H, m), 2.56 (4/5H, m), 2.85–2.98 (2H, m), 3.49 (2/5H, s), 3.52 (8/5H, s), 3.94 (3/5H, s), 3.96 (12/5H, s), 5.07 (2H, s), 5.50 (1/5H, dd, J=11.2, 6.0 Hz), 6.17 (4/5H, dd, J=16.0, 6.8 Hz), 6.34 (1/5H, d, J=11.2 Hz), 6.35 (4/5H, d, J=16.0 Hz), 6.80–6.90 (3H, m), 6.93–7.00 (2H, m), 7.18–7.25 (1H, m), 7.20–7.46 (4H, m), 7.65 (1/5H, br d, J=6.4 Hz), 7.67 (4/5H, br d, J=6.4 Hz), 8.06 (1H, dd, J=4.8, 2.0 Hz).

Example 216

1-[(2-Methoxy-3-pyridinyl)methyl]-4-[[(E)-2-(2-phenylethyl)phenyl]-1-ethenyl]piperidine The title compound was obtained from a corresponding raw material in accordance with the method of Example 214.

$^1$H-NMR (400 MHz, CDCl$_3$) δ 1.52–1.66 (2H, m), 1.74–1.83 (11/6H, m), 2.01 (1/6H, m), 2.10–2.24 (17/6H, m), 2.36 (1/6H, m), 2.78–3.00 (6H, m), 3.47 (1/3H, s), 3.53 (5/3H, s), 3.53 (1/2H, s), 3.96 (5/2H, s), 5.91 (1/6H, dd, J=11.2, 10.0 Hz), 6.07 (5/6H, dd, J=15.6, 6.8 Hz), 6.46 (1/6H, d, J=11.2 Hz), 6.64 (5/6H, d, J=15.6 Hz), 6.84–6.92 (1H, m), 7.09–7.24 (6H, m), 7.25–7.33 (2H, m), 7.43 (1H, dd, J=6.8, 2.0 Hz), 7.63 (1/5H, br d, J=6.8 Hz), 7.68 (5/6H, br d, J=6.8 Hz), 8.05 (1/5H, dd, J=5.2, 2.0 Hz), 8.06 (5/6H, dd, J=5.2, 2.0 Hz).

Example 217

1-[(2-Methoxy-3-pyridinyl)methyl]-4-[(E)-2-[2-(isobutyloxy)phenyl]-1-ethenyl]piperidine The title compound was obtained from a corresponding raw material in accordance with the method of Example 214.

$^1$H-NMR (400 MHz, CDCl$_3$) δ 1.02 (6/5H, d, J=6.8 Hz), 1.05 (24/5H, d, J=6.8 Hz), 1.48–1.64 (2H, m), 1.74–1.83 (2H, m), 2.00–2.22 (19/5H, m), 2.51 (1/5H, m), 2.84–2.98 (2H, m), 3.48 (2/5H, s), 3.52 (8/5H, m), 3.72 (2/5H, d, J=6.4 Hz), 3.74 (8/5H, d, J=6.4 Hz), 3.94 (3/5H, s), 3.96 (12/5H, s), 5.12 (1/5H, dd, J=11.6, 10.0 Hz), 6.21 (4/5H, dd, J=16.0, 7.2 Hz), 6.50 (1/5H, d, J=11.6 Hz), 6.73 (4/5H, d, J=16.0 Hz), 6.80–6.93 (3H, m), 7.12–7.24 (1H, m), 7.41 (1H, dd, J=7.6, 1.6 Hz), 7.65 (1/5H, dd, J=6.8, 2.0 Hz), 7.67 (4/5H, dd, J=6.8, 2.0 Hz), 8.05 (1/5H, dd, J=5.2, 2.0 Hz), 8.06 (4/5H, dd, J=5.2, 2.0 Hz).

Example 218

1-[(2-Methoxy-3-pyridinyl)methyl]-4-[(E)-2-[3-(cyclohexylmethyloxy)phenyl]-1-ethenyl]piperidine The title compound was obtained from a corresponding raw material in accordance with the method of Example 214.

$^1$H-NMR (400 MHz, CDCl$_3$) δ 0.98–1.38 (5H, m), 1.49–1.92 (10H, m), 2.03–2.20 (11/4H, m), 2.60 (1/4H, m), 2.86–2.98 (2H, m), 3.49 (1/2H, s), 3.51 (3/2H, m), 3.74 (1/2H, d, J=6.4 Hz), 3.75 (3/2H, d, J=6.4 Hz), 3.94 (3/4H, s), 3.96 (9/4H, s), 5.49 (1/4H, dd, J=11.6, 10.0 Hz), 6.17 (4/5H, dd, J=16.0, 6.8 Hz), 6.32 (1/4H, d, J=11.6 Hz), 6.33 (3/4H, d, J=16.0 Hz), 6.72–6.93 (4H, m), 7.16–7.28 (1H, m), 7.55 (1/4H, dd, J=7.2, 2.0 Hz), 7.57 (3/4H, dd, J=7.2, 2.0 Hz), 8.07 (1H, dd, J=5.6, 2.0 Hz).

Example 219

1-[(2-Methoxy-3-pyridinyl)methyl]-4-[(E)-2-[2-(2-phenylethoxy)phenyl]-1-ethenyl]piperidine The title compound was obtained from a corresponding raw material in accordance with the method of Example 214.

$^1$H-NMR (400 MHz, CDCl$_3$) δ 1.48–1.81 (4H, m), 2.00–2.20 (17/6H, m), 2.48 (1/6H, m), 2.85–3.00 (2H, m), 3.09 (1/3H, t, J=6.8 Hz), 3.13 (5/3H, t, J=6.8 Hz), 3.48 (1/3H, s), 3.53 (5/3H, s), 3.94 (1/2H, s), 3.96 (5/2H, s), 4.179 (1/3H, t, J=6.8 Hz), 4.19 (5/3H, t, J=6.8 Hz), 5.52 (1/6H, dd, J=11.6, 10.0 Hz), 6.15 (5/6H, dd, J=16.0, 7.2 Hz), 6.44 (1/6H, d, J=11.6 Hz), 6.67 (5/6H, d, J=16.0 Hz), 6.80–6.94 (3H, m), 7.11–7.37 (6H, m), 7.40 (1H, dd, J=8.0, 1.6 Hz), 7.65 (1/6H, br d, J=6.8 Hz), 7.69 (5/6H, br d, J=6.8 Hz), 8.05 (1/6H, dd, J=4.8, 2.0 Hz), 8.06 (5/6H, dd, J=4.8, 2.0 Hz).

Example 220

1-[(2-Methoxy-3-pyridinyl)methyl]-4-[(E)-2-[2-(phenoxymethyl)phenyl]-1-ethenyl]piperidine The title compound was obtained from a corresponding raw material in accordance with the method of Example 214.

$^1$H-NMR (400 MHz, CDCl$_3$) δ 1.46–1.78 (4H, m), 1.95–2.20 (17/6H, m), 2.31 (1/6H, m), 2.82–2.96 (2H, m), 3.43 (1/3H, s), 3.50 (5/3H, s), 3.93 (1/2H, s), 3.95 (5/2H, s), 5.00 (1/3H, s), 5.07 (5/3H, s), 5.61 (1/6H, dd, J=11.6, 10.0 Hz), 6.11 (5/6H, dd, J=16.0, 6.8 Hz), 6.48 (1/6H, dd, J=11.6 Hz), 6.62 (5/6H, dd, J=16.0 Hz), 6.85–6.90 (1H, m), 6.92–7.02 (2H, m), 7.17–7.36 (5H, m), 7.41 (1H, dd, J=, 6.0, 2.0 Hz), 7.50 (1H, dd, J=7.6, 1.2 Hz), 7.63 (1/6H, br d, J=7.2 Hz), 7.65 (5/6H, br d, J=7.2 Hz), 8.06 (1H, dd, J=5.2, 2.0 Hz).

Example 221

1-[(2-Methoxy-3-pyridinyl)methyl]-4-[(E)-2-[2-(cyclopentylmethyloxy)phenyl]-1-ethenyl]piperidine The title compound was obtained from a corresponding raw material in accordance with the method of Example 214.

$^1$H-NMR (400 MHz, CDCl$_3$) δ 1.30–1.44 (2H, m), 1.50–1.73 (8H, m), 1.74–1.91 (11/4H, m), 2.00–2.22 (9/4H, m), 2.39 (3/4H, m), 2.51 (1/4H, m), 2.98 (1/2H, br d, J=11.6 Hz), 2.95 (3/2H, br d, J=11.6 Hz), 3.48 (1/2H, s), 3.52 (3/2H, s), 3.84 (1/2H, d, J=6.8 Hz), 3.85 (3/2H, d, J=6.8 Hz), 3.94 (3/4H, d, J=6.8 Hz), 3.96 (9/4H, s), 5.51 (1/4H, dd, J=12.0, 10.0 Hz), 6.21 (3/4H, dd, J=15.6, 7.2 Hz), 6.48 (1/4H, d, J=12.0 Hz), 6.70 (4/5H, d, J=15.6 Hz), 6.80–6.94 (3H, m), 7.12–7.23 (1H, m), 7.40 (1H, dd, J=7.6, 1.2 Hz), 7.65 (1/4H, dd, J=7.2, 2.0 Hz), 7.67 (3/4H, dd, J=7.2, 2.0 Hz), 8.06 (1/4H, dd, J=5.2, 2.0 Hz), 8.07 (3/4H, dd, J=5.2, 2.0 Hz).

Example 222

1-[(2-Methoxy-3-pyridinyl)methyl]-4-[(E)-[2-(2-cyclohexylethyl)phenyl]-1-ethenyl]piperidine The title compound-was obtained from a corresponding raw material in accordance with the method of Example 214.

$^1$H-NMR (400 MHz, CDCl$_3$) δ 0.85–1.00 (2H, m), 1.10–1.83 (15H, m), 1.65–2.04 (3/4H, m), 2.10–2.23 (2H, m), 2.32 (1/4H, m), 2.53–2.59 (1/2H, m), 2.60–2.67 (3/2H, m), 2.82–2.88 (1/2H, m), 2.91–2.99 (3/2H, m), 3.46 (1/2H, s), 3.53 (3/2H, s), 3.93 (3/4H, s), 3.96 (9/4H, s), 5.54 (1/4H, dd, J=11.2, 10.0 Hz), 6.04 (3/4H, d, J=16.0, 6.8 Hz), 6.44 (1/4H, d, J=11.2 Hz), 6.60 (3/4H, d, J=16.0 Hz), 6.84–6.92 (1H, m), 7.06–7.22 (3H, m), 7.38–7.44 (1H, m), 7.63 (1/4H, dd, J=7.2, 2.0 Hz), 7.67 (1/4H, dd, J=7.2, 2.0 Hz), 8.05 (1/4H, dd, J=4.8, 2.0 Hz), 8.06 (3/4Hi dd, J=4.8, 2.0 Hz).

Example 223

1-[(2-Methoxy-3-pyridinyl)methyl]-4-[(E)-2-[2-(cyclohexylmethyloxy)-5-fluorophenyl]-1-ethenyl]piperidine The title compound was obtained from a corresponding raw material in accordance with the method of Example 214.

$^1$H-NMR (400 MHz, CDCl$_3$) δ 0.97–1.38 (5H, m), 1.48–1.92 (10H, m), 2.01–2.23 (8/3H, m), 2.48 (1/3H, m), 2.85–2.98 (2H, m), 3.48 (2/3H, s), 3.52 (4/3H, s), 3.71 (2/3H, d, J=6.4 Hz), 3.72 (4/3H, d, J=6.4 Hz), 3.94 (1H, s), 3.96 (2H, s), 5.55 (1/3H, t, J=11.6 Hz), 6.20 (2/3H, dd, J=16.0, 6.8 Hz), 6.43 (1/3H, d, J=11.6 Hz), 6.67 (2/3H, d, J=16.0 Hz), 6.71–6.93 (3H, m), 7.11 (1H, dd, J=9.6, 3.2 Hz), 7.62–7.70 (1H, m), 8.06 (1H, m).

Example 224

1-[(2-Methoxy-3-pyridinyl)methyl]-4-[(E)-2-(2-(cyclohexylmethyloxy)-4-fluorophenyl]-1-ethenyl]piperidine The title compound was obtained from a corresponding raw material in accordance with the method of Example 214.

$^1$H-NMR (400 MHz, CDCl$_3$) δ 0.97–1.38 (5H, m), 1.47–1.81 (10H, m), 1.99–2.21 (8/3H, m), 2.43 (1/3H, m), 2.85–2.97 (2H, m), 3.47 (2/3H, s), 3.51 (4/3H, s), 3.72 (2/3H, d, J=6.8 Hz), 3.73 (4/3H, d, J=6.0 Hz), 3.94 (1H, s), 3.96 (2H, s), 5.50 (1/3H, dd, J=11.6, 10.0 Hz), 6.12 (2/3H, dd, J=16.0, 7.2 Hz), 6.38 (1/3H, d, J=11.6 Hz), 6.52–6.66 (8/3H, m), 6.84–6.93 (1H, m), 7.11 (1/3H, t, J=7.6 Hz), 7.33 (2/3H, dd, J=8.4, 6.8 Hz), 7.62–7.70 (1H, m), 78.03–8.11 (1H, m).

Example 225

1-[(2-Methoxy-3-pyridinyl)methyl]-4-[(E)-2-(2-(cyclohexylmethyloxy)-6-fluorophenyl]-1-ethenyl]piperidine The title compound was obtained from a corresponding raw material in accordance with the method of Example 214.

$^1$H-NMR (400 MHz, CDCl$_3$) δ 1.04–1.38 (6H, m), 1.44 (1H, m), 1.52–1.65 (2H, m), 1.68–1.91 (6H, m), 2.10–2.22 (3H, m), 2.90–2.98 (2H, m), 3.52 (2H, s), 3.78 (2H, d, J=6.0 Hz), 3.96 (3H, s), 6.48–6.68 (4H, m), 6.88 (1H, dd, J=7.6, 5.2 Hz), 7.05 (1H, dt, J=8.0, 6.4 Hz), 7.67 (1H, dd, J=7.2, 2.0 Hz), 8.06 (1H, dd, J=5.2, 2.0 Hz).

Example 226

1-[(2-Methoxy-3-pyridinyl)methyl]-4-[(E)-2-(2-methoxy-5-methylphenyl]-1-ethenyl]piperidine oxalate The free compound was obtained from a corresponding raw material in accordance with the method of Example 214, and it was conventionally converted into an oxalate, to give the title compound.

$^1$H-NMR (400 MHz, CDCl$_3$) δ 1.54–1.72 (2H, m), 1.89 (2H, brd, J=11.6 Hz), 2.23 (3H, s), 2.30–2.54 (1H, m), 2.90–3.06 (2H, m), 3.35 (2H, br d, J=10.8 Hz), 3.75 (3H, s), 3.94 (3H, s), 4.20 (2H, s), 6.10–6.26 (1H, m), 6.62 (1H, d, J=16.4 Hz), 6.86 (1H, d, J=8.4 Hz), 7.02 (1H, dd, J=8.4, 1.6 Hz), 7.10 (1H, dd, J=7.2, 4.8 Hz), 7.27 (1H, s), 7.88 (1H, d, J=6.4 Hz), 7.27 (1H, d, J=4.4 Hz).

Example 227

1-[(2-Methoxy-3-pyridinyl)methyl]-4-[(E)-2-(3-bromophenyl)-1-ethenyl]piperidine oxalate The title compound was obtained from a corresponding raw material in accordance with the method of Example 226.

$^1$H-NMR (400 MHz, CDCl$_3$) δ 1.56–1.74 (2H, m), 1.91 (2H, br d, J=12.8 Hz), 2.36–2.50 (1H, m), 2.90–3.06 (2H, m), 3.35 (2H, br d, J=11.2 Hz), 3.94 (3H, s), 4.19 (2H, s), 6.30–6.48 (2H, m), 7.06–7.14 (1H, m), 7.24–7.38 (1H, m), 7.38–7.50 (2H, m), 7.65 (1H, s), 7.88 (1H, d, J=7.6 Hz), 8.27 (1H, d, J=4.4 Hz).

Example 228

1-[(2-Methoxy-3-pyridinyl)methyl]-4-[(E)-2-[2-(cyclopentyloxy)phenyl]-1-ethenyl]piperidine 786 mg of diethyl 2-(cyclopentyloxy)benzylphosphonate was dissolved in 10 ml of tetrahydrofuran. To the mixture was added 281 mg of potassium tert-butoxide, followed by stirring for 15 minutes under ice-cooling. A solution of 500 mg of 1-[(2-methoxy-3-pyridinyl)methyl]-4-piperidinecarboxaldehyde dissolved in 3 ml of tetrahydrofuran was added dropwise thereinto, followed by stirring at room temperature for 2 hours. Ice water was added to the reaction solution, and the mixture was extracted with ethyl acetate. The organic layer was washed with water and brine, and then dried over anhydrous magnesium sulfate. The solvent was evaporated, and the resulting crude product was purified by silica gel column chromatography (n-hexane:ethyl acetate=1:1), to give 473 mg of the title compound as a pale yellow oil.

$^1$H-NMR (400 MHz, CDCl$_3$) δ 1.48–1.94 (12H, m), 2.00–2.22 (11/4H, m), 2.50 (1/4H, m), 2.85–3.00 (2H, m), 3.48 (1/2H s), 3.52 (3/2H, s), 3.94 (3/4H, s), 3.96 (9/4H, s), 4.78 (1H, m), 5.48 (1/4H, dd, J=12.0, 10.0 Hz), 6.18 (3/4H, dd, J=15.6, 7.2 Hz), 6.44 (1/4H, d, J=12.0 Hz), 6.66 (3/4H, d, J=15.6 Hz), 6.82–6.92 (11/4H, m), 7.10–7.22 (5/4H, m), 7.40 (1H, dd, J=7.2, 1.6 Hz), 7.63–7.52 (1H, m), 8.03–8.09 (1H, m).

Example 229

1-[(2-Methoxy-3-pyridinyl)methyl]-4-[(E)-2-(2-phenoxyphenyl)-1-ethenyl]piperidine The title compound was obtained from a corresponding raw material in accordance with the method of Example 228.

$^1$H-NMR (400 MHz, CDCl$_3$) δ 1.44–1.74 (4H, m), 1.98–2.16 (2H, m), 2.40–2.55 (1H, m), 2.84–2.94 (2H, m), 3.48 (2H, s), 3.94 (3H, s), 6.20 (1H, dd, J=16, 7.2 Hz), 6.63 (1H, d, J=16 Hz), 6.84–7.40 (10H, m), 7.60–7.66 (1H, m), 8.02–8.06 (1H, m).

Example 230

1-[(2-Methoxy-3-pyridinyl)methyl]-4-[(E)-2-[3-(cyclopentyloxy)phenylphenyl]-1-ethenyl]piperidine The title compound was obtained from a corresponding raw material in accordance with the method of Example 228.

$^1$H-NMR (400 MHz, CDCl$_3$) δ 1.48–1.96 (12H, m), 2.04–2.18 (14/5H, m), 2.61 (1/5H, m), 2.86–2.99 (2H, m), 3.50 (2/5H s), 3.52 (8/5H, s), 3.94 (3/5H, s), 3.96 (12/5H, s), 4.72–4.80 (1H, m), 5.49 (1/5H, dd, J=11.6, 10.0 Hz), 6.16 (4/5H, dd, J=15.6, 6.8 Hz), 6.33 (4/5H, d, J=15.6 Hz), 6.34 (1/5H, d, J=11.6 Hz), 6.70–6.94 (4H, m), 7.15–7.25 (1H, m), 7.63–7.70 (1H, m), 8.04–8.08 (1H, m).

Example 231

1-[(2-Methoxy-3-pyridinyl)methyl]-4-[(E)-2-[2-(benzyloxy)phenyl]-1-ethenyl]piperidine The title compound was obtained from a corresponding raw material in accordance with the method of Example 228.

$^1$H-NMR (400 MHz, CDCl$_3$) δ 1.48–1.82 (4H, m), 2.00–2.23 (14/5H, m), 2.50 (1/5H, m), 2.85–2.98 (2H, m), 3.48 (2/5H s), 3.51 (8/5H, s), 3.94 (3/5H, s), 3.95 (12/5H, s), 5.10 (2H, s), 5.55 (1/5H, dd, J=11.6, 10.0 Hz), 6.18 (4/5H, dd, J=16.0, 7.2 Hz), 6.54 (1/5H, d, J=11.6 Hz), 6.78 (4/5H, d, J=16.0 Hz), 6.84–6.97 (3H, m), 7.12–7.24 (2H, m), 7.28–7.48 (5H, m), 7.64 (1/5H, br d, J=6.8 Hz), 7.66 (4/5H, br d, J=6.8 Hz), 8.05 (1/5H, dd, J=4.8, 2.4 Hz), 8.06 (4/5H, dd, J=4.8, 2.4 Hz).

Example 232

1-[(2-Methoxy-3-pyridinyl)methyl]-4-[(E)-2-(2,5-dimethylphenyl]-1-ethenyl]piperidine oxalate The title compound was obtained by obtaining a free body from a corresponding raw material in accordance with the method of Example 228 and converting it into an oxalate in a conventional method.

$^1$H-NMR (400 MHz, CDCl$_3$) δ 1.54–1.74 (2H, m), 1.88 (2H, br d, J=13.2 Hz), 2.22 (3H, s), 2.25 (3H, s), 2.30–2.50 (1H, m), 2.64–2.90 (2H, m), 3.26 (2H, br d, J=10.8 Hz), 3.92 (3H, s), 4.06 (2H, s), 6.09 (1H, dd, J=16.0, 6.8 Hz), 6.57 (1H, d, J=16.0 Hz), 6.94 (1H, d, J=7.6 Hz), 7.03 (1H, d, J=7.6 Hz), 7.08 (1H, dd, J=7.6, 5.2 Hz), 7.26 (1H, s), 7.85 (1H, dd, J=7.6, 1.2 Hz), 8.23 (1H, dd, J=5.2, 1.2 Hz).

Example 233

1-[(2-Methoxy-3-pyridinyl)methyl]-4-[(E)-2-(3,5-dimethylphenyl]-1-ethenyl]piperidine oxalate The title compound was obtained from a corresponding raw material in accordance with the method of Example 232.

$^1$H-NMR (400 MHz, CDCl$_3$) δ 1.56–1.74 (2H, m), 1.90 (2H, brd, J=12.0 Hz), 2.24 (6H, s), 2.30–2.50 (1H, m), 2.90–3.08 (2H, m), 3.35 (2H, br d, J=11.2 Hz), 3.93 (3H, s), 4.20 (2H, s), 6.10–6.26 (1H, m), 6.30–6.40 (1H, m), 6.86 (1H, s), 7.01 (2H, s), 7.06–7.14 (1H, m), 7.89 (1H, d, J=7.2 Hz), 8.27 (1H, d, J=4.8 Hz).

Example 234

1-[(2-Methoxy-3-pyridinyl)methyl]-4-[(Z)-4-[2,3-(methylenedioxy)phenyl]-1-butenyl]piperidine The title compound was obtained from a corresponding raw material in accordance with the method of Example 214.

¹H-NMR (400 MHz, CDCl₃) δ 1.30–1.46 (4H, m), 1.98–2.08 (2H, m), 2.19 (1H m), 2.26–2.42 (2H, m), 2.63 (2H, t, J=8.0 Hz), 2.84 (2H, br d, J=11.6 Hz), 3.47 (2H s), 3.95 (3H, s), 5.24 (1H, dd, J=10.4, 9.6 Hz), 5.34 (1H, m), 5.93 (2H, s), 6.66 (1H, dd, J=8.0, 2.0 Hz), 6.78 (1H, dd, J=8.0, 2.0 Hz), 6.74 (1H, t, J=8.0 Hz), 6.87 (1H, dd, J=7.2, 4.8 Hz), 7.63 (1H, dd, J=7.2, 2.0 Hz), 8.05 (1H, dd, J=4.8, 2.0 Hz).

Example 235

1-[(2-Methoxy-3-pyridinyl)methyl]-4-[(Z)-2-[(2-cyclohexylmethyloxy)phenyl]-1-ethenyl]piperidine To dichloromethane (5 ml) were added 2.355 g of [[(2-cyclohexylmethyloxy)phenyl]methyl] triphenylphosphonium chloride, 650 mg of potassium carbonate and 18-crown-6 (11 mg). While heating under reflux, a solution of 1.000 g of 1-[(2-methoxy-3-pyridinyl)methyl]-4-piperidinecarboxaldehyde dissolved in 10 ml of dichloromethane was added dropwise thereinto over 20 minutes. After heating under reflux for 6 hours, ethyl acetate was added to the reaction solution, and filtered through NH-form silica gel. The filtrate was evaporated, and the resulting crude product was purified by silica gel column chromatography (n-hexane:ethyl acetate=6:1), to give 1.047 g of a pale yellow oil. The oil was dissolved in ethyl acetate, 944 mg of di-O-benzoyl-D-tartaric acid was added thereto, and the resulting crystals were separated by filtration. An aqueous saturated sodium carbonate was added to the filtrate, and the mixture was extracted with ethyl acetate. The organic layer was washed with water and brine, and dried over anhydrous magnesium sulfate. The solution was filtered through alumina, and the filtrate was evaporated, to give 374 mg of the title compound as a slight yellow oil.

¹H-NMR (400 MHz, CDCl₃) δ 0.98–1.36 (5H, m), 1.52–1.92 (10H, m), 2.00–2.10 (2H, m), 2.51 (1H, m), 2.84–2.92 (2H, m), 3.48 (2H, s), 3.75 (2H, d, J=6.4 Hz), 3.94 (3H, s), 5.52 (1H, dd, J=11.6, 10.4 Hz), 6.49 (1H, d, J=11.6 Hz), 6.80–6.94 (3H, m), 7.15–7.25 (2H, m), 7.65 (1H, br d, J=7.2 Hz), 8.05 (1H, dd, J=5.2, 2.0 Hz).

Example 236

1-[(2-Methoxy-3-pyridinyl)methyl]-4-(2,2-diphenyl-1-ethenyl)piperidine

The title compound was obtained from a corresponding raw material in accordance with the method of Example 214.

¹H-NMR (400 MHz, CDCl₃) δ 1.52–1.68 (4H, m), 1.90–2.02 (2H, m), 2.14 (1H, m), 2.86 (2H, br d, J=10.8 Hz), 3.46 (2H s), 3.93 (3H s), 5.92 (1H, d, J=10.0 Hz), 6.87 (1H, dd, J=7.2, 4.8 Hz), 7.14–7.40 (10H, m), 7.64 (1H, br d, J=6.8 Hz), 8.05 (1H, dd, J=5.2, 2.0 Hz).

Example 237 1-[(2-Methoxy-3-pyridinyl)methyl]-4-[3-[2,3-(methylenedioxy)phenyl]propyl]piperidine The title compound was obtained from a corresponding raw material in accordance with the method of Example 201.

¹H-NMR (400 MHz, CDCl₃) δ 1.18–1.34 (4H, m), 1.58–1.62 (5H, m), 2.01 (2H, br t, J=10.8 Hz), 2.55 (2H, t, J=7.6 Hz), 2.89 (2H, br d, J=11.2 Hz), 3.48 (2H s), 3.94 (3H, s), 5.92 (2H, s), 6.66 (1H, dd, J=7.6, 2.0 Hz), 6.68 (1H, dd, J=7.6, 2.0 Hz), 6.75 (1H, t, J=7.6 Hz), 6.86 (1H, dd, J=7.2, 4.8 Hz), 7.64 (1H, dd, J=7.2, 2.0 Hz), 8.05 (1H, dd, J=4.8, 2.0 Hz).

Example 238

1-[(2-Methoxy-3-pyridinyl)methyl]-4-[5-[2,3-(methylenedioxy)phenyl]pentyl]piperidine The title compound was obtained from a corresponding raw material in accordance with the method of Example 201.

¹H-NMR (400 MHz, CDCl₃) δ 1.16–1.38 (8H, m), 1.55–1.70 (5H, m), 2.01 (2H, br t, J=11.6 Hz), 2.56 (2H, t, J=8.0 Hz), 2.89 (2H, br d, J=11.6 Hz), 3.48 (2H s), 3.93 (3H, s), 5.92 (2H, s), 6.66 (1H, dd, J=8.0, 1.2 Hz), 6.68 (1H, dd, J=8.0, 1.2 Hz), 6.75 (1H, t, J=8.0 Hz), 6.86 (1H, dd, J=7.2, 4.8 Hz), 7.64 (1H, dd, J=7.2, 2.0 Hz), 8.05 (1H, dd, J=4.8, 2.0 Hz).

Example 239

1-[(6-Methyl-2-methoxy-3-pyridinyl)methyl]-4-[2-[2,3-(methylenedioxy)phenyl]ethyl]piperidine The title compound was obtained from a corresponding raw material in accordance with the method of Example 201.

¹H-NMR (400 MHz, CDCl₃) δ 1.24–1.38 (3H, m), 1.52–1.59 (2H, m), 1.67–1.76 (2H, m), 1.99 (2H, m), 2.42 (3H, s), 2.55–2.62 (2H, m), 2.88 (2H, br d, J=11.6 Hz), 3.45 (2H s), 3.92 (3H, s), 5.92 (2H, s), 6.07 (1H, br d, J=6.8 Hz), 6.65 (1H, dd, J=7.6, 1.2 Hz), 6.68 (1H, dd, J=7.6, 1.2 Hz), 6.75 (1H, t, J=7.6 Hz), 7.49 (1H, d, J=7.2 Hz).

Example 240

1-[(2-Methoxy-3-pyridinyl)methyl]-4-(2,2-diphenylethyl)piperidine

The title compound was obtained from a corresponding raw material in accordance with the method of Example 256.

¹H-NMR (400 MHz, CDCl₃) δ 1.17 (1H, m), 1.24–1.40 (2H, m), 1.67–1.75 (2H, m), 1.87–2.02 (4H, m), 2.84 (2H, br d, J=11.6 Hz), 3.44 (2H, s), 3.92 (3H, s), 4.04 (1H, t, J=7.6 Hz), 6.85 (1H, dd, J=6.8, 4.8 Hz), 7.14–7.30 (10H, m), 7.62 (1H, br d, J=6.8 Hz), 8.04 (1H, dd, J=5.2, 2.0 Hz).

Example 241

1-[(5-Bromo-2-methoxy-3-pyridinyl)methyl]-4-[2-[2,3-(methylenedioxy)phenyl]ethyl]piperidine The title compound was obtained from a corresponding raw material in accordance with the method of Example 201.

¹H-NMR (400 MHz, CDCl₃) δ 1.23–1.40 (3H, m), 1.54–1.65 (2H, m), 1.68–1.79 (2H, m), 1.98–2.09 (2H, m), 2.56–2.64 (2H, m), 2.86 (2H, br d, J=11.6 Hz), 3.43 (2H, s), 3.91 (3H, s), 5.93 (2H, s), 6.66 (1H, dd, J=7.6, 1.2 Hz), 6.68 (1H, dd, J=7.6, 1.2 Hz), 6.76 (1H, t, J=7.6 Hz), 7.78 (1H, br d, J=1.2 Hz), 8.07 (1H, d, J=2.8 Hz).

Example 242

1-[(5-Methyl-2-methoxy-3-pyridinyl)methyl]-4-[2-[2,3-(methylenedioxy)phenyl]ethyl]piperidine The title compound was obtained from a corresponding raw material in accordance with the method of Example 201.

¹H-NMR (400 MHz, CDCl₃) δ 1.23–1.40 (3H, m), 1.54–1.62 (2H, m), 1.68–1.79 (2H, m), 2.01 (2H, br t, J=11.2 Hz), 2.24 (3H, s), 2.59 (2H, br t, J=8.0 Hz), 2.89 (2H, br d, J=11.6 Hz), 3.45 (2H s), 3.91 (3H, s), 5.92 (2H, s), 6.66 (1H, dd, J=7.6, 1.2 Hz), 6.68 (1H, dd, J=7.6, 1.2 Hz), 6.75 (1H, t, J=7.6 Hz), 7.47 (1H, br s), 7.84 (1H, br s).

Example 243

1-[(2-Methoxy-3-pyridinyl)methyl]-4-[2-[2-(benzyloxy)phenyl]ethyl]piperidine

The title compound was obtained from a corresponding raw material in accordance with the method of Example 201.

¹H-NMR (400 MHz, CDCl₃) δ 1.23–1.39 (3H, m), 1.52–1.60 (2H, m), 1.66–1.77 (2H, m), 1.96–2.08 (2H, m), 2.65–2.72 (2H, m), 2.87 (2H, br d, J=10.8 Hz), 3.48 (2H, s), 3.95 (3H, s), 5.08 (2H, s), 6.85–6.93 (3H, m), 7.12–7.18 (2H, m), 7.28–7.46 (5H, m), 7.66 (1H, br d, J=6.8 Hz), 8.06 (1H, dd, J=5.2, 2.0 Hz).

Example 244

1-[(5-Phenyl-2-methoxy-3-pyridinyl)methyl]-4-[2-[2,3-(methylenedioxy)phenyl]ethyl]piperidine The title compound was obtained from a corresponding raw material in accordance with the method of Example 201.

¹H-NMR (400 MHz, CDCl₃) δ 1.23–1.40 (3H, m), 1.52–1.78 (4H, m), 2.00–2.10 (2H, m), 2.55–2.62 (2H, m), 2.90–2.96 (2H, m), 3.54 (2H, s), 3.99 (3H, s), 5.92 (2H, s), 6.65 (1H, dd, J=7.6, 1.2 Hz), 6.68 (1H, dd, J=7.6, 1.2 Hz), 6.75 (1H, t, J=7.6 Hz), 7.35 (1H, m), 7.42–7.48 (2H, m), 7.53–7.58 (2H, m), 7.89 (1H, d, J=2.4 Hz), 8.28 (1H, d, J=2.4 Hz).

Example 245

1-[(2-Methoxy-3-pyridinyl)methyl]-4-[[2-(2-piperidino-2-oxoethoxy)phenyl]ethyl]piperidine The title compound was obtained from a corresponding raw material in accordance with the method of Example 201.

¹H-NMR (400 MHz, CDCl₃) δ 1.26–1.38 (2H, m), 1.51–1.78 (1H, m), 1.98–2.08 (2H, m), 2.62–2.68 (2H, m), 2.90 (2H, br d, J=10.8 Hz), 3.45–3.60 (6H, m), 3.95 (3H, s), 4.67 (2H, s), 6.84–6.95 (3H, m), 7.12–7.18 (2H, m), 7.66 (1H, br d, J=6.8 Hz), 8.05 (1H, dd, J=5.2, 2.0 Hz).

Example 246

1-[(2-Methoxy-3-pyridinyl)methyl]-4-[[2-(4-pyridinyloxy)phenyl]ethyl]piperidine

The title compound was obtained from a corresponding raw material in accordance with the method of Example 201.

¹H-NMR (400 MHz, CDCl₃) δ 1.15–1.32 (3H, m), 1.45–1.54 (2H, m), 1.57–1.68 (2H, m), 1.99 (2H, br d, J=10.4 Hz), 2.48–2.55 (2H, m), 2.87 (2H, br d, J=10.4 Hz), 3.48 (2H, s), 3.94 (3H, s), 6.74–6.79 (2H, m), 6.86 (1H, dd, J=7.2, 5.2 Hz), 7.00 (1H, dd, J=7.6, 1.6 Hz), 7.17–7.34 (3H, m), 7.64 (1H, br d, J=6.8 Hz), 8.05 (1H, dd, J=4.8, 2.0 Hz), 8.41–8.46 (2H, m).

Example 247

1-[(2-Methoxy-3-pyridinyl)methyl]-4-[2-[2-(1-(dimethylcarbamoyl)cyclopentyloxy)phenyl]ethyl]piperidine The title compound was obtained from a corresponding raw material in accordance with the method of Example 201.

¹H-NMR (400 MHz, CDCl₃) δ 1.24–1.41 (3H, m), 1.47–1.58 (2H, m), 1.68–1.82 (6H, m), 1.98–2.10 (2H, m), 2.11–2.20 (2H, m), 2.38–2.40 (2H, m), 2.56–2.64 (2H, m), 2.91 (2H, m), 2.92 (3H, s), 3.09 (3H, s), 3.51 (2H, s), 3.95 (3H, s), 6.67 (1H, dd, J=7.6, 1.2 Hz), 6.82–6.91 (2H, m), 7.04 (1H, dd, J=7.6, 1.6 Hz), 7.11 (1H, dd, J=7.6, 1.6 Hz), 7.66 (1H, br d, J=6.0 Hz), 8.06 (1H, dd, J=5.2, 2.0 Hz).

Example 248

1-[(5-Chloro-2-methoxy-3-pyridinyl)methyl]-4-[2-[2-(benzyloxy)phenyl]ethyl]piperidine The title compound was obtained from a corresponding raw material in accordance with the method of Example 201.

¹H-NMR (400 MHz, CDCl₃) δ 1.23–1.39 (3H, m), 1.52–1.60 (2H, m), 1.66–1.77 (2H, m), 1.96–2.08 (2H, m), 2.65–2.72 (2H, m), 2.87 (2H, br d, J=10.8 Hz), 3.48 (2H, s), 3.95 (3H, s), 5.08 (2H, s), 6.87–6.94 (2H, m), 7.13–7.20 (2H, m), 7.29–7.46 (5H, m), 7.66 (1H, br s), 7.98 (1H, d, J=2.0 Hz).

Example 249

1-[(5-Chloro-2-methoxy-3-pyridinyl)methyl]-4-[2-[2-(2-methoxyethoxy)phenyl]ethyl]piperidine The title compound was obtained from a corresponding raw material in accordance with the method of Example 201.

¹H-NMR (400 MHz, CDCl₃) δ 1.20–1.40 (3H, m), 1.50–1.60 (2H, m), 1.70–1.80 (2H, m), 2.00–2.10 (2H, m), 2.65 (2H, t, J=8.0 Hz), 2.87 (2H, br d, J=10.8 Hz), 3.44 (2H, s), 3.46 (3H, s), 3.76 (2H, t, J=4.8 Hz), 3.92 (3H, s), 4.12 (2H, t, J=4.8 Hz), 6.84 (1H, d, J=8.0 Hz), 6.89 (1H, t, J=7.6 Hz), 7.10–7.18 (2H, m), 7.66 (1H, d, J=2.8 Hz), 7.97 (1H, d, J=2.4 Hz).

Example 250

1-[(2-Methoxy-3-pyridinyl)methyl]-4-[2-[2-(benzylamino)phenyl]ethyl]piperidine

The title compound was obtained from a corresponding raw material in accordance with the method of Example 201.

¹H-NMR (400 MHz, CDCl₃) δ 1.23–1.39 (3H, m), 1.55–1.80 (4H, m), 1.98–2.08 (2H, m), 2.46–2.54 (2H, m), 2.89 (2H, br d, J=11.2 Hz), 3.49 (2H, s), 3.94 (3H, s), 4.37 (2H, s), 6.62 (1H, d, J=9.6 Hz), 6.70 (1H, dt, J=8.0, 1.2 Hz), 6.87 (1H, dd, J=7.2, 5.2 Hz), 7.05–7.14 (2H, m), 7.24–7.42 (5H, m), 7.64 (1H, dd, J=7.2, 2.0 Hz), 8.06 (1H, dd, J=4.8, 2.0 Hz).

Example 251

1-[(2-Methoxy-3-pyridinyl)methyl]-4-[2-[2-(N-benzyl-N-methylamino)phenyl]ethyl]piperidine The title compound was obtained from a corresponding raw material in accordance with the method of Example 201.

¹H-NMR (400 MHz, CDCl₃) δ 1.26–1.40 (3H, m), 1.47–1.65 (2H, m), 1.71–1.78 (2H, m), 1.98–2.08 (2H, m), 2.56 (3H, s), 2.75–2.81 (2H, m), 2.89 (2H, br d, J=11.2 Hz), 3.49 (2H, s), 3.95 (3H, s), 4.00 (2H, s), 6.87 (1H, dd, J=8.8, 5.2 Hz), 7.02–7.07 (1H, m), 7.13–7.40 (8H, m), 7.66 (1H, dd, J=7.2, 1.6 Hz), 8.05 (1H, dd, J=5.2, 2.0 Hz).

Example 252

1-[(2-Methoxy-3-pyridinyl)methyl]-4-[2-[2-[(cyclohexylmethyl)amino]phenyl]ethyl]piperidine The above compound was obtained from a corresponding raw material in accordance with the method of Example 201.

¹H-NMR (400 MHz, CDCl₃) δ 0.95–1.08 (2H, m), 1.12–1.42 (5H, m), 1.52–1.86 (1H, m), 2.00–2.12 (2H, m), 2.43–2.49 (2H, m), 2.92 (2H, br d, J=7.2 Hz), 2.98 (2H, d, J=6.4 Hz), 3.50 (2H, s), 3.95 (3H, s), 6.60 (1H, dd, J=1.2, 7.6 Hz), 6.65 (1H, dt, J=7.6, 1.2 Hz), 6.87 (1H, dd, J=7.2, 4.8 Hz), 7.02 (1H, dd, J=7.6, 1.2 Hz), 7.11 (1H, dt, J=7.6, 1.2 Hz), 7.65 (1H, dd, J=7.2, 2.0 Hz), 8.06 (1H, dd, J=4.8, 2.0 Hz).

Example 253

1-[(2-Methoxy-3-pyridinyl)methyl]-4-[2-[2-[N-(cyclohexylmethyl)N-methylamino]phenyl]ethyl]piperidine The title compound was obtained from a corresponding raw material in accordance with the method of Example 201.

¹H-NMR (400 MHz, CDCl₃) δ 0.81–0.93 (2H, m), 1.08–1.40 (6H, m), 1.44–1.60 (3H, m), 1.61–1.78 (6H, m), 1.79–1.87 (2H, m), 1.99–2.08 (2H, m), 2.56 (3H, s), 2.65 (2H, d, J=7.2 Hz), 2.68–2.74 (2H, m), 2.90 (2H, br d, J=11.2 Hz), 3.49 (2H, s), 3.95 (3H, s), 6.87 (1H, dd, J=7.2, 4.8 Hz), 7.01 (1H, dt, J=7.6, 2.0 Hz), 7.08–7.20 (3H, m), 7.66 (1H, dd, J=7.2, 2.0 Hz), 8.05 (1H, dd, J=4.8, 2.0 Hz).

Example 254

1-[(2-Methoxy-3-pyridinyl)methyl]-4-[2-cyclohexylmethyloxy)phenyl]piperidine

The title compound was obtained from a corresponding raw material in accordance with the method of Example 201.

¹H-NMR (400 MHz, CDCl₃) δ 1.05–1.38 (5H, m), 1.60–1.90 (10H, m), 2.18–2.26 (2H, m), 2.97 (1H, m), 3.01–3.07 (2H, m), 3.56 (2H, s), 3.76 (2H, d, J=6.0 Hz), 3.97 (3H, s), 6.83 (1H, dd, J=8.0, 1.2 Hz), 6.86–6.94 (2H, m), 7.15 (1H, dt, J=8.0, 1.2 Hz), 7.21 (1H, dt, J=8.0, 1.2 Hz), 7.71 (1H, dd, J=7.2, 2.0 Hz), 8.07 (1H, dd, J=7.2, 2.0 Hz).

Example 255

1-[(2-Methoxy-3-pyridinyl)methyl]-4-[2-(2-phenoxyphenyl)ethyl]piperidine oxalate A free compound was obtained from a corresponding raw material in accordance with the method of Example 201 and converting it into an oxalate in a conventional method.

¹H-NMR (400 MHz, DMSO-d₆) δ 1.20–1.50 (3H, m), 1.40–1.55 (2H, m), 1.75 (2H, br d, J=12.8 Hz), 2.56 (2H, t, J=8.0 Hz), 2.60–2.80 (2H, m), 3.18 (2H, br d, J=11.2 Hz), 3.90 (3H, s), 4.04 (2H, s), 6.89 (3H, d, J=8.4 Hz), 7.04–7.18 (3H, m), 7.23 (1H, dt, J=1.4, 7.6 Hz), 7.35 (3H, d, J=8.0 Hz), 7.81 (1H, dd, J=7.6, 1.6 Hz), 8.22 (1H, dd, J=5.2, 1.6 Hz).

Example 256

1-[(2-Methoxy-3-pyridinyl)methyl]-4-[2-(2-methylphenyl)ethyl]piperidine

In ethanol (10 ml) was dissolved 473 mg of 1-[(2-methoxy-3-pyridinyl)methyl]-4-[(E)-2-(2-methylphenyl)-1-ethenyl]piperidine. To the mixture was added 100 mg of 10% palladium-carbon powder (water-containing product) was added thereto, followed by stirring at room temperature under normal pressure overnight in a hydrogen atmosphere for 1.5 hours. The reaction solution was filtered, and then the filtrate was evaporated, to give 465 mg of the title compound as a colorless oil.

¹H-NMR (400 MHz, CDCl₃) δ 1.28–1.42 (2H, m), 1.47–1.55 (2H, m), 1.66–1.84 (3H, m), 2.06 (2H, m), 2.29 (3H, s), 2.56–2.64 (2H, m), 2.92 (2H, br d, J=11.2 Hz), 3.50 (2H, s), 3.95 (3H, s), 6.87 (1H, dd, J=8.8, 4.2 Hz), 7.06–7.16 (4H, m), 7.66 (1H, dd, J=8.8, 2.0 Hz), 8.06 (1H, dd, J=4.2, 2.0 Hz).

Example 257

1-[(2-Methoxy-3-pyridinyl)methyl]-4-[4-[2,3-(methylenedioxy)phenyl]butyl]piperidine The title compound was obtained from a corresponding raw material in accordance with the method of Example 256.

¹H-NMR (400 MHz, CDCl₃) δ 1.16–1.39 (6H, m), 1.55–1.68 (4H, m), 1.72 (1H, m), 2.00 (2H, t, J=11.2 Hz), 2.57 (2H, t, J=8.0 Hz), 2.88 (2H, br d, J=11.2 Hz), 3.48 (2H, s), 3.94 (3H, s), 5.92 (2H, s), 6.65 (1H, dd, J=8.0, 2.0 Hz), 6.68 (1H, dd, J=8.0, 2.0 Hz), 6.75 (1H, d, J=8.0 Hz), 6.86 (1H, dd, J=7.2, 4.8 Hz), 7.64 (1H, dd, J=7.2, 2.0 Hz), 8.05 (1H, dd, J=4.8, 2.0 Hz).

Example 258

1-[(2-Methoxy-3-pyridinyl)methyl]-4-[2-[2-(trifluoromethoxy)phenyl]ethyl]piperidine The title compound was obtained from a corresponding raw material in accordance with the method of Example 256.

¹H-NMR (400 MHz, CDCl₃) δ 1.20–1.45 (3H, m), 1.48–1.60 (2H, m), 1.73 (2H, br d, J=9.6 Hz), 2.04 (2H, br d, J=10.8 Hz), 2.66 (2H, t, J=8.4 Hz), 2.91 (2H, br d, J=11.2 Hz), 3.50 (2H, s), 3.94 (3H, s), 6.87 (1H, dd, J=7.2, 5.2 Hz), 7.14–7.32 (3H, m), 7.66 (1H, dd, J=7.2, 1.2 Hz), 8.05 (1H, dd, J=4.8, 2.0 Hz).

Example 259

1-[(2-Methoxy-3-pyridinyl)methyl]-4-[2-[2-(cyclopentyloxy)phenyl]ethyl]piperidine The title compound was obtained from a corresponding raw material in accordance with the method of Example 256.

¹H-NMR (400 MHz, CDCl₃) δ 1.22–1.38 (3H, m), 1.46–1.54 (2H, m), 1.55–1.94 (10H, m), 1.98–2.10 (2H, m), 2.54–2.62 (2H, m), 2.90 (2H, br d, J=11.2 Hz), 3.50 (2H, s), 3.95 (3H, s), 4.77 (1H, m), 6.78–6.90 (3H, m), 7.08–7.16 (2H, m), 7.66 (1H, br d, J=6.8 Hz), 8.05 (1H, dd, J=4.8, 2.0 Hz).

Example 260

1-[(2-Methoxy-3-pyridinyl)methyl]-4-[2-[3-(cyclopentyloxy)phenyl]ethyl]piperidine The title compound was obtained from a corresponding raw material in accordance with the method of Example 256.

¹H-NMR (400 MHz, CDCl₃) δ 1.24–1.38 (3H, m), 1.52–1.95 (12H, m), 1.96–2.08 (2H, m), 2.54–2.62 (2H, m), 2.90 (2H, br d, J=11.2 Hz), 3.49 (2H, s), 3.94 (3H, s), 4.75 (1H, m), 6.66–6.76 (3H, m), 6.84 (1H, dd, J=7.2, 4.8 Hz), 7.16 (1H, m), 7.66 (1H, br d, J=6.8 Hz), 8.05 (1H, dd, J=4.8, 2.0 Hz).

Example 261

1-[(2-Methoxy-3-pyridinyl)methyl]-4-[2-[2-(3-pyridinyl)phenyl]ethyl]piperidine

In methanol (50 ml) were dissolved 0.3 g of 1-[(2-methoxy-3-pyridinyl)methyl]-4-[(E)-2-(3-bromophenyl)-1-ethenyl]piperidine and 0.3 g of 3-pyridineboronic acid. To the mixture were added 0.3 ml of an aqueous sodium carbonate and 0.1 g of tetrakis(triphenylphosphine) palladium, followed by heating under reflux for 3 hours under a nitrogen gas stream. The reaction solution was cooled to room temperature, and the solvent was evaporated. The residue was purified by silica gel column chromatography, to give 0.3 g of a yellow oil. The oil was treated in accordance with the method of Example 256, to give 0.3 g of the title compound as a yellow oil.

¹H-NMR (400 MHz, CDCl₃) δ 1.24–1.44 (3H, m), 1.44–1.80 (2H, m), 1.60–1.84 (2H, m), 1.96–2.10 (2H, m), 2.64–2.74 (2H, m), 2.86–2.96 (2H, m), 3.49 (2H, s), 3.94 (3H, s), 6.84–6.90 (1H, m), 7.18–7.30 (1H, m), 7.32–7.44 (4H, m), 7.65 (1H, d, J=6.8 Hz), 7.87 (1H, d, J=7.6 Hz), 8.05 (1H, d, J=5.2 Hz), 8.58 (1H, d, J=4.4 Hz), 8.84 (1H, d, J=2.0 Hz).

Example 262

1-[(2-Methoxy-3-pyridinyl)methyl]-4-[2-[3-[(tetrahydropyran-2-yl)methyloxy]phenyl]ethyl]piperidine The title compound was obtained from a corresponding raw material in accordance with the method of Example 256.

$^1$H-NMR (400 MHz, CDCl$_3$) δ 1.10–2.00 (15H, m), 2.20–2.40 (2H, m), 2.55–2.63 (2H, m), 3.00–3.20 (2H, m), 3.40–4.10 (5H, m), 3.96 (3H, s), 6.70–6.80 (2H, m), 6.86–6.98 (1H, m), 7.14–7.22 (1H, m), 7.42–7.52 (1H, m), 7.62–7.72 (1H, m), 8.06–8.16 (1H, m).

Example 263

1-[(2-Methoxy-3-pyridinyl)methyl]-4-[2-[2-[(tetrahydropyran-2-yl)methyloxy]phenyl]ethyl]piperidine The title compound was obtained from a corresponding raw material in accordance with the method of Example 256.

$^1$H-NMR (400 MHz, CDCl$_3$) δ 1.20–1.40 (3H, m), 1.40–2.00 (10H, m), 1.97–2.10 (2H, m), 2.57–2.68 (2H, m), 2.90 (2H, br d, J=11.2 Hz), 3.49 (2H, s), 3.45–3.55 (1H, m), 3.65–3.75 (1H, m), 3.80–3.90 (1H, m), 3.95 (3H, s), 3.93–4.10 (2H, m), 6.78–6.92 (3H, m), 7.08–7.18 (2H, m), 7.66 (1H, dd, J=7.6, 2.0 Hz), 8.05 (1H, dd, J=5.2, 2.0 Hz).

Example 264

1-[(2-Methoxy-3-pyridinyl)methyl]-4-[2-[3-[(benzyloxy)phenyl]ethyl]piperidine

The title compound was obtained from a corresponding raw material in accordance with the method of Example 256.

$^1$H-NMR (400 MHz, CDCl$_3$) δ 1.22–1.38 (3H, m), 1.52–1.76 (4H, m), 1.96–2.08 (2H, m), 2.56–2.64 (2H, m), 2.85–2.94 (2H, m), 3.49 (2H, s), 3.95 (3H, s), 5.05 (2H, s), 6.76–6.83 (3H, m), 6.87 (1H, dd, J=7.2, 5.2 Hz), 7.19 (1H, t, J=8.4 Hz), 7.28–7.46 (5H, m), 7.66 (1H, br d, J=6.8 Hz), 8.05 (1H, dd, J=4.8, 2.0 Hz).

Example 265

1-[(2-Methoxy-3-pyridinyl)methyl]-4-[[2-(2-phenylethyl)phenyl]ethyl]piperidine

The title compound was obtained from a corresponding raw material in accordance with the method of Example 256.

$^1$H-NMR (400 MHz, CDCl$_3$) δ 1.26–1.40 (3H, m), 1.48–1.56 (2H, m), 1.70–1.78 (2H, m), 2.00–2.10 (2H, m), 2.58–2.64 (2H, m), 2.84–2.94 (6H, m), 3.50 (2H, s), 3.95 (3H, s), 6.87 (1H, dd, J=7.2, 5.2 Hz), 7.11–7.33 (9H, m), J=7.66 (1H, br d, J=7.2 Hz), 8.05 (1H, dd, J=4.8, 1.6 Hz).

Example 266

1-[(2-Methoxy-3-pyridinyl)methyl]-4-[2-[2-(cyclohexylmethyloxy)phenyl]ethyl]piperidine The title compound was obtained from a corresponding raw material in accordance with the method of Example 256.

$^1$H-NMR (400 MHz, CDCl$_3$) δ 1.05–1.40 (8H, m), 1.49–1.58 (2H, m), 1.65–1.90 (8H, m), 1.992.10 (2H, m), 2.58–2.66 (2H, m), 2.86–2.95 (2H, m), 3.50 (2H, s), 3.74 (2H, d, J=6.0 Hz), 3.95 (3H, s), 6.78–6.90 (3H, m), 7.08–7.16 (2H, m), 7.66 (1H, br d, J=7.6 Hz), 8.05 (1H, dd, J=5.2, 2.0 Hz).

Example 267

1-[(2-Methoxy-3-pyridinyl)methyl]-4-[2-[2-(isobutyloxy)phenyl]ethyl]piperidine

The title compound was obtained from a corresponding raw material in accordance with the method of Example 256.

$^1$H-NMR (400 MHz, CDCl$_3$) δ 1.04 (6H, d, J=6.8 Hz), 1.26–1.38 (3H, m), 1.50–1.58 (2H, m), 1.70–1.78 (2H, m), 1.99–2.15 (3H, m), 2.60–2.67 (2H, m), 2.86–2.94 (2H, m), 3.49 (2H, s), 3.72 (2H, d, J=6.4 Hz), 3.95 (3H, s), 6.80 (1H, d, J=8.0 Hz), 6.82–6.90 (2H, m), 7.08–7.16 (2H, m), 7.66 (I1H, br dd, J=7.2, 2.0 Hz), 8.05 (1H, dd, J=4.8, 2.0 Hz).

Example 268

1-[(2-Methoxy-3-pyridinyl)methyl]-4-[2-[3-(cyclohexylmethyloxy)phenyl]ethyl]piperidine The title compound was obtained from a corresponding raw material in accordance with the method of Example 256.

$^1$H-NMR (400 MHz, CDCl$_3$) δ 0.98–1.11 (2H, m), 1.14–1.38 (6H, m), 1.52–1.60 (2H, m), 1.62–1.91 (8H, m), 1.97–2.08 (2H, m), 2.54–2.62 (2H, m), 2.85–2.93 (2H, m), 3.48 (2H, s), 3.73 (2H, d, J=6.4 Hz), 3.94 (3H, s), 6.68–6.76 (3H, m), 6.87 (1H, dd, J=5.2, 7.6 Hz), 7.17 (1H, m), 7.65 (1H, br dd, J=7.2, 2.0 Hz), 8.05 (1H, dd, J=5.2, 2.0 Hz).

Example 269

1-[(2-Methoxy-3-pyridinyl)methyl]-4-[2-[2-(2-methoxyethoxy)phenyl]ethyl]piperidine The above compound was obtained from a corresponding raw material in accordance with the method of Example 256.

$^1$H-NMR (400 MHz, CDCl$_3$) δ 1.45–1.70 (5H, m), 1.60–1.80 (2H, m), 1.95–2.10 (2H, m), 2.64 (2H, t, J=8.0 Hz), 2.90 (2H, br d, J=10.4 Hz), 3.45 (3H, t), 3.48 (2H, s), 3.64–3.80 (2H, 1), 3.95 (3H, s), 4.11 (2H, t, J=4.8 Hz), 6.80–6.92 (2H, m), 7.10–7.18 (1H, m), 7.42–7.74 (3H, m), 8.02–8.08 (1H, m).

Example 270

1-[(2-Methoxy-3-pyridinyl)methyl]-4-[2-[2-(2-phenylethoxy)phenyl]ethyl]piperidine The above compound was obtained from a corresponding raw material in accordance with the method of Example 256.

$^1$H-NMR (400 MHz, CDCl$_3$) δ 1.20–1.36 (3H, m), 1.43–1.51 (2H, m), 1.62–1.75 (2H, m), 1.99–2.08 (2H, m), 2.54–2.26 (2H, m), 2.86–2.94 (2H, m), 3.10 (2H, t, J=6.8 Hz), 3.50 (2H, s), 3.95 (3H, s), 4.17 (2H, t, J=6.8 Hz), 6.78–6.90 (3H, m), 7.07–7.16 (2H, m), 7.19–7.36 (5H, m), 7.67 (1H, br d, J=7.2 Hz), 8.06 (1H, dd, J=5.2, 2.0 Hz).

Example 271

1-[(2-Methoxy-3-pyridinyl)methyl]-4-[2-[2-(phenoxymethyl)phenyl]ethyl]piperidine The title compound was obtained from a corresponding raw material in accordance with the method of Example 256.

$^1$H-NMR (400 MHz, CDCl$_3$) δ 1.25–1.39 (3H, m), 1.54–1.78 (4H, m), 1.96–2.08 (2H, m), 2.65–2.73 (2H, m), 2.84–2.93 (2H, m), 3.48 (2H, s), 3.94 (3H, s), 5.04 (2H, s), 6.87 (1H, dd, J=7.6, 5.2 Hz), 6.95–7.01 (2H, m), 7.18–7.34 (6H, m), 7.42 (1H, d, J=7.6 Hz), 7.64 (1H, br d, J=6.4 Hz), 8.05 (1H, dd, J=4.8, 2.0 Hz).

Example 272

1-[(2-Methoxy-3-pyridinyl)methyl]-4-[2-[2-(cyclopentylmethyloxy)phenyl]ethyl]piperidine The title compound was obtained from a corresponding raw material in accordance with the method of Example 256.

$^1$H-NMR (400 MHz, CDCl$_3$) δ 1.24–1.45 (5H, m), 1.49–1.88 (10H, m), 1.98–2.10 (2H, m), 2.37 (1H, septet, J=7.4 Hz), 2.58–2.66 (2H, m), 2.86–2.96 (2H, m), 3.50 (2H, s), 3.82 (2H, d, J=6.8 Hz), 3.95 (3H, s), 6.78–6.90 (3H, m), 7.09–7.17 (2H, m), 7.66 (1H, dd, J=7.2, 2.0 Hz), 8.05 (1H, dd, J=5.2, 2.0 Hz).

Example 273

1-[(2-Methoxy-3-pyridinyl)methyl]-4-[2-[(2-cyclohexylethyl)phenyl]ethyl]piperidine The title compound was obtained from a corresponding raw material in accordance with the method of Example 256.

$^1$H-NMR (400 MHz, CDCl$_3$) δ 0.89–1.01 (2H, m), 1.10–1.56 (10H, m), 1.62–1.83 (8H, m), 2.02–2.11 (2H, m), 2.56–2.63 (4H, m), 2.89–2.96 (2H, m), 3.51 (2H, s), 3.95 (3H, s), 6.87 (1H, dd, J=6.8, 4.8 Hz), 7.08–7.16 (4H, m), 7.66 (1H, dd, J=7.2, 2.0 Hz), 8.06 (1H, dd, J=4.8, 2.0 Hz).

Example 274

1-[(2-Methoxy-3-pyridinyl)methyl]-4-[2-(2,5-dimethylphenyl)ethyl]piperidine oxalate The title compound was obtained from a corresponding raw material in accordance with the method of Example 256 and converting into an oxalate in a conventional method.

$^1$H-NMR (400 MHz, DMSO-d$_6$) γ 1.30–1.55 (5H, m), 1.80–1.90 (2H, m), 2.19 (3H, s), 2.22 (3H, s), 2.45–2.55 (2H, m), 2.65–2.85 (2H, m), 3.15–3.25 (2H, m), 3.91 (3H, s), 4.04 (2H, s), 6.87 (1H, d, J=9.2 Hz), 6.93 (1H, s), 6.99 (1H, d, J=8.0 Hz), 7.07 (1H, dd, J=7.2, 4.8 Hz), 7.80–7.85 (1H, m), 8.20–8.25 (1H, m).

Example 275

1-[(2-Methoxy-3-pyridinyl)methyl]-4-[2-(3,5-dimethylphenyl)ethyl]piperidine oxalate The title compound was obtained from a corresponding raw material in accordance with the method of Example 274.

$^1$H-NMR (400 MHz, DMSO-d$_6$) δ 1.30–1.55 (5H, m), 1.84 (2H, br d, J=12.8 Hz), 2.22 (3H, s), 2.50 (3H, s), 2.45–2.55 (2H, m), 2.75–2.90 (2H, m), 3.26 (2H, br d, J=10.8 Hz), 3.92 (3H, s), 4.12 (2H, s), 6.79 (3H, s), 7.08 (1H, dd, J=7.6, 5.2 Hz), 7.82–7.86 (1H, m), 8.25 (1H, dd, J=5.2, 2.0 Hz).

Example 276

1-[(2-methoxy-3-pyridinyl)methyl]-4-[2-(2-methoxy-5-methylphenyl)ethyl]piperidine oxalate The title compound was obtained from a corresponding raw material in accordance with the method of Example 274.

$^1$H-NMR (400 MHz, DMSO-d$_6$) δ 1.30–1.55 (5H, m), 1.87 (2H, br d, J=11.2 Hz), 2.20 (3H, s), 2.40–2.60 (2H, m), 2.80–3.00 (2H, m), 3.25–3.35 (2H, m), 3.72 (3H, s), 3.93 (3H, s), 4.10–4.20 (2H, m), 6.81 (1H, d, J=8.4 Hz), 6.90–7.00 (2H, m), 7.10 (1H, dd, J=7.6, 5.6 Hz), 7.85 (1H, d, J=7.6 Hz), 8.24–8.30 (1H, m).

Example 277

1-[[5-(3-Pyridinyl)-2-methoxy-3-pyridinyl]methyl]-4-[2-[2,3-(methylenedioxy)phenyl]ethyl]piperidine The title compound was obtained from a corresponding raw material in accordance with the method of Example 206.

$^1$H-NMR (400 MHz, CDCl$_3$) δ 1.24–1.41 (3H, m), 1.54–1.62 (2H, m), 1.70–1.80 (2H, m), 2.07 (2H, br t, J=10.4 Hz), 2.56–2.64 (2H, m), 2.93 (2H, br d, J=11.2 Hz), 3.15 (2H, s), 4.00 (3H, s), 5.92 (2H, s), 6.66 (1H, dd, J=7.6, 1.6 Hz), 6.68 (1H, dd, J=7.6, 1.6 Hz), 6.75 (1H, t, J=7.6 Hz), 7.38 (1H, ddd, J=8.0, 4.8, 1.2 Hz), 7.85 (1H, ddd, J=8.0, 2.4, 1.6 Hz), 7.92 (1H, br s), 8.27 (1H, d, J=2.4 Hz), 8.59 (1H, dd, J=4.8, 1.6 Hz), 8.82 (1H, dd, J=2.4, 1.2 Hz).

Example 278

1-[[5-(4-Pyridinyl)-2-methoxy-3-pyridinyl]methyl]-4-[2-[2,3-(methylenedioxy)phenyl]ethyl]piperidine The title compound was obtained from a corresponding raw material in accordance with the method of Example 206.

$^1$H-NMR (400 MHz, CDCl$_3$) δ 1.26–1.41 (3H, m), 1.55–1.63 (2H, m), 1.68–1.82 (2H, m), 2.07 (2H, br t, J=11.2 Hz), 2.56–2.64 (2H, m), 2.92 (2H, br d, J=11.2 Hz), 3.54 (2H, s), 4.01 (3H, s), 5.92 (2H, s), 6.66 (1H, dd, J=8.0, 1.2 Hz), 6.68 (1H, dd, J=8.0, 1.2 Hz), 6.75 (1H, t, J=8.0 Hz), 7.46–7.52 (2H, m), 7.97 (1H, br s), 8.35 (1H, d, J=2.4 Hz), 8.63–8.69 (2H, m).

Example 279

1-[(5-Chloro-2-methoxy-3-pyridinyl)methyl]-4-[2-(2-fluorophenyl)ethyl]piperidine The title compound was obtained from a corresponding raw material in accordance with the method of Example 206.

$^1$H-NMR (400 MHz, CDCl$_3$) δ 1.20–1.40 (3H, m), 1.50–1.65 (2H, m), 1.70–1.80 (2H, m), 2.04 (2H, br t, J=10.8 Hz), 2.66 (2H, d, J=7.6 Hz), 2.87 (2H, br d, J=11.6 Hz), 3.43 (2H, s), 3.92 (3H, s), 6.96–7.08 (2H, m), 7.12–7.22 (2H, m), 7.66 (1H, d, J=2.8 Hz), 7.97 (1H, d, J=2.8 Hz).

Example 280

1-[(5-Chloro-2-methoxy-3-pyridinyl)methyl]-4-[2-[2-(cyclohexylmethyloxy)phenyl]ethyl]piperidine The title compound was obtained from a corresponding raw material in accordance with the method of Example 206.

$^1$H-NMR (400 MHz, CDCl$_3$) δ 1.05–1.40 (7H, m), 1.49–1.60 (2H, m), 1.62–1.91 (9H, m), 1.99–2.11 (2H, m), 2.58–2.66 (2H, m), 2.83–2.92 (2H, m), 3.44 (2H, s), 3.75 (2H, d, J=6.0 Hz), 3.92 (3H, s), 6.80 (1H, d, J=8.0 Hz), 6.85 (1H, dt, J=7.2, 1.2 Hz), 7.09–7.20 (2H, m), 7.67 (1H, d, J=2.4 Hz), 7.97 (1H, d, J=2.4 Hz).

Example 281

1-[(5-Chloro-2-methoxy-3-pyridinyl)methyl]-4-[2-[2-(isobutyloxy)phenyl]ethyl]piperidine The title compound was obtained from a corresponding raw material in accordance with the method of Example 206.

$^1$H-NMR (400 MHz, CDCl$_3$) δ 1.05 (6H, d, J=6.8 Hz), 1.24–1.40 (3H, m), 1.51–1.59 (2H, m), 1.72–1.80 (2H, m), 2.00–2.19 (3H, m), 2.61–2.68 (2H, m), 2.84–2.92 (2H, m), 3.44 (2H, s), 3.72 (2H, d, J=6.4 Hz), 3.92 (3H, s), 6.80 (1H,

Example 282

1-[(5-Chloro-2-methoxy-3-pyridinyl)methyl]-4-[[2-(2-phenylethyl)phenyl]ethyl]piperidine

The title compound was obtained from a corresponding raw material in accordance with the method of Example 206.

$^1$H-NMR (400 MHz, CDCl$_3$) δ 1.26–1.42 (3H, m), 1.39–1.56 (2H, m), 1.70–1.80 (2H, m), 2.02–2.11 (2H, m), 2.58–2.65 (2H, m), 2.84–2.95 (6H, m), 3.44 (2H, s), 3.92 (3H, s), 7.12–7.34 (9H, m), 7.66 (1H, d, J=2.4 Hz), 7.98 (1H, d, J=2.4 Hz).

Example 283

1-[(5-(Methylsulfonyl)-2-methoxy-3-pyridinyl)methyl]-4-[2-[2-(cyclohexylmethyloxy)phenyl]ethyl]piperidine

The title compound was obtained from a corresponding raw material in accordance with the method of Example 206.

$^1$H-NMR (400 MHz, CDCl$_3$) δ 1.04–1.40 (8H, m), 1.51–1.58 (2H, m), 1.64–1.90 (8H, m), 2.04–2.12 (2H, m), 2.60–2.68 (2H, m), 2.82–2.91 (2H, m), 3.08 (3H, s), 3.49 (2H, s), 3.75 (2H, d, J=6.0 Hz), 4.04 (3H, s), 6.80 (1H, d, J=8.0 Hz), 6.85 (1H, dt, J=8.0, 1.2 Hz), 7.11 (1H, dd, J=8.0, 1.2 Hz), 7.15 (1H, dt, J=8.0, 2.0 Hz), 8.18 (1H, d, J=2.4 Hz), 8.61 (1H, d, J=2.4 Hz).

Example 284

1-[(4-Methoxy-3-pyridinyl)methyl]-4-[2-[2,3-(methylenedioxy)phenyl]ethyl]piperidine

The title compound was obtained from a corresponding raw material in accordance with the method of Example 210.

$^1$H-NMR (400 MHz, CDCl$_3$) δ 1.201.39 (3H, m), 1.52–1.62 (2H, m), 1.66–1.76 (2H, m), 2.00 (2H, br t, J=11.2 Hz), 2.54–2.64 (2H, m), 2.92 (2H, br d, J=12.0 Hz), 3.53 (2H, s), 3.86 (3H, s), 5.92 (2H, s), 6.65 (1H, dd, J=7.6, 1.2 Hz), 6.67 (1H, dd, J=7.6, 1.2 Hz), 6.75 (1H, t, J=7.6 Hz), 6.77 (1H, d, J=5.6 Hz), 8.40 (1H, d, J=5.6 Hz), 8.41 (1H, s).

Example 285

1-[(2-Oxo-1,2-dihydro-3-pyridinyl)methyl]-4-[2-(2-methylphenyl)ethyl]piperidine

In ethanol (10 ml) was dissolved 465 mg of 1-[(2-methoxy-3-pyridyl)methyl]-4-[2-(2-methylphenyl)ethyl]piperidine. To the mixture was added 1.75 ml of a 4N-hydrogen chloride-ethyl acetate solution, followed by heating under reflux for 3 hours. The solvent was evaporated, an aqueous sodium bicarbonate was added to the residue, and the mixture was extracted with chloroform. The extract was dried over anhydrous magnesium sulfate, and then the solvent was evaporated. The resulting solid was recrystallized from ethyl acetate, to give 344 mg of the title compound as white needles.

$^1$H-NMR (400 MHz, CDCl$_3$) δ 1.30–1.42 (3H, m), 1.47–1.56 (2H, m), 1.72–1.83 (2H, br d, J=9.2 Hz), 2.10 (2H, br t, J=10.4 Hz), 2.30 (3H, s), 2.56–2.64 (2H, m), 2.95 (2H, br d, J=11.2 Hz), 3.48 (2H, s), 6.33 (1H, t, J=6.4 Hz), 7.06–7.18 (4H, m), 7.37 (1H, br d, J=5.2 Hz), 7.57 (1H, br d, J=6.0 Hz).

Example 286

1-[(2-Oxo-1,2-dihydro-3-pyridinyl)methyl]-4-[4-[2,3-(methylenedioxy)phenyl]butyl]piperidine

The title compound was obtained from a corresponding raw material in accordance with the method of Example 285.

$^1$H-NM (400 MHz, CDCl$_3$) δ 1.18–1.40 (7H, m), 1.55–1.70 (4H, m), 2.06 (2H, t, J=10.4 Hz), 2.57 (2H, t, J=7.6 Hz), 2.92 (2H, brd, J=11.2 Hz), 3.47 (2H, s), 5.93 (2H, s), 6.34 (1H, t, J=6.8 Hz), 6.66 (1H, dd, J=8.0, 2.0 Hz), 6.80 (1H, dd, J=8.0, 2.0 Hz), 6.75 (1H, t, J=8.0 Hz), 7.38 (1H, m), 7.53 (1H, br d, J=6.8 Hz).

Example 287

1-[(2-Oxo-1,2-dihydro-3-pyridinyl)methyl]-4-[3-[2,3-(methylenedioxy)phenyl]propyl]piperidine

The title compound was obtained from a corresponding raw material in accordance with the method of Example 285.

$^1$H-NMR (400 MHz, CDCl$_3$) δ 1.22–1.35 (4H, m), 1.48–1.53 (5H, m), 2.08 (2H, br t, J=10.4 Hz), 2.56 (2H, t, J=8.0 Hz), 2.92 (2H, br d, J=11.2 Hz), 3.48 (2H, s), 5.92 (2H, s), 6.34 (1H, t, J=6.8 Hz), 6.66 (1H, dd, J=7.6, 1.2 Hz), 6.68 (1H, dd, J=7.6, 1.2 Hz), 6.75 (1H, t, J=7.2 Hz), 7.37 (1H, m), 7.54 (1H, br d, J=6.4 Hz).

Example 288

1-[(2-Oxo-1,2-dihydro-3-pyridinyl)methyl]-4-[5-[2,3-(methylenedioxy)phenyl]pentyl]piperidine

The title compound was obtained from a corresponding raw material in accordance with the method of Example 285.

$^1$H-NMR (400 MHz, CDCl$_3$) δ 1.16–1.36 (8H, m), 1.56–1.90 (5H, m), 2.07 (2H, br t, J=10.0 Hz), 2.57 (2H, t, J=7.6 Hz), 2.92 (2H, br d, J=10.8 Hz), 3.48 (2H, s), 3.93 (3H, s), 5.92 (2H, s), 6.66 (1H, dd, J=7.6, 1.2 Hz), 6.68 (1H, dd, J=7.6, 1.2 Hz), 6.75 (1H, t, J=7.6 Hz), 7.38 (1H, m), 7.54 (1H, br d, J=6.0 Hz).

Example 289

1-[(6-Methyl-2-oxo-1,2-dihydro-3-pyridinyl)methyl]-4-[2-[2,3-(methylenedioxy)phenyl]ethyl]piperidine

The title compound was obtained from a corresponding raw material in accordance with the method of Example 285.

$^1$H-NMR (400 MHz, CDCl$_3$) δ 1.24–1.38 (3H, m), 1.53–1.60 (2H, m), 1.68–1.77 (2H, m), 2.06 (2H, m), 2.31 (3H, s), 2.55–2.62 (2H, m), 2.93 (2H, br d, J=11.6 Hz), 3.45 (2H s), 5.92 (2H, s), 6.07 (1H, br d, J=6.8 Hz), 6.66 (1H, dd, J=7.6, 1.6 Hz), 6.68 (1H, dd, J=7.6, 1.6 Hz), 6.75 (1H, t, J=7.6 Hz), 7.41 (1H, br d, J=6.8 Hz).

Example 290

1-[(2-Oxo-1,2-dihydro-3-pyridinyl)methyl]-4-(2,2-diphenylethyl)piperidine

The title compound was obtained from a corresponding raw material in accordance with the method of Example 285.

$^1$H-NMR (400 MHz, CDCl$_3$) δ 1.20 (1H, m), 1.30–1.42 (2H, m), 1.69–1.76 (2H, m), 1.94–2.04 (4H, m), 2.88 (2H, br d, J=11.6 Hz), 3.43 (2H, s), 4.04 (1H, t, J=8.0 Hz), 6.31 (1H, t, J=6.4 Hz), 7.14–7.19 (2H, m), 7.21–7.30 (8H, m), 7.34 (1H, br d, J=5.2 Hz), 7.54 (1H, br d, J=6.4 Hz).

Example 291

1-[(5-Bromo-2-oxo-1,2-dihydro-3-pyridinyl)methyl]-4-[2-[2,3-(methylenedioxy)phenyl]ethyl]piperidine

The title compound was obtained from a corresponding raw material in accordance with the method of Example 285.

¹H-NMR (400 MHz, CDCl₃) δ 1.30–1.44 (3H, m), 1.56–1.64 (2H, m), 1.76–1.86 (2H, m), 2.09–2.20 (2H, m), 2.56–2.64 (2H, m), 2.95 (2H, br d, J=11.6 Hz), 3.57 (2H, s), 5.93 (2H, s), 6.65 (1H, dd, J=7.6, 1.2 Hz), 6.68 (1H, dd, J=7.6, 1.2 Hz), 6.76 (1H, t, J=7.6 Hz), 7.48 (1H, br s), 7.94 (1H, br s).

Example 292

1-[(5-Methyl-2-oxo-1,2-dihydro-3-pyridinyl)methyl]-4-[2-[2,3-(methylenedioxy)phenyl]ethyl]piperidine The title compound was obtained from a corresponding raw material in accordance with the method of Example 285.

¹H-NMR (400 MHz, CDCl₃) δ 1.28–1.41 (3H, m), 1.54–1.6 2 (2H, m), 1.72–1.80 (2H, m), 2.08 (2H, br t, J=11.2 Hz), 2.11 (3H, s), 2.56–2.64 (2H, m), 2.94 (2H, br d, J=11.2 Hz), 3.46 (2H, s), 5.92 (2H, s), 6.66 (1H, dd, J=8.0, 1.6 Hz), 6.68 (1H, dd, J=8.0, 1.6 Hz), 6.76 (1H, t, J=8.0 Hz), 7.17 (1H, br s), 7.39 (1H, br s).

Example 293

1-[(5-Phenyl-2-oxo-1,2-dihydro-3-pyridinyl)methyl]-4-[2-[2,3-(methylenedioxy)phenyl]ethyl]piperidine The title compound was obtained from a corresponding raw material in accordance with the method of Example 285.

¹H-NMR (400 MHz, CDCl₃) δ 1.25–1.44 (3H, m), 1.54–1.63 (2H, m), 1.74–1.82 (2H, m), 2.14 (2H, br t, J=10.8 Hz), 2.56–2.64 (2H, m), 3.00 (2H, br d, J=11.2 Hz), 3.58 (2H, s), 5.92 (2H, s), 6.65 (1H, dd, J=8.0, 1.2 Hz), 6.68 (1H, dd, J=8.0, 1.2 Hz), 6.75 (1H, t, J=8.0 Hz), 7.33 (1H, m), 7.40–7.50 (5H, m), 7.70 (1H, br s), 7.87 (1H, br s).

Example 294

1-[(2-Oxo-1,2-dihydro-3-pyridinyl)methyl]-4-[2-(2-piperidino-2-oxoethoxy)phenyl]ethyl]piperidine The title compound was obtained from a corresponding raw material in accordance with the method of Example 285.

¹H-NMR (400 MHz, CDCl₃) δ 1.30–1.40 (2H, m), 1.46–1.81 (1H, m), 2.02–2.14 (2H, m), 2.62–2.68 (2H, m), 2.90–2.99 (2H, m), 3.43–3.60 (6H, m), 4.68 (2H, s), 6.35 (1H, m), 6.83–6.95 (2H, m), 7.11–7.20 (2H, m), 7.38 (1H, m), 7.58 (1H, m).

Example 295

1-[(2-Oxo-1,2-dihydro-3-pyridinyl)methyl]-4-[[2-(4-pyridinyloxy)phenyl]ethyl]piperidine The title compound was obtained from a corresponding raw material in accordance with the method of Example 285.

¹H-NMR (400 MHz, CDCl₃) δ 1.18–1.32 (3H, m), 1.46–1.54 (2H, m), 1.58–1.68 (2H, m), 2.02 (2H, br d, J=10.4 Hz), 2.48–2.56 (2H, m), 2.88 (2H, br d, J=11.2 Hz), 3.44 (2H, s), 6.32 (1H, t, J=6.4 Hz), 6.74–6.80 (2H, m), 7.00 (1H, dd, J=1.2, 8.0 Hz), 7.18–7.32 (3H, m), 7.35 (1H, br d, J=6.0 Hz), 7.52 (1H, br d, J=6.0 Hz), 8.42–8.46 (2H, m).

Example 296

1-[(2-Oxo-1,2-dihydro-3-pyridinyl)methyl]-4-[2-[2-[1-(dimethylcarbamoyl)cyclopentyloxy]phenyl]ethyl]piperidine The title compound was obtained from a corresponding raw material in accordance with the method of Example 285.

¹H-NMR (400 MHz, CDCl₃) δ 1.28–1.43 (3H, m), 1.47–1.56 (2H, m), 1.70–1.82 (6H, m), 2.06–2.21 (4H, m), 2.38–2.50 (2H, m), 2.57–2.64 (2H, m), 2.93 (3H, s), 2.96 (2H, br d, J=11.2 Hz), 3.09 (3H, s), 3.50 (2H, s), 6.34 (1H, t, J=6.4 Hz), 6.68 (1H, dd, J=8.4, 1.2 Hz), 6.86 (1H, dd, J=7.6, 1.2 Hz), 7.04 (1H, dd, J=7.6, 2.0 Hz), 7.12 (1H, dd, J=7.6, 2.0, Hz), 7.37 (1H, m), 7.56 (1H, br d, J=5.6 Hz).

Example 297

1-[[5-(3-Pyridinyl)-2-oxo-1,2-dihydro-3-pyridinyl)methyl]-4-[2-[2,3-(methylenedioxy)phenyl]ethyl]piperidine The title compound was obtained from a corresponding raw material in accordance with the method of Example 285.

¹H-NMR (400 MHz, CDCl₃) δ 1.28–1.43 (3H, m), 1.56–1.64 (2H, m), 1.74–1.83 (2H, m), 2.14 (2H, br t, J=10.8 Hz), 2.56–2.64 (2H, m), 2.88 (2H, br d, J=10.8 Hz), 3.58 (2H, s), 5.93 (2H, s), 6.66 (1H, dd, J=7.6, 1.6 Hz), 6.69 (1H, dd, J=7.6, 1.6 Hz), 6.76 (1H, t, J=7.6 Hz), 7.37 (1H, ddd, J=8.0, 5.2, 0.8 Hz), 7.74 (1H, br s), 7.78 (1H, ddd, J=8.0, 2.4, 1.6 Hz), 8.84 (1H, br s), 8.58 (1H, dd, J=5.2, 1.6 Hz), 8.76 (1H, dd, J=2.4, 0.8 Hz).

Example 298

1-[[5-(4-Pyridinyl)-2-oxo-1,2-dihydro-3-pyridinyl)methyl]-4-[2-[2,3-(methylenedioxy)phenyl]ethyl]piperidine The title compound was obtained from a corresponding raw material in accordance with the method of Example 285.

¹H-NMR (400 MHz, CDCl₃) δ 1.30–1.44 (3H, m), 1.56–1.64 (2H, m), 1.75–1.84 (2H, m), 2.15 (2H, br t, J=10.0 Hz), 2.57–2.64 (2H, m), 2.99 (2H, br d, J=11.2 Hz), 3.58 (2H, s), 5.93 (2H, s), 6.66 (1H, dd, J=7.6, 1.2 Hz), 6.69 (1H, dd, J=7.6, 1.2 Hz), 6.76 (1H, t, J=7.6 Hz), 7.38–7.73 (2H, m), 7.73–7.73 (2H, m), 8.63–8.68 (2H, m).

Example 299

1-[5-Chloro-2-oxo-1,2-dihydro-3-pyridinyl)methyl]-4-[2-[2-(benzyloxy)phenyl]ethyl]piperidine The title compound was obtained from a corresponding raw material in accordance with the method of Example 285.

¹H-NMR (400 MHz, CDCl₃) δ 1.23–1.39 (3H, m), 1.53–1.62 (2H, m), 1.72–1.80 (2H, m), 2.09 (2H, br t, J=10.8 Hz), 2.65–2.72 (2H, m), 2.88 (2H, br d, J=11.6 Hz), 3.51 (2H, s), 5.08 (2H, s), 6.88–6.93 (2H, m), 7.13–7.20 (2H, m), 7.29–7.46 (6H, m), 7.77 (1H, br s).

Example 300

1-[(2-Oxo-1,2-dihydro-3-pyridinyl)methyl]-4-[2-[3-(cyclohexylmethyloxy)phenyl]ethyl]piperidine The title compound was obtained from a corresponding raw material in accordance with the method of Example 285.

¹H-NMR (400 MHz, CDCl₃) δ 0.98–1.11 (2H, m), 1.14–1.42 (6H, m), 1.53–1.62 (2H, m), 1.65–1.92 (8H, m), 2.05–2.16 (2H, m), 2.55–2.63 (2H, m), 2.90–2.99 (2H, m), 3.49 (2H, s), 3.74 (2H, d, J=6.4 Hz), 6.36 (1H, t, J=6.4 Hz), 6.68–6.77 (3H, m), 7.17 (1H, dt, J=7.6, 2.0 Hz), 7.36 (1H, br d, J=6.0 Hz), 7.58 (1H, br d, J=6.4 Hz).

Example 301

1-[(5-Chloro-2-oxo-1,2-dihydro-3-pyridinyl)methyl]-4-2-[2-(cyclohexylmethyloxy)phenyl]ethyl]piperidine The title compound was obtained from a corresponding raw material in accordance with the method of Example 285.

¹H-NMR (400 MHz, CDCl₃) δ 1.05–1.43 (9H, m), 1.52–1.60 (2H, m), 1.66–1.90 (7H, m), 2.10–2.20 (2H, m), 2.592.66 (2H, m), 2.94 (2H, br d, J=10.4 Hz), 3.56 (2H, s), 3.75 (2H, d, J=5.6 Hz), 6.80 (1H, d, J=8.0 Hz), 6.85 (1H, dt, J=8.0, 1.6 Hz), 7.10 (1H, dd, J=8.0, 1.6 Hz), 7.14 (1H, dt, J=8.0, 1.6 Hz), 7.35 (1H, d, J=2.4 Hz), 7.87 (1H, br s).

Example 302

1-[(2-Oxo-1,2-dihydro-3-pyridinyl)methyl]-4-[2-[2-(cyclohexylmethyloxy)phenyl]ethyl]piperidine oxalate In ethanol (4 ml) was dissolved 226 mg of 1-[(2-methoxy-3-pyridyl)methyl]-4-[2-[2-(cyclohexylmethyloxy)phenyl]ethyl]piperidine. To the mixture was added 1 ml of a 4N-hydrogen chloride-ethyl acetate solution, followed by heating under reflux for 1.5 hours. An aqueous sodium bicarbonate was added to the reaction solution, and the mixture was extracted with dichloromethane. The extract was dried over anhydrous magnesium sulfate, and the solvent was evaporated. The resulting oil was dissolved in ethanol, 49 mg of oxalic acid and ethyl acetate were added thereto, and then the resulting precipitates were collected by filtration, to give 229 mg of the title compound as a white powder.

¹H-NMR (400 MHz, DMSO-d₆) δ 1.05–1.35 (6H, m), 1.35–1.55 (4H, m), 1.62–1.90 (8H, m), 2.56 (2H, m), 2.88 (2H, m), 3.23–3.36 (2H, m), 3.77 (2H, d, J=5.6 Hz), 4.00 (2H, s), 6.29 (1H, t, J=6.4 Hz), 6.83 (1H, t, J=7.2 Hz), 6.89 (1H, d, J=8.0 Hz), 7.09–7.17 (2H, m), 7.52 (1H, br d, J=6.4 Hz), 7.68 (1H, br d, J=6.0 Hz).

Example 303

1-[(2-Oxo-1,2-dihydro-3-pyridinyl)methyl]-4-[2-[3-(cyclopentyloxy)phenyl]ethyl]piperidine oxalate The title compound was obtained from a corresponding raw material in accordance with the method of Example 302.

¹H-NMR (400 MHz, DMSO-d₆) δ 1.20–1.38 (3H, m), 1.44–1.80 (10H, m), 1.82–1.94 (2H, m), 2.48–2.58 (2H, m), 3.05 (2H, m), 3.49 (2H, br s), 3.64 (2H, br s), 4.78 (1H, br t, J=6.0 Hz), 6.23 (1H, t, J=6.8 Hz), 6.66–6.75 (3H, m), 7.15 (1H, t, J=7.6 Hz), 7.39 (1H, br d, J=5.2 Hz), 7.53 (1H, br d, J=5.2 Hz).

Example 304

1-[(2-Oxo-1,2-dihydro-3-pyridinyl)methyl]-4-[2-[2-(benzyloxy)phenyl]ethyl]piperidine oxalate The title compound was obtained from a corresponding raw material in accordance with the method of Example 302.

¹H-NMR (400 MHz, DMSO-d₆) δ 1.30–1.44 (5H, m), 1.76–1.86 (2H, m), 2.60 (2H, br t, J=7.6 Hz), 2.83 (2H, m), 3.24 (2H, br d, J=8.8 Hz), 3.98 (2H, s), 5.11 (2H, s), 6.29 (1H, t, J=6.4 Hz), 6.87 (1H, t, J=7.2 Hz), 7.13 (1H, d, J=8.8 Hz), 7.12–7.18 (2H, m), 7.29–7.37 (1H, m), 7.38–7.48 (5H, m), 7.52 (1H, dd, J=6.4, 1.2 Hz), 7.67 (1H, dd, J=6.4, 1.2 Hz).

Example 305

1-[(2-Oxo-1,2-dihydro-3-pyridinyl)methyl]-4-[2-[3-(benzyloxy)phenyl]ethyl]piperidine oxalate The title compound was obtained from a corresponding raw material in accordance with the method of Example 302.

¹H-NMR (400 MHz, DMSO-d₆) δ 1.32–1.58 (5H, m), 1.76–1.88 (2H, m), 2.55 (2H, m), 2.84 (1H, m), 3.28 (2H, m), 3.56 (2H, m), 3.98 (2H, br s), 5.08 (2H, s), 6.29 (1H, t, J=6.4 Hz), 6.76–6.88 (3H, m), 7.19 (1H, t, J=7.6 Hz), 7.24–7.46 (5H, m), 7.52 (1H, br d, J=6.4 Hz), 7.67 (1H, br d, J=6.4 Hz).

Example 306

1-[(2-Oxo-1,2-dihydro-3-pyridinyl)methyl]-4-[[2-(2-phenylethyl)phenyl]ethyl]piperidine oxalate The title compound was obtained from a corresponding raw material in accordance with the method of Example 302.

¹H-NMR (400 MHz, DMSO-d₆) δ 1.34–1.58 (3H, m), 1.80–1.90 (2H, m), 2.57 (2H, br t, J=8.0 Hz), 2.74–2.92 (6H, m), 3.26 (2H, m), 3.62 (2H, m), 3.94 (2H, br s), 6.29 (1H, d, J=6.4 Hz), 7.08–7.33 (9H, m), 7.50 (1H, br d, J=2.4 Hz), 7.66 (1H, br d, J=6.4 Hz).

Example 307

1-[(2-Oxo-1,2-dihydro-3-pyridinyl)methyl]-4-[2-[2-(cyclopentyloxy)phenyl]ethyl]piperidine oxalate The above compound was obtained from a corresponding raw material in accordance with the method of Example 302.

¹H-NMR (400 MHz, DMSO-d₆) δ 1.32–1.50 (5SH, m), 1.55–1.76 (6H, m), 1.78–1.93 (4H, m), 2.54–2.62 (2H, m), 2.82 (2H, br s), 3.26 (2H m), 3.95 (2H, br s), 4.83 (1H, br t, J=5.6 Hz), 6.28 (1H, t, J=6.8 Hz), 6.81 (1H, t, J=8.0 Hz), 6.90 (1H, d, J=8.0 Hz), 7.08–7.16 (2H, m), 7.50 (1H, dd, J=6.4, 2.0 Hz), 7.66 (I1H, br d, J=6.4 Hz).

Example 308

1-[(2-Oxo-1,2-dihydro-3-pyridinyl)methyl]-4-[2-[2-(isobutyloxy)phenyl]ethyl]piperidine oxalate The title compound was obtained from a corresponding raw material in accordance with the method of Example 302.

¹H-NMR (400 MHz, DMSO-d₆) δ 1.01 (6H, d, J=6.4 Hz), 1.26–1.40 (3H, m), 1.42–1.51 (2H, m), 1.72–1.81 (2H, m), 2.03 (1H, m), 2.46 (2H, m), 2.53–2.60 (2H, m), 3.06 (2H, br d, J=11.2 Hz), 3.64 (2H, br s), 3.72 (2H, d, J=6.4 Hz), 6.23 (1H, t, J=6.8 Hz), 6.83 (1H, t, J=7.2 Hz), 6.89 (1H, d, J=8.0 Hz), 7.09–7.16 (2H, m), 7.40 (1H, br dd, J=6.4, 2.0 Hz), 7.54 (1H, d, J=5.2 Hz).

Example 309

1-[(2-Oxo-1,2-dihydro-3-pyridinyl)methyl]-4-[2-[2-(2-phenylethoxy)phenyl]ethyl]piperidine oxalate The above compound was obtained from a corresponding raw material in accordance with the method of Example 302.

¹H-NMR (400 MHz, DMSO-d₆) δ 1.28–1.44 (5H, m), 1.72–1.81 (2H, m), 2.43–2.50 (2H, m), 2.86 (2H, m), 3.03 (2H, t, J=6.4 Hz), 3.28 (2H, m), 4.00 (2H, br s), 4.18 (2H, t, J=5.2 Hz), 6.31 (1H, t, J=6.8 Hz), 6.83 (1H, t, J=7.2 Hz), 6.94 (1H, d, J=7.6 Hz), 7.06–7.16 (2H, m), 7.18–7.25 (1H, m), 7.28–7.36 (3H, m), 7.53 (1H, dd, J=6.0, 2.0 Hz), 7.68 (1H, br d, J=5.6 Hz).

Example 310

1-[(2-Oxo-1,2-dihydro-3-pyridinyl)methyl]-4-[2-[2-(phenoxymethyl)phenyl]ethyl]piperidine oxalate The title compound was obtained from a corresponding raw material in accordance with the method of Example 302.

¹H-NMR (400 MHz, DMSO-d₆) δ 1.32–1.58 (5H, m), 1.78–1.86 (2H, m), 2.62–2.68 (2H, m), 2.85 (2H, m), 3.58 (2H, m), 3.98 (2H, br s), 5.08 (2H, s), 6.29 (1H, t, J=6.8 Hz), 6.95 (1H, t, J=7.2 Hz), 6.99–7.04 (2H, m), 7.18–7.24 (5H, m), 7.42 (1H, dd, J=7.6, 1.2 Hz), 7.52 (1H, dd, J=6.8, 2.0 Hz), 7.66 (1H, br d, J=6.8 Hz).

Example 311

1-[(2-Oxo-1,2-dihydro-3-pyridinyl)methyl]-4-[2-[2-(cyclopentylmethyloxy)phenyl]ethyl]piperidine oxalate The title compound was obtained from a corresponding raw material in accordance with the method of Example 302.

¹H-NMR (400 MHz, DMSO-d₆) δ 1.28–1.67 (11H, m), 1.73–1.86 (4H, m), 2.31 (1H, septet, J=7.3 Hz), 2.52–2.58 (2H, m), 2.67 (2H, m), 3.15–3.24 (2H, m), 3.83 (2H, d, J=6.4 Hz), 3.84 (2H, br s), 6.26 (1H, t, J=6.4 Hz), 6.82 (1H, dt, J=6.8, 1.2 Hz), 6.90 (1H, d, J=8.0 Hz), 7.09–7.16 (2H, m), 7.46 (1H, dd, J=6.4, 1.2 Hz), 7.61 (1H, br d, J=5.6 Hz).

Example 312

1-[(2-Oxo-1,2-dihydro-3-pyridinyl)methyl]-4-[2-[(2-cyclohexylethyl)phenyl]ethyl]piperidine oxalate The title compound was obtained from a corresponding raw material in accordance with the method of Example 302.

¹H-NMR (400 MHz, DMSO-d₆) δ 0.87–0.99 (2H, m), 1.10–1.79 (16H, m), 1.83–1.92 (2H, m), 2.51–2.60 (4H, m), 2.92 (2H, br s), 3.34 (2H, br s), 4.04 (2H, br s), 6.03 (1H, t, J=6.8 Hz), 7.06–7.16 (4H, m), 7.54 (1H, dd, J=6.8, 2.4 Hz), 7.69 (1H, br d, J=10.0 Hz).

Example 313

1-[(2-Oxo-1,2-dihydro-3-pyridinyl)methyl]-4-[2-[2-(benzylamino)phenyl]ethyl]piperidine dihydrochloride In ethanol (8 ml) was dissolved 294 mg of 1-[(2-methoxy-3-pyridinyl)methyl]-4-[2-[2-(benzylamino)phenyl]ethyl]piperidine. To the mixture was added 3 ml of a 4N-hydrogen chloride-ethyl acetate solution, followed by heating under reflux for 3 hours. After cooling as it was, the resulting precipitates were collected by filtration and recrystallized from ethanol, to give 273 mg of the title compound as a white powder.

¹H-NMR (400 MHz, DMSO-d₆) δ 1.42–1.58 (4H, m), 1.61–1.76 (1H, m), 1.86–1.96 (2H, m), 2.51–2.60 (2H, m), 2.95 (2H, br t, J=11.6 Hz), 3.28 (2H, br d, J=12.4 Hz), 4.06 (2H, s), 4.36 (2H, s), 6.31 (1H, t, J=6.4 Hz), 6.53 (1H, m), 6.63 (1H, m), 6.94 (1H, br t J=7.6 Hz), 7.00 (1H, br d, J=7.2 Hz), 7.18–7.37 (5H, m), 7.54 (1H, dd, J=6.4, 2.0 Hz), 7.79 (1H, dd, J=6.8, 2.0 Hz).

Example 314

1-[(2-Oxo-1,2-dihydro-3-pyridinyl)methyl]-4-[2-[2-(N-benzyl-N-methylamino)phenyl]ethyl]piperidine oxalate The title compound was obtained from a corresponding raw material in accordance with the method of Example 302.

¹H-NMR (400 MHz, DMSO-d₆) δ 1.36–1.61 (5H, m), 1.80–1.92 (2H, m), 2.51 (3H, s), 2.68–2.76 (2H, m), 2.87 (2H, m), 3.28 (2H, br d, J=9.6 Hz), 3.98 (2H, s), 4.00 (2H, s), 6.29 (1H, t, J=6.8 Hz), 7.01 (1H, dt, J=7.6 Hz), 7.02 (1H, dt, J=7.2, 1.6 Hz), 7.12–7.28 (4H, m), 7.30–7.36 (4H, m), 7.52 (1H, dd, J=6.4, 2.0 Hz), 7.68 (1H, dd, J=6.8, 2.0 Hz).

Example 315

1-[(2-Oxo-1,2-dihydro-3-pyridinyl)methyl]-4-[2-[2-[(cyclohexylmethyl)amino]phenyl]ethyl]piperidine dihydrochloride The title compound was obtained from a corresponding raw material in accordance with the method of Example 313.

¹H-NMR (400 MHz, CDCl₃) δ 0.93–1.06 (2H, m), 1.10–1.26 (3H, m), 1.46–1.66 (5H, m), 1.66–1.81 (4H, m), 1.82–1.96 (4H, m), 2.67 (2H, m), 2.90–3.04 (2H, m), 3.00 (2H, d, J=6.4 Hz), 3.34–3.42 (2H, m), 4.06 (2H, s), 6.31 (1H, t, J=6.8 Hz), 7.06–7.42 (4H, m), 7.54 (1H, dd, J=6.8, 2.0 Hz), 7.83 (1H, dd, J=6.8, 2.0 Hz).

Example 316

1-[(2-Oxo-1,2-dihydro-3-pyridinyl)methyl]-4-[2-[2-[N-(cyclohexylmethyl)-N-methylamino]phenyl]ethyl]piperidine oxalate The title compound was obtained from a corresponding raw material in accordance with the method of Example 302.

¹H-NMR (400 MHz, DMSO-d₆) δ 1.03–1.34 (5H, m), 1.63–2.00 (10H, m), 3.04–3.18 (3H, m), 3.42 (2H, br d, J=12.8 Hz), 3.78 (2H, d, J=5.6 Hz), 4.08 (2H, s), 6.30 (1H, t, J=6.8 Hz), 6.91 (1H, dt, J=7.6, 1.2 Hz), 6.94 (1H, dd, J=7.6, 1.2 Hz), 7.13 (1H, br d, J=6.8 Hz), 7.18 (1H, dt, J=8.0, 1.2 Hz), 7.54 (1H, dd, J=6.8, 2.0 Hz), 7.73 (1H, dd, J=6.8, 2.0 Hz).

Example 317

1-[(2-Oxo-1,2-dihydro-3-pyridinyl)methyl]-4-[2-(cyclohexylmethyloxy)phenyl]piperidine oxalate The title compound was obtained from a corresponding raw material in accordance with the method of Example 302.

¹H-NMR (400 MHz, CDCl₃) δ 0.80–0.92 (2H, m), 1.08–1.23 (3H, m), 1.37–1.56 (6H, m), 1.57–1.70 (3H, m), 1.72–1.81 (2H, m), 1.81–1.90 (2H, m), 2.51 (3H, s), 2.62 (2H, d, J=7.2 Hz), 2.62–2.70 (2H, m), 2.92 (2H, m), 3.26–3.38 (2H, m), 4.04 (2H, s), 6.29 (1H, t, J=6.8 Hz), 6.97–7.02 (1H, m), 7.10–7.20 (3H, m), 7.54 (1H, dd, J=6.8, 2.0 Hz), 7.70 (1H, dd, J=6.8, 2.0 Hz).

Example 318

1-[(5-(Methylsulfonyl)-2-oxo-1,2-dihydro-3-pyridinyl)methyl]-4-[2-[2-(cyclohexylmethyloxy)phenyl]ethyl]piperidine In ethanol (10 ml) was dissolved 138 mg of 1-[(5-(methylsulfonyl)-2-methoxy-3-pyridinyl)methyl]-4-[2-[2-(cyclohexylmethyloxy)phenyl]ethyl]piperidine. To the mixture was added 1 ml of thionyl chloride, followed by heating under reflux for 2.5 hours. An aqueous sodium carbonate aqueous solution was added to the reaction solution, and the resulting precipitates were collected by filtration, to give 127 mg of the title compound as a white powder.

¹H-NMR (400 MHz, CDCl₃) δ 1.05–1.45 (8H, m), 1.53–1.61 (2H, m), 1.67–1.90 (8H, m), 2.15–2.27 (2H, m), 2.60–2.68 (2H, m), 2.92 (2H, br d, J=10.8 Hz), 3.08 (3H, s), 3.60 (2H, s), 3.76 (2H, d, J=6.0 Hz), 6.81 (1H, d, J=8.0 Hz), 6.86 (1H, dt, J=8.0, 1.2 Hz), 7.11 (1H, dd, J=8.0, 1.2 Hz), 7.15 (1H, dt, J=8.0, 2.0 Hz), 7.83 (1H, br d, J=2.4 Hz), 8.35 (1H, br m).

Example 319

1-[(5-Chloro-2-oxo-1,2-dihydro-3-pyridinyl)methyl]-4-[2-[2-[2,3-(methylenedioxy)phenyl]ethyl]piperidine The title compound was obtained from a corresponding raw material in accordance with the method of Example 318.

$^1$H-NMR (400 MHz, DMSO-d$_6$) δ 1.08–1.23 (3H, m), 1.42–1.50 (2H, m), 1.60–1.70 (2H, m), 1.88–2.00 (2H, m), 2.40–2.60 (2H, m), 2.73–2.83 (2H, m), 3.24 (2H, s), 5.95 (2H, s), 6.64–6.76 (3H, m), 7.34 (1H, s), 7.50 (1H, s).

Example 320

1-[(5-Chloro-2-oxo-1,2-dihydro-3-pyridinyl)methyl]-4-[2-[2-(2-fluorophenyl)ethyl]piperidine The title compound was obtained from a corresponding raw material in accordance with the method of Example 318.

$^1$H-NMR (400 MHz, DMSO-d$_6$) δ 1.00–1.26 (3H, m), 1.40–1.54 (2H, m), 1.67 (2H, br d, J=9.6 Hz), 1.94 (2H, br t, J=10.4 Hz), 2.60 (2H, d, J=7.6 Hz), 2.77 (2H, br d, J=11.6 Hz), 3.24 (2H, s), 7.06–7.13 (2H, m), 7.17–7.24 (1H, m), 7.27 (1H, t, J=7.6 Hz), 7.34 (1H, d, J=2.0 Hz), 7.50 (1H, d, J=3.2 Hz).

Example 321

1-[(5-Chloro-2-oxo-1,2-dihydro-3-pyridinyl)methyl]-4-[2-[2-(2-methoxyethoxy)phenyl]ethyl]piperidine The title compound was obtained from a corresponding raw material in accordance with the method of Example 318.

$^1$H-NMR (400 MHz, DMSO-d$_6$) δ 1.10–1.25 (3H, m), 1.40–1.50 (2H, m), 1.67 (2H, br d, J=8.8 Hz), 1.95 (2H, br t, J=10.8 Hz), 2.54 (2H, t, J=8.0 Hz), 2.76 (2H, br d, J=11.2 Hz), 3.24 (2H, s), 3.31 (3H, s), 3.65 (2H, t, J=4.4 Hz), 4.05 (2H, t, J=4.4 Hz), 6.83 (1H, t, J=7.2 Hz), 6.90 (1H, d, J=8.0 Hz), 7.10 (1H, d, J=7.6 Hz), 7.06–7.14 (1H, m), 7.34 (1H, d, J=2.8 Hz), 7.50 (1H, d, J=2.8 Hz).

Example 322

1-[(2-Oxo-1,2-dihydro-3-pyridinyl)methyl]-4-[2-(2,5-dimethylphenyl)ethyl]piperidine The title compound was obtained from a corresponding raw material in accordance with the method of Example 318.

$^1$H-NMR (400 MHz, DMSO-d$_6$) δ 1.16–1.36 (3H, m), 1.32–1.46 (2H, m), 1.72 (2H, br d, J=10.8 Hz), 2.03 (1H, br s), 2.19 (3H, s), 2.22 (3H, s), 2.51 (2H, t, J=7.6 Hz), 2.85 (2H, br d, J=10.4 Hz), 3.20–3.42 (2H, m), 6.18 (1H, t, J=6.4 Hz), 6.87 (1H, d, J=7.6 Hz), 6.92 (1H, s), 6.99 (1H, d, J=7.6 Hz), 7.28 (1H, d, J=6.4 Hz), 7.41 (1H, d, J=6.0 Hz).

Example 323

1-[(5-Chloro-2-oxo-1,2-dihydro-3-pyridinyl)methyl]-4-[2-[2-(isobutyloxy)phenyl]ethyl]piperidine oxalate In ethanol (10 ml) was dissolved 443 mg of 1-[(5-chloro-2-methoxy-3-pyridinyl)methyl]-4-[2-[2-(isobutyloxy)phenyl]ethyl]piperidine. To the mixture was added 0.5 ml of thionyl chloride, followed by heating under reflux for 3 hours. An aqueous sodium carbonate was added to the reaction solution, and the mixture was extracted with dichloromethane. The extract was dried over anhydrous magnesium sulfate, and then the solvent was evaporated. The resulting oil was dissolved in ethanol, 99 mg of oxalic acid was added thereto, and then the resulting precipitates were collected by filtration, to give 382 mg of the title compound as a white powder.

$^1$H-NMR (400 MHz, DMSO-d$_6$) δ 1.01 (6H, d, J=6.8 Hz), 1.24–1.42 (3H, m), 1.43–1.51 (2H, m), 1.73–1.82 (2H, m), 2.03 (1H, m), 2.45 (2H, m), 2.54–2.60 (2H, m), 3.08 (2H, br d, J=11.6 Hz), 3.64 (2H, br s), 3.73 (2H, d, J=6.4 Hz), 6.83 (1H, dt, J=7.6, 1.2 Hz), 6.89 (1H, d, J=7.6 Hz), 7.09–7.16 (2H, m), 7.58 (1H, d, J=2.4 Hz), 7.65 (1H, d, J=2.4 Hz).

Example 324

1-[(2-Oxo-1,2-dihydro-3-pyridinyl)methyl]-4-[2-(3,5-dimethylphenyl)ethyl]piperidine oxalate The title compound was obtained from a corresponding raw material in accordance with the method of Example 323.

$^1$H-NMR (400 MHz, DMSO-d$_6$) δ 1.48 (5H, br s), 1.84 (2H, br d, J=9.2 Hz), 2.22 (6H, s), 2.45–2.55 (2H, m), 2.85–3.00 (2H, m), 3.25–3.40 (2H, m), 4.04 (2H, s), 6.29 (1H, t, J=6.4 Hz), 6.79 (3H, s), 7.53 (1H, dd, J=6.4, 2.0 Hz), 7.73 (1H, dd, J=6.8, 2.0 Hz).

Example 325

1-[(2-Oxo-1,2-dihydro-3-pyridinyl)methyl]-4-[2-(2-methoxy-5-methylphenyl)ethyl]piperidine oxalate The title compound was obtained from a corresponding raw material in accordance with the method of Example 323.

$^1$H-NMR (400 MHz, DMSO-d$_6$) δ 1.45 (5H, br s), 1.86 (2H, br d, J=10.4 Hz), 2.20 (3H, s), 2.44–2.54 (2H, m), 2.93 (2H, br s), 3.24–3.40 (2H, m), 3.73 (3H, s), 4.05 (2H, s), 6.30 (1H, t, J=6.4 Hz), 6.82 (1H, d, J=8.0 Hz), 6.94 (1H, s), 6.95 (1H, d, J=8.4 Hz), 7.54 (1H, dd, J=6.4, 2.0 Hz), 7.72 (1H, d, J=5.2 Hz).

Example 326

1-[(2-Oxo-1,2-dihydro-3-pyridinyl)methyl]-4-[2-[2-(trifluoromethoxy)phenyl]ethyl]piperidine oxalate The title compound was obtained from a corresponding raw material in accordance with the method of Example 323.

$^1$H-NMR (400 MHz, DMSO-d$_6$) δ 1.34–1.60 (5H, br s), 1.86 (2H, br d, J=11.2 Hz), 2.64 (2H, t, J=7.6 Hz), 2.94 (2H, br s), 3.24–3.44 (2H, m), 4.05 (2H, s), 6.30 (1H, t, J=6.4 Hz), 7.28–7.40 (3H, m), 7.38–7.48 (1H, m), 7.54 (1H, d, J=6.4 Hz), 7.71 (1H, d, J=5.6 Hz).

Example 327

1-[(2-Oxo-1,2-dihydro-3-pyridinyl)methyl]-4-[2-[2-(3-pyridinyl)phenyl]ethyl]piperidine oxalate The title compound was obtained from a corresponding raw material in accordance with the method of Example 323.

$^1$H-NMR (400 MHz, DMSO-d$_6$) δ 1.34–1.65 (5H, m), 1.80–1.94 (2H, m), 2.66 (2H, t, J=7.6 Hz), 2.85–3.00 (2H, m), 3.25–3.40 (2H, m), 3.95–4.10 (2H, m), 6.28 (1H, t, J=6.4 Hz), 7.26 (1H, d, J=7.2 Hz), 7.40 (1H, d, J=7.2 Hz), 7.47 (1H, dd, J=7.2, 4.8 Hz), 7.40–7.60 (3H, m), 7.69 (1H, d, J=6.4 Hz), 8.00–8.10 (1H, m), 8.55 (1H, dd, J=4.8, 1.6 Hz), 8.87 (1H, d, J=1.6 Hz).

Example 328

1-[(2-Oxo-1,2-dihydro-3-pyridinyl)methyl]-4-[2-[3-[(tetrahydropyran-2-yl)methyloxy]phenyl]ethyl]piperidine The title compound was obtained from a corresponding raw material in accordance with the method of Example 323.

¹H-NMR (400 MHz, DMSO-d₆) δ 1.20–1.60 (9H, m), 1.62 (1H, br d, J=12.4 Hz), 1.70–1.90 (3H, m), 2.40–2.60 (2H, m), 2.80–3.00 (2H, m), 3.20–3.43 (3H, m), 3.50–3.63 (1H, m), 3.75–3.95 (3H, m), 4.02 (2H, s), 6.27 (1H, t, J=6.4 Hz), 6.66–6.80 (3H, m), 7.14 (1H, t, J=8.0 Hz), 7.52 (1H, d, J=6.4 Hz), 7.68 (1H, d, J=6.0 Hz).

Example 329

1-[(2-Oxo-1,2-dihydro-3-pyridinyl)methyl]-4-[2-[2-[(tetrahydropyran-2-yl)methyloxy]phenyl]ethyl]piperidine The title compound was obtained from a corresponding raw material in accordance with the method of Example 323.

¹H-NMR (400 MHz, DMSO-d₆) δ 1.25–1.55 (9H, m), 1.64 (1H, br d, J=12.0 Hz), 1.75–1.93 (3H, m), 2.53 (2H, t, J=6.4 Hz), 2.80–3.00 (2H, m), 3.20–3.43 (3H, m), 3.53–3.63 (1H, m), 3.83–3.93 (3H, m), 4.03 (2H, s), 6.28 (1H, t, J=6.4 Hz), 6.82 (1H, t, J=7.2 Hz), 6.89 (1H, d, J=8.0 Hz), 7.10 (1H, d, J=7.2 Hz), 7.11 (1H, t, J=7.2 Hz), 7.52 (1H, dd, J=6.0, 2.0 Hz), 7.64–7.72 (1H, m).

Example 330

1-[(2-Oxo-1,2-dihydro-3-pyridinyl)methyl]-4-[2-[2-(2-methoxyethoxy)phenyl]ethyl]piperidine oxalate The title compound was obtained from a corresponding raw material in accordance with the method of Example 323.

¹H-NMR (400 MHz, DMSO-d₆) δ 1.34–1.50 (5H, m), 1.76–1.90 (2H, m), 2.46–2.56 (2H, m), 2.80–2.98 (2H, m), 3.20–3.38 (2H, m), 3.30 (3H, s), 3.64 (2H, t, J=4.0 Hz), 4.02 (2H, s), 4.06 (2H, t, J=4.0 Hz), 6.28 (1H, t, J=6.4 Hz), 6.83 (1H, t, J=7.2 Hz), 6.91 (1H, d, J=8.0 Hz), 7.11 (1H, d, J=7.6 Hz), 7.12 (1H, t, J=7.6 Hz), 7.52 (1H, d, J=6.0 Hz), 7.66–7.76 (1H, m).

Example 331

1-[(2-Oxo-1,2-dihydro-3-pyridinyl)methyl]-4-[2-(2-phenoxyphenyl)ethyl]piperidine oxalate The title compound was obtained from a corresponding raw material in accordance with the method of Example 323.

¹H-NMR (400 MHz, DMSO-d₆) δ 1.25–1.60 (5H, m), 1.78 (2H, br d, J=12.8 Hz), 2.56 (2H, t, J=7.6 Hz), 2.66–2.95 (2H, m), 3.20–3.35 (2H, m), 4.02 (2H, s), 6.29 (1H, t, J=6.4 Hz), 6.84–6.92 (3H, m), 7.08 (1H, t, J=7.2 Hz), 7.13 (1H, t, J=7.2 Hz), 7.23 (1H, t, J=7.2 Hz), 7.30–7.40 (3H, m), 7.54 (1H, d, J=5.2 Hz), 7.68 (1H, d, J=6.0 Hz).

Example 332

1-[(5-Chloro-2-oxo-1,2-dihydro-3-pyridinyl)methyl]-4-[[2-(2-phenylethyl)phenyl]ethyl]piperidine oxalate The title compound was obtained from a corresponding raw material in accordance with the method of Example 323.

¹H-NMR (400 MHz, DMSO-d₆) δ 1.25–1.48 (5H, m), 1.74–1.84 (2H, m), 2.48 (2H, m), 2.53–2.61 (2H, m), 2.76–2.89 (4H, m), 3.06 (2H, br d, J=10.8 Hz), 3.65 (2H, br s), 6.98–7.32 (9H, m), 7.58 (1H, m), 7.65 (1H, d, J=2.8 Hz).

Example 333

1-[(2-Oxo-1,2-dihydro-3-pyridinyl)methyl]-4-(2,2-diphenyl-1-ethenyl)piperidine

The title compound was obtained from a corresponding raw material in accordance with the method of Example 285.

¹H-NMR (400 MHz, CDCl₃) δ 1.52–1.76 (4H, m), 1.98–2.09 (2H, m), 2.16 (1H, m), 2.90 (2H, br d, J=10.4 Hz), 3.46 (2H, s), 5.92 (1H, d, J=9.6 Hz), 6.33 (1H, br t, J=6.4 Hz), 7.14–7.40 (1H, m), 7.55 (1H, m).

Example 334

1-[(5-Chloro-2-oxo-1,2-dihydro-3-pyridinyl)methyl]-4-[(E)-2-(2-fluorophenyl)-1-ethenyl]piperidine In ethanol (8 ml) was dissolved 245 mg of 1-[(5-chloro-2-methoxy-3-pyridinyl)methyl]-4-[(E)-2-(2-fluorophenyl)-1-ethenyl]piperidine. To the mixture was added 7 ml of a 4N-hydrogen chloride-ethyl acetate solution, followed by heating under reflux for 7 hours. An aqueous sodium carbonate was added to the reaction solution, and the mixture was extracted with ethyl acetate. The extract was dried over anhydrous magnesium sulfate, and then the solvent was evaporated. Ether was added to the resulting oil to be crystallized, and 116 mg of the title compound was obtained as a slight yellow powder.

¹H-NMR (400 Hz, CDCl₃) δ 1.56–1.68 (2H, m), 1.80–1.89 (2H, m), 2.18–2.30 (3H, m), 2.96–3.02 (2H, m), 3.56 (2H, s), 6.24 (1H, dd, J=7.2, 16.0 Hz), 6.56 (1H, d, J=16.0 Hz), 7.01 (1H, ddd, J=10.8, 8.4, 1.6 Hz), 7.08 (1H, dt, J=8.0, 1.2 Hz), 7.17 (1H, m), 7.40–7.48 (2H, m), 7.73 (1H, br s).

Example 335

1-[(5-Fluoro-2-oxo-1,2-dihydro-3-pyridinyl)methyl]-4-[(E)-2-(2-fluorophenyl)-1-ethenyl]piperidine In ethanol (12 ml) was dissolved 221 mg of 1-[(5-chloro-2-methoxy-3-pyridinyl)methyl]-4-[(E)-2-(2-fluorophenyl)-1-ethenyl]piperidine. To the mixture was added 12 ml of a 4N-hydrogen chloride-ethyl acetate solution, followed by heating under reflux for 11 hours. An aqueous sodium carbonate was added to the reaction solution, and the mixture was extracted with ethyl acetate. The extract was dried over anhydrous magnesium sulfate, and then the solvent was evaporated. Ether was added to the obtained oil, to crystallize. The title compound (176 mg) was obtained as a light pink powder.

¹H-NMR (400 MHz, CDCl₃) δ 1.57–1.69 (2H, m), 1.81–1.89 (2H, m), 2.20–2.31 (3H, m), 2.96–3.04 (2H, m), 3.60 (2H, s), 6.23 (1H, dd, J=16.0, 7.2 Hz), 6.56 (1H, d, J=16.0 Hz), 7.02 (1H, ddd, J=10.8, 8.0, 1.2 Hz), 7.08 (1H, dt, J=8.0, 1.2 Hz), 7.17 (1H, m), 7.28 (1H, dd, J=8.0, 2.8 Hz), 7.44 (1H, dt, J=7.6, 2.0 Hz), 7.72 (1H, br m).

Example 336

1-[(5-Chloro-2-oxo-1,2-dihydro-3-pyridinyl)methyl]-4-[(E)-2-(2-chlorophenyl)-1-ethenyl]piperidine The title compound was obtained from a corresponding raw material in accordance with the method of Example 285.

¹H-NMR (400 MHz, CDCl₃) δ 1.46–1.69 (2H, m), 1.82–1.90 (2H, m), 2.18–2.34 (3H, m), 2.95–3.02 (2H, m), 3.55 (2H, s), 6.15 (1H, dd, J=16.0, 6.8 Hz), 6.78 (1H, d, J=16.0 Hz), 7.15 (1H, dd, J=8.0, 1.6 Hz), 7.20 (1H, dt, J=8.0, 1.6 Hz), 7.34 (1H, dd, J=8.0, 1.6 Hz), 7.45 (1H, d, J=2.8 Hz), 7.51 (1H, dd, J=8.0, 1.6 Hz), 7.69 (1H, br s).

Example 337

1-[(5-Chloro-2-oxo-1,2-dihydro-3-pyridinyl)methyl]-4-[(E)-2-(2-methylphenyl)-1-ethenyl]piperidine The title compound was obtained from a corresponding raw material in accordance with the method of Example 285.

¹H-NMR (400 MHz, CDCl₃) δ 1.56–1.68 (2H, m), 1.81–1.88 (2H, m), 2.16–2.29 (3H, m), 2.33 (3H, s), 2.94–3.02 (2H, m), 3.54 (2H, s), 6.04 (1H, dd, J=16.0, 7.2 Hz), 6.59 (1H, dd, J=16.0, 0.8 Hz), 7.09–7.19 (3H, m), 7.41 (1H, dd, J=7.6, 1.6 Hz), 7.45 (1H, d, J=2.4 Hz), 7.69 (1H, br s).

Example 338

1-[(2-Oxo-1,2-dihydro-3-pyridinyl)methyl]-4-[(E)-2-[2-(benzyloxy)phenyl]-1-ethenyl]piperidine oxalate The title compound was obtained from a corresponding raw material in accordance with the method of Example 302.

¹H-NMR (400 MHz, DMSO-d₆) δ 1.58–1.78 (4H, m), 1.83–1.94 (2H, m), 2.40 (7/8H, m), 2.64 (1/8H, m), 2.82–3.05 (2H, m), 3.20–3.42 (2H, m), 4.01 (2H, br s), 5.12 (1/4H, s), 5.14 (7/4H, s), 6.18–6.28 (1H, m), 6.30 (1H, t, J=6.4 Hz), 6.50 (1/8H, d, J=11.6 Hz), 6.72 (7/8H, d, J=16.0 Hz), 6.89–7.04 (1H, m), 7.05–7.15 (1H, m), 7.18–7.55 (8H, m), 7.66 (1/8H, br d, J=5.2 Hz), 7.69 (7/8H, br d, J=5.2 Hz).

Example 339

1-[(2-Oxo-1,2-dihydro-3-pyridinyl)methyl]-4-[(E)-2-[(2-phenylethyl)phenyl]-1-ethenyl]piperidine oxalate The title compound was obtained from a corresponding raw material in accordance with the method of Example 302.

¹H-NMR (400 MHz, DMSO-d₆) δ 1.60–1.78 (2H, m), 1.86–1.96 (2H, m), 2.45 (1H, m), 2.52–3.04 (6H, m), 3.21 (2/7H, br d, J=11.2 Hz), 3.34 (12/7H, br d, J=11.2 Hz), 3.92 (2/7H, br s), 4.00 (12/7H, br s), 6.06–6.16 (1H, m), 6.27 (1/7H, t, J=6.8 Hz), 6.30 (6/7H, t, J=6.8 Hz), 6.57 (1/7H, d, J=11.2 Hz), 6.68 (6/7H, d, J=16.0 Hz), 7.10–7.32 (9H, m), 7.42–7.47 (1H, m), 7.49 (1/7H, dd, J=6.8, 2.0 Hz), 7.52 (6/7H, dd, J=6.8, 2.0 Hz), 7.62 (1/7H, br d, J=6.8 Hz), 7.68 (6/7H, dd, J=6.8, 1.6 Hz).

Example 340

1-[(2-Oxo-1,2-dihydro-3-pyridinyl)methyl]-4-[(E)-2-[2-(isobutyloxy)phenyl]-1-ethenyl]piperidine oxalate The title compound was obtained from a corresponding raw material in accordance with the method of Example 302.

¹H-NMR (400 MHz, DMSO-d₆) δ 0.97 (3/2H, d, J=6.8 Hz), 1.01 (9/2H, d, J=6.8 Hz), 1.58–1.94 (4H, m), 1.95–2.10 (1H, m), 2.40 (1/4H, m), 2.66 (3/4H, m), 2.94 (2H, m), 3.20–3.38 (2H, m), 3.74 (1/2H, d, J=6.8 Hz), 3.76 (3/2H, d, J=6.8 Hz), 3.92–4.05 (2H, m), 6.20–6.33 (2H, m), 6.48 (1/4H, d, J=11.6 Hz), 6.64 (3/4H, d, J=16.0 Hz), 6.86–6.99 (2H, m), 7.15–7.29 (5/4H, m), 7.44 (3/4H, dd, J=8.0, 1.6 Hz), 7.50 (1/4H, dd, J=6.4, 2.0 Hz), 7.52 (3/4H, dd, J=6.4, 2.0 Hz), 7.65 (1/4H, br d, J=6.4 Hz), 8.06 (3/4H, br d, J=6.4 Hz).

Example 341

1-[(2-Oxo-1,2-dihydro-3-pyridinyl)methyl]-4-[(E)-2-[2-(cyclopentylmethyloxy)phenyl]-1-ethenyl]piperidine oxalate The title compound was obtained from a corresponding raw material in accordance with the method of Example 302.

¹H-NMR (400 MHz, DMSO-d₆) δ 1.12–1.96 (13H, m), 2.12–2.54 (1H, m), 2.64 (1/4H, m), 2.80–3.02 (7/4H, m), 3.08–3.39 (2H, m), 3.82 (1/2H, d, J=6.8 Hz), 3.83 (3/2H, d, J=6.8 Hz), 4.00 (2H, m), 5.45 (1/4H, dd, J=12.0, 10.0 Hz), 6.20–6.35 (7/4H, m), 6.45 (1/4H, d, J=12.0 Hz), 6.62 (3/4H, d, J=15.6 Hz), 6.85–7.00 (2H, m), 7.15–7.30 (7/4H, m), 7.42 (5/4H, d, J=7.6 Hz), 7.50 (1/4H, dd, J=7.2, 2.0 Hz), 7.52 (3/4H, dd, J=7.2, 2.0 Hz), 7.64 (1/4H, dd, J=5.2, 2.0 Hz), 7.65 (3/4H, dd, J=5.2, 2.0 Hz).

Example 342

1-[(2-Oxo-1,2-dihydro-3-pyridinyl)methyl]-4-[(E)-2-[2-(2-cyclohexylethyl)phenyl]-1-ethenyl]piperidine oxalate The title compound was obtained from a corresponding raw material in accordance with the method of Example 302.

¹H-NMR (400 MHz, DMSO-d₆) δ 0.85–0.98 (2H, m), 1.07–1.29 (4H, m), 1.30–1.40 (2H, m), 1.57–1.76 (7H, m), 1.86–1.95 (2H, m), 2.33 (1/7H, m), 2.43 (6/7H, m), 2.51–2.56 (2/7H, m), 2.58–2.64 (12/7H, m), 3.19–3.27 (2/7H, m), 3.27–3.38 (12/7H, m), 3.92 (2/7H, s), 4.00 (12/7H, s), 6.05–6.14 (1H, m), 6.27 (1/7H, t, J=6.4 Hz), 6.30 (6/7H, t, J=6.4 Hz), 6.53 (1/7H, d, J=11.6 Hz), 6.62 (6/7H, d, J=15.2 Hz), 7.07–7.22 (3H, m), 7.40–7.46 (1H, m), 7.49 (1/7H, dd, J=6.4, 2.0 Hz), 7.52 (6/7H, dd, J=6.4, 2.0 Hz), 7.63 (1/7H, dd, J=5.6, 2.0 Hz), 7.69 (6/7H, dd, J=5.6, 2.0 Hz).

Example 343

1-[(2-Oxo-1,2-dihydro-3-pyridinyl)methyl]-4-[(E)-2-[(2-cyclohexylmethyloxy)phenyl]-1-ethenyl]piperidine oxalate In ethanol (12 ml) was dissolved 221 mg of 1-[(5-chloro-2-methoxy-3-pyridinyl)methyl]-4-[(E)-2-(2-fluorophenyl)-1-ethenyl]piperidine. To the mixture was added 12 ml of a 4N-hydrogen chloride-ethyl acetate solution, followed by heating under reflux for 11 hours. An aqueous sodium carbonate was added to the reaction solution, and the mixture was extracted with ethyl acetate. The extract was dried over anhydrous magnesium sulfate, and then the solvent was evaporated. Ether was added to the obtained oil, to crystallize. The title compound (176 mg) was obtained as a light pink powder.

¹H-NMR (400 MHz, DMSO-d₆) δ 1.02–1.34 (5H, m), 1.57–1.93 (10H, m), 2.39 (1H, m), 2.88 (2H, m), 3.29 (2H, br d, J=9.6 Hz), 3.79 (2H, d, J=6.0 Hz), 3.94 (2H, s), 6.19–6.32 (2H, m), 6.64 (1H, d, J=16.4 Hz), 6.88 (1H, t, J=7.2 Hz), 6.95 (1H, d, J=7.2 Hz), 7.18 (1H, dt, J=7.2, 1.2 Hz), 7.41 (1H, dd, J=7.2, 1.2 Hz), 7.50 (1H, dd, J=7.2, 2.0 Hz), 7.67 (1H, br d, J=5.6 Hz).

Example 344

1-[(2-Oxo-1,2-dihydro-3-pyridinyl)methyl]-4-[(Z)-2-[(2-cyclohexylmethyloxy)phenyl]-1-ethenyl]piperidine oxalate The title compound was obtained from a corresponding raw material in accordance with the method of Example 302.

¹H-NMR (400 MHz, DMSO-d₆) δ 0.97–1.32 (5H, m), 1.60–1.84 (10H, m), 2.65 (1H, m), 2.70–3.00 (2H, m), 3.26 (2H, br d, J=12.0 Hz), 3.77 (2H, d, J=7.2 Hz), 3.96 (2H, s), 5.47 (1H, m), 6.28 (1H, t, J=6.8 Hz), 6.47 (1H, d, J=11.6 Hz), 6.91 (1H, t, J=7.6 Hz), 6.95 (1H, d, J=8.0 Hz), 7.18 (1H, dd, J=7.6, 1.2 Hz), 7.23 (1H, dt, J=7.6, 1.2 Hz), 7.50 (1H, dd, J=6.8, 2.0 Hz), 7.66 (1H, br d, J=6.0 Hz).

Example 345

1-[(5-Fluoro-2-oxo-1,2-dihydro-3-pyridinyl)methyl]-4-[(E)-2-[(2-cyclohexylmethyloxy)phenyl]-1-ethenyl]piperidine oxalate The title compound was obtained from a corresponding raw material in accordance with the method of Example 302.

¹H-NMR (400 MHz, DMSO-d₆) δ 1.03–1.34 (5H, m), 1.47–1.88 (10H, m), 2.28 (1H, m), 2.42–2.60 (2H, m), 3.00–3.18 (2H, m), 3.62–3.74 (2H, m), 3.79 (2H, d, J=6.0 Hz), 6.26 (1H, dd, J=16.0, 6.8 Hz), 6.64 (1H, d, J=16.0 Hz), 6.88 (1H, t, J=7.6 Hz), 6.96 (1H, d, J=7.6 Hz), 7.17 (1H, dt, J=7.6, 2.0 Hz), 7.42 (1H, dd, J=7.6, 2.0 Hz), 7.65 (2H, br s).

Example 346

1-[(2-Oxo-1,2-dihydro-3-pyridinyl)methyl]-4-[(E)-2-[2-(cyclohexylmethyloxy)-5-fluorophenyl]-1-ethenyl]piperidine The title compound was obtained from a corresponding raw material in accordance with the method of Example 302.

¹H-NMR (400 MHz, DMSO-d₆) δ 0.96–1.32 (5H, m), 1.57–1.92 (10H, m), 2.41 (7/4H, m), 2.66 (1/4H, m), 2.84–3.00 (2H, m), 3.21–3.36 (2H, m), 3.75 (1/2H, d, J=6.4 Hz), 3.77 (3/2H, d, J=6.4 Hz), 3.94 (1/2H, m), 3.98 (3/2H, m), 5.23 (1/4H, m), 6.25–6.38 (7/4H, m), 6.42 (1/4H, d, J=11.6 Hz), 6.62 (3/4H, d, J=15.6 Hz), 6.93–7.10 (2H, m), 7.32 (1H, dd, J=10.0, 2.8 Hz), 7.50 (1/4H, dd, J=6.4, 2.0 Hz), 7.52 (3/4H, dd, J=6.4, 2.0 Hz), 7.65 (1/4H, dd, J=6.4, 2.0 Hz), 7.68 (3/4H, dd, J=6.4, 2.0 Hz).

Example 347

1-[(2-Oxo-1,2-dihydro-3-pyridinyl)methyl]-4-[(E)-2-[2-(cyclohexylmethyloxy)-4-fluorophenyl]-1-ethenyl]piperidine The title compound was obtained from a corresponding raw material in accordance with the method of Example 302.

¹H-NMR (400 MHz, DMSO-d₆) δ 0.96–1.34 (5H, m), 1.57–1.92 (10H, m), 2.38 (1H, m), 2.59 (1/5H, m), 2.78–3.02 (9/5H, m), 3.20–3.38 (2H, m), 3.79 (2/5H, d, J=6.4 Hz), 3.81 (8/5H, d, J=6.0 Hz), 3.94 (2/5H, br s), 3.99 (8/5H, br s), 5.56 (1/5H, m), 6.215–6.34 (9/5H, m), 6.38 (1/5H, d, J=11.6 Hz), 6.56 (4/5H, d, J=16.0 Hz), 6.67–6.79 (1H, m), 6.83–6.92 (1H, m), 7.20 (1/5H, t, J=7.2 Hz), 7.26 (1/5H, d, J=7.2 Hz), 7.42–7.56 (8/5H, m), 7.63–7.73 (1H, m).

Example 348

1-[(2-Oxo-1,2-dihydro-3-pyridinyl)methyl]-4-[(E)-2-[2-(cyclohexylmethyloxy)-6-fluorophenyl]-1-ethenyl]piperidine The title compound was obtained from a corresponding raw material in accordance with the method of Example 302.

¹H-NMR (400 MHz, DMSO-d₆) δ 1.04–1.34 (5H, m), 1.56–1.92 (10H, m), 2.39 (1H, m), 2.83–2.98 (2H, m), 3.24–3.36 (2H, m), 3.84 (2H, d, J=5.6 Hz), 3.97 (2H, br s), 6.29 (1H, t, J=6.4 Hz), 6.39–6.51 (2H, m), 7.78 (1H, dd, J=10.8, 8.4 Hz), 6.84 (1H, d, J=8.4 Hz), 7.19 (1H, dd, J=8.4, 6.8 Hz), 7.51 (1H, dd, J=6.4, 2.0 Hz), 7.68 (1H, br d, J=4.8 Hz).

Example 349

1-[(2-Oxo-1,2-dihydro-3-pyridinyl)methyl]-4-[2-[(2-cyclohexylmethyloxy)phenyl]-1-ethynyl]piperidine oxalate In 1,2-dichloroethane (3 ml) was dissolved 111 mg of 4-[2-[(2-cyclohexylmethyloxy)phenyl]-1-ethynyl] piperidine. To the mixture were added 50 mg of 2-oxo-1,2-dihydro-3-pyridinecarboxaldehyde, 0.03 ml of acetic acid and 94 mg of sodium triacetoxyborohydride, followed by stirring at room temperature for 5.5 hours. To the mixture were added 50 mg, of 2-oxo-1,2-dihydro-3-pyridinecarboxaldehyde, 0.03 ml of acetic acid and 94 mg of sodium triacetoxyborohydride, followed by stirring overnight. An aqueous saturated sodium bicarbonate was added to the reaction solution, and the mixture was extracted with ethyl acetate. The organic layer was washed with water and brine, and then dried over anhydrous magnesium sulfate. The solvent was evaporated, and the crude product was purified by NH-from silica gel column chromatography (ethyl acetate:methanol=30:1), to give 140 mg of a colorless oil. The oil was dissolved in ethanol, 33 mg of oxalic acid and ethyl acetate were added thereto, and the resulting precipitates were collected by filtration, to give 120 mg of the title compound as a white powder.

¹H-NMR (400 MHz, DMSO-d₆) δ 1.02–1.32 (5H, m), 1.60–1.87 (8H, m), 1.99–2.08 (2H, m), 2.86–3.04 (3H, m), 3.11–3.22 (2H, m), 3.82 (2H, d, J=6.0 Hz), 3.92 (2H, br s), 6.28 (1H, t, J=6.8 Hz), 6.88 (1H, dt, J=8.0, 0.8 Hz), 7.00 (1H, d, J=8.0 Hz), 7.25–7.33 (2H, m), 7.49 (1H, dd, J=7.6, 2.0 Hz), 7.66 (1H, dd, J=7.6, 2.0 Hz).

Example 350

1-[(2-Oxo-1,2-dihydro-3-pyridinyl)methyl]-4-[(E)-2-(2-phenoxyphenyl)-1-ethenyl]piperidine oxalate The title compound was obtained from a corresponding raw material in accordance with the method of Example 323.

¹H-NMR (400 MHz, DMSO-d₆) δ 1.56–1.78 (3H, m), 1.76–1.88 (1H, m), 2.10–2.50 (1H, m), 2.90–3.10 (2H, m), 3.22–3.40 (2H, m), 4.05 (2H, s), 6.29 (1H, t, J=6.4 Hz), 6.39 (0.3H, d, J=11.6 Hz), 6.56 (0.7H, d, J=16.4 Hz), 6.84–7.40 (8H, m), 7.54 (1H, dd, J=6.4, 2.0 Hz), 7.64–7.74 (1H, m).

Example 351

1-[(5-Cyano-2-oxo-1,2-dihydro-3-pyridinyl)methyl]-4-[(E)-2-(2-fluorophenyl)-1-ethenyl]piperidine To acetonitrile (10 ml) were added 214 mg of 1-[(5-cyano-2-methoxy-3-pyridinyl)methyl]-4-[(E)-2-(2-fluorophenyl)-1-ethenyl]piperidine, 137 mg of sodium iodide and 0.1 ml of chlorotrimethylsilane, followed by stirring at room temperature. After 5 hours, 685 mg of sodium iodide and 0.5 ml of chlorotrimethylsilane were added thereto, followed by stirring at room temperature for 20 minutes. Water was added to the reaction solution, and the mixture was extracted with ethyl acetate. The organic layer was washed with an aqueous sodium carbonate, an aqueous sodium thiosulfate and brine, and then dried over anhydrous magnesium sulfate. The solvent was evaporated, and the crude product was suspended in an aqueous sodium carbonate, followed by stirring at room temperature. The crystals were collected by filtration, to give 185 mg of the title compound as a slight yellow powder.

¹H-NMR (400 MHz, DMSO-d₆) δ 1.41–1.54 (2H, m), 1.68–1.74 (2H, m), 2.08 (2H, br t, J=10.8 Hz), 2.17 (1H, m), 2.85 (2H, br d, J=11.6 Hz), 3.29 (2H, s), 6.38 (1H, dd, J=16.0, 6.8 Hz), 6.50 (1H, d, J=16.0 Hz), 7.12–7.21 (2H, m), 7.25 (1H, m), 7.53 (1H, d, J=2.4 Hz), 7.58 (1H, dt, J=8.4, 1.6 Hz), 8.19 (1H, d, J=2.4 Hz).

Example 352

1-[(2-Oxo-1,2-dihydro-3-pyridinyl)methyl]-4-[2-(cyclohexylmethyloxy)benzyloxy]piperidine oxalate The title compound was obtained from a corresponding raw material in accordance with the method of Example 302.

¹H-NMR (400 MHz, DMSO-d₆) δ 1.00–1.32 (5H, m), 1.62–2.07 (10H, m), 3.01 (2H, m), 3.17 (2H, m), 3.66 (1H, m), 3.79 (2H, d, J=6.4 Hz), 4.00 (2H, s), 4.49 (2H, s), 6.29 (1H, t, J=6.4 Hz), 6.91 (1H, t, J=7.6 Hz), 6.95 (1H, d, J=7.6 Hz), 7.24 (1H, dt, J=7.6, 1.2, Hz), 7.32 (1H, dd, J=7.6, 1.2 Hz), 7.52 (1H, dd, J=6.4, 2.0 Hz), 7.68 (1H, dd, J=6.4, 2.0 Hz).

Example 353

1-[(2-Oxo-1,2-dihydro-3-pyridinyl)methyl]-4-[2-(benzyloxy)benzyloxy]piperidine oxalate The title compound was obtained from a corresponding raw material in accordance with the method of Example 349.

$^1$H-NMR (400 MHz, DMSO-d$_6$) δ 1.72–1.86 (2H, m), 1.90–2.02 (2H, m), 2.85–2.98 (2H, m), 3.05–3.17 (2H, m), 3.64 (1H, m), 3.93 (2H, s), 4.53 (2H, s), 5.14 (2H, s), 6.29 (1H, t, J=6.8 Hz), 6.95 (1H, dt, J=7.6, 1.2 Hz), 7.17 (1H, d, J=7.6 Hz), 7.26–7.42 (5H, m), 7.43–7.48 (2H, m), 7.51 (1H, dd, J=6.8, 2.0 Hz), 7.65 (1H, dd, J=6.8, 2.0 Hz).

Example 354

1-[(2-Oxo-1,2-dihydro-3-pyridinyl)methyl]-4-(2-chloro-6-fluorobenzyloxy)piperidine The title compound was obtained from a corresponding raw material in accordance with the method of Example 318.

$^1$H-NMR (400 MHz, DMSO-d$_6$) δ 1.40–1.55 (2H, m), 1.78–1.90 (2H, m), 2.10 (2H, br t, J=9.2 Hz), 2.58–2.70 (2H, m), 3.22 (2H, s), 3.33–3.45 (1H, m), 4.56 (2H, d, J=2.0 Hz), 6.15 (1H, t, J=6.4 Hz), 7.18–7.28 (2H, m), 7.30–7.46 (3H, m), 11.50 (1H, s).

Example 355

1-[(5-Chloro-2-oxo-1,2-dihydro-3-pyridinyl)methyl]-4-(2-chloro-6-fluorobenzyloxy)piperidine The title compound was obtained from a corresponding raw material in accordance with the method of Example 318.

$^1$H-NMR (400 MHz, DMSO-d$_6$) δ 1.42–1.55 (2H, m), 1.80–1.90 (2H, m), 2.14 (2H, br t, J=9.2 Hz), 2.58–2.70 (2H, m), 3.25 (2H, s), 3.30–3.50 (1H, m), 4.56 (2H, d, J=2.4 Hz), 7.20–7.26 (1H, m), 7.31–7.37 (2H, m), 7.37–7.44 (1H, m), 7.50 (1H, d, J=2.8 Hz).

Example 356

1-[(2-Oxo-1,2-dihydro-3-pyridinyl)methyl]-4-(2,6-difluorobenzyloxy)piperidine

The title compound was obtained from a corresponding raw material in accordance with the method of Example 318.

$^1$H-NMR (400 MHz, DMSO-d$_6$) δ 1.38–1.52 (2H, m), 1.78–1.90 (2H, m), 2.08 (2H, br t, J=9.6 Hz), 2.56–2.70 (2H, m), 3.21 (2H, s), 3.30–3.43 (1H, m), 4.50 (2H, s), 6.14 (1H, t, J=6.4 Hz), 7.09 (2H, t, J=8.0 Hz), 7.23 (1H, dd, J=6.4, 1.6 Hz), 7.35 (1H, dd, J=6.4, 1.2 Hz), 7.36–7.48 (1H, m).

Example 357

1-[(5-Chloro-2-oxo-1,2-dihydro-3-pyridinyl)methyl]-4-(2,6-difluorobenzyloxy)piperidine The title compound was obtained from a corresponding raw material in accordance with the method of Example 318.

$^1$H-NMR (400 MHz, DMSO-d$_6$) δ 1.40–1.53 (2H, m), 1.78–1.90 (2H, br t, J=9.2 Hz), 2.56–2.70 (2H, m), 3.24 (2H, s), 3.30–3.48 (1H, m), 4.50 (2H, s), 7.09 (2H, t, J=8.0 Hz), 7.35 (1H, d, J=2.0 Hz), 7.38–7.48 (1H, m), 7.50 (1H, d, J=2.8 Hz).

Example 358

1-[(2-Oxo-1,2-dihydro-3-pyridinyl)methyl]-4-(2-chlorobenzyloxy)piperidine

The title compound was obtained from a corresponding raw material in accordance with the method of Example 318.

$^1$H-NMR (400 MHz, DMSO-d$_6$) δ 1.45–1.60 (2H, m), 1.82–1.93 (2H, bt, d, J=10.0 Hz), 2.12 (2H, br t, J=10.0 Hz), 2.60–2.73 (2H, m), 3.23 (2H, s), 3.38–3.50 (1H, m), 4.54 (2H, s), 6.15 (1H, t, J=6.4 Hz), 7.24 (1H, d, J=6.4 Hz), 7.26–7.44 (4H, m), 7.50 (1H, d, J=7.6 Hz), 11.50 (1H, s).

Example 359

1-[(5-Chloro-2-oxo-1,2-dihydro-3-pyridinyl)methyl]-4-(2-chlorobenzyloxy)piperidine The above compound was obtained from a corresponding raw material in accordance with the method of Example 318.

$^1$H-NMR (400 MHz, DMSO-d$_6$) δ 1.47–1.62 (2H, m), 1.82–1.94 (2H, m), 2.16 (2H, br t, J=9.6 Hz), 2.60–2.75 (2H, m), 3.27 (2H, s), 3.46 (1H, m), 4.54 (2H, s), 7.26–7.45 (4H, m), 7.48–7.56 (2H, m).

Example 360

1-[(2-Oxo-1,2-dihydro-3-pyridinyl)methyl]-4-(2-fluorobenzyloxy)piperidine oxalate The above compound was obtained from a corresponding raw material in accordance with the method of Example 323.

$^1$H-NMR (400 MHz, DMSO-d$_6$) δ 1.70–1.90 (2H, m), 1.90–2.10 (2H, m), 2.90–3.10 (2H, m), 3.00–3.20 (2H, m), 3.60–3.70 (1H, m), 3.97 (2H, s), 4.53 (2H, s), 6.26 (1H, t, J=6.4 Hz), 7.10–7.22 (2H, m), 7.30–7.38 (1H, m), 7.45 (1H, t, J=6.8 Hz), 7.49 (1H, d, J=4.8 Hz), 7.67 (1H, d, J=5.2 Hz).

Example 361

1-[(5-Chloro-2-oxo-1,2-dihydro-3-pyridinyl)methyl]-4-(2-fluorobenzyloxy)piperidine The above compound was obtained from a corresponding raw material in accordance with the method of Example 323.

$^1$-NMR (400 MHz, DMSO-d$_6$) δ 1.70–1.85 (2H, m), 1.90–2.05 (2H, m), 2.77–3.00 (2H, m), 3.05–3.20 (2H, m), 3.60–3.70 (1H, m), 3.92 (2H, s), 4.54 (2H, s), 7.14–7.22 (2H, m), 7.31–7.38 (1H, m), 7.45 (1H, dt, J=7.6, 2.0 Hz), 7.73 (1H, d, J=3.2 Hz), 7.74 (1H, d, J=2.8 Hz).

Example 362

1-[(2-Oxo-1,2-dihydro-3-pyridinyl)methyl]-4-[(2-methoxyphenoxy)methyl]piperidine The title compound was obtained from a corresponding raw material in accordance with the method of Example 285.

$^1$H-NMR (400 MHz, CDCl$_3$) δ 1.38–1.52 (2H, m), 1.85–2.00 (3H, m), 2.15 (2H, m), 2.98 (2H, br d, J=11.6 Hz), 3.50 (2H s), 3.86 (3H, s), 3.88 (2H, s), 6.33 (1H, d, J=6.8 Hz), 6.86–6.94 (4H, m), 7.36 (1H, br dd, J=6.0, 1.2 Hz), 7.57 (1H, br d, J=6.0 Hz).

Example 363

1-[(5-Chloro-2-oxo-1,2-dihydro-3-pyridinyl)methyl]-4-[2-(cyclohexylmethyloxy)phenoxymethyl]piperidine The title compound was obtained from a corresponding raw material in accordance with the method of Example 285.

¹H-NMR (400 MHz, CDCl₃) δ 1.00–1.36 (5H, m), 1.41–1.54 (2H, m), 1.65–2.00 (7H, m), 2.16–2.26 (2H, m), 2.99 (2H, br d, J=11.6 Hz), 3.58 (2H, s), 3.78 (2H, d, J=6.0 Hz), 3.85 (2H, d, J=6.0 Hz), 6.86–6.94 (4H, m), 7.39 (1H, d, J=2.4 Hz), 7.80 (1H, br s).

Example 364

1-[(2-Oxo-1,2-dihydro-3-pyridinyl)methyl]-4-[2-(cyclohexylmethyloxy)phenoxymethyl]piperidine oxalate The above compound was obtained from a corresponding raw material in accordance with the method of Example 302.

¹H-NMR (400 MHz, DMSO-d₆) δ 0.98–1.12 (2H, m), 1.12–1.30 (3H, m), 1.46–1.84 (8H, m), 1.88–2.08 (3H, m), 3.12 (2H, m), 3.33 (2H, m), 3.75 (2H, d, J=6.4 Hz), 3.83 (2H, m), 3.99 (2H, m), 6.30 (1H, t, J=6.8 Hz), 6.82–6.91 (2H, m), 6.92–7.00 (2H, m), 7.52 (1H, br d, J=5.2 Hz), 7.68 (1H, br d, J=6.4 Hz).

Example 365

1-[(2-oxo-1,2-dihydro-3-pyridinyl)methyl]-4-[[2-(cyclohexylethyl)phenoxy]methyl]piperidine oxalate The title compound was obtained from a corresponding raw material in accordance with the method of Example 302.

¹H-NMR (400 MHz, DMSO-d₆) δ 0.84–0.96 (2H, m), 1.06–1.27 (4H, m), 1.35–1.43 (2H, m), 1.50–1.77 (7H, m), 1.86–1.96 (2H, m), 2.00 (1H, m), 2.55–2.58 (2H, m), 2.88 (2H, m), 3.04 (2H, m), 3.83 (2H, m), 3.95 (2H, s), 6.29 (1H, t, J=6.8 Hz), 6.84 (1H, dt, J=7.6, 0.8 Hz), 6.91 (1H, d, J=7.6 Hz), 7.08–7.16 (2H, m), 7.50 (1H, br d, J=5.2 Hz), 7.66 (1H, br d, J=4.8 Hz).

Example 366

1-[(2-Oxo-1,2-dihydro-3-pyridinyl)methyl]-4-[2-(benzyloxy)phenoxymethyl]piperidine oxalate The above compound was obtained from a corresponding raw material in accordance with the method of Example 349.

¹H-NMR (400 MHz, DMSO-d₆) δ 1.40–1.65 (2H, m), 1.86–1.96 (2H, m), 2.02 (1H, m), 2.85–2.96 (2H, m), 3.26–3.36 (2H, m), 3.88 (2H, d, J=6.4 Hz), 3.97 (2H, s), 5.10 (2H, s), 6.29 (1H, t, J=6.4 Hz), 6.84–6.93 (2H, m), 6.97–7.06 (2H, m), 7.28–7.47 (5H, m), 7.51 (1H, dd, J=6.4, 2.0 Hz), 7.67 (1H, dd, J=6.8, 2.0 Hz).

Example 367

1-[(2-Oxo-1,2-dihydro-3-pyridinyl)methyl]-4-[(2-fluorophenoxy)methyl]piperidine

The title compound was obtained from a corresponding raw material in accordance with the method of Example 318.

¹H-NMR (400 MHz, DMSO-d₆) δ 1.24–1.38 (2H, m), 1.72 (3H, br d, J=10 Hz), 1.98 (2H, br t, J=10.8 Hz), 2.83 (2H, br d, J=11.2 Hz), 3.25 (2H, s), 3.88 (2H, d, J=5.6 Hz), 6.15 (1H, t, J=6.4 Hz), 6.86–6.94 (1H, m), 7.04–7.20 (3H, m), 7.24 (1H, d, J=6.4 Hz), 7.37 (1H, d, J=6.8 Hz), 11.50 (1H, s).

Example 368

1-[(5-Chloro-2-oxo-1,2-dihydro-3-pyridinyl)methyl]-4-[(2-fluorophenoxy)methyl]piperidine The title compound was obtained from a corresponding raw material in accordance with the method of Example 318.

¹H-NMR (400 MHz, DMSO-d₆) δ 1.24–1.40 (2H, m), 1.74 (3H, br d, J=9.6 Hz), 2.01 (2H, br t, J=10.8 Hz), 2.82 (2H, br d, J=10.8 Hz), 3.27 (2H, s), 3.86 (2H, d, J=6.0 Hz), 6.86–6.93 (1H, m), 7.05–7.20 (3H, m), 7.36 (1H, d, J=2.8 Hz), 7.51 (1H, d, J=3.2 Hz).

Example 369

1-[(2-Oxo-1,2-dihydro-3-pyridinyl)methyl]-4-[(2,4-difluorophenoxy)methyl]piperidine The title compound was obtained from a corresponding raw material in accordance with the method of Example 318.

¹H-NMR (400 MHz, DMSO-d₆) δ 1.22–1.38 (2H, m), 1.71 (3H, br d, J=10.8 Hz), 1.96 (2H, br t, J=10.8 Hz), 2.82 (2H, br d, J=11.2 Hz), 3.23 (2H, s), 3.86 (2H, d, J=5.6 Hz), 6.15 (1H, t, J=6.4 Hz), 6.93–7.02 (1H, m), 7.12–7.20 (1H, m), 7.20–7.28 (1H, m), 7.36 (1H, dd, J=6.4, 1.2 Hz), 11.41 (1H, s).

Example 370

1-[(5-Chloro-2-oxo-1,2-dihydro-3-pyridinyl)methyl]-4-[(2,4-difluorophenoxy)methyl]piperidine The above compound was obtained from a corresponding raw material in accordance with the method of Example 318.

¹H-NMR (400 MHz, DMSO-d₆) δ 1.24–1.38 (2H, m), 1.72 (3H, br d, J=10.4 Hz), 2.01 (2H, br t, J=10.4 Hz), 2.82 (2H, br d, J=11.6 Hz), 3.27 (2H, s), 3.87 (2H, d, J=6.0 Hz), 6.93–7.01 (1H, m), 7.13–7.21 (1H, m), 7.21–7.28 (1H, m), 7.36 (1H, d, J=2.8 Hz), 7.50 (1H, d, J=2.8 Hz).

Example 371

1-[(2-Oxo-1,2-dihydro-3-pyridinyl)methyl]-4-[(2,5-difluorophenoxy)methyl]piperidine The title compound was obtained from a corresponding raw material in accordance with the method of Example 318.

¹H-NMR (400 MHz, DMSO-d₆) δ 1.20–1.38 (2H, m), 1.65–1.83 (1H, m), 1.71 (2H, br d, J=10.8 Hz), 1.97 (2H, br t, J=11.2 Hz), 2.82 (2H, br d, J=11.2 Hz), 3.24 (2H, s), 3.90 (2H, d, J=6.0 Hz), 6.15 (1H, t, J=6.4 Hz), 6.68–6.76 (1H, m), 7.06–7.14 (1H, m), 7.17–7.28 (2H, m), 7.36 (1H, dd, J=6.4, 1.2 Hz), 11.51 (1H, m).

Example 372

1-[(5-Chloro-2-oxo-1,2-dihydro-3-pyridinyl)methyl]-4-[(2,5-difluorophenoxy)methyl]piperidine The above compound was obtained from a corresponding raw material in accordance with the method of Example 318.

¹H-NMR (400 MHz, DMSO-d₆) δ 1.24–1.39 (2H, m), 1.67–1.80 (1H, m), 1.73 (2H, br d, J=11.2 Hz), 1.95–2.08 (2H, m), 2.82 (2H, br d, J=11.2 Hz), 3.27 (2H, s), 3.91 (2H, d, J=6.0 Hz), 6.68–6.76 (1H, m), 7.06–7.13 (1H, m), 7.18–7.26 (1H, m), 7.36 (1H, d, J=2.8 Hz), 7.51 (1H, d, J=2.8 Hz).

Example 373

1-[(2-Oxo-1,2-dihydro-3-pyridinyl)methyl]-4-[(2,6-difluorophenoxy)methyl]piperidine The above compound was obtained from a corresponding raw material in accordance with the method of Example 318.

¹H-NMR (400 MHz, DMSO-d₆) δ 1.20–1.38 (2H, m), 1.60–1.80 (1H, m), 1.72 (2H, br d, J=12.4 Hz), 1.96 (2H, br t, J=11.2 Hz), 2.81 (2H, br d, J=11.2 Hz), 3.23 (2H, s), 3.93 (2H, d, J=6.0 Hz), 6.15 (1H, t, J=6.8 Hz), 7.04–7.18 (3H, m), 7.23 (1H, d, J=6.4 Hz), 7.36 (1H, d, J=6.4 Hz), 11.49 (1H, s).

Example 374

1-[(5-Chloro-2-oxo-1,2-dihydro-3-pyridinyl)methyl]-4-[(2,6-difluorophenoxy)methyl]piperidine The title compound was obtained from a corresponding raw material in accordance with the method of Example 318.

$^1$H-NMR (400 MHz, DMSO-$d_6$) δ 1.22–1.38 (2H, m), 1.60–1.80 (1H, m), 1.73 (2H, br d, J=12.8 Hz), 1.95–2.05 (2H, m), 2.81 (2H, br d, J=11.2 Hz), 3.26 (2H, s), 3.94 (2H, d, J=6.0 Hz), 7.04–7.16 (3H, m), 7.35 (1H, d, J=2.0 Hz), 7.50 (1H, d, J=2.8 Hz).

Example 375

1-[(5-Chloro-2-oxo-1,2-dihydro-3-pyridinyl)methyl]-4-[(2-methoxyphenoxy)methyl]piperidine The title compound was obtained from a corresponding raw material in accordance with the method of Example 318.

$^1$H-NMR (400 MHz, DMSO-$d_6$) δ 1.22–1.36 (2H, m), 1.66–1.78 (3H, m), 2.01 (2H, br t, J=10.4 Hz), 2.82 (2H, br d, J=11.6 Hz), 3.27 (2H, s), 3.72 (3H, s), 3.78 (2H, d, J=6.0 Hz), 6.80–6.88 (2H, m,), 6.88–6.95 (2H, m), 7.36 (1H, d, J=2.8 Hz), 7.51 (1H, d, J=3.2 Hz).

Example 376

1-[(2-Oxo-1,2-dihydro-3-pyridinyl)methyl]-4-[(2-chlorophenoxy)methyl]piperidine

The title compound was obtained from a corresponding raw material in accordance with the method of Example 318.

$^1$H-NMR (400 MHz, DMSO-$d_6$) δ 1.26–1.40 (2H, m), 1.74 (3H, br d, J=10.8 Hz), 1.98 (2H, br t, J=11.2 Hz), 2.83 (2H, br d, J=11.2 Hz), 3.24 (2H, s), 3.89 (2H, d, J=5.6 Hz), 6.16 (1H, t, J=6.8 Hz), 6.91 (1H, t, J=7.6 Hz), 7.11 (1H, d, J=8.0 Hz), 7.20–7.30 (2H, m), 7.34–7.41 (2H, m), 11.5 (1H, br s).

Example 377

1-[(5-Chloro-2-oxo-1,2-dihydro-3-pyridinyl)methyl]-4-[(2-fluoro-6-methoxyphenoxy)methyl]piperidine The title compound was obtained from a corresponding raw material in accordance with the method of Example 318.

$^1$H-NMR (400 MHz, DMSO-$d_6$) δ 1.22–1.36 (2H, m), 1.58–1.73 (1H, m), 1.74 (2H, br d, J=12 Hz), 1.94–2.04 (2H, m), 2.80 (2H, br d, J=11.6 Hz), 3.26 (2H, s), 3.79 (3H, s), 3.79 (2H, d, J=6.0 Hz), 6.80 (1H, t, J=9.6 Hz), 6.85 (1H, d, J=7.6 Hz), 6.96–7.05 (2H, m), 7.36 (1H, d, J=2.0 Hz), 7.50 (1H, d, J=2.8 Hz).

Example 378

1-[(5-Chloro-2-oxo-1,2-dihydro-3-pyridinyl)methyl]-4-[(2,3-difluorophenoxy)methyl]piperidine The title compound was obtained from a corresponding raw material in accordance with the method of Example 318.

$^1$H-NMR (400 MHz, DMSO-$d_6$) δ 1.26–1.38 (2H, m), 1.73 (3H, brd, J=12.8 Hz), 1.96–2.10 (2H, m), 2.83 (2H, br d, J=11.6 Hz), 3.28 (2H, s), 3.93 (2H, d, J=6.4 Hz), 6.90–7.04 (2H, m), 7.06–7.14 (1H, m), 7.36 (1H, d, J=2.8 Hz), 7.51 (1H, d, J=2.4 Hz).

Example 379

1-[(4-Oxo-1,4-dihydro-3-pyridinyl)methyl]-4-[2-[2,3-(methylenedioxy)phenyl]ethyl]piperidine 259 mg of 1-[(4-methoxy-3-pyridinyl)methyl]-4-[2-(2-methylphenyl)ethyl]piperidine was dissolved in 5 ml of ethanol. To the mixture was added 1.91 ml of a hydrogen chloride-ethyl acetate solution, followed by heating under reflux overnight. The solvent was evaporated, and to the residue was added a 2N hydrochloric acid (15 ml), followed by heating under reflux for further 7 hours. A sodium carbonate aqueous solution was added to the reaction solution, and the mixture was extracted with chloroform. The extract was dried over anhydrous magnesium sulfate, and then the solvent was evaporated. The crude product was purified by NH-silica gel column chromatography (n-hexane:ethyl acetate=2:1), to give 42 mg of the title compound as a white powder.

$^1$H-NMR (400 MHz, CDCl$_3$) δ 1.24–1.44 (3H, m), 1.56–1.64 (2H, m), 1.78–1.88 (2H, m), 2.10–2.20 (2H, m), 2.56–2.64 (2H, m), 3.00 (2H, br d, J=11.6 Hz), 3.73 (2H, s), 5.93 (2H, s), 6.64 (1H, dd, J=7.6, 1.6 Hz), 6.69 (1H, dd, J=7.6, 1.6 Hz), 6.69 (1H, d, J=5.6 Hz), 6.76 (1H, t, J=7.6 Hz), 8.10 (1H, s), 8.25 (1H, d, J=5.6 Hz).

Example 380

1-[(2-Oxo-1,2-dihydro-3-quinolinyl)methyl]-4-[2-[2,3-(methylenedioxy)phenyl]ethyl]piperidine In 50 ml of tetrahydrofuran were dissolved 0.24 g of 2-oxo-1,2-dihydro-3-quinolinecarboxaldehyde and 0.3 g of 4-[2-[2,3-(methylenedioxy)phenyl]ethyl]piperidine. To the mixture were added 0.5 ml of acetic acid and 0.42 g of sodium triacetoxyborohydride were added thereto, followed by stirring at room temperature for 12 hours. An aqueous saturated sodium bicarbonate aqueous solution was added to the reaction solution, and then the mixture was extracted with ethyl acetate. The organic layer was washed with water and brine, and then dried over anhydrous magnesium sulfate. The solvent was evaporated, and the resulting solid was collected by filtration, to give 130 mg of the title compound as a light brown solid.

$^1$H-NMR (400 MHz, DMSO-$d_6$) δ 1.18–1.28 (3H, m), 1.68 (2H, br d, J=7.6 Hz), 1.90–2.00 (2H, m), 2.53 (2H, br t, J=8.0 Hz), 2.84 (2H, br d, J=10.0 Hz), 3.30 (2H, s), 5.95 (2H, s), 6.66–6.77 (3H, m), 7.14 (1H, t, J=7.6 Hz), 7.27 (1H, d, J=7.6 Hz), 7.43 (1H, t, J=7.6 Hz), 7.66 (1H, d, J=7.6 Hz), 7.80 (1H, s), 11.74 (1H, s).

Example 381

1-[(2-Oxo-1,2-dihydro-3-quinolinyl)methyl]-4-[2-(3-(phenylphenyl)ethyl]piperidine oxalate The title compound was obtained from a corresponding raw material in accordance with the method of Example 349.

$^1$H-NMR (400 MHz, DMSO-$d_6$) δ 1.30–1.70 (5H, m), 1.86 (2H, br d, J=10.8 Hz), 2.54–2.76 (2H, m), 2.88 (2H, br s), 3.33 (2H, br d, J=10.8 Hz), 4.07 (2H, s), 7.14–7.26 (2H, m), 7.30–7.40 (3H, m), 7.40–7.50 (4H, m), 7.55 (1H, t, J=7.6 Hz), 7.60–7.70 (3H, m), 8.14 (1H, s).

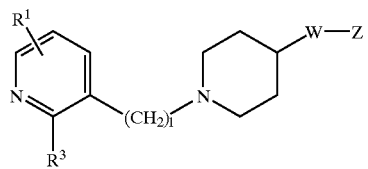
Example 1–86
| Ex.No. | R¹ | R³ | l | —W— | -Z |
|---|---|---|---|---|---|
| 1 | H | —OCH₃ | 1 | —(CH₂)₂— | 2-methylphenyl-SO₂CH₃ |
| 2 | H | —OCH₃ | 1 | —(CH₂)₂— | benzo[1,3]dioxol-5-yl |
| 3 | H | —OCH₃ | 1 | —(CH₂)₂— | 2-methylphenyl |
| 4 | H | —OCH₃ | 1 | —(CH₂)₂— | 2-methylphenyl-OH |
| 5 | H | —OCH₃ | 1 | —(CH₂)₂— | 3-fluoro-phenyl |
| 6 | H | —OCH₃ | 1 | —(CH₂)₂— | 2-methylphenyl-CF₃ |
| 7 | H | —OCH₃ | 1 | —(CH₂)₂— | 2-methylphenyl-pyrazol-1-yl |
| 8 | H | —OCH₃ | 1 | —(CH₂)₂— | 2-methylphenyl-(4-acetyl-piperazin-1-yl) |
| 9 | H | —OCH₃ | 1 | —(CH₂)₂— | methyl-benzo[1,3]dioxol-SO₂CH₃ |
| 10 | H | —OCH₃ | 1 | —(CH₂)₂— | 5-methyl-thiophen-2-yl |

-continued

| | | | | |
|---|---|---|---|---|
| 11 | H | —OCH₃ | 1 —(CH₂)₂— | 2-methyl-3-methoxythiophene |
| 12 | H | —OCH₃ | 1 —(CH₂)₂— | 2-methyl-3-cyanothiophene |
| 13 | H | —OCH₃ | 1 —(CH₂)₂— | 2-methyl-3-phenylthiophene |
| 14 | H | —OCH₃ | 1 —(CH₂)₂— | 2-methylthiophene |
| 15 | H | —OCH₃ | 1 —(CH₂)₂— | 3-methyl-4-(methylsulfonyl)thiophene |
| 16 | H | —OCH₃ | 1 —(CH₂)₂— | 2-methylbenzothiophene |
| 17 | H | —OCH₃ | 1 —(CH₂)₂— | 3-methyl-2-(methylsulfonyl)pyridine |
| 18 | H | —OCH₃ | 1 —(CH₂)₂— | 3-methyl-2-butylpyridine |
| 19 | H | —OCH₃ | 1 —(CH₂)₂— | 3-methylpyridine |
| 20 | H | —OCH₃ | 1 —(CH₂)₂— | 3-methyl-2-phenoxypyridine |
| 21 | H | —OCH₃ | 1 —(CH₂)₂— | 2-methyl-5-methoxypyridine |
| 22 | H | —OCH₃ | 1 —(CH₂)₂— | 3-methyl-2-(4-methoxyphenyl)pyridine |

-continued
| | | | | |
|---|---|---|---|---|
| 23 | H | —OCH₃ | 1 —(CH₂)₂— | 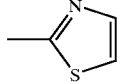 |
| 24 | H | —OCH₃ | 1 —(CH₂)₂— | 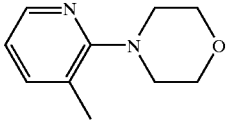 |
| 25 | H | —OCH₃ | 1 —(CH₂)₂— | 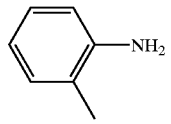 |
| 26 | H | —OCH₃ | 1 —(CH₂)₂— | 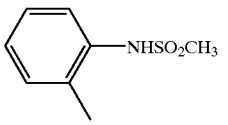 |
| 27 | H | —OCH₃ | 1 —(CH₂)₂— | 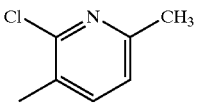 |
| 28 | H | —OCH₃ | 1 —(CH₂)₂— | 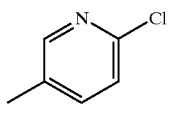 |
| 29 | H | —OCH₃ | 1 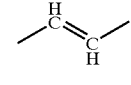 | 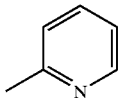 |
| 30 | H | —OCH₃ | 1 —(CH₂)₂— | 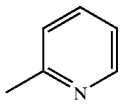 |
| 31 | H | —OCH₃ | 1 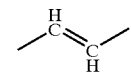 | 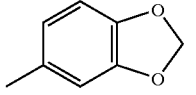 |
| 32 | H | —OCH₃ | 1 —(CH₂)₂— | 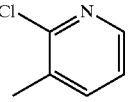 |
| 33 | H | —OCH₃ | 1 —(CH₂)₂— | 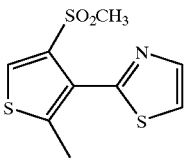 |
| 34 | H | —OCH₃ | 1 —(CH₂)₂— | 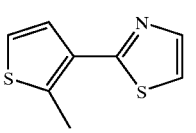 |

-continued
| | | | | | |
|---|---|---|---|---|---|
| 35 | H | —OCH₃ | 1 | —(CH₂)₂— | 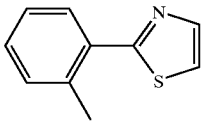 |
| 36 | H | —OCH₃ | 1 | —(CH₂)₂— | 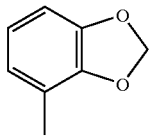 |
| 37 | H | —OCH₃ | 1 | —(CH₂)₂— | 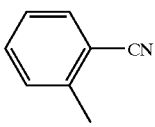 |
| 38 | H | —OCH₃ | 1 | —(CH₂)₂— | 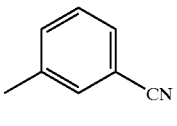 |
| 39 | H | —OCH₃ | 1 | —(CH₂)₂— | 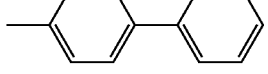 |
| 40 | H | —OCH₃ | 1 | —(CH₂)₂— | 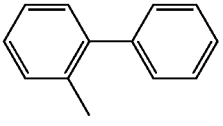 |
| 41 | H | —OCH₃ | 1 | —(CH₂)₂— | 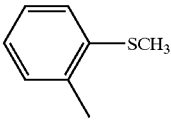 |
| 42 | H | —OCH₃ | 1 | —(CH₂)₂— | 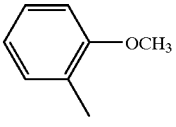 |
| 43 | H | —OCH₃ | 1 | —(CH₂)₂— | 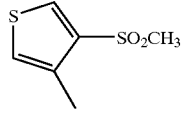 |
| 44 | H | —OCH₃ | 1 | —C≡C— | 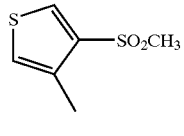 |
| 45 | H | —OCH₃ | 1 | —(CH₂)₂— | 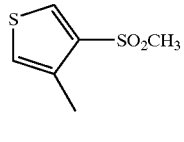 |

-continued

| | | | | | |
|---|---|---|---|---|---|
| 46 | H | —OCH₃ | 1 | —(CH₂)₂— | 5-methyl-benzo[1,3]dioxol-4-yl methyl sulfone |
| 47 | H | —OCH₃ | 1 | —(CH₂)₂— | 3-methyl-2-oxo-pyridin-1-yl |
| 48 | H | —OCH₃ | 1 | —(CH₂)₂— | 3-methyl-2-(thiazol-2-yl)pyridine |
| 49 | H | —OCH₃ | 1 | —(CH₂)₂— | 1-(3-methylpyridin-2-yl)piperidin-4-ol |
| 50 | H | —OCH₃ | 1 | —(CH₂)₂— | 3-(3-methylpyridin-2-yloxy)propanenitrile |
| 51 | H | —OCH₃ | 1 | —(CH₂)₂— | 1-(2-fluorobenzyl)-3-methylpyridin-2(1H)-one |
| 52 | H | —O—CH₂—C₆H₅ | 1 | —(CH₂)₂— | 4-methylbenzo[1,3]dioxole |
| 53 | H | —OCH₃ | 1 | —CH₂—CH(OH)— | 2-methylthiophene |
| 54 | H | —OCH₃ | 1 | —CH₂—C(=O)— | 2-methylthiophene |
| 55 | H | —OCH₃ | 1 | —CH₂—C(=O)— | —N(CH₃)—O—CH₃ |
| 56 | H | —OCH₃ | 1 | —CH₂—C(=O)— | 2-methylthiophene |
| 57 | H | —OCH₃ | 1 | —CH₂—CH(OH)— | 3-methylpyridine |

-continued

| | | | | | |
|---|---|---|---|---|---|
| 58 | H | —OCH₃ | 1 | —CH₂—C(=O)— | phenyl (o-methyl) |
| 59 | H | —OCH₃ | 1 | —CH₂—CH(OH)— | 2-chlorophenyl (o-methyl) |
| 60 | H | —OCH₃ | 1 | —CH₂—C(=O)— | 2-chlorophenyl (o-methyl) |
| 61 | H | —OCH₃ | 1 | —CH₂—CH(OH)— | 2-chloro-3-methylpyridyl |
| 62 | H | —OCH₃ | 1 | —CH₂—C(=O)— | 2-chloro-3-methylpyridyl |
| 63 | H | —OCH₃ | 1 | —CH₂—C(=O)— | 2-(NHCOCF₃)-phenyl (o-methyl) |
| 64 | H | —OCH₃ | 1 | —CH₂—C(=O)— | 2-NH₂-phenyl (o-methyl) |
| 65 | H | —OCH₃ | 1 | —CH₂—C(=O)— | 2-(NHSO₂CH₃)-phenyl (o-methyl) |
| 66 | H | —OCH₃ | 1 | —CH₂—C(=O)— | 2-(SO₂CH₃)-phenyl (o-methyl) |
| 67 | H | —OCH₃ | 1 | —CH₂—C(=O)— | 2-OCH₃-phenyl (o-methyl) |
| 68 | H | —OCH₃ | 1 | —CH₂—C(=O)— | 2-(O—CH₂-cyclopropyl)-phenyl (o-methyl) |
| 69 | H | —OCH₃ | 1 | —CH₂—C(=O)— | 2-CF₃-phenyl (o-methyl) |

-continued
| | | | | |
|---|---|---|---|---|
| 70 | H | —OCH₃ | 1 —CH₂—C(=O)— | 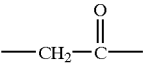 |
| 71 | H | —OCH₃ | 1 —CH₂—C(=O)— | 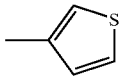 |
| 72 | H | —OCH₃ | 1 —CH₂—C(=O)— | 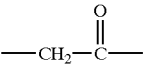 |
| 73 | H | —OCH₃ | 1 —CH₂—C(=O)— | 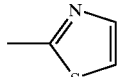 |
| 74 | H | —OCH₃ | 1 —CH₂—C(=O)— | 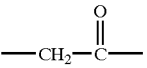 |
| 75 | H | —OCH₃ | 1 —CH₂—C(=O)— | 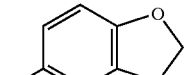 |
| 76 | H | —OCH₃ | 1 —(CH₂)₃— |  |
| 77 | H | —OCH₃ | 1 —(CH₂)₃— | 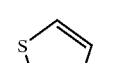 |
| 78 | H | —OCH₃ | 1 —CH₂— |  |
| 79 | H | —OCH₃ | 1 —(CH₂)₄— | 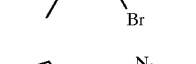 |
| 80 | H | —OCH₃ | 1 —C(=O)— |  |
| 81 | H | —OCH₃ | 1 —C(=O)— | —NH₂ |
| 82 | H | —OCH₃ | 1 —C(=O)— | —NH—CH₂— 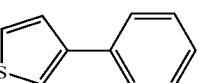 |

-continued
| | | | | | |
|---|---|---|---|---|---|
| 83 | H | —OCH₃ | 1 | —CH₂—O— | 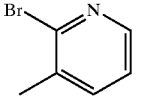 |
| 84 | H | —OCH₃ | 1 | —CH₂—O— | 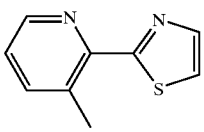 |
| 85 | H | —OCH₃ | 1 | —CH₂—CH(CN)— | 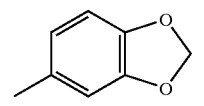 |
| 86 | H | —OCH₃ | 1 | —CH₂—CH(CN)— | 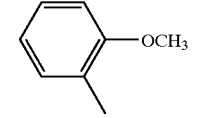 |
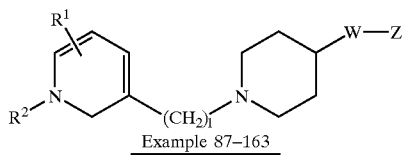
Example 87–163
| Ex.No. | R¹ | R² | I | —W— | -Z |
|---|---|---|---|---|---|
| 87 | H | H | 1 | —(CH₂)₂— | 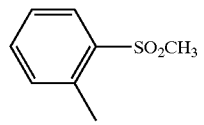 |
| 88 | H | H | 1 | —(CH₂)₂— | 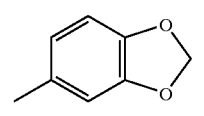 |
| 89 | H | H | 1 | —(CH₂)₂— | 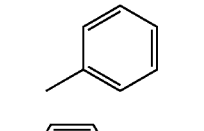 |
| 90 | H | H | 1 | —(CH₂)₂— | 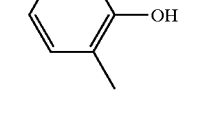 |
| 91 | H | H | 1 | —(CH₂)₂— | 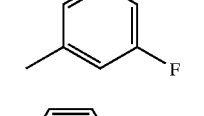 |
| 92 | H | H | 1 | —(CH₂)₂— | 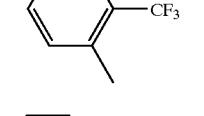 |
| 93 | H | H | 1 | —(CH₂)₂— | 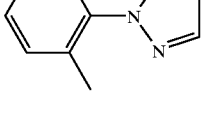 |

-continued
| | | | | |
|---|---|---|---|---|
| 94 | H | H | 1 —(CH$_2$)$_2$— | 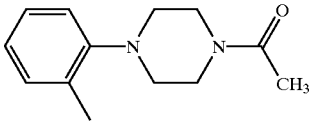 |
| 95 | H | H | 1 —(CH$_2$)$_2$— | 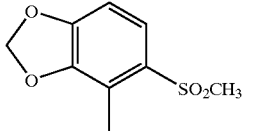 |
| 96 | H | H | 1 —(CH$_2$)$_2$— | 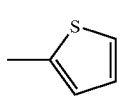 |
| 97 | H | H | 1 —(CH$_2$)$_2$— | 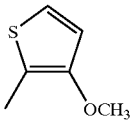 |
| 98 | H | H | 1 —(CH$_2$)$_2$— | 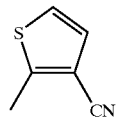 |
| 99 | H | H | 1 —(CH$_2$)$_2$— | 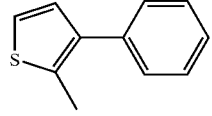 |
| 100 | H | H | 1 —(CH$_2$)$_2$— | 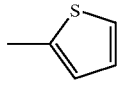 |
| 101 | H | H | 1 —(CH$_2$)$_2$— | 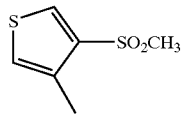 |
| 102 | H | H | 1 —(CH$_2$)$_2$— | 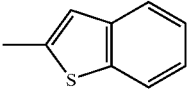 |
| 103 | H | H | 1 —(CH$_2$)$_2$— | 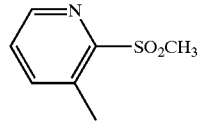 |
| 104 | H | H | 1 —(CH$_2$)$_2$— | 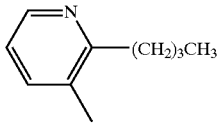 |
| 105 | H | H | 1 —(CH$_2$)$_2$— | 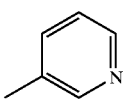 |

-continued
| | | | | | |
|---|---|---|---|---|---|
| 106 | H | H | 1 | —(CH₂)₂— | 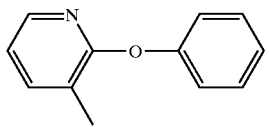 |
| 107 | H | H | 1 | —(CH₂)₂— | 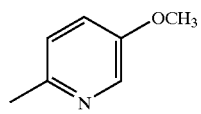 |
| 108 | H | H | 1 | —(CH₂)₂— | 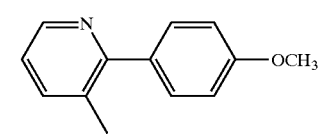 |
| 109 | H | H | 1 | —(CH₂)₂— | 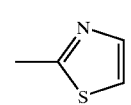 |
| 110 | H | H | 1 | —(CH₂)₂— | 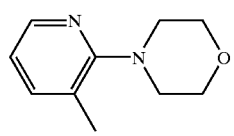 |
| 111 | H | H | 1 | —(CH₂)₂— | 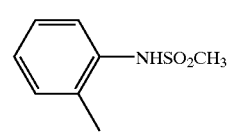 |
| 112 | H | H | 1 | —(CH₂)₂— | 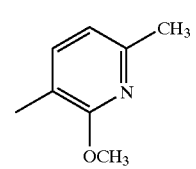 |
| 113 | H | H | 1 | —(CH₂)₂— | 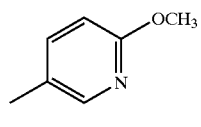 |
| 114 | H | H | 1 | 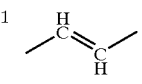 | 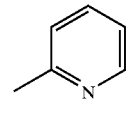 |
| 115 | H | H | 1 | —(CH₂)₂— | 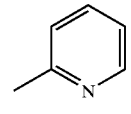 |
| 116 | H | H | 1 | 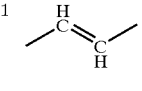 | 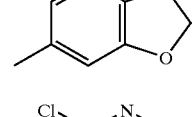 |
| 117 | H | H | 1 | —(CH₂)₂— | 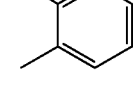 |

-continued

| | | | | |
|---|---|---|---|---|
| 118 | H | H | 1 —(CH₂)₂— | 3-methyl-2-methoxypyridine |
| 119 | H | H | 1 —(CH₂)₂— | 3-methyl-2-(methylthio)pyridine |
| 120 | H | H | 1 —(CH₂)₂— | 3-methyl-2-(2-methoxyethoxy)pyridine |
| 121 | H | H | 1 —(CH₂)₂— | 3-methyl-2-(cyclopropylmethoxy)pyridine |
| 122 | H | H | 1 —(CH₂)₂— | 3-methyl-2-(2,2,2-trifluoroethoxy)pyridine |
| 123 | H | H | 1 —(CH₂)₂— | 3-methyl-2-(2-hydroxyethoxy)pyridine |
| 124 | H | H | 1 —(CH₂)₂— | 3-methyl-2-(2-(dimethylamino)ethoxy)pyridine |
| 125 | H | H | 1 —(CH₂)₂— | 2-methyl-3-(thiazol-2-yl)-4-(methylsulfonyl)thiophene |
| 126 | H | H | 1 —(CH₂)₂— | 2-methyl-3-(thiazol-2-yl)thiophene |
| 127 | H | H | 1 —(CH₂)₂— | 3-methyl-2-(thiazol-2-yl)pyridine |
| 128 | H | H | 1 —(CH₂)₂— | 5-methyl-1,3-benzodioxole |

-continued

| 129 | H | H | 1 | —(CH$_2$)$_2$— | 2-methyl-benzonitrile |
| 130 | H | H | 1 | —(CH$_2$)$_2$— | 3-methyl-benzonitrile |
| 131 | H | H | 1 | —(CH$_2$)$_2$— | 4-methylbiphenyl |
| 132 | H | H | 1 | —(CH$_2$)$_2$— | 2-methylbiphenyl |
| 133 | H | H | 1 | —(CH$_2$)$_2$— | 2-methyl-thioanisole |
| 134 | H | H | 1 | —(CH$_2$)$_2$— | 2-methylanisole |
| 135 | H | H | 1 | —(CH$_2$)$_2$— | 2-methyl-3-(methylsulfonyl)thiophene |
| 136 | H | H | 1 | —(CH$_2$)$_2$— | methyl-methylsulfonyl-benzodioxole |
| 137 | H | H | 1 | —(CH$_2$)$_2$— | 3-methyl-2-(thiazol-2-yl)pyridine |
| 138 | H | H | 1 | —(CH$_2$)$_2$— | 1-(3-methylpyridin-2-yl)piperidin-4-ol |
| 139 | H | H | 1 | —(CH$_2$)$_2$— | 3-(3-methylpyridin-2-yloxy)propanenitrile |

-continued
| | | | | | |
|---|---|---|---|---|---|
| 140 | H | H | 1 | —(CH₂)₂— | 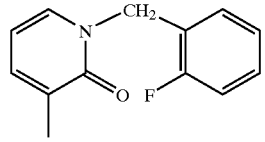 |
| 141 | H | H | 1 | 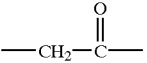 | 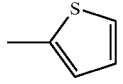 |
| 142 | H | H | 1 | 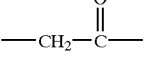 | 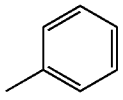 |
| 143 | H | H | 1 | 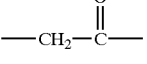 | 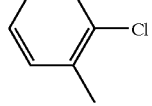 |
| 144 | H | H | 1 | 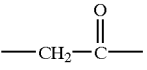 | 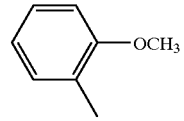 |
| 145 | H | H | 1 | 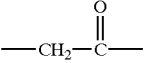 | 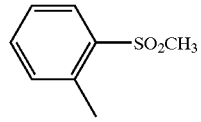 |
| 146 | H | H | 1 | 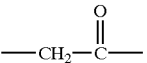 | 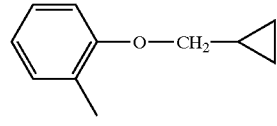 |
| 147 | H | H | 1 | 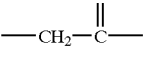 | 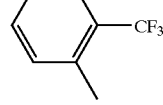 |
| 148 | H | H | 1 | 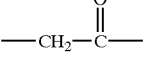 | 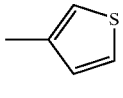 |
| 149 | H | H | 1 | 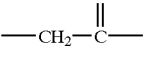 | 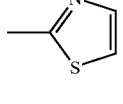 |
| 150 | H | H | 1 | 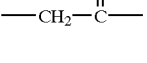 | 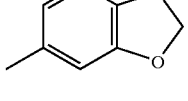 |
| 151 | H | H | 1 | 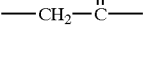 | 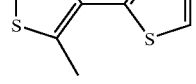 |

-continued
| | | | | | |
|---|---|---|---|---|---|
| 152 | H | H | 1 | —CH₂—C(=O)— | 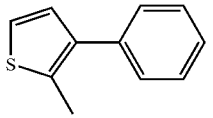 |
| 153 | H | H | 1 | —CH₂—C(=O)— | 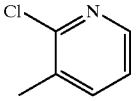 |
| 154 | H | H | 1 | —CH₂—C(=O)— | 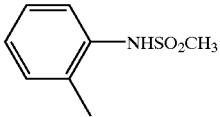 |
| 155 | H | H | 1 | —(CH₂)₃— | 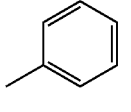 |
| 156 | H | H | 1 | —CH₂— | 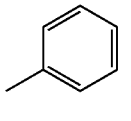 |
| 157 | H | H | 1 | —(CH₂)₄— | 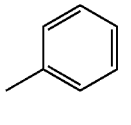 |
| 158 | H | H | 1 | —C(=O)— | 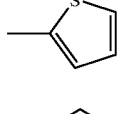 |
| 159 | H | H | 1 | —(CH₂)₂—C(=O)— | 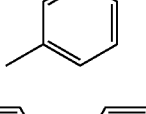 |
| 160 | H | H | 1 | —C(=O)— | 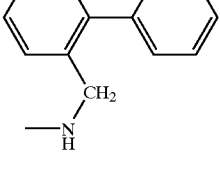 |
| 161 | H | H | 1 | —CH₂—O— | 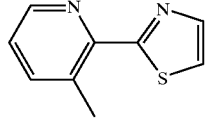 |
| 162 | H | H | 1 | —CH₂—CH(CN)— | 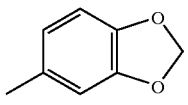 |
| 163 | H | H | 1 | —CH₂—CH(CN)— | 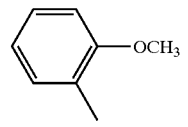 |

-continued
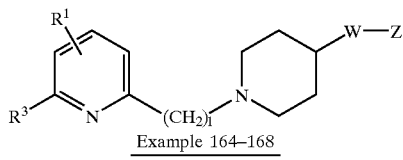
Example 164–168
| Ex.No. | R¹ | R³ | I | —W— | -Z |
|---|---|---|---|---|---|
| 164 | H | —OCH₃ | 1 | —(CH₂)₂— | benzodioxole-5-yl |
| 165 | H | —OCH₃ | 1 | —(CH₂)₂— | 3-thienyl |
| 166 | H | —OCH₃ | 1 | —(CH₂)₂— | 2-methoxy-3-methylpyridinyl |
| 167 | H | —OCH₃ | 1 | —(CH₂)₂— | benzodioxole-4-yl |
| 168 | H | —O(CH₂)₂OH | 1 | —(CH₂)₂— | benzodioxole-4-yl |
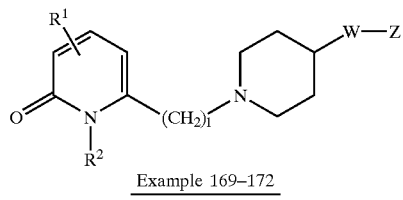
Example 169–172
| Ex.No. | R¹ | R² | I | —W— | -Z |
|---|---|---|---|---|---|
| 169 | H | H | 1 | —(CH₂)₂— | benzodioxole-5-yl |
| 170 | H | H | 1 | —(CH₂)₂— | 3-thienyl |
| 171 | H | H | 1 | —(CH₂)₂— | 2-methoxy-3-methylpyridinyl |
| 172 | H | H | 1 | —(CH₂)₂— | benzodioxole-4-yl |

-continued
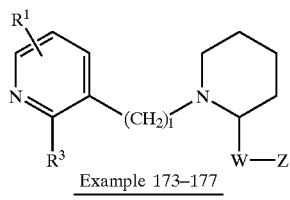
Example 173–177
| Ex.No. | R¹ | R³ | l | —W— | -Z |
|---|---|---|---|---|---|
| 173 | H | —OCH₃ | 1 | —CH₂—N(CH₃)—C(O)— | phenyl |
| 174 | H | —OCH₃ | 1 | —CH₂—C(O)— | —N(CH₃)—CH₂—(3-F-phenyl) |
| 175 | H | —OCH₃ | 1 | (R) —CH₂—C(O)— | —N(CH₃)(CH₂C≡CH)₂ (N,N-dipropargyl methylamine) |
| 176 | H | —OCH₃ | 1 | —(CH₂)₂—C(O)— | —N(CH₃)(CH₂C≡CH)₂ |
| 177 | H | —OCH₃ | 2 | —CH₂—C(O)— | —N(CH₃)—CH₂—(3-F-phenyl) |
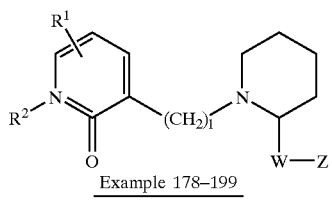
Example 178–199
| Ex.No. | R¹ | R² | l | —W— | -Z |
|---|---|---|---|---|---|
| 178 | H | H | 1 | —(CH₂)₃— | 2-methylpyridyl |
| 179 | H | H | 1 | —(CH₂)₂— | tolyl |
| 180 | H | —CH₂-cyclopropyl | 1 | —(CH₂)₃— | 2-methylpyridyl |
| 181 | H | H | 1 | —CH₂—C(O)— | —N(CH₃)—CH₂—phenyl |

-continued

| | | | | | |
|---|---|---|---|---|---|
| 182 | H | H | 1 | —CH₂—C(=O)— | —NH—CH₂-(3-fluorophenyl) |
| 183 | H | H | 1 | —CH₂—C(=O)— | —NH—CH₂—CH₂-cyclopropyl |
| 184 | H | H | 1 | —CH₂—C(=O)— | —NH—CH₂-cyclopropyl |
| 185 | H | H | 1 | —CH₂—C(=O)— | —NH-(4-fluorophenyl) |
| 186 | H | H | 1 | —CH₂—C(=O)— | —NH—CH₂-(2-pyridyl) |
| 187 | H | —CH₂-cyclopropyl | 1 | —CH₂—C(=O)— | —NH—CH₂—CH₂-cyclopropyl |
| 188 | H | —CH₂-cyclopropyl | 1 | —CH₂—C(=O)— | —NH—CH₂-(3-fluorophenyl) |
| 189 | H | —CH₂-cyclopropyl | 1 | —CH₂—C(=O)— | —NH-(4-fluorophenyl) |
| 190 | H | —CH₂-phenyl | 1 | —CH₂—C(=O)— | —NH—CH₂-(2-pyridyl) |
| 191 | H | H | 1 | (R) —CH₂—C(=O)— | —N(CH₂C≡CH)(CH₂C≡CH) (with N-methyl: dipropargyl methylamino) |
| 192 | H | —CH₂-cyclopropyl | 1 | (R) —CH₂—C(=O)— | N-methyl-N,N-dipropargylamino |
| 193 | H | —(CH₂)₂OCH₃ | 1 | (R) —CH₂—C(=O)— | N-methyl-N,N-dipropargylamino |
| 194 | H | —CH₂—CF₃ | 1 | (R) —CH₂—C(=O)— | N-methyl-N,N-dipropargylamino |

-continued
| Ex. | R¹ | R² | n | | |
|---|---|---|---|---|---|
| 195 | H | (i-Pr)₂N—CH₂— | 1 | (R) —CH₂—C(=O)— | 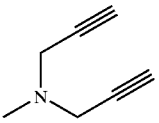 |
| 196 | H | H | 1 | —(CH₂)₂—C(=O)— | 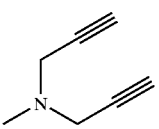 |
| 197 | H | —CH₂-cyclopropyl | 1 | —(CH₂)₂—C(=O)— | 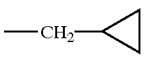 |
| 198 | H | H | 2 | —CH₂—C(=O)— | 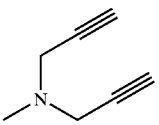 |
| 199 | H | —CH₂-cyclopropyl | 2 | —CH₂—C(=O)— | 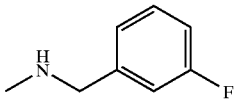 |
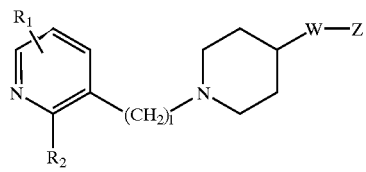
Example 201–283
| Ex.No. | R¹ | R² | l | —W— | -Z |
|---|---|---|---|---|---|
| 201 | H | —OCH₃ | 1 | —CH₂—O— | 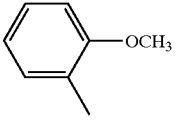 |
| 202 | H | —OCH₃ | 1 | —CH₂—O— | 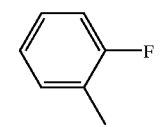 |
| 203 | 5-Cl | —OCH₃ | 1 | —CH₂—O— | 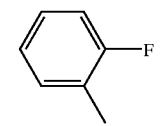 |
| 204 | H | —OCH₃ | 1 | —CH₂—O— | 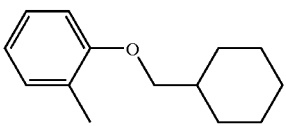 |
| 205 | H | —OCH₃ | 1 | —CH₂—O— | 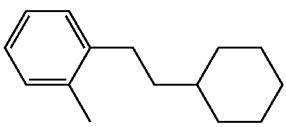 |

-continued
| | | | | |
|---|---|---|---|---|
| 206 | 5-Cl | —OCH₃ | 1 —CH₂—O— | 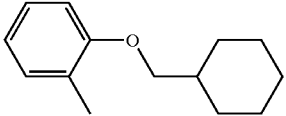 |
| 207 | H | —OCH₃ | 1 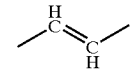 | 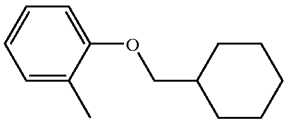 |
| 208 | 5-Cl | —OCH₃ | 1 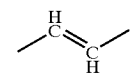 | 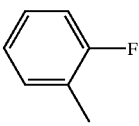 |
| 209 | 5-CN | —OCH₃ | 1 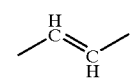 | 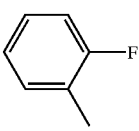 |
| 210 | 5-F | —OCH₃ | 1 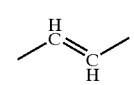 | 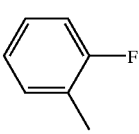 |
| 211 | 5-F | —OCH₃ | 1 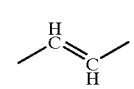 | 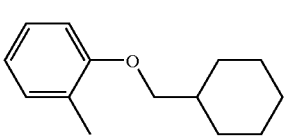 |
| 212 | 5-Cl | —OCH₃ | 1 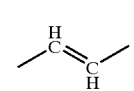 | 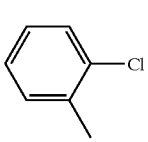 |
| 213 | 5-Cl | —OCH₃ | 1 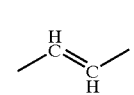 | 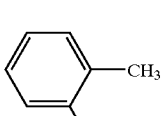 |
| 214 | H | —OCH₃ | 1 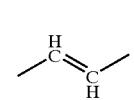 | 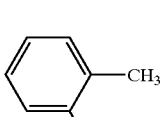 |
| 215 | H | —OCH₃ | 1 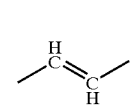 | 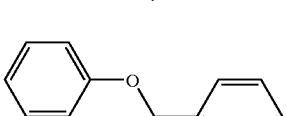 |
| 216 | H | —OCH₃ | 1 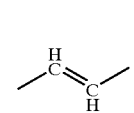 | 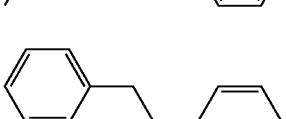 |

-continued

| | | | | |
|---|---|---|---|---|
| 217 | H | —OCH₃ | 1 | CH₂=CH-CH₃ | 2-methylphenyl isobutyl ether |
| 218 | H | —OCH₃ | 1 | CH₂=CH-CH₃ | 3-methylphenyl cyclohexylmethyl ether |
| 219 | H | —OCH₃ | 1 | CH₂=CH-CH₃ | 2-methylphenyl benzyl ether |
| 220 | H | —OCH₃ | 1 | CH₂=CH-CH₃ | 2-methylbenzyl phenyl ether |
| 221 | H | —OCH₃ | 1 | CH₂=CH-CH₃ | 2-methylphenyl cyclopentylmethyl ether |
| 222 | H | —OCH₃ | 1 | CH₂=CH-CH₃ | 1-methyl-2-(2-cyclohexylethyl)benzene |
| 223 | H | —OCH₃ | 1 | CH₂=CH-CH₃ | 4-fluoro-2-methylphenyl cyclohexylmethyl ether |
| 224 | H | —OCH₃ | 1 | CH₂=CH-CH₃ | 5-fluoro-2-methylphenyl cyclohexylmethyl ether |
| 225 | H | —OCH₃ | 1 | CH₂=CH-CH₃ | 3-fluoro-2-methylphenyl cyclohexylmethyl ether |
| 226 | H | —OCH₃ | 1 | CH₂=CH-CH₃ | 4-methoxy-2,5-dimethyl (substituted benzene) |
| 227 | H | —OCH₃ | 1 | CH₂=CH-CH₃ | 1-bromo-3-methylbenzene |

-continued
| | | | | | |
|---|---|---|---|---|---|
| 228 | H | —OCH₃ | 1 | 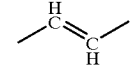 | 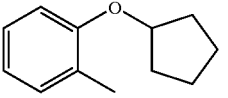 |
| 229 | H | —OCH₃ | 1 | 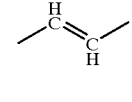 | 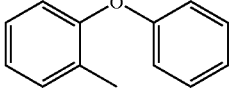 |
| 230 | H | —OCH₃ | 1 | 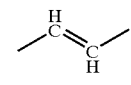 | 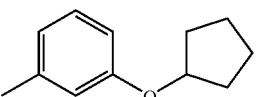 |
| 231 | H | —OCH₃ | 1 | 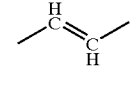 | 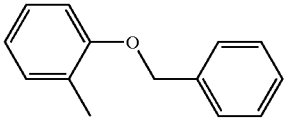 |
| 232 | H | —OCH₃ | 1 | 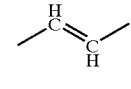 | 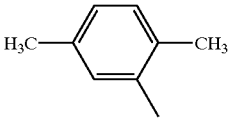 |
| 233 | H | —OCH₃ | 1 | 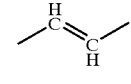 | 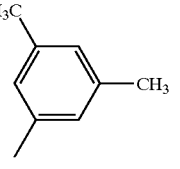 |
| 234 | H | —OCH₃ | 1 | 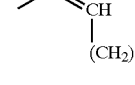 | 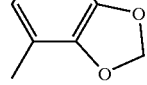 |
| 235 | H | —OCH₃ | 1 | 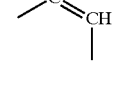 | 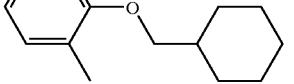 |
| 236 | H | —OCH₃ | 1 | 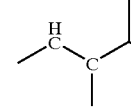 | 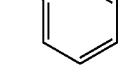 |
| 237 | H | —OCH₃ | 1 | —(CH₂)₃— | 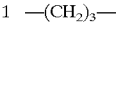 |
| 238 | H | —OCH₃ | 1 | —(CH₂)₅— | 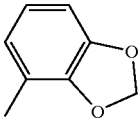 |

-continued

| | | | | |
|---|---|---|---|---|
| 239 | 6-CH₃ | —OCH₃ | 1 —(CH₂)₂— | 7-methyl-1,3-benzodioxole |
| 240 | H | —OCH₃ | 1 isobutylbenzene-type (CH₂CH(CH₃)Ph) | toluene |
| 241 | 5-Br | —OCH₃ | 1 —(CH₂)₂— | 7-methyl-1,3-benzodioxole |
| 242 | 5-CH₃ | —OCH₃ | 1 —(CH₂)₂— | 7-methyl-1,3-benzodioxole |
| 243 | H | —OCH₃ | 1 —(CH₂)₂— | 2-methylphenyl benzyl ether |
| 244 | 5-phenyl | —OCH₃ | 1 —(CH₂)₂— | 7-methyl-1,3-benzodioxole |
| 245 | H | —OCH₃ | 1 —(CH₂)₂— | 2-(2-methylphenoxy)-1-(piperidin-1-yl)ethanone |
| 246 | H | —OCH₃ | 1 —(CH₂)₂— | 4-(2-methylphenoxy)pyridine |
| 247 | H | —OCH₃ | 1 —(CH₂)₂— | N,N-dimethyl-1-(2-methylphenoxy)cyclopentanecarboxamide |
| 248 | 5-Cl | —OCH₃ | 1 —(CH₂)₂— | 2-methylphenyl benzyl ether |
| 249 | 5-Cl | —OCH₃ | 1 —(CH₂)₂— | 1-(2-methoxyethoxy)-2-methylbenzene |

-continued
| | | | | |
|---|---|---|---|---|
| 250 | H | —OCH₃ | 1 —(CH₂)₂— | 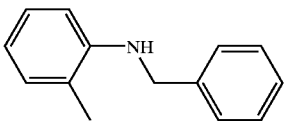 |
| 251 | H | —OCH₃ | 1 —(CH₂)₂— | 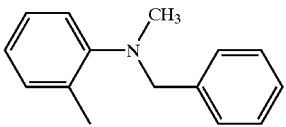 |
| 252 | H | —OCH₃ | 1 —(CH₂)₂— | 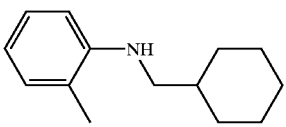 |
| 253 | H | —OCH₃ | 1 —(CH₂)₂— | 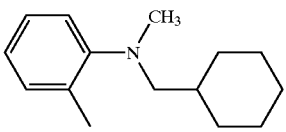 |
| 254 | H | —OCH₃ | 1 single bond | 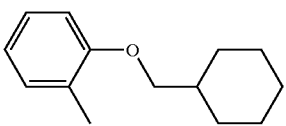 |
| 255 | H | —OCH₃ | 1 —(CH₂)₂— | 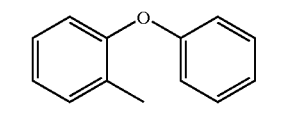 |
| 256 | H | —OCH₃ | 1 —(CH₂)₂— | 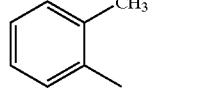 |
| 257 | H | —OCH₃ | 1 —(CH₂)₄— | 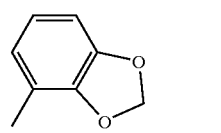 |
| 258 | H | —OCH₃ | 1 —(CH₂)₂— | 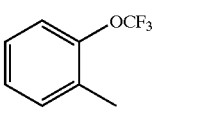 |
| 259 | H | —OCH₃ | 1 —(CH₂)₂— | 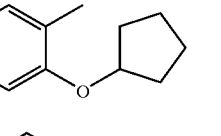 |
| 260 | H | —OCH₃ | 1 —(CH₂)₂— | 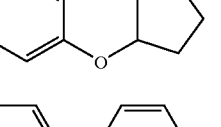 |
| 261 | H | —OCH₃ | 1 —(CH₂)₂— | 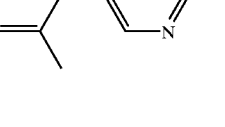 |

-continued
| 262 | H | —OCH₃ | 1 | —(CH₂)₂— | 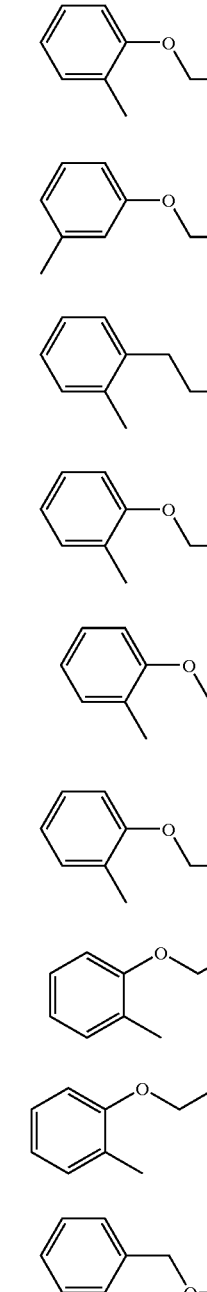 |
| 263 | H | —OCH₃ | 1 | —(CH₂)₂— | 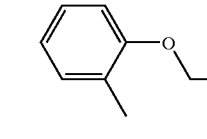 |
| 264 | H | —OCH₃ | 1 | —(CH₂)₂— | 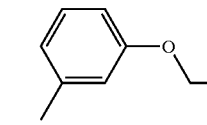 |
| 265 | H | —OCH₃ | 1 | —(CH₂)₂— | 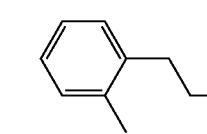 |
| 266 | H | —OCH₃ | 1 | —(CH₂)₂— | 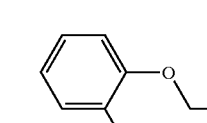 |
| 267 | H | —OCH₃ | 1 | —(CH₂)₂— | 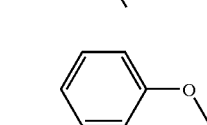 |
| 268 | H | —OCH₃ | 1 | —(CH₂)₂— | 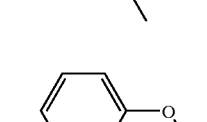 |
| 269 | H | —OCH₃ | 1 | —(CH₂)₂— | 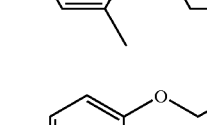 |
| 270 | H | —OCH₃ | 1 | —(CH₂)₂— | 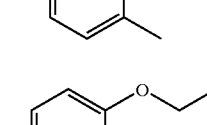 |
| 271 | H | —OCH₃ | 1 | —(CH₂)₂— | 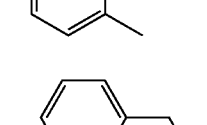 |
| 272 | H | —OCH₃ | 1 | —(CH₂)₂— | 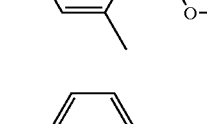 |

-continued
| | | | | | |
|---|---|---|---|---|---|
| 273 | H | —OCH$_3$ | 1 | —(CH$_2$)$_2$— | 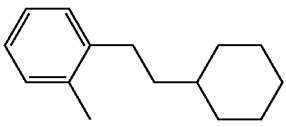 |
| 274 | H | —OCH$_3$ | 1 | —(CH$_2$)$_2$— | 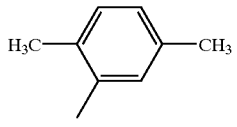 |
| 275 | H | —OCH$_3$ | 1 | —(CH$_2$)$_2$— | 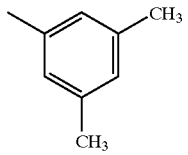 |
| 276 | H | —OCH$_3$ | 1 | —(CH$_2$)$_2$— | 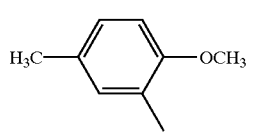 |
| 277 | 5-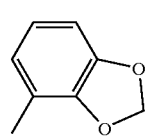 | —OCH$_3$ | 1 | —(CH$_2$)$_2$— | 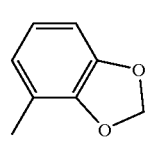 |
| 278 | 5-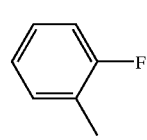 | —OCH$_3$ | 1 | —(CH$_2$)$_2$— | 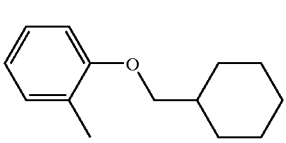 |
| 279 | 5-Cl | —OCH$_3$ | 1 | —(CH$_2$)$_2$— | 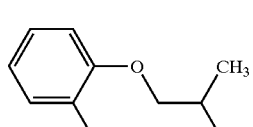 |
| 280 | 5-Cl | —OCH$_3$ | 1 | (CH$_2$)$_2$— | 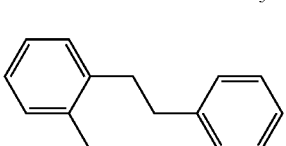 |
| 281 | 5-Cl | —OCH$_3$ | 1 | —(CH$_2$)$_2$— | 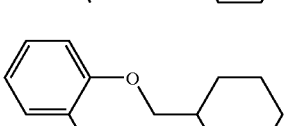 |
| 282 | 5-Cl | —OCH$_3$ | 1 | —(CH$_2$)$_2$— | |
| 283 | 5-H$_3$C—S(=O)$_2$— | —OCH$_3$ | 1 | —(CH$_2$)$_2$— | |

-continued
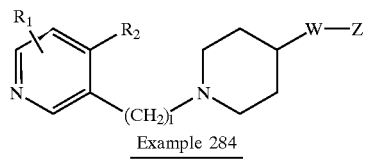
Example 284
| Ex.No. | R¹ | R² | I | —W— | -Z |
|---|---|---|---|---|---|
| 284 | H | —OCH₃ | 1 | —(CH₂)₂— | 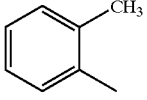 |
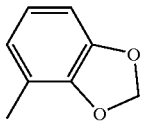
Example 285–378
| Ex.No. | R¹ | R² | I | —W— | -Z |
|---|---|---|---|---|---|
| 285 | H | H | 1 | —(CH₂)₂— | 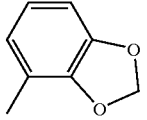 |
| 286 | H | H | 1 | —(CH₂)₄— | 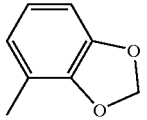 |
| 287 | H | H | 1 | —(CH₂)₃— | 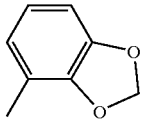 |
| 288 | H | H | 1 | —(CH₂)₅— | 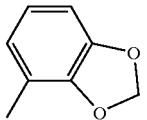 |
| 289 | 6-CH₃ | H | 1 | —(CH₂)₂— | 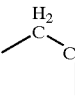 |
| 290 | H | H | 1 | 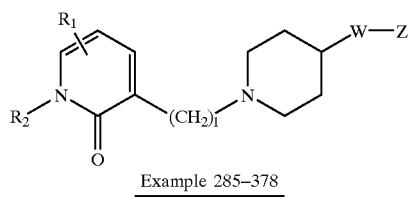 | 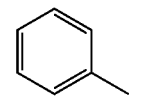 |
| 291 | 5-Br | H | 1 | —(CH₂)₂— | 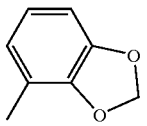 |

-continued

| | | | | | |
|---|---|---|---|---|---|
| 292 | 5-CH₃ | H | 1 | —(CH₂)₂— | 4-methyl-1,3-benzodioxole |
| 293 | 5-phenyl | H | 1 | —(CH₂)₂— | 4-methyl-1,3-benzodioxole |
| 294 | H | H | 1 | —(CH₂)₂— | 2-(2-methylphenoxy)-1-(piperidin-1-yl)ethanone |
| 295 | H | H | 1 | —(CH₂)₂— | 4-(2-methylphenoxy)pyridine |
| 296 | H | H | 1 | —(CH₂)₂— | 1-(2-methylphenoxy)-N,N-dimethylcyclopentanecarboxamide |
| 297 | 5-(pyridin-3-yl) | H | 1 | —(CH₂)₂— | 4-methyl-1,3-benzodioxole |
| 298 | 5-(pyridin-4-yl) | H | 1 | —(CH₂)₂— | 4-methyl-1,3-benzodioxole |
| 299 | 5-Cl | H | 1 | —(CH₂)₂— | 1-(benzyloxy)-2-methylbenzene |
| 300 | H | H | 1 | —(CH₂)₂— | 1-(cyclohexylmethoxy)-3-methylbenzene |
| 301 | 5-Cl | H | 1 | —(CH₂)₂— | 1-(cyclohexylmethoxy)-2-methylbenzene |
| 302 | H | H | 1 | —(CH₂)₂— | 1-(cyclohexylmethoxy)-2-methylbenzene |

-continued

| | | | | |
|---|---|---|---|---|
| 303 | H | H | 1 —(CH₂)₂— | 3-methylphenyl cyclopentyl ether |
| 304 | H | H | 1 —(CH₂)₂— | 2-methylphenyl benzyl ether |
| 305 | H | H | 1 —(CH₂)₂— | 3-methylphenyl benzyl ether |
| 306 | H | H | 1 —(CH₂)₂— | 2-methylphenyl-CH₂CH₂-phenyl |
| 307 | H | H | 1 —(CH₂)₂— | 2-methylphenyl cyclopentyl ether |
| 308 | H | H | 1 —(CH₂)₂— | 2-methylphenyl isobutyl ether |
| 309 | H | H | 1 —(CH₂)₂— | 2-methylphenyl phenethyl ether |
| 310 | H | H | 1 —(CH₂)₂— | 2-methylbenzyl phenyl ether |
| 311 | H | H | 1 —(CH₂)₂— | 2-methylphenyl cyclopentylmethyl ether |
| 312 | H | H | 1 —(CH₂)₂— | 2-methylphenyl-CH₂CH₂-cyclohexyl |
| 313 | H | H | 1 —(CH₂)₂— | N-benzyl-2-methylaniline |

-continued
| | | | | | |
|---|---|---|---|---|---|
| 314 | H | H | 1 | —(CH₂)₂— | 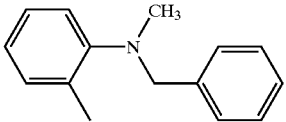 |
| 315 | H | H | 1 | —(CH₂)₂— | 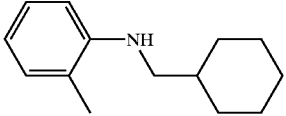 |
| 316 | H | H | 1 | —(CH₂)₂— | 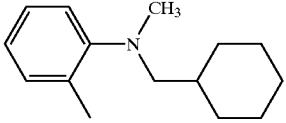 |
| 317 | H | H | 1 | —(CH₂)₂— | 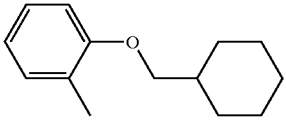 |
| 318 | 5- H₃C—S(=O)(=O)— | H | 1 | —(CH₂)₂— | 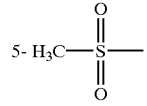 |
| 319 | 5-Cl | H | 1 | —(CH₂)₂— | 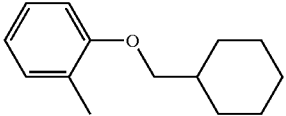 |
| 320 | 5-Cl | H | 1 | —(CH₂)₂— | 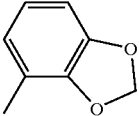 |
| 321 | 5-Cl | H | 1 | —(CH₂)₂— | 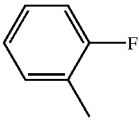 |
| 322 | H | H | 1 | —(CH₂)₂— | 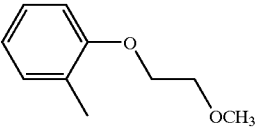 |
| 323 | 5-Cl | H | 1 | —(CH₂)₂— | 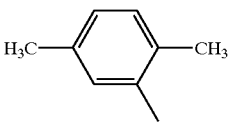 |
| 324 | H | H | 1 | —(CH₂)₂— | 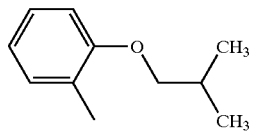 |

-continued

| | | | | |
|---|---|---|---|---|
| 325 | H | H | 1 —(CH₂)₂— | 2,4-dimethyl-methoxyphenyl (H₃C, OCH₃, CH₃) |
| 326 | H | H | 1 —(CH₂)₂— | 2-methyl-(trifluoromethoxy)phenyl |
| 327 | H | H | 1 —(CH₂)₂— | 3-(pyridin-3-yl)-methylphenyl |
| 328 | H | H | 1 —(CH₂)₂— | 3-((tetrahydropyran-2-yl)methoxy)-methylphenyl |
| 329 | H | H | 1 —(CH₂)₂— | 2-((tetrahydropyran-2-yl)methoxy)-methylphenyl |
| 330 | H | H | 1 —(CH₂)₂— | 2-(2-methoxyethoxy)-methylphenyl |
| 331 | H | H | 1 —(CH₂)₂— | 2-phenoxy-methylphenyl |
| 332 | 5-Cl | H | 1 —(CH₂)₂— | 2-(2-phenylethyl)-methylphenyl |
| 333 | H | H | 1  —CH=C(CH₃)(Ph)— | methylphenyl |
| 334 | 5-Cl | H | 1  —CH=CH(CH₃)— | 2-fluoro-methylphenyl |
| 335 | 5-F | H | 1  —CH=CH(CH₃)— | 2-fluoro-methylphenyl |

-continued
| | | | | | |
|---|---|---|---|---|---|
| 336 | 5-Cl | H | 1 | 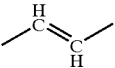 | 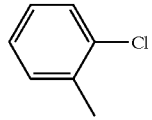 |
| 337 | 5-Cl | H | 1 | 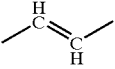 | 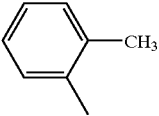 |
| 338 | H | H | 1 | 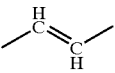 | 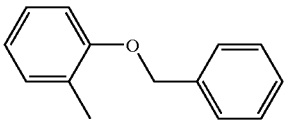 |
| 339 | H | H | 1 | 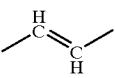 | 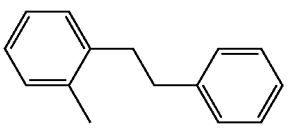 |
| 340 | H | H | 1 | 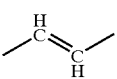 | 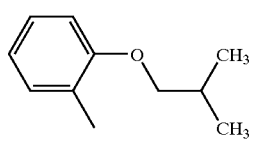 |
| 341 | H | H | 1 | 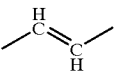 | 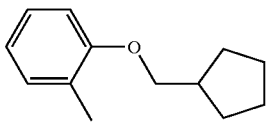 |
| 342 | H | H | 1 | 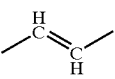 | 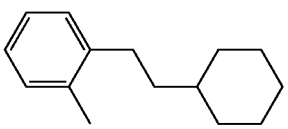 |
| 343 | H | H | 1 | 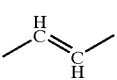 | 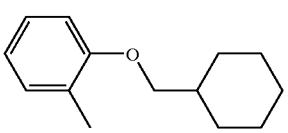 |
| 344 | H | H | 1 | 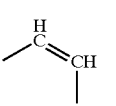 | 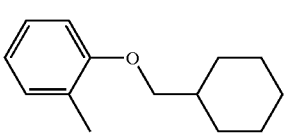 |
| 345 | 5-F | H | 1 | 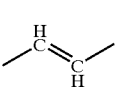 | 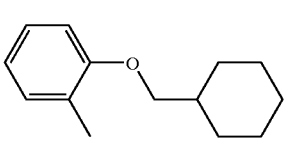 |
| 346 | H | H | 1 | 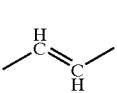 | 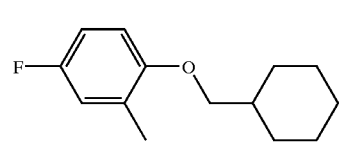 |

-continued
| | | | | | |
|---|---|---|---|---|---|
| 347 | H | H | 1 | 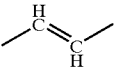 | 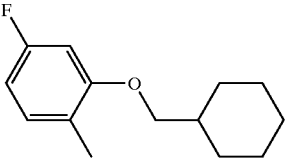 |
| 348 | H | H | 1 | 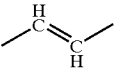 | 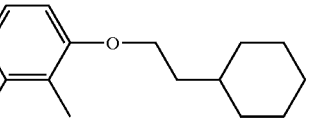 |
| 349 | H | H | 1 | —C≡C— |  |
| 350 | H | H | 1 | 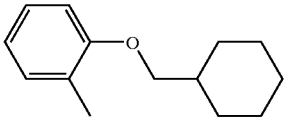 | 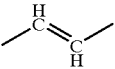 |
| 351 | 5-CN | H | 1 | 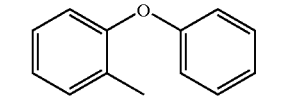 | 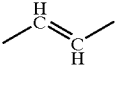 |
| 352 | H | H | 1 | —O—CH$_2$— | 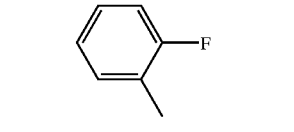 |
| 353 | H | H | 1 | —O—CH$_2$— |  |
| 354 | H | H | 1 | —O—CH$_2$— | 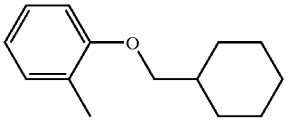 |
| 355 | 5-Cl | H | 1 | —O—CH$_2$— |  |
| 356 | H | H | 1 | —O—CH$_2$— | 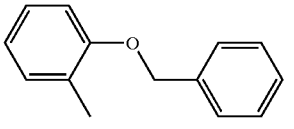 |
| 357 | 5-Cl | H | 1 | —O—CH$_2$— |  |

-continued
| | | | | | |
|---|---|---|---|---|---|
| 358 | H | H | 1 | —O—CH₂— | 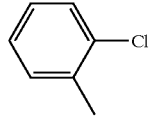 |
| 359 | 5-Cl | H | 1 | —O—CH₂— | 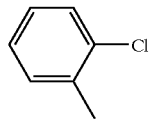 |
| 360 | H | H | 1 | —O—CH₂— | 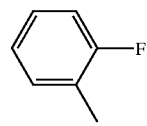 |
| 361 | 5-Cl | H | 1 | —O—CH₂— | 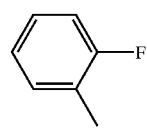 |
| 362 | H | H | 1 | —CH₂—O— | 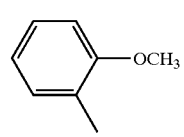 |
| 363 | 5-Cl | H | 1 | —CH₂—O— | 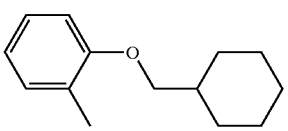 |
| 364 | H | H | 1 | —CH₂—O— | 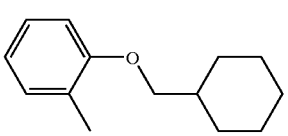 |
| 365 | H | H | 1 | —CH₂—O— | 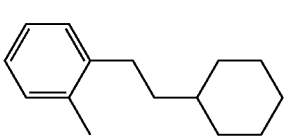 |
| 366 | H | H | 1 | —CH₂—O— | 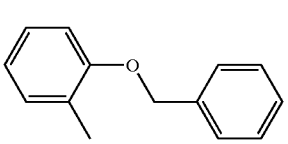 |
| 367 | H | H | 1 | —CH₂—O— | 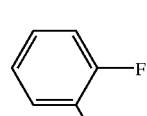 |
| 368 | 5-Cl | H | 1 | —CH₂—O— | 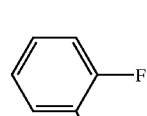 |

-continued
| | | | | |
|---|---|---|---|---|
| 369 | H | H | 1 —CH₂—O— | 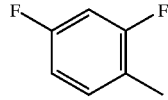 |
| 370 | 5-Cl | H | 1 —CH₂—O— | 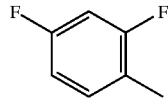 |
| 371 | H | H | 1 —CH₂—O— | 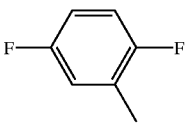 |
| 372 | 5-Cl | H | 1 —CH₂—O— | 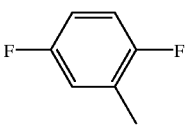 |
| 373 | H | H | 1 —CH₂—O— | 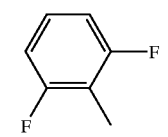 |
| 374 | 5-Cl | H | 1 —CH₂—O— | 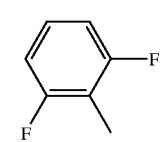 |
| 375 | 5-Cl | H | 1 —CH₂—O— | 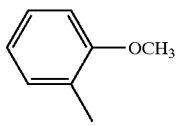 |
| 376 | H | H | 1 —CH₂—O— | 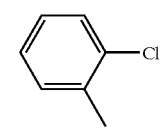 |
| 377 | 5-Cl | H | 1 —CH₂—O— | 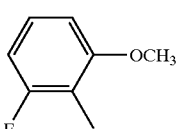 |
| 378 | 5-Cl | H | 1 —CH₂—O— | 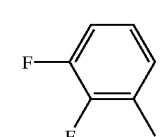 |

-continued

Example 379

| Ex.No. | R¹ | R² | l | —W— | -Z |
|---|---|---|---|---|---|
| 379 | H | H | 1 | —(CH₂)₂— | (benzodioxole) |

Example 380–381

| Ex.No. | R¹ | R² | l | —W— | -Z- |
|---|---|---|---|---|---|
| 380 | H | H | 2 | —(CH₂)₂— | (benzodioxole) |
| 381 | H | H | 2 | —(CH₂)₂— | (biphenyl) |

Test Example 1

Effect of Termination and Prevention of Atrium Fibrillation (AF) in Anesthetized Thoracotomy Dog (1) An anesthetized thoracotomy dog was used for the present experiment. After opening brisket at a median line and cutting epicardium, bipolar electrodes for determination of a potential wave form were respectively stitched at the free walls of right and left atriums. Further, a wire electrode was inserted in the free wall of a right atrium to be fixed and used for electrical simulation. After cutting cervix at a median line, right and left vagal nerves were peeled. Wire electrodes for stimulating vagal nerves were inserted along the surface layers of the respective both sides to be fixed and used as stimulation for vagal nerves.

(2) Electrical stimulation was carried out under conditions: a stimulation duration of 0.1 mess; a x stimulation frequency of 20 Hz; and a stimulation intensity of 3 to 7 V. After 5 minutes of the start of the stimulation, high frequency stimulation (10 Hz, 1 sec) was applied to the right atrium, and the induction of atrial fibrillation (hereinafter, abbreviated as "AF") was tried. The stimulation intensity of high frequency stimulation of the right atrium was carried out from 1.0 V, and when AF was not induced, induction was tried by increasing the stimulation intensity to 5.0 V. After AF was induced, observation for 30 minutes was carried out, it was confirmed that AF is kept (control experiment). Further, when AF induced was not kept for 30 minutes, the experiment was stopped.

(3) After confirming that AF was kept for 30 minutes or more in the control experiment, the stimulation of vagal nerve was intercepted, and the dog was rested for about one hour to be recovered. After that, similarly, AF was induced again. Further, the stimulation of vagal nerve at this time was carried out at the higher stimulation intensity by about 2 V than at the control experiment. After 5 minutes of the induction of AF, the administration of a tested substance was carried out. The tested substance was administered intravenously over 5 minutes. After completion of the administration, observation was carried out for 5 minutes, and when the termination of AF was not observed, the dose was increased and the observation was similarly carried out. When AF was stopped, the induction of AF was tried again just after termination. At this time, when AF which was continued for one minute or more was induced again, it was judged as no effect of prevention, and experiment was similarly carried out by increasing the dose.

(4) Result (Table 1): 1/3 of the samples exhibited termination effect at a dose of 0.3 mg/kg. Prevention effect was also confirmed at the same dose for the one sample. Test was carried out by increasing the dose to 1 mg/kg for two samples for which no termination effect was confirmed at a dose of 0.3 mg/kg. As a result, the termination effect was confirmed for 2/2 samples and the prevention effect was also confirmed.

TABLE 1

| Ex. No. | Dose | the termination effect | the prevention effect |
|---|---|---|---|
| 135 | 0.3 mg/kg | 1/3 | 1/1 |
|  | 1 mg/kg | 2/2 | 2/2 |

In the Table, the number of the denominator indicates the number of the sample used for test, and the number of the numerator indicates the number of the sample in which the effect was confirmed.

Test Example 2

Effective Refractory Period (ERP) in Anesthetized Thoracotomy Dog (1) An anesthetized thoracotomy dog was used for the present experiment. After opening brisket at a median line and cutting epicardium, bipolar electrodes for determination of a potential wave form were respectively stitched at the free walls of right and left atriums. Further, a wire electrode was inserted in the free wall of a right atrium to be fixed and used for electrical simulation.

(2) A program electrical stimulation equipment was connected with the electrode for electrical stimulation at the right atrium, the electrical stimulation was carried out at a stimulation periodical length of 500 mess, and a threshold for the electrical stimulation was measured. The electrical stimulation intensity for the experiments below was set to carry out stimulation at 3-fold of this threshold. However, when the threshold was 0.7 V or less, the electrical stimulation was carried out at 2.0 V. Effective refractory period (ERP) provided early premature stimulation (S2) after the basic stimulation (S1) of 10 times, and the longest linking period in which atrium potential was not generated by the premature stimulation was referred to as ERP, while shortening the linking period (S1–S2) by 5 mess. Similar experiments were also carried out for the respective basic stimulation length (BCL) of 400, 300, 250 and 200 mess (control experiment: 1 series). After carrying out 2 times or more of the control experiments and confirming that ERP was stable, the tested substance was subsequently administered, and similar measurement was carried out. After the tested substance was administered once intravenously for 5 minutes, its keeping dose was subsequently administered intravenously. After 10 minutes of the administration start of the keeping dose, ERP was measured in the respective stimulation frequency. After completion of the one series of measurements, the concentration of the tested substance was increased and the similar experiments were repeated. The ERP and conduction time in the atrium in the respective stimulation frequency were compared with various indices under control condition. The result is shown by mean.

(3) Result: The compound according to the present invention or a salt thereof and a hydrate of them can effectively terminate and prevent atrial fibrillation, and exhibited a superior effect for the extension of effective refractory period of atrial muscle (Tables 2 and 3).

(1) Measurement Value of ERP (Mess)

TABLE 2

| Ex. No. | Dose | BCL (msec) | | | | |
|---|---|---|---|---|---|---|
| | | 500 | 400 | 300 | 250 | 200 |
| 109 | (Pre) | 165 | 155 | 135 | — | 105 |
| | 0.1 mg/kg | 185 | 165 | 140 | — | 110 |
| | 0.3 mg/kg | 200 | 185 | 155 | — | 130 |
| | 1 mg/kg | 235 | 215 | 175 | — | 150 |
| 118 | (Pre) | 170 | 160 | 150 | — | 120 |
| | 0.3 mg/kg | 190 | 180 | 160 | — | 130 |
| | 1 mg/kg | 220 | 215 | 190 | — | — |
| 128 | (Pre) | 175 | 165 | 150 | — | 125 |
| | 0.1 mg/kg | 185 | 175 | 160 | — | 125 |
| | 0.3 mg/kg | 210 | 195 | 180 | — | 155 |
| | 1 mg/kg | 280 | 250 | 215 | — | — |
| 135 | (Pre) | 173.3 | 165.0 | 146.7 | 133.3 | 116.7 |
| | 0.1 mg/kg | 178.3 | 170.0 | 155.0 | 138.3 | 125.0 |
| | 0.3 mg/kg | 190.0 | 181.7 | 166.7 | 150.0 | 138.3 |
| | 1 mg/kg | 208.3 | 203.3 | 195.0 | 183.3 | — |
| 144 | (Pre) | 190 | 180 | 160 | 150 | 130 |
| | 0.1 mg/kg | 200 | 190 | 165 | 155 | 140 |
| | 0.3 mg/kg | 215 | 200 | 180 | 165 | 155 |
| 191 | (Pre) | 160 | 155 | 135 | — | 110 |
| | 0.3 mg/kg | 175 | 165 | 155 | — | 135 |
| | 1 mg/kg | 195 | 185 | 170 | — | 150 |
| 194 | (Pre) | 155 | 145 | 130 | 115 | 105 |
| | 0.1 mg/kg | 165 | 155 | 135 | 120 | 110 |
| | 0.3 mg/kg | 175 | 165 | 145 | 126 | 125 |
| | 1 mg/kg | 210 | 195 | 170 | 155 | 145 |

(2) Variation Coefficient (D %) of ERP

TABLE 3

| Ex. No. | Dose | BCL (msec) | | | | |
|---|---|---|---|---|---|---|
| | | 500 | 400 | 300 | 250 | 200 |
| 135 | 0.1 mg/kg | 3.1 | 3.0 | 5.7 | 3.9 | 7.1 |
| | 0.3 mg/kg | 9.8 | 10.1 | 13.7 | 12.6 | 18.6 |
| | 1 mg/kg | 20.6 | 23.4 | 33.2 | 37.9 | — |
| 191 | 0.3 mg/kg | 9.4 | 6.5 | 14.8 | — | — |
| | 1 mg/kg | 21.9 | 19.4 | 25.9 | — | — |

Test Example 3

Assessment for Sodium Channel of Synaptosome of Rat Cerebral Cortex

In the present experiment the synaptosome which was extracted from rat cerebral cortex was used. After sodium ion-sensitive dye, SBFI was taken in, the synaptosome was reacted with the respective tested substances (3 samples in 6 concentrations) at room temperature for 15 minutes in a 96 wells plate. The sodium channel inhibitory activity was measured using FDSS2000 of HAMAMATSU Photonics Co., Ltd. The sodium ion concentration in the synaptosome was measured once per 5 seconds using the fluorescent intensity of SBFI as an index. After measuring the control value 10 times, Veratridine was added so that the final concentration was 20 $\mu$M, and further measurement was carried out 30times. The inhibitory activity value of the tested substances for sodium channel was calculated, setting the action only by a measurement solution without the tested substance, as 0%, and the inhibitory activity caused by 2 $\mu$M of TTX which was a positive control, as 100%, as an inhibitory activity value corresponding to this action, using the increase of the fluorescent intensity of SBFI to the control value which was generated after addition of Veratridine, as an index. As a result, the compound according to the present invention exhibited a superior sodium channel inhibitory action as shown in Table 4 (SBFI value ($IC_{50}$ μM)).

Test Example 4

Assessment for Rabbit Atrial Muscle, Vmax

The specimen of the right atrial muscle which was enucleated from rabbit was used for the present experiment. The electrical stimulation was applied for the right atrial muscle which was enucleated, under conditions: a stimulation duration of 1 mess; a stimulation frequency of 4 Hz; and a stimulation intensity of about 1.2-fold of the threshold. The stimulation was provided from 30 minutes to 60 minutes before start of the experiment, and the condition of the specimen was stabilized. The action potential was recorded according to a glass microelectrode method. 3 M KCl was charged in the glass electrode, inserted in the specimen of the right atrium, and the action potential was recorded. Vmax is the parameter of the maximum upstroke slope of the action potential recorded, and a value which was automatically calculated by an action potential analysis soft (CAPA 1.23 manufactured by Physiotec. Co., Ltd.) was used. After the action potential in a normal Tyrode solution was recorded as control, the action potential after flowing the tested substances at respective concentrations for 15 minutes was recorded. The action of the tested substance for Vmax was calculated as an $IC_{50}$ value. As a result, as shown in Table 4 (Vmax($IC_{50}$ μM)), it was confirmed that the compound according to the present invention has a superior action on Vmax.

Test Example 5

Suppression of Spontaneous Nerve Discharge

In order to assess the suppression action for spontaneous nerve discharge, the experiment was carried out by a method below, referring to "Burchiel, K J., Exp. Nuerol., 102, 249–253 (1988)". Namely, for the rat in which spontaneous discharge was observed, the left saphenous nerve was cut off nearby knee articulatio before 1 week or more, and around 3 mm of the nerve was cut off so that the nerve was not adhered again. The left saphenous nerve was exposed under urethane (1 g/kg body weight) anesthetized, and about 1 cm of adjacent portion from the cut portion was peeled from a periphery tissue. Further, a catheter was preliminarily inserted in the vein of a right neck for administration of a compound. The peeled nerve was mounted on a platinum hook electrode, and liquid paraffin was put on it so that the nerve was not dried. The electrode was connected with a fine electrode amplifier, and the value was recorded on a computer through an AD/converter from an oscilloscope. The nerve discharge recorded was assessed by the number of ignition per 10 seconds using an analysis soft (AcqKnowledge). As a result, as shown in Table 4 (Ectopic Firing ($ID_{50}$ mg/kg)), the compound according to the present invention exhibited a superior suppression action on the spontaneous nerve discharge.

TABLE 4

| Ex. No. | Test Example 3 SBFI ($IC_{50}$ μM) | Test Example 4 Vmax ($IC_{50}$ μM) | Test Example 5 Ectopic Firing ($ID_{50}$ mg/kg) |
| --- | --- | --- | --- |
| 285 | 7.7 | 2.9 | 0.13 |
| 291 | 14.5 | 6 | 0.1 |

TABLE 4-continued

| Ex. No. | Test Example 3 SBFI ($IC_{50}$ μM) | Test Example 4 Vmax ($IC_{50}$ μM) | Test Example 5 Ectopic Firing ($ID_{50}$ mg/kg) |
| --- | --- | --- | --- |
| 299 | 5.3 | 50 | 0.1 |
| 301 | 6.5 | 100 | 0.18 |
| 302 | 1.2 | 22.5 | 0.14 |
| 306 | 1.3 | 1.9 | 0.17 |
| 308 | 0.5 | 3.1 | 0.22 |
| 309 | 1 | 6.3 | 0.19 |
| 311 | 0.7 | 2 | 0.13 |
| 313 | 1.5 | 8.6 | 0.16 |
| 319 | 10.2 | 10 | 0.082 |
| 320 | 17 | 14.8 | 0.041 |
| 323 | 4.8 | 3.9 | 0.083 |
| 326 | 1.9 | 3.98 | 0.18 |
| 333 | 5.4 | 4.9 | 0.15 |
| 334 | — | 17.5 | 0.03 |
| 335 | — | 7.8 | 0.034 |
| 337 | — | — | 0.3 |
| 338 | 1.2 | 11.4 | 0.19 |
| 343 | — | 30 | 0.13 |
| 344 | — | 30 | 0.19 |
| 345 | — | — | 0.4 |
| 349 | — | — | 0.17 |
| 351 | — | — | 0.17 |
| 370 | 33.6 | 45 | 0.081 |
| 372 | 21.8 | 9.3 | 0.11 |
| 376 | 20.3 | — | 0.07 |
| 380 | 3.9 | 8.6 | 0.1 |
| 381 | 3 | 100 | 0.56 |

What is claimed is:

1. A compound represented by the following formula (I), a salt thereof or a hydrate of them:

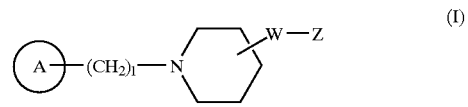

wherein in formula (I), the ring A is a ring represented by the formula:

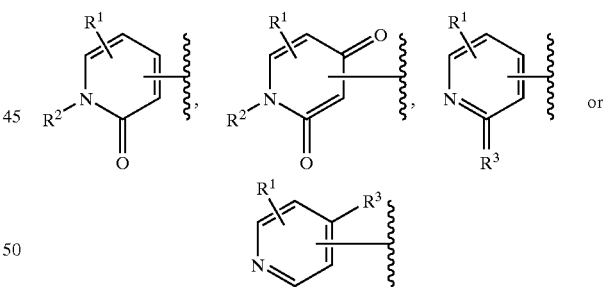

wherein $R^1$ is (1) a hydrogen atom, (2) a halogen atom, (3) a cyano group, (4) an optionally substituted $C_{1-6}$ alkyl group, (5) an optionally substituted $C_{2-6}$ alkenyl group, (6) an optionally substituted $C_{2-6}$ alkynyl group, (7) an optionally substituted $C_{3-8}$ cycloalkyl group, (8) an optionally substituted $C_{3-8}$ cycloalkenyl group, (9) an optionally substituted $C_{1-6}$ alkoxy group, (10) an optionally substituted $C_{1-6}$ alkylthio group, (11) an optionally substituted $C_{1-6}$ alkylsulfinyl group, (12) an optionally substituted $C_{1-6}$ alkylsulfonyl group, (13) an optionally substituted $C_{1-14}$ aromatic hydrocarbon cyclic group or (14) an optionally substituted 5- to 14-membered aromatic heterocyclic group;

$R^2$ is (1) a hydrogen atom, (2) an optionally substituted $C_{1-6}$ alkyl group, (3) an optionally substituted $C_{2-6}$ alkenyl group, (4) an optionally substituted $C_{2-6}$ alkynyl group, (5) an optionally substituted $C_{3-8}$ cycloalkyl group, (6) an optionally substituted $C_{3-8}$ cycloalkenyl group, (7) an optionally substituted amino group, (8) an additional substituted $C_{5-14}$ aromatic hydrocarbon cyclic group or (9) an optionally substituted 5- to 14-membered aromatic heterocyclic group; and $R^3$ is (1) an optionally substituted $C_{1-6}$ alkoxy group, (2) an optionally substituted $C_{2-6}$ alkenyloxy group, (3) an optionally substituted $C_{3-7}$ cycloalkyloxy group or (4) an optionally substituted $C_{3-7}$ cycloalkenyloxy group;

W is (1) a single bond, (2) an optionally substituted $C_{1-6}$ alkylene group, (3) an optionally substituted $C_{2-6}$ alkenylene group, (4) an optionally substituted $C_{2-6}$ alkynylene group or (5) a group represented by the formula —U—V— (wherein U is (i) a single bond, (ii) an oxygen atom, (iii) a sulfur atom, (iv) a group represented by the formula —NH—, (v) an optionally substituted $C_{1-6}$ alkylene group, (vi) an optionally substituted $C_{2-6}$ alkenylene group or (vii) an optionally substituted $C_{2-6}$ alkynylene group; V is (i) a single bond, (ii) an optionally substituted $C_{1-6}$ alkylene group, (iii) an optionally substituted $C_{2-6}$ alkenylene group, (iv) an optionally substituted $C_{2-6}$ alkynylene group, (v) an oxygen atom, (vi) a sulfur atom, or (vii) a group represented by the formula —CO—, (viii) —SO— or (ix) —SO$_2$—, provided that the case where U and V mean the same group in the above definition is excluded, and one of U and V is a single bond, an optionally substituted $C_{1-6}$ alkylene group, an optionally substituted $C_{2-6}$ alkenylene group or an optionally substituted $C_{2-6}$ alkynylene group);

Z is (1) an optionally substituted $C_{6-14}$ aromatic hydrocarbon cyclic group, (2) an optionally substituted 5- to 14-membered aromatic heterocyclic group or (3) a group represented by the formula —N($R^4$)$R^5$ (wherein $R^4$ and $R^5$ may be the same as or different from each other and each represents (i) a hydrogen atom, (ii) an optionally substituted $C_{1-6}$ alkyl group, (iii) an optionally substituted $C_{2-6}$ alkenyl group, (iv) an optionally substituted $C_{2-6}$ alkynyl group, (v) an optionally substituted $C_{3-8}$ cycloalkyl group, (vi) an optionally substituted $C_{3-8}$ cycloalkenyl group, (vii) an optionally substituted $C_{6-14}$ aromatic hydrocarbon cyclic group, (viii) an optionally substituted 5- to 14-membered aromatic heterocyclic group or (ix) a $C_{1-6}$ aliphatic acyl group, with the proviso that Z is not —NH$_2$); and l represents an integer of 0 to 6.

2. The compound according to claim 1, the salt thereof or the hydrate of them, wherein W is a group represented by the formula —CH$_2$—, —CH$_2$—CH$_2$—, —(CH$_2$)$_3$—, —(CH$_2$)$_4$—, —(CH$_2$)$_5$—, —CH=CH—, —C≡C—, —CO—, —O—, —O—CH$_2$—, —CH$_2$—O—, —CH$_2$—CO—, —(CH$_2$)$_2$—CO—, —CH$_2$—CH(CN)—, —CH$_2$—CH(OH)—, —SO$_2$—, —CH$_2$—SO$_2$—, —NH—CO—, —CH$_2$—NH—CO—, —NH—SO$_2$— or —CH$_2$—NH—SO$_2$—.

3. The compound according to claim 1, the salt thereof or the hydrate of them, wherein W is a group represented by the formula —CH$_2$—CH$_2$—, —CH=CH—, —CH≡CH— or —CH$_2$—O—.

4. The compound according to claim 1, the salt thereof or the hydrate of them, wherein Z is an optionally substituted $C_{6-14}$ aromatic hydrocarbon cyclic group or an optionally substituted 5- to 14-membered aromatic heterocyclic group.

5. The compound according to claim 1, the salt thereof or the hydrate of them, wherein Z is an optionally substituted phenyl group, pyridyl group or thienyl group.

6. The compound according to claim 1, the salt thereof or the hydrate of them, wherein Z is a $C_{6-14}$ aromatic hydrocarbon cyclic group or a 5- to 14-membered aromatic heterocyclic group, and the ring may be respectively substituted with one or more groups selected from (1) a hydroxyl group, (2) a halogen atom, (3) a cyano group, (4) an optionally substituted $C_{1-6}$ alkyl group, (5) an optionally substituted $C_{3-8}$ cycloalkyl group, (6) an optionally substituted $C_{1-6}$ alkoxy group, (7) an optionally substituted $C_{3-8}$ cycloalkyloxy group, (8) an optionally substituted $C_{1-6}$ alkylthio group, (9) an optionally substituted $C_{6-14}$ aryloxy group, (10) an optionally substituted 5- to 14-membered hetero aryloxy group, (11) an optionally substituted amino group, (12) an optionally substituted 5- to 14-membered aromatic heterocyclic group, (13) an optionally substituted 5- to 14-membered non aromatic heterocyclic group, (14) a $C_{1-6}$ alkylsulfonyl group and (15) a $C_{1-4}$ alkylenedioxy group.

7. The compound according to claim 1, the salt thereof or the hydrate of them, wherein Z is a group represented by the formula —N($R^4$)$R^5$.

8. The compound according to claim 7, the salt thereof or the hydrate of them, wherein $R^4$ and $R^5$ are the same as or different from each other and each represents an optionally substituted $C_{1-6}$ alkyl group, an optionally substituted $C_{2-6}$ alkynyl group, an optionally substituted $C_{6-14}$ aryl $C_{1-6}$ alkyl group or an optionally substituted heteroaryl $C_{1-6}$ alkyl group.

9. The compound according to claim 8, the salt thereof or the hydrate of them, wherein Z is an optionally substituted piperidyl group, an optionally substituted piperazyl group or an optionally substituted morpholinyl group.

10. The compound according to claim 1, the salt thereof or the hydrate of them, wherein l is 1.

11. A compound according to claim 1, a salt thereof or a hydrate of them:

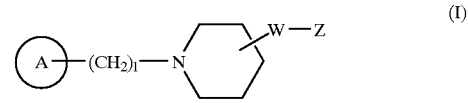

wherein in formula (I), wherein the ring A is represented by the formula:

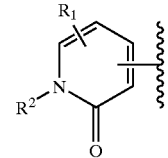

wherein $R^1$ is (1) a hydrogen atom, (2) a halogen atom, (3) a cyano group, (4) an optionally substituted $C_{1-6}$ alkyl group, (5) an optionally substituted $C_{2-6}$ alkenyl group, (6) an optionally substituted $C_{2-6}$ alkynyl group, (7) an optionally substituted $C_{3-8}$ cycloalkyl group, (8) an optionally substituted $C_{3-8}$ cycloalkenyl group, (9) an optionally substituted $C_{1-6}$ alkoxy group, (10) an optionally substituted $C_{1-6}$ alkylthio group, (11) an optionally substituted $C_{1-6}$ alkylsulfinyl group, (12) an optionally substituted $C_{1-6}$ alkylsulfonyl group, (13) an optionally substituted $C_{6-14}$ aromatic hydrocarbon cyclic group or (14) an optionally substituted 5- to 14-membered aromatic heterocyclic group;

$R^2$ is (1) a hydrogen atom, (2) an optionally substituted $C_{1-6}$ alkyl group, (3) an optionally substituted $C_{2-6}$ alkenyl group, (4) an optionally substituted $C_{2-6}$ alkynyl group, (5) an optionally substituted $C_{3-8}$ cycloalkyl group, (6) an optionally substituted $C_{3-8}$ cycloalkenyl group, (7) an optionally substituted amino group, (8) an optionally substituted $C_{6-14}$ aromatic hydrocarbon cyclic group or (9) an optionally substituted 5- to 14-membered aromatic heterocyclic group; and $R^3$ is (1) an optionally substituted $C_{1-6}$ alkoxy group, (2) an optionally substituted $C_{2-6}$ alkenyloxy group, (3) an optionally substituted $C_{3-7}$ cycloalkyloxy group or (4) an optionally substituted $C_{3-7}$ cycloalkenyloxy group;

W is (1) a single bond, (2) an optionally substituted $C_{1-6}$ alkylene group, (3) an optionally substituted $C_{1-6}$ alkenylene group, (4) an optionally substituted $C_{2-6}$ alkynylene group or (5) a group represented by the formula —U—V— (wherein U is (i) a single bond, (ii) an oxygen atom, (iii) a sulfur atom, (iv) a group represented by the formula —NH—, (v) an optionally substituted $C_{1-6}$ alkylene group, (vi) an optionally substituted $C_{2-6}$ alkenylene group or (vii) an optionally substituted $C_{2-6}$ alkynylene group; V is (i) a single bond, (ii) an optionally substituted $C_{1-6}$ alkylene group, (iii) an optionally substituted $C_{2-6}$ alkenylene group, (iv) an optionally substituted $C_{2-6}$ alkynylene group, (v) an oxygen atom, (vi) a sulfur atom, or (vii) a group represented by the formula —CO—, (viii) —SO— or (ix) —SO$_2$—, provided that the case where U and V mean the same group in the above definition is excluded, and one of U and V is a single bond, an optionally substituted $C_{1-6}$ alkylene group, an optionally substituted $C_{2-6}$ alkenylene group or an optionally substituted $C_{2-6}$ alkynylene group);

Z is (1) an optionally substituted $C_{6-14}$ aromatic hydrocarbon cyclic group, (2) an optionally substituted 5- to 14-membered aromatic heterocyclic group or (3) a group represented b the formula —N($R^4$)$R^5$ (wherein $R^4$ and $R^5$ may be the same as or different from each other and each represents (i) a hydrogen atom, (ii) an optionally substituted $C_{1-6}$ alkyl group, (iii) an optionally substituted $C_{2-6}$ alkenyl group, (iv) an optionally substituted $C_{2-6}$ alkynyl group, (v) an optionally substituted $C_{3-8}$ cycloalkyl group, (vi) an optionally substituted $C_{3-8}$ cycloalkenyl group, (vii) an optionally substituted $C_{6-14}$ aromatic hydrocarbon cyclic group, (viii) an optionally substituted 5- to 14-membered aromatic heterocyclic group or (ix) a $C_{1-6}$ aliphatic acyl group, or (x) $R^4$ and $R^5$ may be bound together to form a 3- to 8-membered nitrogen-containing cyclic group); and l represents an integer of 0 to 6.

12. The compound according to claim 11, the salt thereof or the hydrate of them, wherein $R^1$ is a hydrogen atom, a halogen atom or a $C_{1-6}$ alkyl group.

13. The compound according to claim 11, the salt thereof or the hydrate of them, wherein $R^1$ is a hydrogen atom.

14. The compound according to claim 11, the salt thereof or the hydrate of them, wherein $R^2$ is a hydrogen atom or an optionally substituted $C_{1-6}$ alkyl group.

15. The compound according to claim 1, the salt thereof or the hydrate of them, wherein the ring A is represented by the formula:

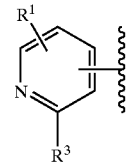

wherein $R^1$ and $R^3$ have the same meanings as defined in claim 1, respectively.

16. The compound according to claim 15, the salt thereof or the hydrate of them, wherein $R^3$ is a hydroxyl group or a $C_{1-6}$ alkoxy group.

17. The compound according to claim 1, the salt thereof or the hydrate of them, wherein the bonding position of the group —W—Z is 2- or 4-position of a piperidine ring.

18. A compound represented by the following formula, a salt thereof or a hydrate of them:

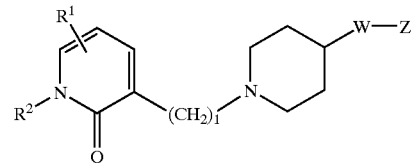

wherein $R^1$ is (1) a hydrogen atom, (2) a halogen atom, (3) a cyano group, (4) an optionally substituted $C_{1-6}$ alkyl group, (5) an optionally substituted $C_{2-6}$ alkenyl group, (6) an optionally substituted $C_{2-6}$ alkynyl group, (7) an optionally substituted $C_{3-8}$ cycloalkyl group, (8) an optionally substituted $C_{3-8}$ cycloalkenyl group, (9) an optionally substituted $C_{1-6}$ alkoxy group, (10) an optionally substituted $C_{1-6}$ alkylthio group, (11) an optionally substituted $C_{1-6}$ alkylsulfinyl group, (12) an optionally substituted $C_{1-6}$ alylsulfonyl group, (13) an optionally substituted $C_{6-14}$ aromatic hydrocarbon cyclic group or (14) an optionally substituted 5- to 14-membered aromatic heterocyclic group;

$R^2$ is (1) a hydrogen atom, (2) an optionally substituted $C_{1-6}$ alkyl group, (3) an optionally substituted $C_{2-6}$ alkenyl group, (4) an optionally substituted $C_{2-6}$ alkynyl group, (5) an optionally substituted $C_{3-8}$ cycloalkyl group, (6) an optionally substituted $C_{3-8}$ cycloalkenyl group, (7) an optionally substituted amino group, (8) an optionally substituted $C_{6-14}$ aromatic hydrocarbon cyclic group or (9) an optionally substituted 5- to 14-membered aromatic heterocyclic group;

W is (1) a single bond, (2) an optionally substituted $C_{1-6}$ alkylene group, (3) an optionally substituted $C_{2-6}$ alkenylene group, (4) an optionally substituted $C_{2-6}$ alkynylene group or (5) a group represented by the formula —U—V— (wherein U is (i) a single bond, (ii) an oxygen atom, (iii) a sulfur atom, (iv) a group represented by the formula —NH—, (v) an optionally substituted $C_{1-6}$ alkylene group, (vi) an optionally substituted $C_{2-6}$ alkenylene group or (vii) an optionally substituted $C_{2-6}$ alkynylene group; V is (i) a single bond, (ii) an optionally substituted $C_{1-6}$ alkylene group, (iii) an optionally substituted $C_{2-6}$ alkenylene group, (iv) an optionally substituted $C_{2-6}$ alkynylene group, (v) an oxygen atom, (vi) a sulfur atom, or (vii) a group represented by the formula —CO—, (viii) —SO— or (ix) —SO$_2$—, provided that the case where U and V mean the same group in the above definition is excluded, and one of U and V is a single bond, an optionally substituted $C_{1-6}$ alkylene group, an optionally substituted $C_{2-6}$ alkenylene group or an optionally substituted $C_{2-6}$ alkynylene group);

Z is (1) an optionally substituted $C_{6-14}$ aromatic hydrocarbon cyclic group, (2) an optionally substituted 5- to 14-membered aromatic heterocyclic group or (3) a group represented by the formula —N(R$^4$)R$^5$ (wherein R$^4$ and R$^5$ may be the same as or different from each other and each represents (i) a hydrogen atom, (ii) an optionally substituted $C_{1-6}$ alkyl group, (iii) an optionally substituted $C_{2-6}$ alkenyl group, (iv) an optionally substituted $C_{2-6}$ alkynyl group, (v) an optionally substituted $C_{3-8}$ cycloalkyl group, (vi) an optionally substituted $C_{3-8}$ cycloalkenyl group, (vii) an optionally substituted $C_{6-14}$ aromatic hydrocarbon cyclic group, (viii) an optionally substituted 5 to 14-membered aromatic heterocyclic group or (ix) a $C_{1-6}$ aliphatic acyl group, or (x) R$^4$ and R$^5$ may be bound together to form a 3- to 8-membered nitrogen-containing cyclic group); and l represents an integer of 0 to 6.

19. A compound represented by the following formula, a salt thereof or a hydrate of them:

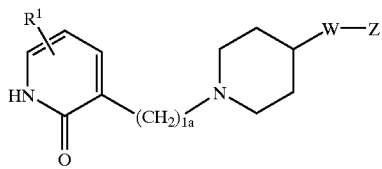

wherein R$^1$ is (1) a hydrogen atom, (2) a halogen atom, (3) a cyano group, (4) an optionally substituted $C_{1-6}$ alkyl group, (5) an optionally substituted $C_{1-6}$ alkenyl group, (6) an optionally substituted $C_{2-6}$ alkynyl group, (7) an optionally substituted $C_{3-8}$ cycloalkyl group, (8) an optionally substituted $C_{3-8}$ cycloalkenyl group, (9) an optionally substituted $C_{1-6}$ alkoxy group, (10) an optionally substituted $C_{1-6}$ alkylthio group, (11) an optionally substituted $C_{1-6}$ alkylsulfinyl group, (12) an optionally substituted $C_{1-6}$ aralkylsulfonyl group, (13) an optionally substituted $C_{6-14}$ aromatic hydrocarbon cyclic group or (14) an optionally substituted 5- to 14-membered aromatic heterocyclic group;

W is (1) a single bond, (2) an optionally substituted $C_{1-6}$ alkylene group, (3) an optionally substituted $C_{2-6}$ alkenylene group, (4) an optionally substituted $C_{2-6}$ alkynylene group or (5) a group represented by the formula —U—V— (wherein U is (i) a single bond, (ii) an oxygen atom, (iii) a sulfur atom, (iv) a group represented by the formula —NH—, (v) an optionally substituted $C_{1-6}$ alkylene group, (vi) an optionally substituted $C_{2-6}$ alkenylene group or (vii) an optionally substituted $C_{2-6}$ alkynylene group; V is (i) a single bond, (ii) an optionally substituted $C_{1-6}$ alkylene group, (iii) an optionally substituted $C_{2-6}$ alkenylene group, (iv) an optionally substituted $C_{2-6}$ alkynylene group, (v) an oxygen atom, (vi) a sulfur atom, or (vii) a group represented by the formula —CO—, (viii) —SO— or (ix) —SO$_2$—, provided that the case where U and V mean the same group in the above definition is excluded, and one of U and V is a single bond, an optionally substituted $C_{1-6}$ alkylene group, an optionally substituted $C_{2-6}$ alkenylene group or an optionally substituted $C_{2-6}$ alkynylene group);

Z is (1) an optionally substituted $C_{6-14}$ aromatic hydrocarbon cyclic group, (2) an optionally substituted 5- to 14-membered aromatic heterocyclic group or (3) a group represented by the formula —N(R$^4$)R$^5$ (wherein R$^4$ and R$^5$ may be the same as or different from each other and each represents (i) a hydrogen atom, (ii) an optionally substituted $C_{1-6}$ alkyl group, (iii) an optionally substituted $C_{2-6}$ alkenyl group, (iv) an optionally substituted $C_{2-6}$ alkynyl group, (v) an optionally substituted $C_{3-8}$ cycloalkyl group, (vi) an optionally substituted $C_{3-8}$ cycloalkenyl group, (vii) an optionally substituted $C_{6-14}$ aromatic hydrocarbon cyclic group, (viii) an optionally substituted 5- to 14-membered aromatic heterocyclic group or (ix) a $C_{1-6}$ aliphatic acyl group, or (x) R$^4$ and R$^5$ may be bound together to form a 3- to 8-membered nitrogen-containing cyclic group); and la represents an integer of 1 or 2.

20. A compound, a salt thereof or a hydrate of them, selected from the group consisting of 1-[(2-Oxo-1,2-dihydro-3-pyridinyl)methyl]-4-[2-[2-(cyclohexylmethyloxy)phenyl]ethyl]piperidine, 1-[(5-chloro-2-oxo-1,2-dihydro-3-pyridinyl)methyl]-4-[2-[2,3-(methylenedioxy)phenyl]ethyl]piperidine, 1-[(5-chloro-2-oxo-1,2-dihydro-3-pyridinyl)methyl]-4-[2-(2-(fluorophenyl)ethyl]piperidine, 1-[(5-chloro-2-oxo-1,2-dihydro-3-pyridinyl)methyl]-4-[2-[2-(isobutyloxy)phenyl]ethyl]piperidine, 1-[(5-chloro-2-oxo-1,2-dihydro-3-pyridinyl)methyl]-4-[(E)-2-(2-fluorophenyl)-1-ethenyl]piperidine, 1-[(5-fluoro-2-oxo-1,2-dihydro-3-pyridinyl)methyl]-4-[(E)-2-(2-fluorophenyl)-1-ethenyl]piperidine, 1-[(2-oxo-1,2-dihydro-3-pyridinyl)methyl]-4-[(E)-2-[2-(benzyloxy)phenyl]-1-ethenyl]piperidine, 1-[(2-oxo-1,2-dihydro-3-pyridinyl)methyl]-4-[(E)-2-[(2-cyclohexylmethyloxy)phenyl]-1-ethenyl]piperidine, 1-[(2-oxo-1,2-dihydro-3-pyridinyl)methyl]-4-[(Z)-2-[(2-cyclohexylmethyloxy)phenyl]-1-ethenyl]piperidine, 1-[(5-fluoro-2-oxo-1,2-dihydro-3-pyridinyl)methyl]-4-[(E)-2-[(2-cyclohexylmethyloxy)phenyl]-1-ethenyl]piperidine, 1-[(2-oxo-1,2-dihydro-3-pyridinyl)methyl]-4-[2-(2-cyclohexylmethyloxy)phenyl]-1-ethynyl]piperidine, 1-[(5-chloro-2-oxo-1,2-dihydro-3-pyridinyl)methyl]-4-[2,4-(difluorophenoxy)methyl]piperidine; and 1-[(5-chloro-2-oxo-1,2-dihydro-3-pyridinyl)methyl]-4-[2,5-(difluorophenoxy)methyl]piperidine.

21. A process for producing the compound according to claim 1, the salt thereof or the hydrate of them, which comprises the step of reacting a compound represented by the formula:

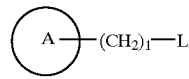

(wherein the ring A and l have the same meaning as claim 1, respectively; and L represents a leaving group), a salt thereof or a reactive derivative of them, with a compound represented by the formula:

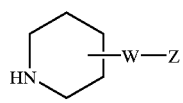

(wherein W and Z have the same meanings as defined in claim 1, respectively).

22. A pharmaceutical composition comprising:

a therapeutically effective amount of the compound, the salt thereof or the hydrate of them as defined in claim 1; and a pharmaceutically acceptable carrier.

23. A method for or treating a disease against which a sodium channel inhibitor or a potassium channel inhibitor is effective for said therapy, wherein said method comprises: administering a pharmacologically effective amount of the compound according to claim 1, the salt thereof or the hydrate of them, to a patient in need thereof.

24. The method of claim 23, wherein said disease is arrhythmia or class III arrhythmia of Vaughan Williams classification.

25. A method for treating a disease against which a sodium channel inhibitor or a potassium channel inhibitor is effective for said therapy, wherein said method comprises:

administering a therapeutically effective amount of the pharmaceutical composition according to claim 22, the salt thereof or the hydrate of them, to a patient in need thereof.

26. The method of claim 25, wherein said disease is arrhythmia or class III arrhythmia of Vaughan Williams classification.

* * * * *

UNITED STATES PATENT AND TRADEMARK OFFICE
CERTIFICATE OF CORRECTION

PATENT NO.    : 6,784,192 B2
DATED         : July 19, 2002
INVENTOR(S)   : Fumihiro Ozaki et al.

It is certified that error appears in the above-identified patent and that said Letters Patent is hereby corrected as shown below:

Title page,
Item [54], Title, should read
-- NOVEL PIPERIDINE COMPOUND AND PHARMACEUTICAL COMPOSITION THEREOF --

Signed and Sealed this

Fifteenth Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,784,192 B2
DATED : August 31, 2004
INVENTOR(S) : Fumihiro Ozaki et al.

It is certified that error appears in the above-identified patent and that said Letters Patent is hereby corrected as shown below:

Column 236,
Lines 40-47, the formula on the right-hand side: the double bond should be a single bond wherein the "=$R_3$" group should read as a -- -$R_3$ -- group.
Line 63, "optionally substituted $C_{1-14}$ aromatic hydrocarbon" should read -- optionally substituted $C_{6-14}$ aromatic hydrocarbon --.

Column 237,
Line 5, "additional substituted $C_{5-14}$ aromatic hydrocarbon" should read -- additional substituted $C_{6-14}$ aromatic hydrocarbon --.

Column 239,
Line 14, "alkylene group, (3) an optionally substituted $C_{1-6}$ alk-" should read -- alkylene group, (3) an optionally substituted $C_{2-6}$ alk- --.

Signed and Sealed this

Tenth Day of May, 2005

JON W. DUDAS
*Director of the United States Patent and Trademark Office*